United States Patent
Aihara et al.

(10) Patent No.: US 6,180,622 B1
(45) Date of Patent: Jan. 30, 2001

(54) IMIDAZO[5,1-B]THIAZOL-3-YL CARBAPENEM ANTIMICROBIALS

(75) Inventors: Kazuhiro Aihara; Toshiro Sasaki; Yumiko Toyooka; Yuko Kano; Kunio Atsumi; Katsuyoshi Iwamatsu; Takashi Ida, all of Yokohama (JP)

(73) Assignee: Meiji Seika Kaisha, Ltd., Tokyo (JP)

( * ) Notice: Under 35 U.S.C. 154(b), the term of this patent shall be extended for 0 days.

(21) Appl. No.: 09/117,167
(22) PCT Filed: Nov. 25, 1997
(86) PCT No.: PCT/JP97/04270
  § 371 Date: Jul. 23, 1998
  § 102(e) Date: Jul. 23, 1998
(87) PCT Pub. No.: WO98/23623
  PCT Pub. Date: Jul. 4, 1998

(30) Foreign Application Priority Data

Nov. 25, 1996 (JP) .................................................. 8-313922

(51) Int. Cl.[7] ...................... C07D 519/06; A61K 31/425; A61P 31/04
(52) U.S. Cl. ................................ 514/210.12; 514/210.13; 540/350
(58) Field of Search .......................... 540/350; 514/210, 514/210.12, 210.13

(56) References Cited

FOREIGN PATENT DOCUMENTS

| | | |
|---|---|---|
| 0 343 499 | 11/1989 | (EP) . |
| 0 424 832 | 5/1991 | (EP) . |
| 0 528 678 | 2/1993 | (EP) . |
| 0 581 500 | 2/1994 | (EP) . |
| 0 590 885 | 4/1994 | (EP) . |
| 0 760 370 | 3/1997 | (EP) . |
| 7-101959 | 4/1995 | (JP) . |
| 8-311071 | 11/1996 | (JP) . |
| 93/21186 | 10/1993 | (WO) . |
| 95/10520 | 4/1995 | (WO) . |

OTHER PUBLICATIONS

Database WPI, Week 9602, Derwent Publications Ltd., London, GB; AN 96–017206, XP002121958 & JP 07 291973 A (Banyu Pharmaceutical. CO., LTD.) Nov. 7, 1995 (1995–11–07) *abstract*.

Database WPI, Week 199533, Derwent Publications Ltd., London, GB; AN 1995–252272, XP002121959 & JP 07 157484 A (Yamanouchi Pharmaceutical. CO., LTD.) Jun. 20, 1995 (1995–06–20) *abstract*.

*Primary Examiner*—Mark L. Berch
(74) *Attorney, Agent, or Firm*—Wenderoth, Lind & Ponack, L.L.P.

(57) ABSTRACT

Compounds of formula (I) and compounds of formula (II) which have potent antimicrobial activity against a wide range of bacteria including Gram-positive bacteria and Gram-negative bacteria as well as heve potent antimicrobial activity against various β-lactamase-producing bacteria, MRSA, and resistant Pseudomonas aeruginosa and are very stable against DHP-1.

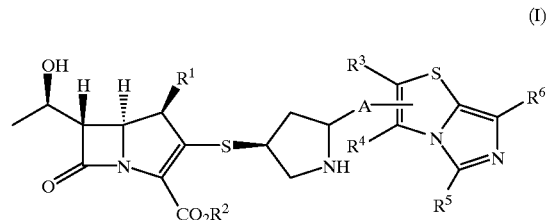

(I)

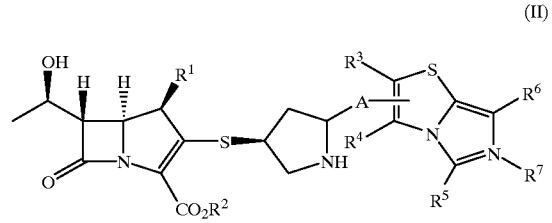

(II)

12 Claims, No Drawings

IMIDAZO[5,1-B]THIAZOL-3-YL CARBAPENEM ANTIMICROBIALS

BACKGROUND OF THE INVENTION

1. Field of the Invention

The present invention relates to carbapenem derivatives which have potent antimicrobial activity against a wide range of bacteria. More particularly, the present invention relates to novel carbapenem derivatives which have a substituted or unsubstituted imidazo[5,1-b]thiazole or imidazo[5,1-b]thiazolium group at the 2-position of the carbapenem ring through a pyrrolidinylthio group.

2. Background Art

Carbapenem derivatives, by virtue of potent antimicrobial activity against a wide spectrum of bacteria, have been energetically studied as a highly useful β-lactam agent, and Imipenem, Panipenem, and Meropenem have been clinically used.

At the present time, both Imipenem and Panipenem, however, are used as a mixture due to instability against renal dehydropeptidase-1 ("DHP-1") in the case of Imipenem and in order to reduce nephrotoxicity in the case of Panipenem. On the other hand, Meropenem, which has been recently put on the market, has increased stability against DHP-1 by virtue of the presence of a methyl group at the 1β-position and hence enabled the use as a single active ingredient in medicaments.

However, the stability against DHP-1 is not yet satisfactory. Further, the antimicrobial activity against methicillin-resistant *Staphylococcus aureus* (MRSA), penicillin-resistant *Streptococcus pneumoniae* (PRSP), and resistant *Pseudomonas aeruginosa* which have risen a serious clinical problem these days are also not always satisfactory. It is therefore strongly demanded to obtain novel carbapenem antibiotics which have improved antimicrobial activity against these bacteria.

WO 96/028455 discloses that carbapenem derivatives having an aromatic heterocyclic imidazo[5,1-b]thiazolium-6-ylmethyl group at the 2-position of the carbapenem ring have antimicrobial activity.

Japanese Patent Laid-Open Nos. 239058/1993 and 291973/1995, WO 95/10520, and WO 93/21186 disclose carbapenem derivatives wherein the 5-position of a pyrrolidinylthio group bonded to the 2-position of the carbapenem ring is bonded to the carbon atom on the aromatic heterocycle through a suitable spacer. None of these publications disclose carbapenem derivatives bonded to a bicyclic aromatic heterocycle.

SUMMARY OF THE INVENTION

The present inventors have now succeeded in synthesizing carbapenem derivatives having a substituted or unsubstituted imidazo[5,1-b]thiazole or substituted imidazo[5,1-b]thiazolium group at the 2-position of the carbapenem ring through a pyrrolidinylthio group (optionally through a pyrrolidinylthio group with a spacer).

According to one aspect of the present invention, there is provided a compound represented by formula (I) or a pharmacologically acceptable salt thereof:

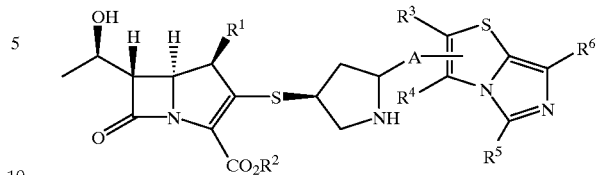

(I)

wherein

A represents a bond, —(CH$_2$)m—, —CHR$^8$—, —(CH$_2$)n—CH=CH—(CH$_2$)n'—, —C(=O)N(—R$^9$)CH$_2$— wherein R$^8$ represents hydroxyl, methoxy, halogen, or amino, R$^9$ represents hydrogen or —(CH$_2$)pCH$_3$ wherein p is an integer of 0 to 3, m is an integer of 1 to 3, and n and n' each represent an integer of 0 to 3;

R$^1$ represents hydrogen or lower alkyl;

R$^2$ represents hydrogen, sodium, or potassium; and any one of R$^3$, R$^4$, R$^5$, and R$^6$ represents a bond and is bonded to A, and the remaining three substituents, which may be the same or different, represent hydrogen, halogen, nitro, cyano, lower alkyl, lower cycloalkyl, lower alkylthio, C$_{2-4}$ alkenyl, formyl, lower alkylcarbonyl, arylcarbonyl, or aryl (one or more hydrogen atoms in said lower alkyl, lower cycloalkyl, C$_{2-4}$ alkenyl, and aryl groups may be substituted by a group selected from the group consisting of halogen, nitro, cyano, lower cycloalkyl, lower alkylthio, lower alkoxy, hydroxyl, amino, N-lower alkylamino, formyl, lower alkylcarbonyl, arylcarbonyl, carboxyl, lower alkoxycarbonyl, formylamino, lower alkylcarbonylamino, carbamoyl, (N-lower alkylamino) carbonyl, aminosulfonyl, (N-lower alkylamino) sulfonyl, aminosulfonylamino, (N-lower alkylamino) sulfonylamino, and aryl);

or any two of R$^3$, R$^4$, R$^5$, and R$^6$ may form together a five-membered heterocyclic saturated ring, containing one oxygen atom and one nitrogen atom, in which the ring may be substituted by oxo (=O), or any two of R$^3$, R$^4$, R$^5$, and R$^6$ may form together C$_{3-6}$ alkylene in which one or more methylene groups in the alkylene group may be substituted by —NH—, —O—, —S—, or —CO—.

According to another aspect of the present invention, there is provided a compound represented by formula (II) or a pharmacologically acceptable salt thereof:

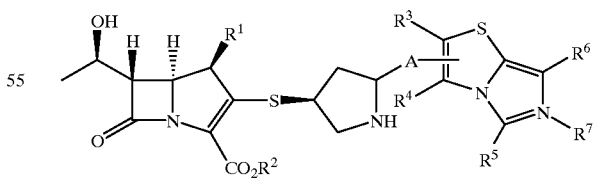

(II)

wherein

A represents a bond, —(CH$_2$)m—, —CHR$^8$—, —(CH$_2$)n—CH=CH—(CH$_2$)n'—, —C(=O)N(—R$^9$)CH$_2$— wherein R$^8$ represents hydroxyl, methoxy, halogen, or amino, R$^9$ represents hydrogen or —(CH$_2$)pCH$_3$ wherein p is an integer of 0 to 3, m is an integer of 1 to 3, and n and n' each represent an integer of 0 to 3;

$R^1$ represents hydrogen or lower alkyl;

$R^2$ represents hydrogen, sodium, or potassium;

any one of $R^3$, $R^4$, $R^5$, and $R^6$ represents a bond and is bonded to A, and the remaining three substituents, which may be the same or different, represent hydrogen, halogen, nitro, cyano, lower alkyl, lower cycloalkyl, lower alkylthio, $C_{2-4}$ alkenyl, formyl, lower alkylcarbonyl, arylcarbonyl, or aryl;

$R^7$ represents lower alkyl, lower cycloalkyl, or aryl; and one or more hydrogen atoms in said lower alkyl, lower cycloalkyl, $C_{2-4}$ alkenyl, and aryl groups each as a group or a portion of a group, which may be represented by $R^3$, $R^4$, $R^5$, $R^6$, and $R^7$, may be substituted by a group selected from the group consisting of halogen, nitro, cyano, lower cycloalkyl, lower alkylthio, lower alkoxy, hydroxyl, amino, N-lower alkylamino, formyl, lower alkylcarbonyl, arylcarbonyl, carboxyl, lower alkoxycarbonyl, formylamino, lower alkylcarbonylamino, carbamoyl, (N-lower alkylamino) carbonyl, aminosulfonyl, (N-lower alkylamino) sulfonyl, aminosulfonylaminq, (N-lower alkylamino) sulfonylamino, and aryl; and or any two of $R^3$, $R^4$, $R^5$, and $R^6$ may form together a five-membered heterocyclic saturated ring, containing one oxygen atom and one nitrogen atom, in which the ring may be substituted by oxo (=O), or any two of $R^3$, $R^4$, $R^5$, and $R^6$ may form together $C_{3-6}$ alkylene in which one or more methylene groups in the alkylene group may be substituted by —NH—, —O—, —S—, or —CO—.

The carbapenem derivatives represented by formulae (I) and (II) have potent antimicrobial activity against a wide range of bacteria including Gram-positive bacteria and Gram-negative acteria as well as have potent antimicrobial activity against various β-lactamase-producing bacteria, MRSA, and resistant *Pseudomonas aeruginosa*. Furthermore, they are very stable against DHP-1. Therefore, the compounds according to the present invention are useful as antimicrobial agents.

DETAILED DESCRIPTION OF THE INVENTION

Definition

As used herein, the term "lower alkyl" or "lower alkoxy" as a group or a part of a group means a straight or branched chain $C_{1-6}$ alkyl or alkoxy, preferably a straight or branched chain $C_{1-4}$ alkyl or alkoxy. The term "lower cycloalkyl" means $C_{3-6}$ monocyclic alkyl.

The term "halogen" means a fluorine, chlorine, bromine, or iodine atom.

Examples of the lower alkyl include methyl, ethyl, n-propyl, i-propyl, n-butyl, i-butyl, s-butyl, t-butyl, n-pentyl, and n-hexyl.

Examples of the lower alkoxy include methoxy, ethoxy, n-propoxy, i-propoxy, n-butoxy, i-butoxy, s-butoxy, and t-butoxy.

Compounds

The group —$(CH_2)m$— represented by A is preferably —$(CH_2)$— (i.e., m=1).

—$CHR^8$— represented by A is preferably —CHOH—.

—$(CH_2)n$—CH=CH—$(CH_2)n'$— represented by A is preferably —CH=CH— (i.e., n=n'=0).

—C(=O)N(—$R^9$)$CH_2$— represented by A is preferably —C(=O)N(—$CH_3$)$CH_2$— or —C(=O)NH—$CH_2$—.

$R^1$ preferably represents hydrogen or methyl.

$R^2$ preferably represents hydrogen.

$R^3$, $R^4$, $R^5$ and $R^6$ preferably represent hydrogen, halogen, cyano, lower alkyl, lower cycloalkyl, lower alkylthio, $C_{2-4}$ alkenyl, formyl, lower alkylcarbonyl, or aryl, more preferably represent hydrogen, halogen, lower alkyl, lower cycloalkyl, or lower alkylthio.

One or more hydrogen atoms in the lower alkyl, lower cycloalkyl, $C_{2-4}$ alkenyl, and aryl groups as a group or a portion of a group, which may be represented by $R^3$, $R^4$, $R^5$, and $R^6$, may be preferably substituted by halogen (for example, a fluorine atom), hydroxyl, amino, lower cycloalkyl (for example, cyclopropyl), lower alkylcarbonyl, lower alkoxy, lower alkoxycarbonyl, carboxyl, carbamoyl, or (N-lower-alkylamino)carbonyl (for example, dimethylaminocarbonyl).

Examples of the alkyl group as a group or a portion of a group, which may be represented by $R^3$, $R^4$, $R^5$, and $R^6$ as well as has been substituted, include aminomethyl, hydroxymethyl, 2-hydroxyethyl, carbamoylmethyl, carbamoylethyl, 2-fluoroethyl, cyclopropylmethyl, N,N-dimethylcarbamoylmethyl, methoxymethyl, ethoxycarbonylmethyl, and formylaminomethyl.

The arylcarbonyl group, which may be represented by $R^3$, $R^4$, $R^5$, and $R^6$, is preferably phenylcarbonyl or naphthyl-carbonyl.

The aryl group, which may be represented by $R^3$, $R^4$, $R^5$, and $R^6$, is preferably phenyl or naphthyl.

One or more hydrogen atoms in the lower alkyl, lower cycloalkyl, and aryl groups each as a group or a portion of a group, which may be represented by $R^7$, may be substituted. Examples of preferred substituents and examples of preferred substituted alkyl groups include those described above in connection with $R^3$, $R^4$, $R^5$, and $R^6$. $R^7$ preferably represents lower alkyl or lower cycloalkyl.

According to a preferred embodiment of the present invention, any two of $R^3$, $R^4$, $R^5$, and $R^6$ may form together a five-membered heterocyclic saturated ring, containing one oxygen atom and one nitrogen atom, in which the ring may be substituted by oxo (=O), or any two of $R^3$, $R^4$, $R^5$, and $R^6$ may form together $C_{3-6}$ alkylene in which one or more methylene groups in the alkylene group may be substituted by —NH—, —O—, —S—, or —CO—. Examples of compounds having such a cyclic structure include compounds wherein $R^3$ and $R^4$ represent 1-oxo-2-azapropano.

When A represents a bond, $R^4$ or $R^5$ preferably represents a bond.

A preferred group of compounds represented by formula (I) include those wherein

A represents a bond, —$CH_2$—, —CH(OH)—, —CH=CH—, —C(O)NHCH$_2$—, or —C(=O)N(—CH$_3$)CH$_2$—;

$R^1$ represents hydrogen or methyl;

$R^2$ represents hydrogen; and $R^3$, $R^4$, $R^5$, and $R^6$ except for those representing a bond, which may be the same or different, represent hydrogen, halogen, cyano, lower alkyl, lower cycloalkyl, lower alkylthio, $C_{2-4}$alkenyl, formyl, lower alkylcarbonyl, or aryl, (wherein one or more hydrogen atoms in the lower alkyl, lower cycloalkyl, $C_{2-4}$ alkenyl, and aryl groups may be optionally substituted by the substituent described above), more preferably hydrogen, halogen, lower alkyl, lower cycloalkyl, or lower alkylthio (wherein one or more hydrogen atoms in the lower alkyl and lower cycloalkyl groups may be optionally substituted by the substituent described above).

A preferred group of compounds represented by formula (II) include those wherein A represents a bond, —$CH_2$—, —CH(OH)—, —CH=CH—, —C(O)NHCH$_2$—, or —C(=O)N(—CH$_3$)CH$_2$—;

$R^1$ represents hydrogen or methyl;

$R^2$ represents hydrogen;

$R^3$, $R^4$, $R^5$, and $R^6$ except for those representing a bond, which may be the same or different, represent hydrogen, halogen, cyano, lower alkyl, lower cycloalkyl, lower alkylthio, $C_{2-4}$ alkenyl, formyl, lower alkylcarbonyl, or aryl (wherein one or more hydrogen atoms in the lower alkyl, lower cycloalkyl, $C_{2-4}$ alkenyl, and aryl groups may be optionally substituted by the substituent described above), more preferably, hydrogen, halogen, lower alkyl, lower cycloalkyl, or lower alkylthio (wherein one or more hydrogen atoms in the lower alkyl and lower cycloalkyl groups may be optionally substituted by the above substituent); and $R^7$ represents lower cycloalkyl or lower alkyl (wherein one or more hydrogen atoms in the lower alkyl and lower cycloalkyl groups may be optionally substituted by the substituent described above).

Specific examples of preferred carbapenem derivatives represented by formulae (I) and (II) according to the present invention include:

1. (1R,5S,6S)-6-((1R)-1-hydroxyethyl)-2-[(3S,5S)-5-[(imidazo[5,1-b]thiazol-5-yl)methylaminocarbonyl]pyrrolidin-3-yl]thio-1-methylcarbapen-2-em-3-carboxylic acid;
2. (1R,5S,6S)-6-((1R)-1-hydroxyethyl)-1-methyl-2-[(3S,5S)-5-[(6-methylimidazo[5,1-b]thiazolium-5-yl)methylaminocarbonyl]pyrrolidin-3-yl]thiocarbapen-2-em-3-carboxylic acid chloride;
3. sodim(1R,5S,6S)-6-((1R)-1-hydroxyethyl)-2-[(3S,5S)-5-[N-(imidazo[5,1-b]thiazol-5-yl)methyl-N-methylaminocarbonyl]pyrrolidin-3-yl]thio-1-methylcarbapen-2-em-3-carboxylate;
4. (1R,5S,6S)-6-((1R)-1-hydroxyethyl)-1-methyl-2-[(3S,5S)-5-[N-methyl-N-(6-methylimidazo[5,1-b]thiazolium-5-yl)methylaminocarbonyl]pyrrolidin-3-yl]thiocarbapen-2-em-3-carboxylic acid chloride;
5. (1R,5S,6S)-2-[(3S,5S)-5-[N-methyl-N-(5-aminomethyl-6-methylimidazo[5,1-b]thiazolium-3-yl)methylaminocarbonyl]pyrrolidin-3-yl]thio-6-((1R)-1-hydroxyethyl)-1-methylcarbapen-2-em-3-carboxylic acid iodide;
6. (1R,5S,6S)-6-((1R)-1-hydroxyethyl)-2-[(3S,5S)-5-[1-hydroxy-1-(imidazo[5,1-b]thiazol-3-yl)methyl]pyrrolidin-3-yl]thio-1-methylcarbapen-2-em-3-carboxylic acid;
7. (1R,5S,6S)-6-((1R)-1-hydroxyethyl)-2-[(3S,5S)-5-[1-hydroxy-1-(6-methylimidazo[5,1-b]thiazolium-3-yl)methyl]pyrrolidin-3-yl]thio-1-methylcarbapen-2-em-3-carboxylic acid iodide;
8. (1R,5S,6S)-6-((1R)-1-hydroxyethyl)-2-[(3S,5S)-5-[1-hydroxy-1-(imidazo[5,1-b]thiazol-3-yl)methyl]pyrrolidin-3-yl]thio-1-methylcarbapen-2-em-3-carboxylic acid;
9. (1R,5S,6S)-6-((1R)-1-hydroxyethyl)-2-[(3S,5S)-5-[1-hydroxy-1-(6-methylimidazo[5,1-b]thiazolium-3-yl)methyl]pyrrolidin-3-yl]thio-1-methylcarbapen-2-em-3-carboxylic acid perchlorate;
10. (1R,5S,6S)-6-((1R)-1-hydroxyethyl)-2-[(3S,5R)-5-(imidazo[5,1-b]thiazol-5-yl)methylpyrrolidin-3-yl]thio-1-methylcarbapen-2-em-3-carboxylic acid;
11. (1R,5S,6S)-6-((1R)-1-hydroxyethyl)-1-methyl-2-[(3S,5R)-5-(6-methylimidazo[5,1-b]thiazolium-5-yl)methylpyrrolidin-3-yl]thiocarbapen-2-em-3-carboxylic acid iodide;
12. (1R,5S,6S)-6-((1R)-1-hydroxyethyl-2-[(3S,5S)-5-[1-hydroxy-1-(imidazo[5,1-b]thiazol-5-yl)methyl]pyrrolidin-3-yl]thio-1-methylcarbapen-2-em-3-carboxylic acid;
13. (1R,5S,6S)-6-((1R)-1-hydroxyethyl)-2-[(3S,5S)-5-[1-hydroxy-1-(6-methylimidazo[5,1-b]thiazolium-5-yl)methyl]pyrrolidin-3-yl]thio-1-methylcarbapen-2-em-3-carboxylic acid iodide;
14. (1R,5S,6S)-6-((1R)-1-hydroxyethyl)-2-[(3S,5S)-5-[1-hydroxy-1-(imidazo[5,1-b]thiazol-7-yl)methyl]pyrrolidin-3-yl]thio-1-methylcarbapen-2-em-3-carboxylic acid;
15-1. (1R,5S,6S)-6-((1R)-1-hydroxyethyl)-2-[(3S,5S)-5-[1-hydroxy-1-(6-methylimidazo[5,1-b]thiazolium-7-yl)methyl]pyrrolidin-3-yl]thio-1-methylcarbapen-2-em-3-carboxylic acid iodide;
15-2. (1R,5S,6S)-6-((1R)-1-hydroxyethyl)-2-[(3S,5S)-5-[1-hydroxy-1-(6-methylimidazo[5,1-b]thiazolium-7-yl)methyl]pyrrolidin-3-yl]thio-1-methylcarbapen-2-em-3-carboxylic acid iodide;
16. (1R,5S,6S)-6-((1R)-1-hydroxyethyl)-2-[(3S,5S)-5-[1-hydroxy-1-(imidazo[5,1-b]thiazol-2-yl)methyl]pyrrolidin-3-yl]thio-1-methylcarbapen-2-em-3-carboxylic acid;
17. (1R,5S,6S)-6-((1R)-1-hydroxyethyl)-2-[(3S,5S)-5-[1-hydroxy-1-(imidazo[5,1-b]thiazol-2-yl)methyl]pyrrolidin-3-yl]thio-1-methylcarbapen-2-em-3-carboxylic acid;
18. (1R,5S,6S)-6-((1R)-1-hydroxyethyl)-2-[(3S,5S)-5-[1-hydroxy-1-(6-methylimidazo[5,1-b]thiazolium-2-yl)methyl]pyrrolidin-3-yl]thio-1-methylcarbapen-2-em-3-carboxylic acid iodide;
19. (1R,5S,6S)-6-((1R)-1-hydroxyethyl)-2-[(3S,5S)-5-[1-hydroxy-1-(6-methylimidazo[5,1-b]thiazolium-2-yl)methyl]pyrrolidin-3-yl]thio-1-methylcarbapen-2-em-3-carboxylic acid iodide;
20. (1R,5S,6S)-6-((1R)-1-hydroxyethyl)-2-[(3S,5R)-5-(imidazo[5,1-b]thiazol-3-yl)methylpyrrolidin-3-yl]thio-1-methylcarbapen-2-em-3-carboxylic acid;
21. (1R,5S,6S)-6-[(1R)-1-hydroxyethyl]-1-methyl-2-[(3S,5R)-5-(6-methylimidazo[5,1-b]thiazolium-3-yl)methylpyrrolidin-3-yl]thiocarbapen-2-em-3-carboxylic acid iodide;
22. (1R,5S,6S)-6-((1R)-1-hydroxyethyl)-2-[(3S,5R)-5-[6-(2-hydroxyethyl)imidazo[5,1-b]thiazolium-3-yl]methylpyrrolidin-3-yl]thio-1-methylcarbapen-2-em-3-carboxylic acid chloride;
23. (1R,5S,6S)-6-((1R)-1-hydroxyethyl)-2-[(3S,5S)-5-(imidazo[5,1-b]thiazol-2-yl)methylpyrrolidin-3-yl]thio-1-methylcarbapen-2-em-3-carboxylic acid;
24. (1R,5S,6S)-6-((1R)-1-hydroxyethyl)-1-methyl-2-[(3S,5S)-5-(6-methylimidazo[5,1-b]thiazolium-2-yl)methylpyrrolidin-3-yl]thiocarbapen-2-em-3-carboxylic acid iodide;
25. (1R,5S,6S)-6-((1R)-1-hydroxyethyl)-2-[(3S,5S)-5-[6-(2-hydroxyethyl)imidazo[5,1-b]thiazolium-2-yl]methylpyrrolidin-3-yl]thio-1-methylcarbapen-2-em-3-carboxylic acid chloride;
26. (1R,5S,6S)-2-[(3S,5S)-5-[6-(carbamoylmethyl)imidazo[5,1-b]thiazolium-2-yl]methylpyrrolidin-3-yl]thio-6-((1R)-1-hydroxyethyl)-1-methylcarbapen-2-em-3-carboxylic acid iodide;
27. (1R,5S,6S)-2-[(3S,5S)-5-[6-(2-fluoroethyl)imidazo[5,1-b]thiazolium-2-yl]methylpyrrolidin-3-yl]thio-6-((1R)-1-hydroxyethyl)-1-methylcarbapen-2-em-3-carboxylic acid chloride;
28. (1R,5S,6S)-6-((1R)-1-hydroxyethyl)-1-methyl-2-[(3S,5S)-5-(3-methylimidazo[5,1-b]thiazol-2-yl)methylpyrrolidin-3-yl]thiocarbapen-2-em-3-carboxylic acid;

29. (1R,5S,6S)-2-[(3S,5S)-5-(3,6-dimethylimidazo[5,1-b]thiazolium-2-yl)methylpyrrolidin-3-yl]thio-6-((1R)-1-hydroxyethyl)-1-methylcarbapen-2-em-3-carboxylic acid iodide;

30. (1R,5S,6S)-2-[(3S,5S)-5-(6-carbamoylmethyl-3-methylimidazo[5,1-b]thiazolium-2-yl)methylpyrrolidin-3-yl]thio-6-((1R)-1-hydroxyethyl)-1-methylcarbapen-2-em-3-carboxylic acid iodide;

31. (1R,5S,6S)-6-((1R)-1-hydroxyethyl)-1-methyl-2-[(3S,5S)-5-(5-methylimidazo[5,1-b]thiazol-2-yl)methylpyrrolidin-3-yl]thiocarbapen-2-em-3-carboxylic acid;

32. (1R,5S,6S)-2-[(3S,5S)-5-(5,6-dimethylimidazo[5,1-b]thiazolium-2-yl)methylpyrrolidin-3-yl]thio-6-((1R)-1-hydroxyethyl)-1-methylcarbapen-2-em-3-carboxylic acid iodide;

33. (1R,5S,6S)-2-[(3S,5S)-5-(6-carbamoylmethyl-5-methylimidazo[5,1-b]thiazolium-2-yl)methylpyrrolidin-3-yl]thio-6-((1R)-1-hydroxyethyl)-1-methylcarbapen-2-em-3 -carboxylic acid iodide;

34. (1R,5S,6S)-6-((1R)-1-hydroxyethyl)-2-[(3S,5R)-5-(imidazo[5,1-b]thiazol-7-yl)methylpyrrolidin-3-yl]thio-1-methylcarbapen-2-em-3-carboxylic acid;

35. (1R,5S,6S)-6-((1R)-1-hydroxyethyl)-1-methyl-2-[(3S,5R)-5-(6-methylimidazo[5,1-b]thiazolium-7-yl)methylpyrrolidin-3-yl]thiocarbapen-2-em-3-carboxylic acid iodide;

36. (1R,5S,6S)-6-((1R)-1-hydroxyethyl)-1-methyl-2-[(3S)-5-(6-methylimidazo[5,1-b]thiazolium-5-yl)pyrrolidin-3-yl]thiocarbapen-2-em-3-carboxylic acid chloride;

37. (1R,5S,6S)-6-((1R)-1-hydroxyethyl)-2-[(3S)-5-[6-(2-hydroxyethyl)imidazo[5,1-b]thiazolium-5-yl]pyrrolidin-3-yl]thio-1-methylcarbapen-2-em-3-carboxylic acid chloride;

38. (1R,5S,6S)-6-((1R)-1-hydroxyethyl)-2-[(3S,5S)-5-[2(Z)-(imidazo[5,1-b]thiazol-3-yl)ethenyl]pyrrolidin-3-yl]thio-1-methylcarbapen-2-em-3-carboxylic acid;

39. (1R,5S,6S)-6-((1R)-1-hydroxyethyl)-1-methyl-2-[(3S,5S)-5-[2(Z)-(6-methylimidazo[5,1-b]thiazolium-3-yl)ethenyl]pyrrolidin-3-yl]thiocarbapen-2-em-3-carboxylic acid chloride;

40. (1R,5S,6S)-6-((1R)-1-hydroxyethyl)-1-methyl-2-[(3S,5S)-5-[2(E)-(6-methylimidazo[5,1-b]thiazolium-3-yl)ethenyl]pyrrolidin-3-yl]thiocarbapen-2-em-3-carboxylic acid chloride;

41. (1R,5S,6S)-2-[(3S,5S)-5-[6-(2-cyclopropylmethyl)-5-methylimidazo[5,1-b]thiazolium-2-yl]methylpyrrolidin-3-yl]thio-6-((1R)-1-hydroxyethyl)-1-methylcarbapen-2-em-3-carboxylic acid;

42. (1R,5S,6S)-2-[(3S,5S)-5-[6-(2-fluoroethyl)-5-methylimidazo[5,1-b]thiazolium-2-yl]methylpyrrolidin-3-yl]thio-6-((1R)-1-hydroxyethyl)-1-methylcarbapen-2-em-3-carboxylic acid trifluoromethanesulfonate;

43. (1R,5S,6S)-6-((1R)-1-hydroxyethyl)-2-[(3S,5S)-5-[6-(2-hydroxyethyl)-5-methylimidazo[5,1-b]thiazolium-2-yl]methylpyrrolidin-3-yl]thio-1-methylcarbapen-2-em-3-carboxylic acid trifluoromethanesulfonate;

44. (1R,5S,6S)-2-[(3S,5S)-5-[6-N,N-dimethylcarbamoylmethyl- 5-methylimidazo[5,1-b]thiazolium-2-yl]methylpyrrolidin-3-yl]thio-6-((1R)-1-hydroxyethyl)-1-methylcarbapen-2-em-3-carboxylate;

45. (1R,5S,6S)-6-((1R)-1-hydroxyethyl)-2-[(3S,5S)-5-[6-methoxymethyl-5-methylimidazo[5,1-b]thiazolium-2-yl]methylpyrrolidin-3-yl]thio-1-methylcarbapen-2-em-3-carboxylate;

46. (1R,5S,6S)-2-[(3S,5S)-5-[6-ethoxycarbonylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate;

47. (1R,5S,6S)-6-(1(R)-hydroxyethyl)-2-[(3S,5S)-5-[2(Z)-(6-methylimidazo[5,1-b]thiazol-2-yl)vinyl]pyrrolidin-3-yl]thio-1-methylcarbapen-2-em-3-carboxylic acid chloride;

48. (1R,5S,6S)-6-(1(R)-hydroxyethyl)-2-[(3S,5S)-5-[2(E)-(6-methylimidazo[5,1-b]thiazol-2-yl)vinyl]pyrrolidin-3-yl]thio-1-methylcarbapen-2-em-3-carboxylic acid chloride;

49. (5S,6S)-6-(1(R)-hydroxyethyl)-2-[(3S,5S)-5-[2(Z)-(6-methylimidazo[5,1-b]thiazol-2-yl)vinyl]pyrrolidin-3-yl]thiocarbapen-2-em-3-carboxylic acid chloride;

50. (5S,6S)-6-(1(R)-hydroxyethyl)-2-[(3S,5S)-5-[2(E)-(6-methylimidazo[5,1-b]thiazol-2-yl)vinyl]pyrrolidin-3-yl]thiocarbapen-2-em-3-carboxylic acid chloride;

51. (1R,5S,6S)-2-[(3S,5S)-5-[imidazo[5,1-b]thiazol-3-yl]pyrrolidin-3-yl]thio-6-((1R)-1-hydroxyethyl)-1-methylcarbapen-2-em-3-carboxylic acid;

52. (1R,5S,6S)-6-((1R)-1-hydroxyethyl)-1-methyl-2-[(3S,5S)-5-[(6-methylimidazo[5,1-b]thiazolium)-3-yl]pyrrolidin-3-yl]thiocarbapen-2-em-3-carboxylic acid chloride;

53. (1R,5S,6S)-2-[(3S,5S)-5-[(6-carbamoylmethylimidazo[5,1-b]thiazolium)-3-yl]pyrrolidin-3-yl]thio-6-((1R)-1-hydroxyethyl)-1-methylcarbapen-2-em-3-carboxylic acid iodide;

54. (1R,5S,6S)-2-[(3S,5S)-5-[2-(imidazo[5,1-b]thiazol-2-yl)ethenyl]pyrrolidin-3-yl]thio-6-((1R)-1-hydroxyethyl)-1-methylcarbapen-2-em-3-carboxylic acid;

55. (1R,5S,6S)-2-[(3S,5S)-5-[2(E)-(6-(carbamoylmethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid iodide;

56. (1R,5S,6S)-2-[(3S,5S)-5-[2(Z)-(6-(carbamoylmethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid iodide;

57. (1R,5S,6S)-2-[(3S,5S)-5-[[2(Z)-(6-(carbamoylmethyl)imidazo[5,1-b]thiazolium-3-yl)ethenyl]pyrrolidin-3-yl]thio-6-((1R)-1-hydroxyethyl)-1-methylcarbapen-2-em-3-carboxylic acid iodide;

58. (1R,5S,6S)-2-[(3S,5S)-5-[2(E)-(6-(carbamoylmethyl)imidazo[5,1-b]thiazol-3-yl)ethenyl]pyrrolidin-3-yl]thio-6-((1R)-1-hydroxyethyl)-1-methylcarbapen-2-em-3-carboxylic acid chloride;

59. (1R,5S,6S)-2-[(3S,5S)-5-[2(E)-(6-(carbamoylethyl)imidazo[5,1-b]thiazol-3-yl)ethenyl]pyrrolidin-3-yl]thio-6-((1R)-1-hydroxyethyl)-1-methylcarbapen-2-em-3-carboxylic acid iodide;

60. (1R,5S,6S)-2-[(3S,5S)-5-[2(Z)-(6-(carbamoylmethyl)imidazo[5,1-b]thiazolium-5-yl)ethenyl]pyrrolidin-3-yl]thio-6-((1R)-1-hydroxyethyl)-1-methylcarbapen-2-em-3-carboxylic acid iodide;

61. (1R,5S,6S)-2-[(3S,5S)-5-[2(E)-(6-(carbamoylmethyl)imidazo[5,1-b]thiazolium-7-yl)ethenyl]pyrrolidin-3-yl]thio-6-((1R)-1-hydroxyethyl)-1-methylcarbapen-2-em-3-carboxylic acid iodide;

62. (1R,5S,6S)-2-[(3S,5S)-5-[2(E)-(6-(carbamoylmethyl)-3-methylimidazo[5,1-b]thiazolium-2-yl)ethenyl]pyrrolidin-3-yl]thio-6-((1R)-1-hydroxyethyl)-1-methylcarbapen-2-em-3-carboxylic acid iodide;

63. (1R,5S,6S)-2-[(3S,5S)-5-[2(Z)-(6-(carbamoylmethyl)-3-methylimidazo[5,1-b]thiazolium-2-yl)ethenyl]pyrrolidin-3-yl]thio-6-((1R)-1-hydroxyethyl)-1-methylcarbapen-2-em-3-carboxylic acid iodide;

64. (1R,5S,6S)-2-[(3S,5S)-5-[2(E)-(6-(carbamoylmethyl)-2-methylimidazo[5,1-b]thiazolium-3-yl)ethenyl]

65. (1R,5S,6S)-2-[(3S,5S)-5-[2(Z)-(6-(carbamoylmethyl)-2-methylimidazo[5,1-b]thiazolium-3-yl)ethenyl]pyrrolidin-3-yl]thio-6-((1R)-1-hydroxyethyl)-1-methylcarbapen-2-em-3-carboxylic acid iodide;
66. (1R,5S,6S)-6-((1R)-1-hydroxyethyl)-1-methyl-2-[(3S,5S)-5-(5-methylthioimidazo[5,1-b]thiazol-2-yl)methylpyrrolidin-3-yl]thiocarbapen-2-em-3-carboxylic acid;
67. (1R,5S,6S)-6-((1R)-1-hydroxyethyl)-1-methyl-2-[(3S,5S)-5-(6-methyl-5-methylthioimidazo[5,1-b]thiazolium-2-yl)methylpyrrolidin-3-yl]thiocarbapen-2-em-3-carboxylate;
68. (1R,5S,6S)-2-[(3S,5S)-5-(6-carbamoylmethyl-5-methylthioimidazo[5,1-b]thiazolium-2-yl)methylpyrrolidin-3-yl]thio-6-((1R)-1-hydroxyethyl)-1-methylcarbapen-2-em-3-carboxylic acid iodide;
69. (1R,5S,6S)-2-[(3S,5S)-5-(5-chloroimidazo[5,1-b]thiazol-2-yl)methylpyrrolidin-3-yl]thio-6-((1R)-1-hydroxyethyl)-1-methylcarbapen-2-em-3-carboxylic acid;
70. (1R,5S,6S)-2-[(3S,5S)-5-(5-chloro-6-methylimidazo[5,1-b]thiazolium-2-yl)methylpyrrolidin-3-yl]thio-6-((1R)-1-hydroxyethyl)-1-methylcarbapen-2-em-3-carboxylic acid iodide;
71. (1R,5S,6S)-2-[(3S,5S)-5-(6-carbamoylmethyl-5-chloroimidazo[5,1-b]thiazolium-2-yl)methylpyrrolidin-3-yl]thio-6-((1R)-1-hydroxyethyl)-1-methylcarbapen-2-em-3-carboxylic acid chloride;
72. (1R,5S,6S)-2-[(3S,5S)-5-(6-(2-carbamoylethyl)-5-methylimidazo[5,1-b]thiazolium-2-yl)methylpyrrolidin-3-yl]thio-6-((1R)-1-hydroxyethyl)-1-methylcarbapen-2-em-3-carboxylic acid chloride;
73. (1R,5S,6S)-2-[(3S,5S)-5-[2(Z)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylic acid chloride;
74. (1R,5S,6S)-2-[(3S,5S)-5-[2(E)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylic acid chloride;
75. (1R,5S,6S)-2-[(3S,5S)-5-[2(Z)-(6-ethylimidazo[5,1-b]thiazolium-3-yl)ethenyl]pyrrolidin-3-yl]thio-6-((1R)-1-hydroxyethyl)-1-methylcarbapen-2-em-3-carboxylate;
76. (1R,5S,6S)-6-((1R)-1-hydroxyethyl)-2-[(3S,5S)-5-[2(Z)-(6-(2-hydroxyethyl)imidazo[5,1-b]thiazolium-3-yl)ethenyl]pyrrolidin-3-yl]thio-1-methylcarbapen-2-em-3-carboxylic acid trifluoromethanesulfonate;
77. (1R,5S,6S)-2-[(3S,5S)-5-[2(Z)-(6-(2-carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate;
78. (1R,5S,6S)-2-[(3S,5S)-5-[2(Z)-(6-(2-fluoroethyl)imidazo[5,1-b]thiazolium-3-yl)ethenyl]pyrrolidin-3-yl]thio-6-((1R)-1-hydroxyethyl)-1-methylcarbapen-2-em-3-carboxylic acid chloride;
79. (1R,5S,6S)-2-[(3S,5S)-5-[2(Z)-(6-(2-carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate;
80. (1R,5S,6S)-6-((1R)-1-hydroxyethyl)-2-[(3S,5S)-5-[2(Z)-(6-(2-hydroxyethyl)imidazo[5,1-b]thiazolium-2-yl)ethenyl]pyrrolidin-3-yl]thio-1-methylcarbapen-2-em-3-carboxylate;
81. (1R,5S,6S)-2-[(3S,5S)-5-[2(Z)-(6-(2-carbamoylethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid chloride;
82. (1R,5S,6S)-2-[(3S,5S)-5-[2(Z)-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid chloride; and
83. (1R,5S,6S)-2-[(3S,5S)-5-[2(E)-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylate.

The compounds of formulae (I) and (II) may be in the form of pharmaceutically acceptable salts thereof. Examples of such salts include pharmaceutically acceptable nontoxic salts. Examples of salts formed at the amino group include: salts of hydrohalogenic acids such as hydrofluoric acid, hydrochloric acid, hydrobromic acid and hydroiodic acid; inorganic acid salts such as nitrate, perchlorate, sulfate, phosphate, and carbonate; salts of lower alkylsulfonic acids such as methanesulfonic acid, trifluoromethanesulfonic acid, and ethanesulfonic acid; salts of arylsulfonic acids such as benzenesulfonic acid and p-toluenesulfonic acid; salts of organic acids such as trichloroacetic acid, trifluoroacetic acid, hydroxyacetic acid, benzoic acid, mandelic acid, butyric acid, propionic acid, formic acid, fumaric acid, succinic acid, citric acid, tartaric acid, oxalic acid, maleic acid, acetic acid, malic acid, lactic acid, and ascorbic acid; and salts of acidic amino acids such as glutamic acid and aspartic acid. Examples of salts formed at the carboxyl group include: alkali metal salts such as sodium, potassium, and lithium salts; alkaline earth metal salts such as calcium and magnesium salts; ammonium salts; salts of organic amines such as triethylamine, trimethylamine, diethylamine, pyridine, ethanolamine, triethanolamine, dicyclohexylamine, procaine, benzylamine, N-methylpiperidine, N-methylmorpholine, and diethylaniline; and salts of basic amino acids such as lysine, arginine and histidine.

Examples of salts formed at the imidazothiazolium group include a pharmaceutically acceptable salt formed with a pharmaceutically acceptable anion. The pharmaceutically acceptable anion includes halogen ions such as a fluoric ion, chloric ion, bromic ion and iodide ion; anions of inorganic acid salts such as nitrate, perchlorate, sulfate, phosphate, and carbonate; pharmaceutically acceptable anions of lower alkylsulfonic acid salts such as methanesulfonic acid, trifluoromethanesulfonic acid, and ethanesulfonic acid salts; pharmaceutically acceptable anions of arylsulfonic acid salts such as benzenesulfonic acid and p-toluenesulfonic acid salts; pharmaceutically acceptable anions of organic acid salts such as trichloroacetic acid, trifluoroacetic acid, hydroxyacetic acid, benzoic acid, mandelic acid, butyric acid, propionic acid, formic acid, fumaric acid, succinic acid, citric acid, tartaric acid, oxalic acid, maleic acid, acetic acid, malic acid, lactic acid, and ascorbic acid salts; and pharmaceutically acceptable anions of acidic amino acid salts such as glutamic acid and asparatic acid salts.

Compounds represented by formula (II) may form internal salts. Such salts also are included in the pharmacologically acceptable salts of the compounds according to the present invention.

In the compounds represented by formulae (I) and (II), isomers exist. Any of the isomers and any mixture thereof are within the scope of the present invention.

Preparation of Compounds

Preferably, the compounds represented by formula (I) according to the present invention may be prepared according to the following scheme:

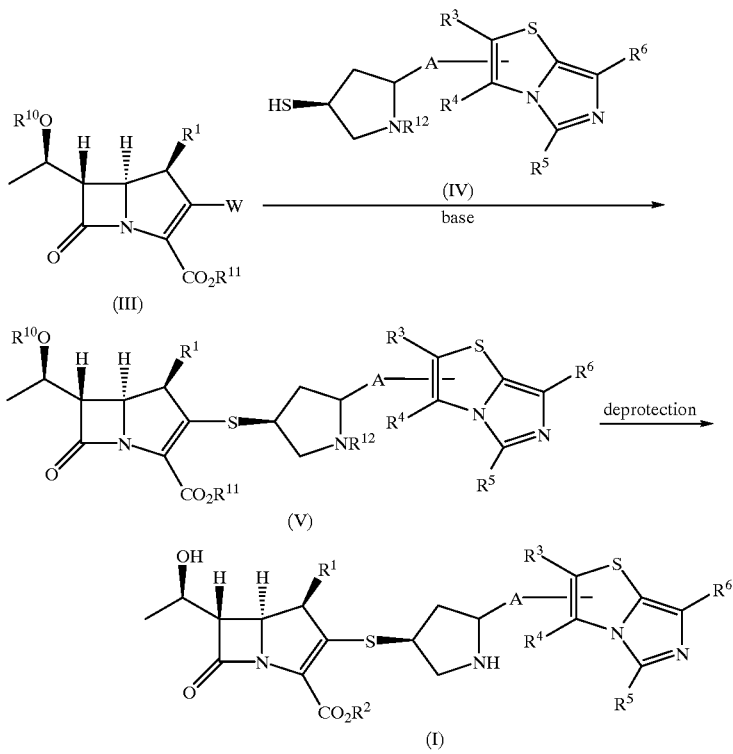

In the scheme, A, $R^1$, $R^2$, $R^3$, $R^4$, $R^5$, $R^6$ are as defined in formula (I), $R^{10}$ represents hydrogen or a hydroxyl protective group (for example, t-butyldimethylsilyl, trimethylsilyl, triethylsilyl, allyloxycarbonyl, p-methoxybenzyloxycarbonyl, or p-nitrobenzyloxycarbonyl), $R^{11}$ represents a carboxyl protective group (for example, allyl, diphenylmethyl, p-methoxybenzyl, or p-nitrobenzyl), $R^{12}$ represents an amino protective group (for example, allyloxycarbonyl, p-methoxybenzyloxycarbonyl, or p-nitrobenzyloxycarbonyl), and W represents an elimination group (preferably, diphenylphosphoryloxy, or trifluoromethanesulfonyloxy).

In the first step, the compound of formula (III) may be prepared by a conventional method described, for example, in WO 96/28455. Further, the compound represented by formula (IV) may be synthesized by a method which will be described below.

In the first step, the compound (III) can be converted to the compound (V) by the following method. Specifically, the compound (III) may be reacted with the compound (IV) in an equivalent or excess amount based on the compound (III) in the presence of an equivalent or excess amount, based on the compound (IV), of a base, such as diisopropylethylamine, triethylamine, N,N-dimethylaminopyridine, or pyridine, in an equivalent or excess amount based on the compound (IV) in a solvent, such as acetonitrile, acetone, N,N-dimethylformamide, N,N-dimethylacetamide, tetrahydrofuran, dioxane, methanol, ethanol, dichloromethane, toluene, or hexamethylphosphoric triamide, or a solvent mixture of the above solvents at −80° C. to +60° C. for 15 min to 72 hr, followed by conventional post-treatment to give the compound (V).

Finally, in the second step, the protective groups $R^{10}$, $R^{11}$, and $R^{12}$ of the compound (V) are removed in one stage or a plurality of stages depending upon the kind of the protective group to give the compound represented by formula (I) according to the present invention.

The deprotection reaction for removal of $R^{10}$, $R^{11}$, and $R^{12}$ may be carried out by a conventional method commonly known in the art although the method varies depending upon the protective group used. When a part of or all the protective groups can be removed under acidic conditions, a mineral acid, such as hydrochloric acid, an organic acid, such as formic acid, acetic acid, or citric acid, or a Lewis acid, such as aluminum chloride, may be used. On the other hand, the removal can be achieved under reduction conditions, catalytic reductions using various catalysts or a metallic reducing agent, such as zinc or iron, may be used. When $R^{10}$ represents a silyl-based protective group (for example, t-butyldimethylsilyl, trimethylsilyl, or triethylsilyl), a fluoride ion reagent (for example, tetrabutylammonium fluoride) may be used. When $R^{10}$ represents allyloxycarbonyl with $R^{11}$ representing allyl, the protective groups can be easily removed using various palladium complexes.

Among the compounds represented by formula (I), those wherein A represents —CH(OH)—, that is, compounds (I-1), may be produced according to the following scheme:

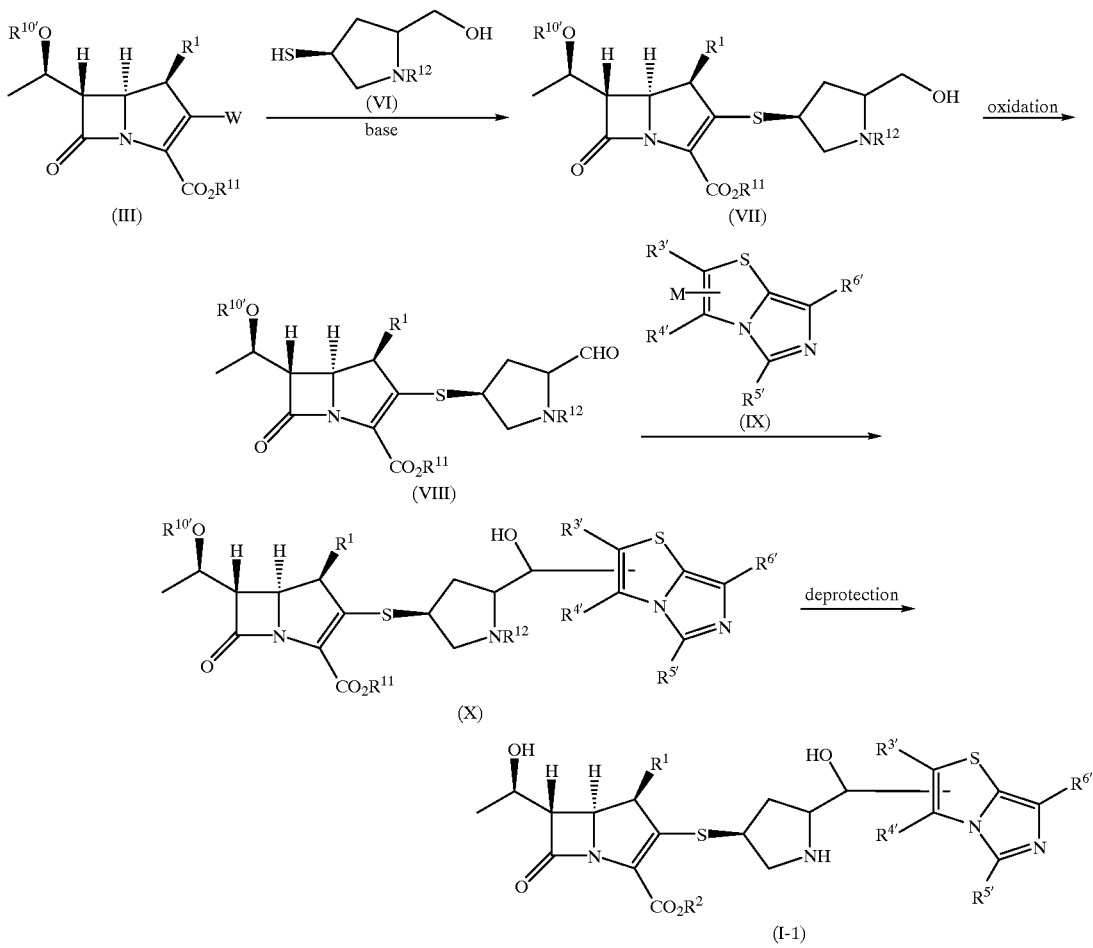

In the scheme, M represents lithium, MgCl, MgBr, or MgI, $R^1$ and $R^2$ are as defined in formula (I), any one of $R^{3'}$, $R^{4'}$ $R^{5'}$, and $R^{6'}$ represents M, and the remaining three substituents, which may be the same or different, represent hydrogen; halogen; nitro; cyano; lower alkyl; lower cycloalkyl lower alkylthio; $C_{2-4}$ alkenyl; or aryl, $R^{10'}$ represents a hydroxyl protective group (for example, t-butyldimethylsilyl, trimethylsilyl, triethylsilyl, allyloxycarbonyl, p-methoxybenzyloxycarbonyl, or p-nitrobenzyloxycarbonyl), and $R^{11}$, $R^{12}$, and W are as defined in formula (III).

In the first step, the compound (III) can be converted to the compound (VII) by the following method. The compound (III) may be reacted with the compound (VI) in an equivalent or excess amount based on the compound (III) in the presence of a base, such as diisopropylethylamine, triethylamine, N,N-dimethylaminopyridine, or pyridine, in an equivalent or excess amount based on the compound (VI) in a solvent, such as acetonitrile, acetone, N,N-dimethylformamide, N,N-dimethylacetamide, tetrahydrofuran, dioxane, methanol, ethanol, dichloromethane, toluene, or hexamethylphosphoric triamide, or a solvent mixture of the above solvents at −50° C. to +50° C. for 15 min to 24 hr, followed by conventional post-treatment to give the compound (VII).

Then, in the second step, the compound (VII) can be converted to the compound (VIII) by conventional alcohol oxidation (for example, Swern oxidation, DMSO oxidation, or chromic acid oxidation). Preferably, however, the conversion is carried out using a catalytic amount of tetra-n-propylammonium perruthenate and a slightly excessive amount of N-methylmorpholine N-oxide in an inert solvent, such as dichloromethane, in the presence of Molecular Sieves 4A.

An organometallic compound of imidazo[5,1-b]thiazole represented by formula (IX) may be synthesized by a method described below.

In the third step, the compound (VIII) can be converted to the compound (X) by the following method. The compound (X) may be prepared by adding the compound (VIII) in an amount of 0.5 to 1 equivalent to a solution of the compound (IX) in an inert solvent (for example, tetrahydrofuran, dioxane, diethyl ether, dimethoxyethane, toluene, or benzene), allowing a reaction to proceed at −80° C. to +50° C. for 15 min to 24 hr, and conducting conventional post-treatment.

In the fourth step, the protective groups $R^{10'}$, $R^{11}$, and $R^{12}$ of the compound (x) are removed in one stage or a plurality of stages depending upon the kind of the protective group to give the compound represented by formula (I-1) according to the present invention.

The deprotection reaction for removal of $R^{10'}$, $R^{11}$, and $R^{12}$ may be carried out by a conventional method commonly known in the art although the method varies depending upon the protective group used. When a part of or all the protective groups can be removed under acidic conditions, a mineral acid, such as hydrochloric acid, an organic acid, such as formic acid, acetic acid, or citric acid, or a Lewis acid, such as aluminum chloride, may be used. On the other hand, the removal can be achieved under reduction conditions, catalytic reductions using various catalysts or a metallic reducing agent, such as zinc or iron, may be used. When $R^{10'}$ represents a silyl-based protective group (for example, t-butyldimethylsilyl, trimethylsilyl, or triethylsilyl), a fluoride ion reagent (for example, tetrabutylammonium fluoride) may be used. When $R^{10'}$ represents allyloxycarbonyl with $R^{11}$ representing allyl, the protective groups can be easily removed using various palladium complexes.

The compounds represented by formulae (I) and (I-1) thus obtained can be isolated and purified by chromatography using a nonionic macro high porous resin, gel filtration using Sephadex or the like, reversed phase silica gel column chromatography and the like.

The compounds represented by formula (II) according to the present invention may be preferably produced according to the following scheme:

or $R^{10'}$ in the compound (X) is t-butyldimethylsilyl. This compound can be synthesized by the method described above in the process for producing the compounds represented by formulae (I) and (I-1).

In the first step, the compound (XI) may be reacted with a fluoride anion reagent (preferably, tetrabutylammonium fluoride or the like) in an inert solvent, such as tetrahydrofuran, at $-20°$ C. to $+50+$ C. for one hr to one week, thereby removing the t-butyldimethylsilyl group as the protective group, followed by conventional post-treatment to give the compound (XII).

The compound (XII) is a compound wherein $R^{10}$ in the compound (V) is a hydrogen atom. This compound may be synthesized also from a compound represented by formula (III) wherein $R^{10'}$ represents t-butyldimethylsilyl according to the method described in the production of the compounds represented by formula (I).

In the second step, the conversion of the compound (XII) to the compound (XIII) may be carried out as follows. Specifically, the compound (XII) may be reacted with $R^7$—Y as an electrophilic reagent in an amount of 1 to 100

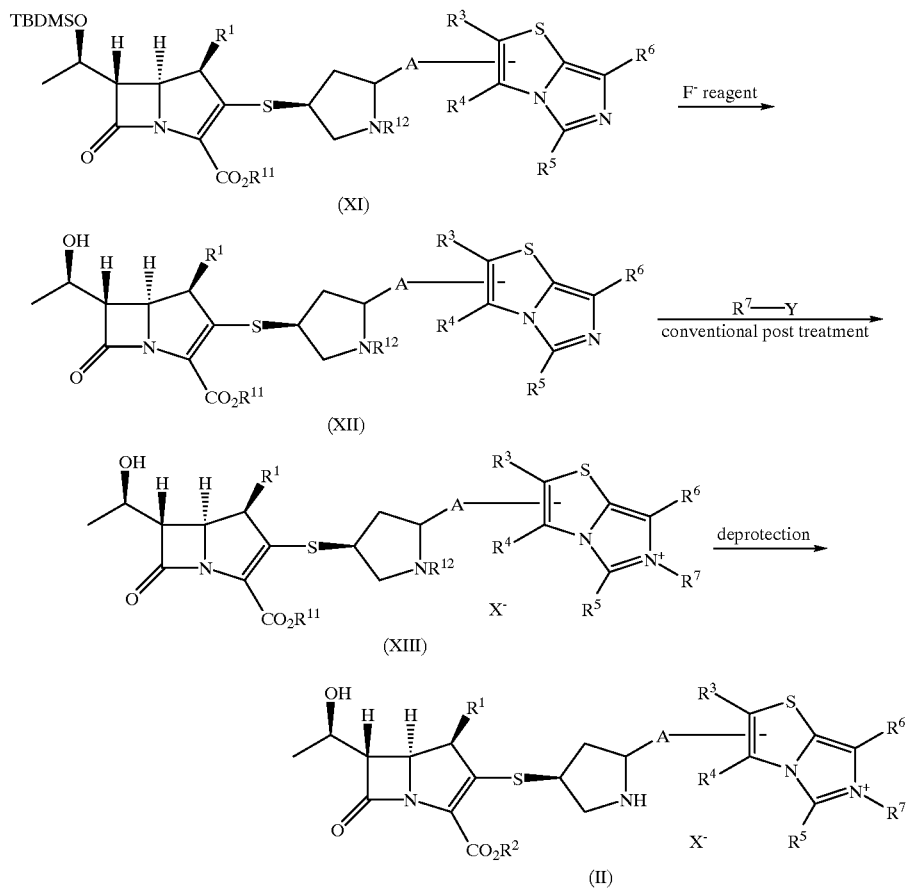

In the scheme, A, $R^1$, $R^2$, $R^3$, $R^4$, $R^5$, $R^6$, and $R^7$ are as defined in formula (II), $R^{11}$ and $R^{12}$ are as defined in formula (V), $X^-$ represents a pharmaceutically acceptable halogen ion, organic acid anion, or inorganic acid anion, Y represents an elimination group (preferably, a halogen atom, p-toluenesulfonyloxy, trifluromethanesulfonyloxy, or methanesulfonyloxy).

The compound (XI), which is a starting compound in the first step, is a compound wherein $R^{10}$ in the compound (V)

equivalents in the absence of a solvent or in an inert solvent (for example, benzene, toluene, dichloromethane, chloroform, tetrahydrofuran, N,N-dimethylformamide, or acetonitrile) at $-80°$ C. to $+60°$ C. for 15 min to one week, followed by conventional post-treatment to give the compound (XIII).

Finally, in the third step, the deprotection reaction for removal of $R^{11}$ and $R^{12}$ as protective groups of the compound (XIII) may be carried out by a conventional method commonly known in the art although the method varies depending upon the protective group used. Thus, the compound represented by formula (II) according to the present invention can be prepared.

When a part of or all the protective groups can be removed under acidic conditions, a mineral acid, such as hydrochloric acid, an organic acid, such as formic acid, acetic acid, or citric acid, or a Lewis acid, such as aluminum chloride, may be used. When $R^{11}$ represents allyl, the protective group can be easily removed using various palladium complexes.

In the case of the deprotection under reduction conditions or the deprotection using a palladium complex, the compound (II) thus obtained is such that $X^-$ represents an ion of the elimination group Y or an anion, while in the case of the deprotection using an acid, the compound (II) thus obtained is such that $X^-$ represents an anion of the organic acid or inorganic acid used.

The compounds represented by formulae (II) thus obtained can be isolated and purified by chromatography using a nonionic macro high porous resin, gel filtration using Sephadex or the like, reversed phase silica gel column chromatography, or using an ion exchange resin.

The compounds represented by the formula (IV) may be produced by the following methods which may vary depending upon A.

The compound (IV-1), which is a compound wherein A in the formula (IV) represents —C(=O)N(—$R^9$)CH$_2$—, may be preferably produced according to the following scheme:

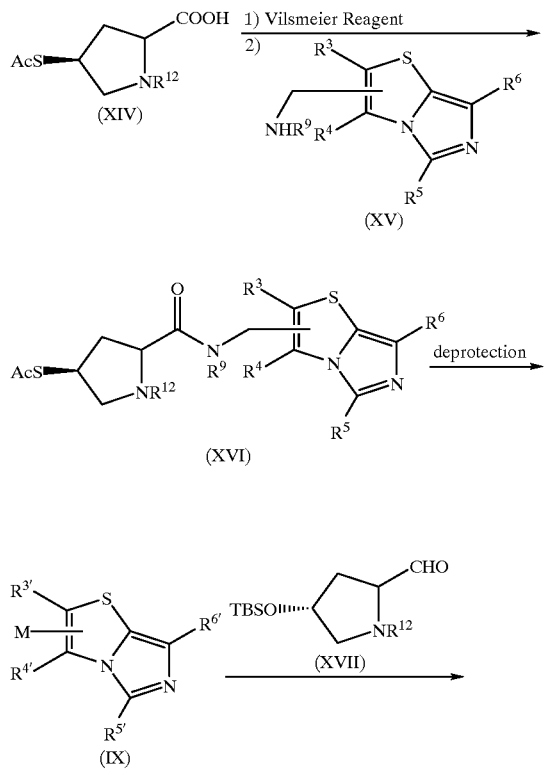

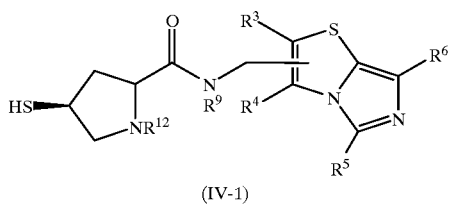

(IV-1)

In the above scheme, $R^3$, $R^4$, $R^5$, $R^6$, and $R^9$ are as defined in formula (I) and $R^{12}$ is as defined above in connection with the formula (IV).

In the first step, the compound represented by the formula (XIV) may be produced by a conventional method described in Japanese Patent Laid-Open No. 104088/1985, and the compound represented by the formula (XV) may be produced by a conventional method described in Japanese Patent Laid-Open No. 311071/1996.

In the first step, the compound (XVI) may be prepared be reacting the compound (XIV) with the compound (XV) by a method using a condensing agent (for example, dicyclohexylcarbodiimide or carbonyldiimidazole), an acid halide method using thionyl chloride, or phosphorus oxychloride or other methods. Alternatively, use of the following method is preferred.

Vilsmeier reagent prepared by a conventional method is added in an amount of 1 to 5 equivalents to a solution of the compound (XIV) in an inert solvent (for example, dichloromethane, chloroform, benzene, toluene, or diethyl ether). The reaction is then allowed to proceed at –50° C. to +50° C. for 15 min to one hr. The compound (XV) and a base (for example, triethylamine, diisopropylethylamine, or pyridine) in an amount of 1 to 10 equivalents are added thereto. The reaction is further allowed to proceed at the same temperature for 30 min to 24 hr, followed by conventional post-treatment to give the compound (XVI).

In the second step, the compound (XVI) is then dissolved in a suitable solvent (for example, methanol, ethanol, distilled water, acetonitrile, tetrahydrofuran, dioxane, N,N-dimethylformamide, or dichloromethane), an alkali (for example, sodium hydroxide, lithium hydroxide, potassium hydroxide, potassium carbonate, sodium methoxide, sodium ethoxide, or ammonia) solution in an equivalent amount based on the compound (XVI) is added to the solution, and a deprotection reaction is allowed to proceed at –80° C. to +50° C. for 10 min to 24 hr, followed by conventional post-treatment to give the compound (IV-1).

The compound (IV-2), which is a compound wherein A in the formula (IV) represents —CH(OH)—, may be preferably produced according to the following scheme:

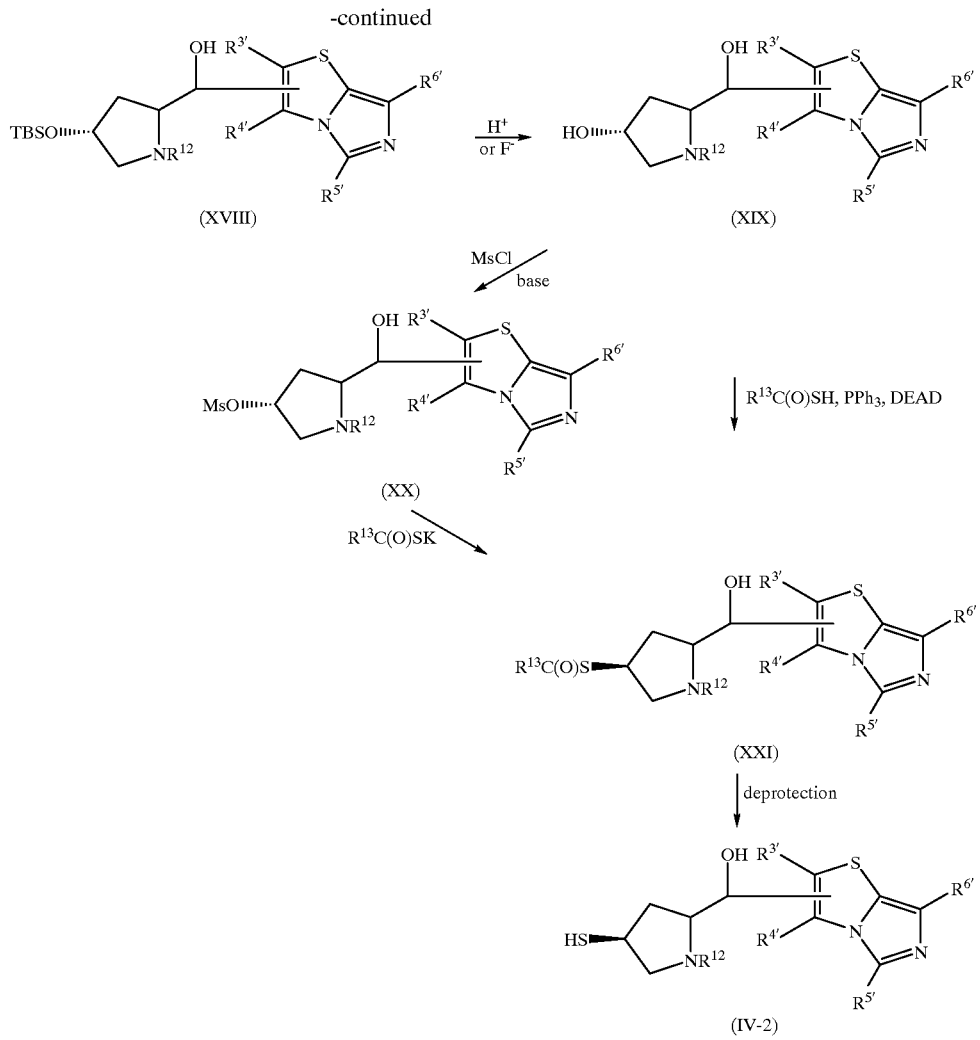

In the scheme, M, $R^{3'}$, $R^{4'}$, $R^{5'}$, and $R^{6'}$ are as defined in formula (IX), $R^{12}$ is as defined in formula (V), $R^{13}$ represents lower alkyl (preferably methyl) or aryl (preferably phenyl).

An organometallic compound of imidazo[5,1-b]thiazole represented by the formula (IX) in the first step may be synthesized by a method described below.

In the first step, the compound (XVII) can be converted to the compound (XVIII) by the following method. The compound (XVIII) may be prepared by adding the compound (XVII) in an amount of 0.5 to 2 equivalents to a solution of the compound (IX) in an inert solvent (for example, tetrahydrofuran, dioxane, diethyl ether, dimethoxyethane, toluene, or benzene), allowing a reaction to proceed at −80° C. to +50° C. for 15 min to 24 hr, and conducting conventional post-treatment.

In the second step, the t-butyldimethylsilyl group as the protective group of the compound (XVIII) is removed using an acid or a fluoride anion reagent to give the compound (XIX).

When an acid is used, the compound (XIX) may be prepared by dissolving the compound (XVIII) in a solvent (for example, acetonitrile, methanol, or ethanol or an aqueous solution of the solvent), adding a mineral acid (preferably hydrochloric acid) in an amount of 1 to 10 equivalents to the solution, allowing a reaction to proceed at −20° C. to +50° C. for 15 min to 24 hr, neutralizing the reaction mixture, and conducting conventional post-treatment.

On the other hand, when a fluoride anion reagent is used, the compound (XIX) may be prepared by dissolving the compound (XVIII) in an inert solvent (for example, tetrahydrofuran, diethyl ether, dioxane, acetonitrile, or dichloromethane), adding a fluoride anion reagent (preferably tetra-n-butylammonium fluoride) in an amount of 1 to 10 equivalents, allowing a reaction to proceed at −50° C. to +50° C. for 30 min to 24 hr, and conducting conventional post-treatment.

In the third and fourth steps, the compound (XIX) can be converted to the acylthio compound (XXI) in one stage by Mitsunobu reaction, or alternatively may be carried out in two stages through the mesylate compound (XX).

The synthesis in one stage by Mitsunobu reaction will be described.

Triphenylphosphine in an equivalent or excess amount based on the compound (XIX) is added to a solution of the compound (XIX) in an inert solvent (for example, tetrahydrofuran, diethyl ether, dioxane, acetonitrile, toluene, dichloromethane, or N,N-dimethylformamide). Thereafter, an equivalent or excess amount, based on the compound (XIX), of a thiol acid ($R^{13}C(=O)SH$ wherein $R^{13}$ preferably represents methyl or phenyl) and a dialkyl azodicarboxylate (preferably diethyl azodicarboxylate or diisopropyl azodicarboxylate) are added simultaneously or in a proper sequence to the mixture, and a reaction is allowed to proceed at −80° C. to +50° C. for 15 min to 24 hr, followed by conventional post-treatment. Thus, the compound (XXI) is prepared.

On the other hand, the synthesis in two stages through the mesylate compound (XX) may be carried out as follows. Specifically, the compound (XIX) is dissolved in an inert solvent (for example, tetrahydrofuran, diethyl ether, dioxane, acetonitrile, toluene, dichloromethane, or N,N-dimethylformamide), an equivalent or excess amount, based on the compound (XIX), of methanesulfonyl chloride is added to the solution in the presence of an equivalent or excess amount, based on the compound (XIX), of an organic base (preferably diisopropylethylamine, triethylamine, 2,6-lutidine, pyridine or the like), and a reaction is allowed to proceed at −80° C. to +50° C. for 15 min to 12 hr, followed by conventional post-treatment to give the compound (XX). In some cases, the post-treatment is omitted, and the reaction is followed by the subsequent step. The compound (XX) can be converted to the acylthio compound (XXI) by treatment with a salt of thiol acid. The compound (XX) is dissolved in an inert solvent (preferably N,N-dimethylformamide or a mixed solvent composed of N,N-dimethylformamide and toluene, xylene, dioxane or the like). When the post-treatment has not been carried out, the reaction solvent is replaced with the inert solvent. An equivalent or excess amount, based on the compound (XX), of a salt of thiol acid (preferably potassium thioacetate) is then added to the solution, and a reaction is allowed to proceed in the temperature range of room temperature to the reflux temperature for 30 min to 48 hr, followed by conventional post-treatment to give the compound (XXI).

Finally, in the fifth step, the thiol compound represented by the formula (IV-2) can be derived from the compound (XXI) in the same manner as described above in connection with the conversion of the compound (XVI) to the compound (IV-1).

The compound (IV-3), which is a compound wherein A in the formula (IV) represents —$CH_2$—, may be preferably produced according to the following scheme:

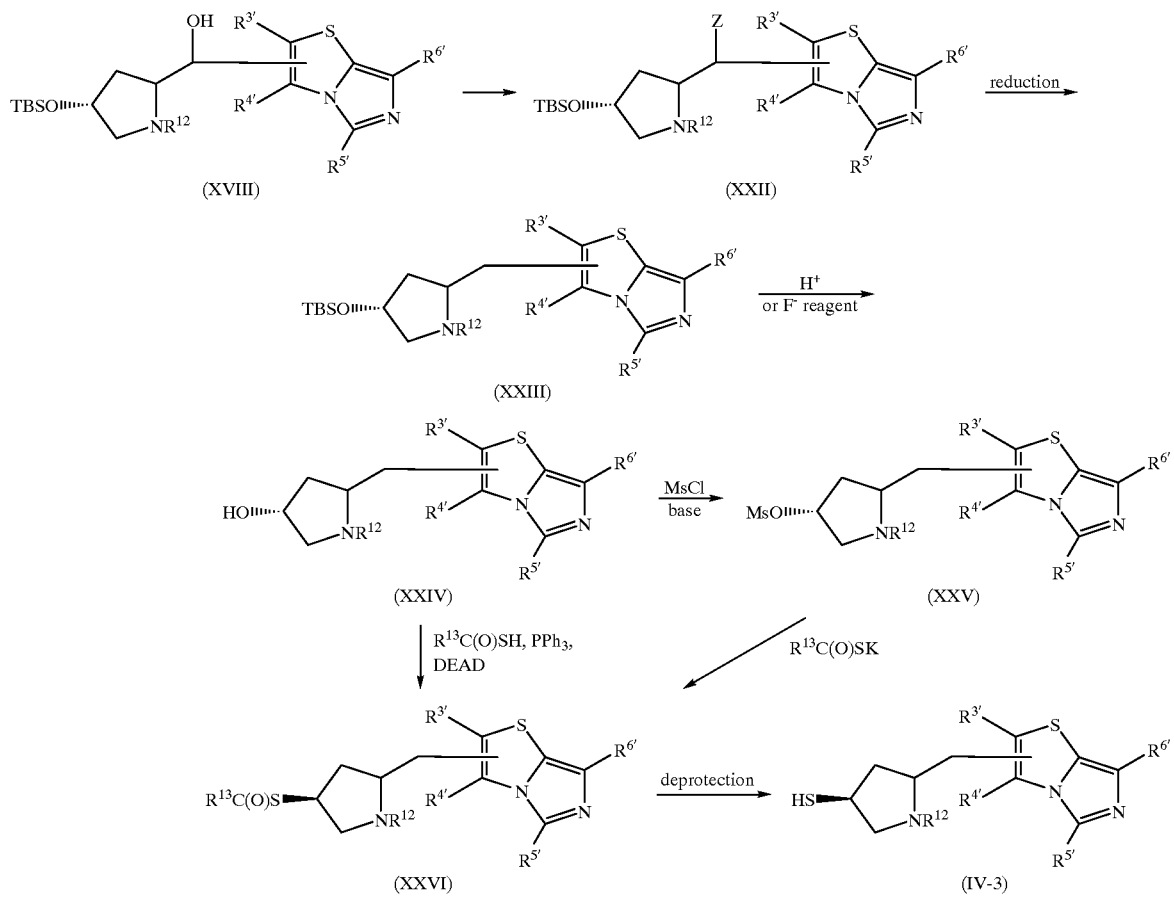

In the scheme, Z represents $OC(S)SR^{14}$ (wherein $R^{14}$ represents lower alkyl or aryl), —$OC(S)OR^{14}$ (wherein $R^{14}$ is as defined above), Cl, Br, I, or —$OSO_2R^{14}$ ($R^{14'}$ is as defined above), preferably —$OC(S)SCH_3$ or Cl, $R^{3'}$, $R^{4'}$, $R^{5'}$, and $R^{6'}$ are as defined in formula (IX), $R^{12}$ is as defined in formula (V), and $R^{13}$ is as defined in formula (XXI).

In the first and second steps, the compound (XVIII) can be converted to the compound (XXII) which is then converted to the compound (XXIII) either step by step or continuously. It may be carried out through the above Z.

For example, the compound (XXII), which is a compound wherein Z represents —$OC(S)SCH_3$, may be produced by the following method. The compound (XVIII) is dissolved in an inert solvent (for example, tetrahydrofuran, diethyl ether, dioxane, dimethoxyethane, toluene, benzene, dichloromethane, or hexamethylphosphoric triamide), an equivalent or excess amount, based on the compound (XVIII), of a deprotonating agent (for example, metal hydride (preferably NaH) or an alkyllithium) and carbon disulfide and a catalytic amount of imidazole are added to the solution, a reaction is allowed to proceed at −50° C. to +50° C. for 15 min to 6 hr, an equivalent or slightly excess amount, based on the compound (XVIII), of iodomethane is added thereto, and a reaction is allowed to proceed at −20° C. to +30° C. for 30 min to 24 hr, followed by conventional post-treatment to give the compound (XXII).

The compound (XXII) is then dissolved in an inert solvent (for example, toluene, xylene, or benzene), an excess amount of a tributyltin hydride and a catalytic amount of azobisisobutyronitrile are added to the solution, and a reaction is allowed to proceed in the temperature range of room temperature to the reflux temperature for 15 min to 24 hr, followed by conventional post-treatment to give the compound (XXIII).

Further, for example, the compound (XXII), which is a compound wherein Z represents Cl, may be produced by a conventional method wherein the hydroxyl group is replaced with Cl. Alternatively, a method using thionyl chloride is preferred. The compound (XVIII) is dissolved in an inert solvent (for example, tetrahydrofuran, diethyl ether, dioxane, dimethoxyethane, toluene, benzene, dichloromethane, or hexamethylphosphoric triamide), an excess amount, based on the compound (XVIII), of thionyl chloride and a catalytic amount of N,N-dimethylformamide are added to the solution, and a reaction is allowed to proceed at −50° C. to +50° C. for 10 min to 6 hr. Thus, the compound (XXII) can be prepared.

The compound (XXII) is then dissolved in an acidic solvent (preferably an aqueous acetic acid solution or a mixed solution composed of an aqueous acetic acid solution and an inert solvent (for example, N,N-dimethylformamide, tetrahydrofuran, or dioxane) or the like), an excess amount of an activated zinc powder is added thereto, and a reaction is allowed to proceed in the temperature range of from ice cooling to +80° C. for 30 min to 24 hr, followed by conventional post-treatment to give the compound (XXIII).

In the third step, the compound (XXIII) can be converted to the compound, as an alcohol compound, represented by the formula (XXIV) in the same manner as described in the conversion of the compound (XVIII) to the compound (XIX).

Thereafter, in the fourth and fifth steps, as with the conversion of the compound (XIX) to the compound (XXI), the compound (XXIV) can be converted to the acylthio compound (XXVI) in one stage by Mitsunobu reaction or alternatively in two stages through the mesylate compound (XXV).

Finally, in the sixth step, a thiol compound represented by the formula (IV-3) may be derived from the compound (XXVI) in the same manner as described in the conversion of the compound (XVI) to the compound (IV-1).

The compound (IV-4), which is a compound wherein A in formula (IV) represents —CH═CH—, may be preferably produced according to the following scheme:

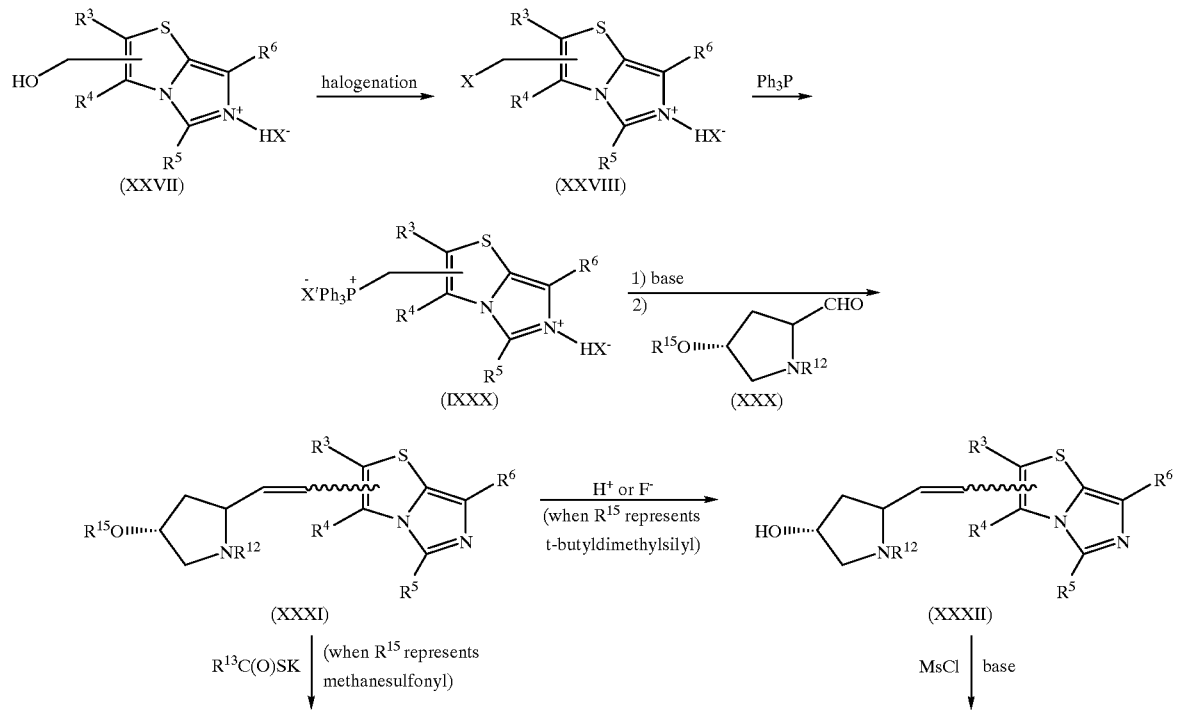

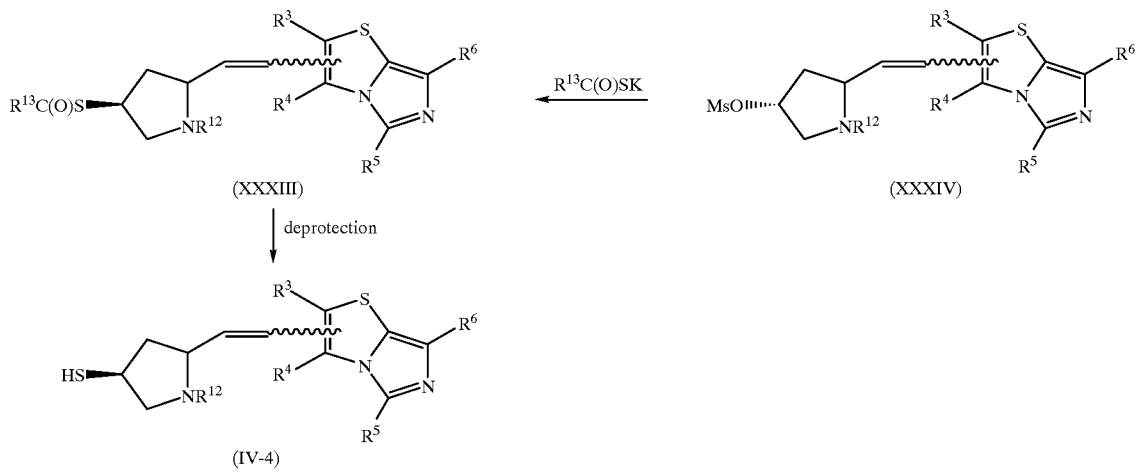

In the above scheme, $R^3$, $R^4$, $R^5$, and $R^6$ are as defined in formula (II), $R^{12}$ is as defined in formula (V), $R^{13}$ represents lower alkyl (preferably methyl) or aryl (preferably phenyl), $X^-$ is as defined in the scheme, $R^{15}$ represents methanesulfonyl or t-butyldimethylsilyl, and X' represents halogen.

In the first step, the compound represented by formula (XXVII) may be produced by a method, proposed by the present inventors, described in Japanese Patent Laid-Open No. 311071/1996.

In the first step, the compound (XXVII) can be converted to the compound (XXVIII) by the following method. An equivalent or excess amount of a halogenating agent (preferably thionyl chloride, phosphorus oxychloride or the like) is added to the compound (XXVII) in the absence or presence of an inert solvent (for example, tetrahydrofuran, dioxane, diethyl ether, dimethoxyethane, toluene, benzene or the like or a mixed solvent composed of at least two of the above solvents). The reaction is completed under cooling or heating, followed by conventional post-treatment to give the compound (XXVIII).

In the second step, the compound (XXVIII) can be converted to the compound (IXXX) by the following method. The compound (XXVIII) is dissolved in an inert solvent (for example, N,N-dimethylformamide, dimethyl sulfoxide, benzene, toluene, xylene, acetonitrile, tetrahydrofuran, dioxane, methanol, or ethanol or a mixed solvent composed of at least two of the solvents. An equivalent or excess amount of triphenylphosphine is added to the solution. The reaction is completed in the temperature range of from room temperature to the reflux temperature, followed by conventional post-treatment to give the compound (IXXX).

In the third step, the compound (IXXX) can be converted to the compound (XXXI) by the following method. The compound (IXXX) is dissolved or suspended in an inert solvent (dimethyl sulfoxide, N,N-dimethylformamide, tetrahydrofuran, or dioxane or a mixed solvent composed of at least two of the above solvents). Two equivalents of a base (for example, potassium t-butoxide, n-butyllithium, lithium diisopropylamide, lithium hexamethyldisilazide, or sodium hydride) is added to the solution. The reaction is allowed to proceed at a temperature of −78° C. to room temperature to produce an ylide, the compound represented by the formula (XXX), which has been diluted with an inert solvent (dimethyl sulfoxide, N,N-dimethylformamide, tetrahydrofuran, dioxane or the like or a mixed solvent composed of at least two of the above solvents) to a proper concentration, is added to the solution. The reaction is completed at a temperature of −78° C. to room temperature, followed by conventional post-treatment to give the compound (XXXI).

For the compound represented by formula (XXXI), cis (Z) and trans (E) geometrical isomers exist with respect to double bond. In this reaction, one of these isomers can be selectively or preferentially produced by properly selecting the above solvent, reaction temperature, base and the like.

In the fourth, fifth, and sixth steps, the compound (XXXI) can be converted to the acylthio compound (XXXIII) by the following methods which vary depending upon $R^{15}$ in formula (XXXI).

The compound represented by formula (XXXI), wherein $R^{15}$ represents methanesulfonyl, may be converted by the following method. The compound (XXXI) is dissolved in an inert solvent (N,N-dimethylformamide or a mixed solvent composed of N,N-dimethylformamide and toluene, xylene, dioxane or the like). An equivalent or excess amount of a salt of thiol acid (preferably potassium thioacetate) is added to the solution. The reaction is completed in the temperature range of from room temperature to the reflux temperature, followed by conventional post-treatment to give the compound (XXXIII).

The compound represented by the formula (XXXI), wherein $R^{15}$ in the compound (XXXI) represents t-butyldimethylsilyl, may be converted by the following method. In the fourth step, t-butyldimethylsilyl, as the protective group, represented by $R^{15}$ in the compound (XXXI) is removed using an acid or a fluoride anion reagent. In the fifth step, methanesulfonation is carried out using methanesulfonyl chloride and a suitable base; and in the sixth step, a salt of thiol acid is used to give the acylthio compound (XXXIII).

When an acid is used in the fourth step, the compound (XXXI) is first dissolved in a solvent (for example, acetonitrile, methanol, or ethanol or an aqueous solution of the above solvent). A mineral acid (preferably hydrochloric acid) is added to the solution. The reaction is allowed to proceed at −20° C. to +50° C. for 15 min to 24 hr, and the reaction mixture is neutralized, followed by conventional post-treatment to give the compound (XXXII). On the other hand, when a fluoride anion reagent is used, the compound (XXXI) is first dissolved in an inert solvent (for example, tetrahydrofuran, diethyl ether, dioxane, acetonitrile, or dichloromethane). A fluoride anion reagent (preferably tetra-n-butylammonium fluoride) is added to the solution. The reaction is allowed to proceed at −50° C. to +50° C. for 30 min to 24 hr, followed by conventional post-treatment to give the compound (XXXII).

In the fifth step, the compound (XXXII) is dissolved in an inert solvent (for example, tetrahydrofuran, diethyl ether, dioxane, acetonitrile, dichloromethane, or N,N-dimethylformamide), an equivalent or excess amount of an organic base (preferably diisopropylethylamine, triethylamine, 2,6-lutidine, pyridine or the like) is added to the solution. An equivalent or excess amount of methanesulfonyl chloride is added to the solution. The reaction is allowed to proceed at −50° C. to +50° C. for 15 min to 24 hr, followed by conventional post-treatment to give the compound (XXXIV). In this case, the post-treatment may be omitted, and the reaction may be followed by the subsequent step.

In the sixth step, the compound (XXXIV) is dissolved in an inert solvent (N,N-dimethylformamide or a mixed solvent composed of N,N-dimethylformamide and toluene, xylene, dioxane or the like). An equivalent or excess amount of a salt of thiol acid (preferably potassium thioacetate) is added to the solution. The reaction is completed in the temperature range of from room temperature to the reflux temperature, followed by post-treatment to give the compound (XXXIII).

In the seventh step, a thiol compound represented by formula (IV-4) may be derived from the compound (XXXVI) in the same manner as described in the conversion of the compound (XVI) to the compound (IV-1).

The compound (IV-5), wherein A in formula (IV) is not present (—(CH$_2$)$_m$— wherein m=0) and the 5-position of the pyrrolidine ring is bonded directly to the 5-position of imidazo[5,1-b]thiazole, may be preferably produced according to the following scheme:

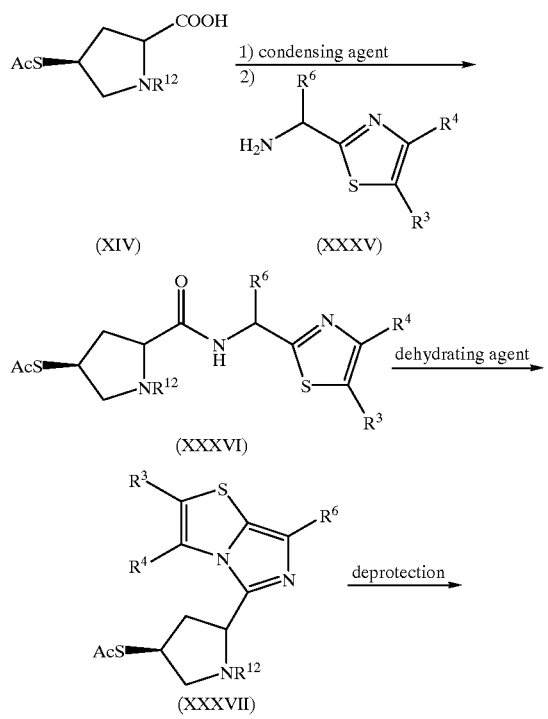

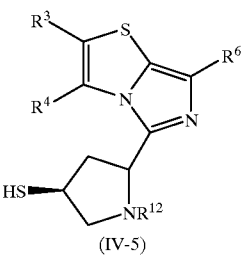

In the above scheme, R$^3$, R$^4$, and R$^6$ are as defined in formula (II) and R$^{12}$ is as defined in the formula (V).

In the first step, the compound (XXXVI) may be synthesized from the compound (XIV) and the compound (XXXV) by the following method or the like. The compound (XIV) is dissolved in an inert solvent (for example, tetrahydrofuran, dioxane, diethyl ether, dimethoxyethane, dichloromethane, chloroform, toluene, or benzene). One equivalent of an additive (preferably 1-hydroxybenzotriazole) and one equivalent of a condensing agent (preferably dicyclohexylcarbodiimide) are added to the solution. The reaction is allowed to proceed at 0° C. to room temperature for 30 min to 12 hr, the compound (XXXV), which has been if necessary diluted with an inert solvent (for example, tetrahydrofuran, dioxane, diethyl ether, dimethoxyethane, dichloromethane, chloroform, toluene, or benzene) to a proper concentration, is added thereto, and a reaction is allowed to proceed at 0° C. to room temperature for 30 min to 12 hr, followed by post-treatment to give the compound (XXXVI).

In the second step, the compound (XXXVII) may be synthesized from the compound (XXXVI) by the following method. An inert solvent (for example, benzene, toluene, xylene, dichloromethane, chloroform, tetrahydrofuran, or dioxane) is added to the compound (XXXVII). In some cases, an equivalent or excess amount of a dehydrating agent (preferably phosphorus oxychloride) is added without adding the solvent. The reaction is allowed to proceed at −20° C. to the reflux temperature for 10 min to 48 hr, followed by conventional post-treatment to give the compound (XXXVII).

In the third step, a thiol compound represented by formula (IV-5) may be derived from the compound (XXXVI) in the same manner as described in the conversion of the compound (XVI) to the compound (IV-1). The compound (IV-6), wherein A in formula (IV) is none (—(CH$_2$)$_m$— wherein m=0) and the 5-position of the pyrrolidine ring is bonded directly to the 3-position of imidazo[5,1-b]thiazole, may be preferably produced according to the following scheme:

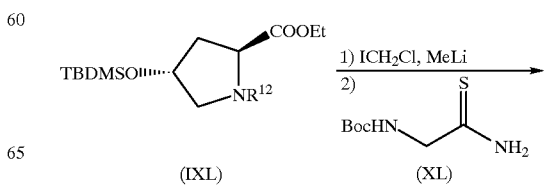

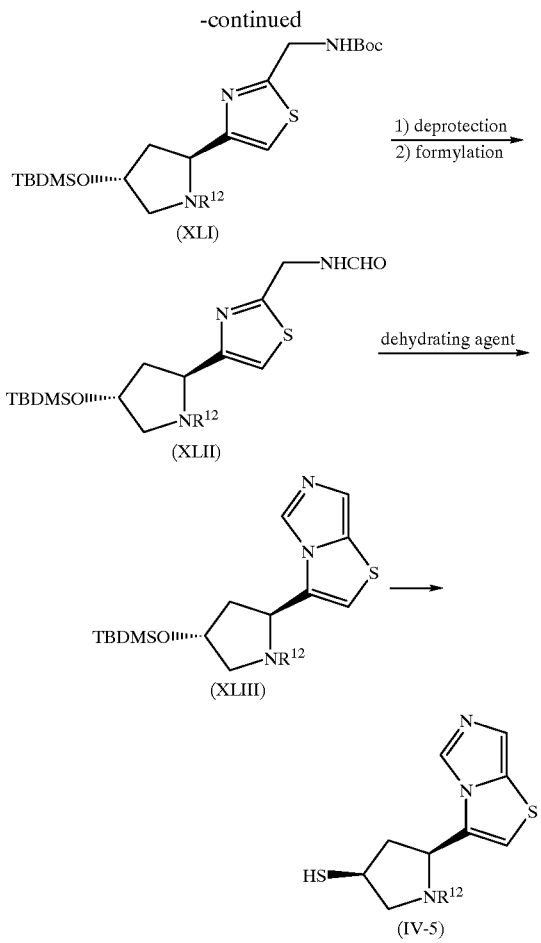

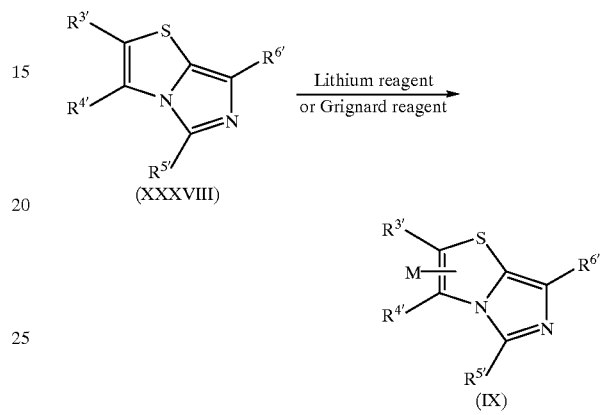

In the scheme, $R^{12}$ is as defined in formula (V).

In the first step, the compound (XLI) may be synthesized from the compound (IXL) and the compound (XL) by the following method or the like. The compound (IXL) is dissolved in an inert solvent (preferably tetrahydrofuran). The reaction is allowed to proceed using two equivalents of methyllithium in the presence of two equivalents of iodochloromethane at −100° C. to room temperature for 30 min to 12 hr, followed by conventional post-treatment. The resultant residue and one equivalent of the compound (XL) is dissolved in an inert solvent (preferably N,N-dimethylformamide). The reaction is allowed to proceed in the presence of one equivalent of sodium bromide at room temperature to 100° C. for 30 min to 12 hr, followed by conventional post-treatment to give the compound (XLI). In the second step, the compound (XLII) may be synthesized from the compound (XLI) by the following method. t-butoxycarbonyl as the protective group in the compound (XLI) is removed using trifluoroacetic acid, the deprotected compound is dissolved in a mixed solvent composed of methylene chloride and water. The reaction is allowed to proceed using a mixed acid anhydride, prepared from formic acid and acetic acid, in the presence of an inorganic base, such as sodium hydrogencarbonate or potassium carbonate, to give the compound (XLII). In the third step, the compound (XLIII) may be synthesized from the compound (XLII) by the following method. The compound (XLII) is dissolved in an inert solvent (for example, benzene, toluene, xylene, or dioxane or a mixed solvent composed of at least two of the above solvents). An equivalent or excess amount of a dehydrating agent (preferably phosphorus oxychloride) can be added without adding the solvent. The reaction is allowed to proceed at −20° C. to the reflux temperature for 10 min to 48 hr, followed by conventional post-treatment to give the compound (XLIII).

In the fourth step, the compound (XLIII) may be converted to a thiol compound represented by formula (IV-6) in the same manner as described in the conversion of the compound (XXXI) to the compound (IV-4).

An organometallic compound of imidazo[5,1-b]thiazole represented by formula (IX) may be preferably produced according to the following scheme:

In the scheme, M represents lithium, MgCl, MgBr, or MgI and any one of $R^{3'}$, $R^{4'}$, $R^{5'}$, and $R^{6'}$ represents a hydrogen, chlorine, bromine, or iodine atom, and the remaining three substituents, which may be the same or different, represent hydrogen; halogen; nitro; cyano; lower alkyl; lower cycloalkyl; lower alkylthio; $C_{2-4}$ alkenyl; or aryl, one or more hydrogen atoms of the lower alkyl, lower cycloalkyl, $C_{2-4}$ alkenyl, and aryl which may be optionally substituted by a group selected from the group consisting of halogen; nitro; lower cycloalkyl; lower alkylthio; lower alkoxy; (N-lower alkylamino)carbonyl; (N-lower alkylamino) sulfonyl; and aryl.

The compound (IX), wherein M is lithium, may be produced by treating a compound represented by formula (XXXVIII) wherein any one of $R^{3'}$, $R^{4'}$, $R^{5'}$, and $R^{6'}$ represents a hydrogen atom (see Japanese Patent Laid-Open No. 311071/1996) with a lithium reagent in the following manner. The compound (XXXVIII) is dissolved in an inert solvent (for example, tetrahydrofuran, diethyl ether, dioxane, dimethoxyethane, toluene, benzene, or hexamethylphosphoric triamide). A lithium reagent (for example, an alkyllithium or aryllithium, preferably n-butyllithium, methyllithium or the like) is added to the solution. The reaction is allowed to proceed at −100° C. to +50° C. for 10 min to 24 hr. Thus, a solution containing the compound (IX), wherein M represents lithium, dissolved therein is obtained.

The compound (IX), wherein M is MgCl, MgBr, or MgI, may be produced by treating a compound represented by formula (XXXVIII) wherein any one of $R^{3'}$, $R^{4'}$, $R^{5'}$, and $R^{6'}$ represents a chlorine, bromine, or iodine atom (see Japanese Patent Laid-Open No. 311071/1996) with a Grignard reagent in the following manner. The compound (XXXVIII) is dissolved in an inert solvent (for example, tetrahydrofuran, diethyl ether, dioxane, dimethoxyethane, toluene, benzene, dichloromethane, or hexamethylphosphoric triamide). Grignard reagent (for example, alkylmagnesium chloride, alkylmagnesium bromide, alkylmagnesium iodide, or arylmagnesium bromide, preferably methylmagnesium iodide, ethylmagnesium bromide or the like) is added to the solution. The reaction is allowed to proceed at −100° C. to +70° C. for 10 min to 24 hr. Thus, a solution containing the compound (IX), wherein M represents MgCl, MgBr, or MgI, dissolved therein is obtained.

Use of Compounds and Pharmaceutical Compositions

The carbapenem derivatives represented by formulae (I) and (II) have potent antimicrobial activity against a wide range of bacteria including Gram-positive bacteria and Gram-negative bacteria. In particular, they have potent antimicrobial activity against various β-lactamase-producing bacteria, resistant *Pseudomonas aeruginosa*, and meticillin-resistant *Staphylococcus aureus* (MRSA) and the like. Further, they are highly stable against kidney dehydropeptidase-I (DHP-I). Therefore, the carbapenem derivatives represented by formula (I) and (II) are useful in the treatment of infectional diseases. The term "treatment" as used herein refers to "prevention".

According to the present invention, there is provided a pharmaceutical composition comprising a carbapenem derivative represented by formula (I) or (II). This pharmaceutical composition can be used as an antimicrobial agent.

A pharmaceutical composition comprising as an active ingredient the compound of the present invention or a pharmaceutically acceptable salt thereof can be administered either orally or parenterally (e.g., intravenous injection, intramuscular injection, subcutaneous administration, rectal administration, or percutaneous administration) to humans or animals other than humans.

The pharmaceutical composition comprising as an active ingredient the compound of the present invention may be made into a preparation suitable for an administration route to be adopted. Specifically, it may be made into any of the following preparations: an injection for intravenous or intramuscular injection; a capsule, a tablet, a granule, a powder, a pill, fine subtilaes, or a troche for oral administration; a preparation for rectal administration; and an oleaginous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include lactose, fructose, glucose, starch, gelatin, magnesium carbonate, synthetic magnesium silicate, talc, magnesium stearate, methyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound of the present invention is properly determined in consideration of the regimen, the age and sex of a patient, and the conditions of disease. However, for the treatment of infectious disease, approximately 100 mg to 2000 mg, preferably 200 mg to 1000 mg of the compound is generally administered per day for an adult human, desirably at one time or several times.

EXAMPLES

The following examples further illustrate the present invention but are not intended to limit it.

Example 1

(1R,5S,6S)-6-((1R)-1-Hydroxyethyl)-2-[(3S,5S)-5-[(imidazo[5,1-b]thiazol-5-yl)methylaminocarbonyl] pyrrolidin-3-yl]thio-1-methylcarbapen-2-em-3-carboxylic acid a) Allyl(1R,5S,6S)-2-[(3S,5S)-1-allyloxycarbonyl-5-[(imidazo[5,1-b]thiazol-5-yl)methylaminocarbonyl] pyrrolidin-3-yl]thio-6-[(1R)-1-(t-butyldimethylsilyloxy)ethyl]-1-methylcarbapen-2-em-3-carboxylate A 2 N aqueous sodium hydroxide solution (0.38 ml) is added to a solution of 293 mg of (3S,5S)-3-acetylthio-1-allyloxycarbonyl-5-[(imidazo[5,1-b]thiazol-5-yl) methylaminocarbonyl]pyrrolidine in 1 ml of methanol under ice cooling, and the mixture is stirred for 20 min. Saturated saline (2 ml) and 1 N hydrochloric acid are added to the mixture to adjust the pH value to 7, and the mixture is then extracted twice with 20 ml of ethyl acetate. The extract is dried over anhydrous magnesium sulfate and filtered, and the solvent is removed under reduced pressure and by filtrate to give 260 mg of a mercaptan compound as a milky white amorphous material. N,N-Diisopropylethylamine (0.15 ml) is added dropwise to a solution of this mercaptan compound and 352 mg of allyl(1R,5R,6S)-6-[(1R)-1-(t-butyldimethylsilyloxy)ethyl]-2-(diphenylphosphono)oxy-1-methylcarbapen-2-em-3-carboxylate in 1 ml of dry acetonitrile under ice cooling in an argon atmosphere, and the mixture is stirred in this state for one hr. 1/15 M phosphate buffer (pH 7.0) (3 ml) is added thereto, and the mixture is successively extracted with 30 ml of ethyl acetate and 15 ml of ethyl acetate. The combined organic layers are dried over a 1:1 mixture of anhydrous magnesium sulfate and potassium carbonate and filtered, and the solvent is removed from the filtrate by evaporation to give a light yellow viscous material. The viscous material is successively purified by column chromatography on silica gel (ethyl acetate:methanol=97:3) and on Sephadex LH-20 (chloroform:methanol=1:1) to give 241 mg of allyl(1R,5S, 6S)-2-[(3S,5S)-1-allyloxycarbonyl-5-[imidazo[5,1-b] thiazol-5-yl)methylaminocarbonyl]pyrrolidin-3-yl]thio-6-[(1R)-1-(t-butyldimethylsilyloxy)ethyl]-1-methylcarbapen-2-em-3-carboxylate as a colorless amorphous material.

NMR (CDCl$_3$) δ: 0.07 (6H, s), 0.88 (9H, s), 1.20 (3H, d, J=7.2 Hz), 1.23 (3H, d, J=5.8 Hz), 1.9–2.4 (2H, br), 2.7 (1H, br.s), 3.15 (1H, br.s), 3.21 (1H, dd, J1=5.8 Hz, J2=2.7 Hz), 3.38 (1H, br.t), 3.70 (1H, br.s), 4.00 (1H, br.s), 4.16–4.27 (4H, m), 5.05 (1H, br), 5.22–5.47 (2H, m), 5.53 (1H, br.s), 5.87–6.00 (1H, m), 6.78 (1H, d, J=4.3 Hz), 6.95 (1H, s), 7.56 (1H, br.s), 7.73 (1H, d, J=4.3 Hz).

MS (SIMS): 730 (M$^+$+H)

b) Allyl(1R,5S,6S)-2-[(3S,5S)-1-allyloxycarbonyl-5-[(imidazo[5,1-b]thiazol-5-yl)methylaminocarbonyl] pyrrolidin-3-yl]thio-6-((1R)-1-hydroxyethyl)-1-methylcarbapen-2-em-3-carboxylate Acetic acid (0.285 ml) and 1.65 ml of a 1 M tetra-n-butylammonium fluoride/THF solution are added to a solution of 241 mg of allyl(1R,5S,6S)-2-[(3S,5S)-1-ayloxycarbonyl-5-[(imidazo-[5,1-b]thiazol-5-yl) methylaminocarbonyl]pyrrolidin-3-yl]thio-6-[(1R)-1-(t-butyldimethylsilyloxy)ethyl]-1-methylcarbapen-2-em-3-carboxylate in 5 ml of anhydrous THF, and the mixture is stirred in an argon atmosphere at room temperature for 47 hr. It is then diluted with 50 ml of ethyl acetate and washed with 10 ml of a 5% aqueous sodium hydrogencarbonate solution to obtain an organic layer. The aqueous layer is re-extracted with 20 ml of ethyl acetate, and the resultant organic layer is combined with the above organic layer. The solution is then dried over a 1:1 mixture of anhydrous magnesium sulfate and potassium carbonate and filtered, and the solvent is removed under reduced pressure and by filtrate to give a yellow oil. The oil is successively purified by column chromatography on silica gel (ethyl acetate:methanol=9:1) and on Sephadex LH-20 (chloroform:methanol=1:1) to give 181.3 mg of allyl(1R,5S,6S)-2-[(3S,5S)-1-allyloxycarbonyl-5-[(imidazo[5,1-b]thiazol-5-yl)methylaminocarbonyl]pyrrolidin-3-yl]thio-6-((1R)-1-hydroxyethyl)-1-methylcarbapen-2-em-3-carboxylate as a colorless amorphous material.

NMR (CDCl$_3$) δ: 1.23 (3H, d, J=7.2 Hz), 1.33 (3H, d, J=5.8 Hz), 1.6–2.4 (3H, br), 2.7 (1H, br.s), 3.21 (1H, dd, J1=6.0 Hz, J2=2.5 Hz), 3.3 (2H, br.s), 3.60 (1H, br), 4.10 (1H, br.s), 4.25–4.60 (6H, br), 4.65–4.87 (3H, m), 5.0 (1H, br.s), 5.24–5.48 (2H, m), 5.50 (1H, br.s), 5.92–6.04 (1H, m), 6.80 (1H, d, J=4.2 Hz), 6.95 (1H, s), 7.4 (1H, br.s), 7.73 (1H, d, J=4.3 Hz).

MS (SIMS): 616 (M$^+$+H)

c) (1R,5S,6S)-2-[(3S,5S)-6-((1R)-1-Hydroxyethyl)-5-[(imidazo[5,1-b]thiazol-5-yl)methylaminocarbonyl]pyrrolidin-3-yl]thio-1-methylcarbapen-2-em-3-carboxylic acid Tetrakis(triphenylphosphine)palladium(0) (8.1 mg) is added to a solution of 43.1 mg of allyl(1R,5S,6S)-2-[(3S,5S)-1-allyloxycarbonyl-5-[imidazo[5,1-b]thiazol-5-yl)methylaminocarbonyl]pyrrolidin-3-yl]thio-6-((1R)-1-hydroxyethyl)-1-methylcarbapen-2-em-3-carboxylate and 0.038 ml of aniline in 0.7 ml of dry dichloromethane, and the mixture is stirred in an argon atmosphere at room temperature for 60 min. Distilled water (2 ml) is added thereto, and the mixture is washed three times with 5 ml of ethyl acetate. The water layer is filtered and concentrated under reduced pressure, and the concentrate is freeze dried to give a colorless solid. This solid is purified by column chromatography on Sephadex LH-20 (water:methanol=1:1) to give 13.2 mg of the title compound as a colorless flocculent material.

NMR (D$_2$O) δ (HOD=4.80 ppm): 1.09 (3H, d, J=6.6 Hz), 1.28 (3H, d, J=6.3 Hz), 1.95–2.05 (1H, m), 2.79–2.89 (1H, m), 3.20–3.43 (3H, m), 3.62–3.75 (1H, m), 3.92–4.00 (1H, m), 4.15–4.28 (2H, m), 4.34–4.39 (1H, m), 4.67 (1H, d, J=13.2 Hz), 4.80 (1H, d, J=13.2 Hz), 7.04 (1H, s), 7.12 (1H, d, J=4.3 Hz), 7.67 (1H, d, J=4.3 Hz).

MS (SIMS): 492 (M$^+$+H)

Example 2

(1R,5S,6S)-6-((1R)-1-Hydroxyethyl)-1-methyl-2-[(3S,5S)- 5-[(6-methylimidazo[5,1-b]thiazolium-5-yl)methylaminocarbonyl]pyrrolidin-3-yl]thiocarbapen-2-em-3-carboxylic acid chloride a) Allyl(1R,5S,6S)-6-((1R)-1-Hydroxyethyl)-1-methyl-2-[(3S,5S)-5-[(6-methylimidazo[5,1-b]thiazolium-5-yl)methylaminocarbonyl]pyrrolidin-3-yl]thiocarbapen-2-em-3-carboxylate iodide Iodomethane (1.00 g) is added to 43.2 mg of allyl(1R,5S,6S)-2-[(3S,5S)-1-allyloxycarbonyl-5-[(imidazo[5,1-b]thiazol-5-yl)methylaminocarbonyl]pyrrolidin-3-yl]thio-6-((1R)-1-hydroxyethyl)-1-methylcarbapen-2-em-3-carboxylate, and the mixture is allowed to stand in an argon atmosphere in a light-shielded state at room temperature for 19 hr. The excess reagent is removed by evaporation under reduced pressure to give 52.6 mg of allyl(1R,5S,6S)-2-[(3S,5S)-1-allyloxycarbonyl-5-[(6-methylimidazo[5,1-b]thiazolium-5-yl)methylaminocarbonyl]pyrrolidin-3-yl]thio-6-((1R)-1-hydroxyethyl)-1-methylcarbapen-2-em-3-carboxylate iodide as a slightly yellowish solid.

NMR (CD$_3$COCD$_3$) δ: 1.26 (3H, d, J 6.9 Hz), 1.27 (3H, d, J=6.0 Hz), 2.00 (1H, m), 3.25 (1H, dd, J1=6.0 Hz, J2=2.5 Hz), 3.26–3.50 (1H, m), 3.59 (1H, m), 3.95 (1H, br), 4.05–4.22 (3H, m+br.s), 4.28–4.37 (3+1H, br.s+shoulder), 4.41 (2H, br.s), 4.52 (1H, br.s), 4.61 (1H, ddt), 4.79 (1H, ddt), 4.95–5.35 (5H, m), 5.47 (1H, m), 5.65–6.04 (2H, m+br), 7.74 (1H, br.s), 7.93 (1H, br.s), 8.50 (1H, br.s), 8.87 & 9.03 (total 1H, br.s each).

MS (SIMS): 630 (M$^+$) (excluding I$^-$)

b) (1R,5S,6S)-6-((1R)-1-Hydroxyethyl)-1-methyl-2-[(3S,5S)-5-[(6-methylimidazo[5,1-b]thiazolium-5-yl)methylaminocarbonyl]pyrrolidin-3-yl]thiocarbapen-2-em-3-carboxylic acid chloride Tetrakis(triphenylphosphine)palladium(0) (7.6 mg) is added to a solution of 50.0 mg of allyl( 1R,5S,6S)-2-[(3S,5S)-1-allyloxycarbonyl-5-[(6-methylimidazo[5,1-b]thiazolium-5-yl)methylaminocarbonyl]pyrrolidin-3-yl]thio-6-((1R)-1-hydroxyethyl)-1-methylcarbapen-2-em-3-carboxylate iodide and 0.036 ml of aniline in 0.7 ml of dry DMF, and the mixture is stirred in an argon atmosphere at room temperature for 70 min. Distilled water (2 ml) is added thereto, and the mixture is washed three times with 5 ml of ethyl acetate. The water layer is filtered and concentrated under reduced pressure to give an orange oil. This oil is dissolved in saturated saline and successively purified by column chromatography on Sephadex LH-20 (water:methanol=1:1) and on Diaion CHP-20P (2% aqueous THF solution) to give 5.3 mg of the title compound as a colorless flocculent material.

NMR (D$_2$O) δ (HOD=4.80 ppm): 1.05 (3H, d, J=7.1 Hz), 1.29 (3H, d, J=6.3 Hz), 1.77 (1H, m), 2.57 (1H, m), 2.88 (1H, dd, J1=11.3 Hz, J2=3.6 Hz), 3.25–3.40 (3H, m), 3.65–3.74 (1H, m), 3.86 (1H, m), 4.10 (3H, s), 4.12–4.28 (2H, m), 4.89 (1H, d, J=16.3 Hz), 4.98 (1H, d, J=16.3 Hz), 7.54 (1H, d, J=4.3 Hz), 7.60 (1H, s), 8.04 (1H, d, J=4.3 Hz).

MS (SIMS): 506 (M$^+$) (excluding Cl$^-$)

Example 3

Sodium(1R,5S,6S)-6-((1R)-1-hydroxyethyl)-2-[(3S,5S)-5-[N-(imidazo[5,1-b]thiazol-5-yl)methyl-N-methylaminocarbonyl]pyrrolidin-3-yl]thio-1-methylcarbapen-2-em-3-carboxylate a) Allyl(1R,5S,6S)-2-[3S,5S)-1-allyloxycarbonyl-6-[(1R)-1-(t-butyldimethylsilyloxy)ethyl]-5-[N-(imidazo[5,1-b]thiazol-5-yl)methyl-N-methylaminocarbonyl]pyrrolidin-3-yl]thio-1-methylcarbapen-2-em-3-carboxylate A 2 N aqueous sodium hydroxide solution (0.24 ml) is added to a solution of 190 mg of (3S,5S)-3-acetylthio-1-allyloxycarbonyl-5-[N-(imidazo[5,1-b]thiazol-5-yl)methyl-N-methylaminocarbonyl]pyrrolidine in 0.9 ml of methanol under ice cooling, and the mixture is stirred for 20 min. Saturated saline (2 ml) and 1 N hydrochloric acid are added to the mixture to adjust the pH value to 8, and the mixture is then extracted twice with 10 ml of ethyl acetate. The extract is dried over anhydrous magnesium sulfate and filtered, and the solvent is removed under reduced pressure and by filtrate to give 168.6 mg of a mercaptan compound as a yellow viscous material. N,N-Diisopropylethylamine (0.094 ml) is added dropwise to a solution of this mercaptan compound and 276 mg of allyl(1R,5R,6S)-6-[(1R)-1-(t-butyldimethylsilyloxy)ethyl]-2-(diphenylphosphono)oxy-1-methylcarbapen-2-em-3-carboxylate in 2 ml of dry acetonitrile under ice cooling in an argon atmosphere, and the mixture is stirred in this state for 2 hr. 1/15 M phosphate buffer (pH 7.0) (3 ml) is added thereto, and the mixture is extracted twice with 20 ml of ethyl acetate. The combined organic layers are dried over anhydrous magnesium sulfate and filtered, and the solvent is removed under reduced pressure and by filtrate to give a yellowish orange amorphous material. This material is successively purified by column chromatography on silica gel (ethyl acetate:methanol=97:3) and on Sephadex LH-20 (chloroform:methanol 1:1) to give 114.4 mg of allyl(1R,5S,6S)-2-[(3S,5S)-1-allyloxycarbonyl-6-[(1R)-1-(t-butyldimethylsilyloxy)ethyl]-5-[N-(imidazo[5,1-b]thiazol-5-yl)methyl-N-methylaminocarbonyl]pyrrolidin-3-yl]thio-1-methylcarbapen-2-em-3-carboxylate as a milky white amorphous material.

NMR (CDCl$_3$) (conformer mixture) δ: 0.09 (6H, s), 0.88 (9H, s), 1.22–1.26 (6H, m), 1.80–2.1.97 (1H, m), 2.66 (1H, m), 3.07 & 3.09 (total 3H, s each), 3.19–3.32 (2H, m), 3.47–3.55 (1H, m), 3.57–3.70 (1H, m), 4.03–4.51 (total 4H, m), 4.58–4.84 (5H, m), 4.94–5.07 (2H, m), 5.22–5.48 (1+2H, m), 5.48–5.61 & 5.88–6.02 (total 2H, m), 6.79 (1H, d, J=4.3 Hz), 6.98 & 7.00 (total 1H, s each), 7.69 & 7.78 (total 1H, d each, J=4.3 Hz each).

MS (SIMS): 743 (M$^+$+H)

b) Allyl(1R,5S,6S)-2-[(3S,5S)-1-allyloxycarbonyl-5-[N-(imidazo[5,1-b]thiazol-5-yl)methyl-N-methylaminocarbonyl]pyrrolidin-3-yl]thio-6-((1R)-1-hydroxyethyl)-1-methylcarbapen-2-em-3-carboxylate Acetic acid (0.132 ml) and 0.77 ml of a 1 M tetra-n-butylammonium fluoride/THF solution are added to a solution of 114 mg of allyl(1R,5S,6S)-2-[(3S,5S)-1-allyloxycarbonyl-5-[N-(imidazo[5,1-b]thiazol-5-yl)methyl-N-methylaminocarbonyl]pyrrolidin-3-yl]thio-6-[(1R)-1-(t-butyldimethylsilyloxy)ethyl]-1-methyl-carbapen-2-em-3-carboxylate in 2.3 ml of anhydrous THF, and the mixture is stirred in an argon atmosphere at room temperature for 22.5 hr. 1/15 M phosphate buffer (pH 7.0) (3 ml) is added thereto, and the mixture is extracted twice with 15 ml of ethyl acetate. The combined organic layers are dried over anhydrous magnesium sulfate and filtered, and the solvent is removed under reduced pressure and by filtrate to give a yellowish orange oil. This oil is purified by column chromatography on silica gel (ethyl acetate:methanol=9:1) to give 78.3 mg of allyl(1R,5S,6S)-2-[(3S,5S)-1-allyloxycarbonyl-5-[N-(imidazo[5,1-b]thiazol-5-yl)methyl-N-methylaminocarbonyl]pyrrolidin-3-yl]thio-6-((1R)-1-hydroxyethyl)-1-methylcarbapen-2-em-3-carboxylate as a colorless solid.

NMR (CDCl$_3$) (conformer mixture) δ: 1.23–1.28 (3H, m), 1.34–1.38 (3H, m), 1.8–2.3 (2H, m+br.s), 2.64–2.85 (1H, m), 3.07 & 3.09 (total 3H, s each), 3.23–3.29 (1H, m), 3.31–3.44 (1H, m), 3.46–3.57 (1H, m), 3.59–3.71 (1H, m), 4.03–4.52 (total 4H, m), 4.57–5.08 (total 7H, m), 5.22–5.51 (3H, m), 5.51–5.61 & 5.88–6.04 (total 2H, m each), 6.79–6.82 (1H, m), 6.98 & 7.00 (total 1H, s each), 7.69 & 7.78 (total 1H, br.d each).

MS (SIMS): 630 (M$^+$+H)

c) Sodium(1R,5S,6S)-6-((1R)-1-hydroxyethyl)-2-[(3S,5S)-5-[N-(imidazo[5,1-b]thiazol-5-yl)methyl-N-methylaminocarbonyl]pyrrolidin-3-yl]thio-1-methylcarbapen-2-em-3-carboxylate Tetrakis(triphenylphosphine)palladium(0) (7.0 mg) is added to a solution of 38.4 mg of allyl(1R,5S,6S)-2-[(3S,5S)-1-allyloxycarbonyl-5-[N-(imidazo[5,1-b]thiazol-5-yl)methyl-N-methylaminocarbonyl]pyrrolidin-3-yl]thio-6-((1R)-1-hydroxyethyl)-1-methylcarbapen-2-em-3-carboxylate and 0.033 ml of aniline in 0.6 ml of dry dichloromethane, and the mixture is stirred in an argon atmosphere at room temperature for 60 min. Distilled water (2 ml) is added thereto, and the mixture is washed three times with 4 ml of ethyl acetate. The water layer is concentrated under reduced pressure to give a yellow amorphous material. This amorphous material is dissolved in 5% aqueous hydrogencarbonate solution so that the resultant solution has pH 8.5. The solution is then purified by column chromatography on Diaion CHP-20P (2% aqueous THF solution) to give 13.4 mg of the title compound as a colorless flocculent material.

NMR (D$_2$O) δ (HOD=4.80 ppm): 1.13 (3H, d, J=7.5 Hz), 1.28 (3H, d, J=6.3 Hz), 1.46–1.55 (1H, m), 2.65–2.75 (1H, m), 2.96 (3H, s), 3.05–3.15 (2H, m), 3.30–3.31 (2H, m), 3.73–3.81 (1H, m), 4.08 (1H, dd, J1=9.0 Hz, J2=6.8 Hz), 4.15–4.27 (2H, m), 4.69 (1H, d, J=15.4 Hz), 5.05 (1H, d, J=15.4 Hz), 7.02 (1H, s), 7.11 (1H, d, J=4.2 Hz), 7.59 (1H, d, J=4.2 Hz).

MS (SIMS): 506 (M$^+$+H) (as COOH)

Example 4

(1R,5S,6S)-6-((1R)-1-Hydroxyethyl)-1-methyl-2-[(3S,5S)-5-[N-methyl-N-(6-methylimidazo[5,1-b]thiazolium-5-yl)methylaminocarbonyl]pyrrolidin-3-yl]thiocarbapen-2-em-3-carboxylic acid chloride a) Allyl(1R,5S,6S)-2-[(3S,5S)-1-allyloxycarbonyl-5-[N-methyl-N-(6-methylimidazo[5,1-b]thiazolium-5-yl)methylaminocarbonyl]pyrrolidin-3-yl]thio-6-((1R)-1-hydroxyethyl)-1-methylcarbapen-2-em-3-carboxylate iodide Iodomethane (0.84 g) is added to 37.0 mg of allyl(1R,5S,6S)-2-[(3S,5S)-1-allyloxycarbonyl-5-[N-(imidazo[5,1-b]thiazol-5-yl)methyl-N-methylaminocarbonyl]pyrrolidin-3-yl]thio-6-((1R)-1-hydroxyethyl)-1-methylcarbapen-2-em-3-carboxylate, and the mixture is stirred in an argon atmosphere in a light-shielded state at room temperature for 18 hr. The excess reagent is removed by evaporation under reduced pressure, and the residue is purified by column chromatography on Sephadex LH-20 (chloroform:methanol=1:1) to give 36.3 mg of allyl(1R,5S,6S)-2-[(3S,5S)-1-allyloxycarbonyl-5-[N-methyl-N-(6-methylimidazo[5,1-b]thiazolium-5-yl)methylaminocarbonyl]pyrrolidin-3-yl]thio-6-((1R)-1-hydroxyethyl)-1-methylcarbapen-2-em-3-carboxylate iodide as a milky white amorphous material.

NMR (CD$_3$COCD$_3$) (conformer mixture) δ: 1.25–1.28 (6H, m), 1.77–1.88 (1H, m), 2.80 (1H, br.s), 2.9–3.1 (1H, m), 3.30 (1H, dd, J1=6.8 Hz, J2=2.6 Hz), 3.34 & 3.43 & 3.47 (total 3H, s each), 3.7 (1H, br.t), 3.9–4.1 (1H, m), 4.1–4.45 (2H, m), 4.33 & 4.36 (total 3H, s each), 4.35–4.45 (1H, m), 4.50–4.55 (1H, m), 4.60–4.67 (1H, m), 4.76–4.83 (1H, m), 4.90–5.05 (1H, m), 5.05–5.35 (4H, m), 5.40–5.55 (2H, m), 5.68–5.82 & 5.85–6.03 (2H, m each), 7.78 & 7.82 (total 1H, d each, J=4.2 Hz each), 8.01–8.04 (1H, m), 8.30–8.36 (1H, m).

MS (SIMS): 644 (M$^+$) (excluding I$^-$)

b) (1R,5S,6S)-6-((1R)-1-Hydroxyethyl)-1-methyl-2-[(3S,5S)-5-[N-methyl-N-(6-methylimidazo[5,1-b]thiazolium-5-yl)methylaminocarbonyl]pyrrolidin-3-yl]thiocarbapen-2-em-3-carboxylic acid chloride Tetrakis(triphenylphosphine)palladium(0) (5.3 mg) is added to a solution of 35.3 mg of allyl(1R,5S,6S)-2-[(3S,5S)-1-allyloxycarbonyl-5-[N-methyl-N-(6-methylimidazo[5,1-b]thiazolium-5-yl)methylaminocarbonyl]pyrrolidin-3-yl]thio-6-((1R)-1-hydroxyethyl)-1-methylcarbapen-2-em-3-carboxylate iodide and 0.025 ml of aniline in a mixture of 0.4 ml of dry dichloromethane and 0.1 ml of dry DMF, and the mixture is stirred in an argon atmosphere at room temperature for 60 min. Distilled water (2 ml) is added thereto, and the mixture is washed three times with 4 ml of ethyl acetate. The water layer is concentrated under reduced pressure, and the concentrate is then freeze dried to give a light orange flocculent material. This material is dissolved in saturated saline, and the solution is then purified by column chromatography on Diaion CHP-20P (distilled water) to give 4.1 mg of the title compound as a colorless flocculent material.

NMR (D$_2$O) (conformer mixture) δ: 1.23–1.31 (6H, m), 1.8–2.1 (1H, m), 2.2–2.65 (total 1H, m), 2.85–3.12 (1H, m), 3.18–3.25 (total 4H, m), 3.35–3.90 (total 4H, m), 4.10 & 4.12 & 4.13 (total 3H, s each), 4.1–4.30 (1H, m), 4.4–4.55 (1H, m), 4.85–5.45 (2H, m), 7.58 (1H, d, J=4.1 Hz), 7.66 & 7.68 (total 1H, s each), 7.96–8.02 (1H, m).

Example 5

(1R,5S,6S)-2-[(3S,5S)-5-[N-Methyl-N-(5-aminomethyl-6-methylimidazo[5,1-b]thiazolium-3-yl)methylaminocarbonyl]pyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-[N-[5-(allyloxycarbonylaminomethyl)imidazo[5,1-b]thiazol-3-yl]methyl-N-methylamino-carbonyl]pyrrolidin-3-yl]thio-6-[(1R)-1-t-butyldimethylsilyloxy)ethyl]-1-methylcarbapen-2-em-3-carboxylate A 2 N aqueous sodium hydroxide solution (0.315 ml) is added to a solution of 320 mg of (3S,5S)-3-acetylthio-1-allyloxycarbonyl-5-[N-[5-(allyloxycarbonylaminomethyl)imidazo[5,1-b]thiazol-3-yl]methyl-N-methylaminocarbonyl]pyrrolidine in 1.2 ml of methanol under ice cooling, and the mixture is stirred for 20 min. Saturated saline (3 ml) and 1 N hydrochloric acid are added to the mixture to adjust the pH value to 7, and the mixture is then extracted twice with 15 ml of ethyl acetate. The extract is dried over anhydrous magnesium sulfate and filtered, and the solvent is removed under reduced pressure and by filtrate to give 286 mg of a mercaptan compound as a colorless powder. N,N-Diisopropylethylamine (0.12 ml) is added dropwise to a solution of this mercaptan compound and 354 mg of allyl(1R,5R,6S)-6-[(1R)-1-(t-butyldimethylsilyloxy)ethyl]-2-(diphenylphosphono)oxy-1-methylcarbapen-2-em-3-carboxylate in a mixture of 2.5 ml of dry acetonitrile with 2.5 ml of dry DMF under ice cooling in an argon atmosphere, and the mixture is stirred in this state for 3.5 hr. 1/15 M phosphate buffer (pH 7.0) (10 ml) is added thereto, and the mixture is extracted twice with 20 ml of ethyl acetate. The combined organic layers are dried over a 1:1 mixture of anhydrous magnesium sulfate and potassium carbonate and filtered, and the solvent is removed under reduced pressure and by filtrate to give a light yellow viscous material. The viscous material is successively purified by column chromatography on silica gel (ethyl acetate) and on Sephadex LH-20 (chloroform:methanol=1:1) to give 305 mg of allyl(1R,5S,6S)-2-[(3S,5S)-1-allyloxycarbonyl-5-[N-[5-(allyloxycarbonylaminomethyl)imidazo[5,1-b]thiazol-3-yl]methyl-N-methylaminocarbonyl]pyrrolidin-3-yl]thio-6-[(1R)-1-(t-butyldimethylsilyloxy)ethyl]-1-methylcarbapen-2-em-3-carboxylate as a colorless amorphous material.

NMR (CDCl$_3$) δ: 0.07–0.09 (6H, m), 0.87–0.91 (9H, m), 1.19–1.29 (6H, m), 1.95–2.15 (1H, m), 2.6–2.9 (1H, br), 3.1–3.35 (5H, m), 3.45–3.55 (1H, m), 3.6–3.8 (1H, br), 3.95–4.1 (1H, m), 4.15–4.3 (3H, m), 4.5–4.85 (10H, m), 5.25–5.5 (6H, m), 5.6–5.75 (1H, br), 5.8–6.05 (3H, m), 6.83 & 6.95 (total 1H, br.s each), 6.99 & 7.14 (total 1H, s each).

MS (FD): 857 (M$^+$+H)

b) Allyl(1R,5S,6S)-2-[(3S,5S)-1-allyloxycarbonyl-5-[N-[5-(allyloxycarbonyl-aminomethyl)imidazo[5,1-b]thiazol-3-yl]methyl-N-methylaminocarbonyl]pyrrolidin-3-yl]thio-6-((1R)-1-hydroxyethyl)-1-methylcarbapen-2-em-3-carboxylate Acetic acid (0.30 ml) and 1.75 ml of a 1 M tetra-n-butylammonium fluoride/THF solution are added to a solution of 300 mg of allyl(1R,5S,6S)-2-[(3S,5S)-1-allyloxycarbonyl-5-[N-[5-(allyloxycarbonylaminomethyl)imidazo[5,1-b]thiazol-3-yl]methyl-N-methylaminocarbonyl]pyrrolidin-3-yl]thio-6-[(1R)-1-(t-butyldimethylsilyloxy)ethyl]-1-methylcarbapen-2-em-3-carboxylate in 5.2 ml of anhydrous THF, and the mixture is stirred in an argon atmosphere at room temperature for 27.5 hr. 1/15 M phosphate buffer (pH 7.0) (10 ml) is added thereto, and the mixture is extracted twice with 30 ml of ethyl acetate. The combined organic layers are dried over a 1:1 mixture of anhydrous magnesium sulfate and potassium carbonate and filtered, and the solvent is removed under reduced pressure and by filtrate to give a colorless viscous material. The viscous material is successively purified by column chromatography on silica gel (ethyl acetate:methanol=97:3 to 95:5) and on Sephadex LH-20 (chloroform:methanol=1:1) to give 212.6 mg of allyl(1R,5S,6S)-2-[(3S,5S)-1-allyloxycarbonyl-5-[N-[5-(allyloxycarbonylaminomethyl)imidazo[5,1-b]thiazol-3-yl]methyl-N-methylaminocarbonyl]pyrrolidin-3-yl]thio-6-((1R)-1-hydroxyethyl)-1-methylcarbapen-2-em-3-carboxylate as a colorless amorphous material.

NMR (CDCl$_3$) δ: 1.27–1.37 (6H, m), 1.95–2.15 (1H, m+br), 2.6–2.9 (1H, m+br), 3.12–3.75 (7H, m), 3.98–4.07 (1H, m), 4.15–4.3 (3H, m), 4.5–4.85 (10H, m), 4.9–5.5 (7H, m), 5.75 (1H, m), 5.8–6.05 (3H, m), 6.40 & 6.53 & 6.84 & 6.95 (total 1H, br.s each), 6.98 & 7.01 & 7.03 & 7.06 (total 1H, s each).

MS (FD): 743 (M$^+$+H)

c) Allyl(1R,5S,6S)-2-[(3S,5S)-1-allyloxycarbonyl-5-[N-[5-(allyloxycarbonylaminomethyl-6-methylimidazo[5,1-b]thiazolium-3-yl]methyl-N-methylaminocarbonyl]pyrrolidin-3-yl]thio-6-((1R)-1-hydroxyethyl)-1-methylcarbapen-2-em-3-carboxylate iodide Iodomethane (2.14 g) is added to 111 mg of allyl(1R,5S,6S)-2-[(3S,5S)-1-allyloxycarbonyl-5-[N-[5-

(allyloxycarbonylaminomethyl)imidazo[5,1-b]thiazol-3-yl]methyl-N-methylaminocarbonyl]pyrrolidin-3-yl]thio-6-((1R)-1-hydroxyethyl)-1-methylcarbapen-2-em-3-carboxylate, and the mixture is stirred at room temperature in a light-shielded state for 18 hr. The excess reagent is removed under reduced pressure to give 132 mg of allyl (1R,5S,6S)-2-[(3S,5S)-1-allyloxycarbonyl-5-[N-(5-(allyloxycarbonylaminomethyl-6-methyl)imidazo[5,1-b]thiazolium-3-yl)methyl-N-methylaminocarbonyl]pyrrolidin-3-yl]thio-6-((1R)-1-hydroxyethyl)-1-methylcarbapen-2-em-3-carboxylate iodide as a bright yellow solid.

NMR (CD$_3$COCD$_3$) δ: 1.25–1.29 (6H, m), 1.65–1.975 (1H, m), 2.95–3.15 (2H, m), 3.20–3.40 (4H, m), 3.63–3.75 (1H, m), 3.85–4.40 (8H, m), 4.55–4.75 (5H, m), 4.75–4.85 (1H, m), 4.95–5.65 (11H, m), 5.85–6.05 (3H, m), 7.23 & 7.48 & 7.55 & 7.67 & 7.80 & 7.97 & 8.03 (total 3H, s or br.s each).

MS (SIMS): 757 (M$^+$) (excluding I$^-$)

d) (1R,5S,6S)-2-[(3S,5S)-5-[N-(5-aminomethyl-6-methylimidazo[5,1-b]thiazolium-3-yl)methyl-N-methylaminocarbonyl]pyrrolidin-3-yl]thio-6-((1R)-1-hydroxyethyl)-1-methylcarbapen-2-em-3-carboxylic acid iodide Tetrakis(triphenylphosphine)palladium(0) (25.9 mg) is added to a solution of 132 mg of allyl(1R,5S,6S)-2-[(3S,5S)-1-allyloxycarbonyl-5-[N-(5-allyloxycarbonylaminomethyl-6-methylimidazo[5,1-b]thiazolium-3-yl)methyl-N-methylaminocarbonyl]pyrrolidin-3-yl]thio-6-((1R)-1-hydroxyethyl)-1-methylcarbapen-2-em-3-carboxylate iodide and 0.125 ml of aniline in a mixture of 1.0 ml of dry dichloromethane and 0.4 ml of dry DMF, and the mixture is stirred in an argon atmosphere at room temperature for 4 hr. Distilled water (5 ml) is added thereto, and the mixture is washed four times with 4 ml of ethyl acetate. The water layer is concentrated under reduced pressure, and the concentrate is then freeze dried to give an orange solid. This material is dissolved in distilled water, and the solution is then purified by column chromatography on Sephadex LH-20 (water:methanol=1:1) to give 27.9 mg of the title compound as a milky white flocculent material.

NMR (D$_2$O) δ (HOD=4.80 ppm): 1.21 (3H, d, J=7.2 Hz), 1.28 (3H, d, J=6.0 Hz), 1.97–2.07 (1H, m), 2.4–3.0 (1H, br), 3.05–3.25 (4H, m), 3.32–3.72 (total 3H, m), 4.07 (4H, br.s), 4.18–4.40 (3H, m), 4.80–5.25 (4H, m), 7.25 & 7.30 & 7.34 (total 1H, s each), 7.64 (3H, s).

Example 6

(1R,5S,6S)-6-((1R)-1-Hydroxyethyl)-2-[(3S,5S)-5-[1-hydroxy-1-(imidazo[5,1-b]thiazol-3-yl)methyl]pyrrolidin-3-yl]thio-1-methylcarbapen-2-em-3-carboxylic acid (stereoisomer A)

a) Allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-[(1R)-1-(t-butyldimethylsilyloxy)ethyl]-1-methylcarbapen-2-em-3-carboxylate (stereoisomer A)

A 2 N aqueous sodium hydroxide solution (0.30 ml) is added to a solution of 214 mg of (3S,5S)-3-acetylthio-1-allyloxycarbonyl-5-[1-hydroxy-1-(imidazo[5,1-b]thiazol-3-yl)methyl]pyrrolidine (stereoisomer A) described in Synthesis Example 4 in 1.7 ml of methanol under ice cooling, and the mixture is stirred for 25 min. Saturated saline (10 ml) and 1 N hydrochloric acid are added to the mixture to adjust the pH value to 7, and the mixture is then extracted twice with 15 ml of ethyl acetate. The extract is dried over anhydrous magnesium sulfate and filtered, and the solvent is removed under reduced pressure and by filtrate to give 187.5 mg of a mercaptan compound as a pale red solid. N,N-Diisopropylethylamine (0.11 ml) is added dropwise to a solution of this mercaptan compound and 344 mg of allyl (1R,5R,6S)-6-[(1R)-1-(t-butyldimethylsilyloxy)ethyl]-2-(diphenylphosphono)oxy-1-methylcarbapen-2-em-3-carboxylate in a mixture of 1.1 ml of dry acetonitrile with 1.1 ml of dry DMF under ice cooling in an argon atmosphere, and the mixture is stirred in this state for 35 min. 1/15 M phosphate buffer (pH 7.0) (10 ml) is added thereto, and the mixture is extracted with 20 ml of ethyl acetate. The organic layer is dried over anhydrous magnesium sulfate and filtered, and the solvent is removed under reduced pressure and by filtrate to give a red viscous material. The viscous material is purified by column chromatography on silica gel (ethyl acetate:methanol=97:3) to give 250 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-[(1R)-1-(t-butyldimethylsilyloxy)ethyl]-1-methylcarbapen-2-em-3-carboxylate (stereoisomer A) as a light yellow amorphous material.

NMR (CDCl$_3$) δ: 0.08 (6H, s), 0.88 (9H, s), 1.21–1.25 (6H, s), 1.75 (1H, br.s), 2.3 (2H, br), 3.20 (1H, dd, J1=5.6 Hz, J2=2.5 Hz), 3.29 (2H, br.t), 3.55 (1H, m), 4.02–4.42 (4H, m), 4.60 (2H, br.s), 4.65–4.82 (2H, m), 5.22–5.60 (5H, m+br.s), 5.67–6.02 (2H, m+br), 6.74 (1H, s), 7.03 (1H, s), 8.07 & 8.23 (1H, br.s each).

MS (FAB$^+$): 703 (M$^+$+H)

b) Allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer A)

Acetic acid (0.30 ml) and 1.8 ml of a 1 M tetra-n-butylammonium fluoride/THF solution are added to a solution of 250 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-[(1R)-1-(t-butyldimethylsilyloxy)ethyl]-1-methylcarbapen-2-em-3-carboxylate (stereoisomer A) in 5.3 ml of anhydrous THF, and the mixture is stirred in an argon atmosphere at room temperature for 35 hr. The reaction solution is diluted with 100 ml of ethyl acetate, and the diluted solution is washed with 50 ml of 1/15 M phosphate buffer (pH 7.0) and 20 ml of saturated saline in that order, dried over anhydrous magnesium sulfate, and filtered. The solvent is removed by evaporation to give 244 mg of a light brown oil. This oil is successively purified by column chromatography on silica gel (ethyl acetate:methanol=9:1) and on Sephadex LH-20 (chloroform:methanol=1:1) to give 150 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer A) as a milky while amorphous material.

NMR (CDCl$_3$) δ: 1.23 (3H, d, J=7.2 Hz), 1.35 (3H, d, J=6.2 Hz), 1.8–2.5 (3H, br), 3.2–3.4 (2+1H, m+dd, J1=7.1 Hz, J2=2.5 Hz), 3.55 (1H, m), 3.9–4.65 (6H, m+br), 4.63–4.86 (2H, m), 5.2–5.6 (6H, m), 5.70–6.05 (2H, br+m), 6.75 (1H, s), 7.05 (1H, s), 8.07 & 8.25 (total 1H, br.s each).

MS (FAB$^+$): 589 (M$^+$+H)

c) (1R,5S,6S)-6-((1R)-1-Hydroxyethyl)-2-[(3S,5S)-5-[1-hydroxy-1-(imidazo[5,1-b]thiazol-3-yl)methyl]pyrrolidin-3-yl]thio-1-methylcarbapen-2-em-3-carboxylic acid (stereoisomer A)

Tetrakis(triphenylphosphine)palladium(0) (13.8 mg) is added to a solution of 70 mg of allyl( 1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer A) and 0.077 ml of N-methylaniline in 1.0 ml of dry dichloromethane, and the mixture is stirred in an argon atmosphere at room temperature for 45 min. Distilled water (3 ml) is added thereto, and the mixture is washed three times with 5 ml of ethyl acetate. The water layer is filtered, followed by concentration under reduced pressure and freeze drying to give a colorless flocculent material. The flocculent material is purified by column chromatography (water-methanol) on Cosmosil 40C18-PREP to give 11.5 mg of the title compound as a colorless flocculent material.

NMR ($D_2O$) δ (HOD=4.80 ppm): 1.21 (3H, d, J=7.2 Hz), 1.28 (3H, d, J=6.5 Hz), 1.96–2.07 (1H, m), 2.65–2.77 (1H, m), 3.29–3.40 (2H, m), 3.45 (1H, dd, J1=6.2 Hz, J2=2.8 Hz), 3.57–3.64 (1H, m), 3.95–4.05 (1H, m), 4.15–4.28 (3H, m), 5.27 (1H, d, J=6.6 Hz), 7.13 (1H, s), 7.19 (1H, s), 8.33 (1H, s).

MS ($FAB^+$): 465 ($M^+$+H)

Example 7

(1R,5S,6S)-6-((1R)-1-Hydroxyethyl)-2-[(3S,5S)-5-[1-hydroxy-1-(6-methylimidazo[5,1-b]thiazolium-3-yl)methyl]pyrrolidin-3-yl]thio-1-methylcarbapen-2-em-3-carboxylic acid iodide (stereoisomer A)

a) Allyl(1R,5S,6S)-6-((1R)-1-hydroxyethyl)-2-[(3S,5S)-1-allyloxycarbonyl-5-[1-hydroxy-1-(6-methylimidazo[5,1-b]thiazolium-3-yl)methyl]pyrrolidin-3-yl]thio-1-methylcarbapen-2-em-3-carboxylate iodide (stereoisomer A)

Iodomethane (1.70 g) is added to 70.6 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer A) described in Example 6-b), and the mixture is stirred in an argon atmosphere at room temperature in a light-shielded state for 14 hr. The excess reagent is removed by evaporation under reduced pressure, and the residue is purified by column chromatography on Sephadex LH-20 (chloroform:methanol=1: 1) to give 83.4 mg of allyl(1R,5S,6S)-6-((1R)-1-hydroxyethyl)-2-[(3S,5S)-1-allyloxycarbonyl-5-[1-hydroxy-1-(6-methylimidazo[5,1-b]thiazolium-3-yl)methyl]pyrrolidin-3-yl]thio-1-methylcarbapen-2-em-3-carboxylate iodide (stereoisomer A) as a light yellow amorphous material.

NMR ($CD_3COCD_3$) δ: 1.25–1.29 (6H, m), 2.18–2.28 (1H, m), 2.75 (1H, br.s), 3.31 (2H, br+dd, J1=6.8 Hz, J2=2.7 Hz), 3.62 (1H, m), 3.98 (1H, br.t), 4.13 (1H, m), 4.22–4.30 (2H, m), 4.33 (3+1H, s+br), 4.44 (3H, br), 4.63 (1H, m), 4.80 (1H, m), 5.05–5.30 (2+1H, br+m), 5.35–5.52 (1+1H, br+m), 5.60–6.15 (2+1H, m+br), 7.59 (1H, br.s), 8.02 (1H, br.s), 9.82 & 9.93 (total 1H, br.s each).

MS ($FAB^+$): 603 (M+) (excluding $I^-$)

b) (1R,5S,6S)-6-((1R)-1-Hydroxyethyl)-2-[(3S,5S)-5-[1-hydroxy-1-(6-methylimidazo[5,1-b]thiazolium-3-yl)methyl]pyrrolidin-3-yl]thio-1-methylcarbapen-2-em-3-carboxylic acid iodide (stereoisomer A)

Tetrakis(triphenylphosphine)palladium(0) (13.1 mg) is added to a solution of 83.0 mg of allyl(1R,5S,6S)-6-((1R)-1-hydroxyethyl)-2-[(3S,5S)-1-allyloxycarbonyl-5-[1-hydroxy-1-(6-methylimidazo[5,1-b]thiazolium-3-yl)methyl]pyrrolidin-3-yl]thio-1-methylcarbapen-2-em-3-carboxylate iodide (stereoisomer A) and 0.074 ml of N-methylaniline in 0.9 ml of dry dichloromethane, and the mixture is stirred in an argon atmosphere at room temperature for 35 min. Distilled water (5 ml) is added thereto, the mixture is washed three times with 5 ml of ethyl acetate, the aqueous layer is concentrated under reduced pressure, and the concentrate is freeze dried to give a milky white flocculent material. The milky white flocculent material is successively purified by column chromatography on Cosmosil 40C18-PREP (water-methanol) and on Sephadex LH-20 (water:methanol=1:1) to give 8.2 mg of the title compound as a light brown powder.

NMR ($D_2O$) δ (HOD=4.80 ppm): 1.21 (3H, d, J=7.2 Hz), 1.28 (3H, d, J=6.4 Hz), 1.78 (1H, m), 2.62 (1H, dt, Jd=14.0 Hz, Jt=8.0 Hz), 2.96 (1H, dd, J1=12.0 Hz, J2=4.1 Hz), 3.26 (1H, dd, J1=12.0 Hz, J2=6.1 Hz), 3.33–3.44 (2H, m), 3.73–3.88 (2H, m), 4.10 (3H, s), 4.16–4.27 (2H, m), 5.05 (1H, d, J=7.7 Hz), 7.50 (1H, s), 7.65 (1H, s), 9.36 (1H, s, gradually exchanged with $D_2O$).

MS ($FAB^+$): 479 ($M^+$) (Excluding $I^-$)

Example 8

(1R,5S,6S)-6-((1R)-1-Hydroxyethyl)-2-[(3S,5S)-5-[1-hydroxy-1-(imidazo[5,1-b]thiazol-3-yl)methyl]pyrrolidin-3-yl]thio-1-methylcarbapen-2-em-3-carboxylic acid stereoisomer B)

a) Allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-[(1R)-1-(t-butyldimethyl-silyloxy)ethyl]-1-methylcarbapen-2-em-3-carboxylate (stereoisomer B)

A 2 N aqueous sodium hydroxide solution (0.30 ml) is added to a solution of 138 mg of (3R,5S)-3-acetylthio-1-allyloxycarbonyl-5-[1-hydroxy-1-(imidazo[5,1-b]thiazol-3-yl)methyl]pyrrolidine (stereoisomer B), described in Synthesis Example 5, in 1.1 ml of methanol at a bath temperature of −20° C., and the mixture is stirred for 25 min and then stirred for 10 min while gradually raising the temperature. Semi-saturated saline (10 ml) and 1 N hydrochloric acid are added thereto to adjust the pH value to 7, and the mixture is extracted twice with 15 ml of ethyl acetate and dried over anhydrous magnesium sulfate, followed by filtration and removal of the solvent by evaporation to give 123.5 mg of a mercaptan compound as a slightly red solid. N,N-Diisopropylethylamine (0.11 ml) is added dropwise to a solution of this mercaptan and 273 mg of allyl(1R,5R,6S)-6-[(1R)-1-(t-butyldimethylsilyloxy)ethyl]-2-(diphenylphosphono)oxy-1-methylcarbapen-2-em-3-carboxylate in 1.0 ml of acetonitrile in an argon atmosphere at a bath temperature of −10° C., and the mixture is stirred in this state for 30 min. A 1/15 M phosphate buffer (pH 7.0) (10 ml) is added thereto, and the mixture is extracted with 20 ml of ethyl acetate. The organic layer is dried over anhydrous magnesium sulfate, followed by filtration and the removal of the solvent by evaporation to give 347 mg of an orange brown oil. This oil is purified by column chromatography on silica gel (ethyl acetate:methanol=96:4) to give 213 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-[(1R)-1-(t-butyldimethyl-silyloxy)ethyl]-1-methylcarbapen-2-em-3-carboxylate (stereoisomer B) as a light yellow amorphous materia.

NMR (CDCl₃) δ: 0.08 (6H, s), 0.89 (9H, s), 1.19–1.25 (6H, m), 1.7 (1H, br.s), 2.22 (1H, br), 3.15–3.23 (1+1H, m+dd, J1=5.6 Hz, J2=2.7 Hz), 3.30–3.41 (1H, m), 3.60 (1H, m), 4.05 (1H, br), 4.19–4.29 (1H, m), 4.49–4.83 (6H, m), 4.98 (1H, d, 8.3 Hz), 5.23–5.48 (4H, m), 5.88–6.02 & 6.27 (total 2H, m+br.s), 6.75 (1H, s), 7.07 (1H, s), 8.26 (1H, br.s).

MS (FAB⁺): 703 (M⁺+H)

b) Allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer B)

Acetic acid (0.26 ml) and 1.52 ml of a 1 M tetra-n-butyl ammonium fluoride/THF solution are added to a solution of 213 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-[(1R)-1-(t-butyldimethylsilyloxy)ethyl]-1-methylcarbapen-2-em- 3-carboxylate (stereoisomer B) in 4.5 ml of anhydrous THF, and the mixture is stirred in an argon atmosphere at room temperature for 38 hr. The reaction solution is diluted with 80 ml of ethyl acetate, the diluted solution is successively washed with 40 ml of a 1/15 M phosphate buffer (pH 7.0) and 20 ml of saturated saline, the washed solution is dried over anhydrous magnesium sulfate and filtered, and the solvent is removed by evaporation to give 193 mg of a slightly yellow oil. This oil is successively purified by column chromatography on silica gel (ethyl acetate:methanol=95:5→9:1) and on Sephadex LH-20 (chloroform:methanol=1:1) to give 119.2 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer B) as a milky white amorphous material.

NMR (CDCl₃) δ: 1.22 (3H, d, J=7.1 Hz), 1.36 (3H, d, J=6.2 Hz), 1.67 (1H, m), 2.25 (1+1H, br+m), 3.20–3.40 (1+2H, dd+m, J1=7.1 Hz, J2=2.7 Hz), 3.59 (1H, quintet, J=7.4 Hz), 4.06 (1H, br.t), 4.20–4.29 (2H, m), 4.57 (1H, dd, J1=14.5 Hz, J2=7.7 Hz), 4.64–4.73 (1+2H, m+br.s), 4.83 (1H, m), 5.00 (1H, d, J=7.9 Hz), 5.25–5.49 (4H, m), 5.90–6.04 & 6.30 (total 3H, m+br), 6.76 (1H, s), 7.07 (1H, s), 8.26 (1H, br.s).

MS (FAB⁺): 589 (M⁺+H)

c) (1R,5S,6S)-6-((1R)-1-Hydroxyethyl)-2-[(3S,5S)-5-[1-hydroxy-1-(imidazo[5,1-b]thiazol-3-yl)methyl]pyrrolidin-3-yl]thio-1-methylcarbapen-2-em-3-carboxylic acid (stereoisomer B)

Tetrakis(triphenylphosphine)palladium(0) (12.7 mg) is added to a solution of 64.8 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer B) and 0.072 ml of N-methylaniline in a mixture of 0.9 ml of dry dichloromethane with 0.9 ml of monochlorobenzene, and the mixture is stirred in an argon atmosphere at room temperature for 70 min. Distilled water (3 ml) is added thereto, the mixture is washed three times with 3 ml of ethyl acetate, and the aqueous layer is filtered, followed by concentration under reduced pressure and freeze drying to give 23 mg of a colorless flocculent material. The colorless flocculent material is successively purified by column chromatography on Diaion CHP-20P (4% aqueous THF solution) and on Cosmosil 5C18-MS (water:methanol=2:1) to give 5.8 mg of the title compound as a colorless flocculent material.

NMR (D₂O) δ (HOD=4.80 ppm): 1.19 (3H, d, J=7.2 Hz), 1.28 (3H, J=6.0 Hz), 1.81 (1H, m), 2.60 (1H, m), 3.33–3.47 (3H, m), 3.67 (1H, m), 4.01 (1H, br.t), 4.19–4.30 (3H, m), 5.22 (1H, d, J=8.5 Hz), 7.12 (1H, s), 7.20 (1H, s), 8.34 (1H, s).

MS (FAB⁺): 465 (M⁺+H)

Example 9

(1R,5S,6S)-6-[(1R)-1-Hydroxyethyl]-2-[(3S,5S)-5-[1-hydroxy-1-(6-methylimidazo[5,1-b]thiazolium-3-yl)methyl]pyrrolidin-3-yl]thio-1-methylcarbapen-2-em-3-carboxylic acid perchlorate (stereoisomer B)

a) Allyl(1R,5S,6S)-2-[(3S,5S)-1-allyloxycarbonyl-5-[1-hydroxy-1-(6-methylimidazo[5,1-b]thiazolium-3-yl)methyl]pyrrolidin-3-yl]thio-6-((1R)-1-hydroxyethyl)-1-methylcarbapen-2-em-3-carboxylate perchlorate (stereoisomer B)

Iodomethane (0.71 g) is added to 58.8 mg of allyl(1R,5S,6S)-2-[(3S,5S)-1-allyloxycarbonyl-5-[1-hydroxy-1-(imidazo[5,1-b]thiazol-3-yl)methyl]pyrrolidin-3-yl]thio-6-((1R)-1-hydroxyethyl)-1-methylcarbapen-2-em-3-carboxylate (stereoisomer B) described in Example 8-b), and the mixture is stirred in an argon atmosphere in a light-shielded state at room temperature for 24 hr. The excess reagent is removed by evaporation under reduced pressure, and the residue is purified by column chromatography on Sephadex LH-20 (chloroform:methanol=1:1) to give 71.1 mg of allyl(1R,5S,6S)-2-[(3S,5S)-1-allyloxycarbonyl-5-[1-hydroxy-1-(6-methylimidazo[5,1-b]thiazolium-3-yl)methyl]pyrrolidin-3-yl]thio-6-((1R)-1-hydroxyethyl)-1-methylcarbapen-2-em-3-carboxylate iodide (stereoisomer B) as a light brown oil. Silver perchlorate (31 mg) is added to a solution of this oil in a mixture of 2 ml of dry dichloromethane with 2 ml of acetonitrile, and the mixture is stirred. The solvent is removed by evaporation, and acetonitrile is again added for suspension, followed by filtration and the removal of the solvent by evaporation to give an oil. The oil is then purified by column chromatography on Sephadex LH-20 (chloroform:methanol=1:1) to give 55 mg of allyl(1R,5S,6S)-2-[(3S,5S)-1-allyloxycarbonyl-5-[1-hydroxy-1-(6-methylimidazo[5,1-b]thiazolium-3-yl)methyl]pyrrolidin-3-yl]thio-6-((1R)-1-hydroxyethyl)-1-methylcarbapen-2-em-3-carboxylate perchlorate (stereoisomer B) as a light brown amorphous material.

NMR (CDCl₃) δ: 1.18 (3H, d, J=6.9 Hz), 1.31 (3H, d, J=6.3 Hz), 1.62 (1H, m), 1.82 & 2.03 (total 1H, br.s each), 2.31 & 2.55 (total 1H, m each), 3.17–3.65 (5H, m), 3.95–4.30 (total 6H, br.s+m), 4.35–4.85 (total 4H, br+m), 5.05–5.48 (total 6H, br+m), 5.70–6.05 (1+1H, m+br.s), 6.98 (1H, m), 7.40 (1H, br.s), 9.64 (1H, br.s).

MS (FAB⁺): 603 (M⁺) (excluding ClO₄)

b) (1R,5S,6S)-6-((1R)-1-Hydroxyethyl)-2-[(3S,5S)-5-[1-hydroxy-1-(6-methylimidazo[5,1-b]thiazolium-3-yl)methyl]pyrrolidin-3-yl]thio-1-methylcarbapen-2-em-3-carboxylic acid perchlorate (stereoisomer B)

Tetrakis(triphenylphosphine)palladium(0) (18.1 mg) is added to a solution of 55 mg of allyl(1R,5S,6S)-2-[(3S,5S)-1-allyloxycarbonyl-5-[1-hydroxy-1-(6-methylimidazo[5,1-b]thiazolium-3-yl)methyl]pyrrolidin-3-yl]thio-6-((1R)-1-hydroxyethyl)-1-methylcarbapen-2-em-3-carboxylate perchlorate (stereoisomer B) and 0.051 ml of N-methylaniline in 0.7 ml of dry dichloromethane, and the mixture is stirred in an argon atmosphere at room temperature for 45 min. Distilled water (3 ml) is added thereto, the mixture is washed three times with 3 ml of ethyl acetate, and the aqueous layer is filtered, followed by concentration under reduced pressure and freeze drying to give 31 mg of a light orange flocculent material. The light orange flocculent material is purified by column chromatography on Cosmosil 5C18-MS (water:methanol=10:1) to give 3.9 mg of the title compound as a colorless flocculent material.

NMR ($D_2O$) δ (HOD=4.80 ppm): 1.14 (3H, J=7.4 Hz), 1.22 (3H, d, J=6.3 Hz), 1.70 (1H, m), 2.52 (1H, m), 3.31 (2H, m), 3.40 (1H, dd, J1=6.3 Hz, J2=2.5 Hz), 3.56 (1H, m), 3.95 (1H, br.s), 4.02–4.12 (3+1H, s+m), 4.14–4.21 (2H, m), 5.20 (1H, d, J=9.2 Hz), 7.54 (1H, s), 7.61 (1H, s), 9.38 (1H, br.s, gradually exchanged with $D_2O$).

Example 10

(1R,5S,6S)-6-((1R)-1-Hydroxyethyl)-2-[(3S,5R)-5-(imidazo[5,1-b]thiazol-5-yl)methylpyrrolidin-3-yl]thio-1-methylcarbapen-2-em-3-carboxylic acid a) Allyl(1R,5S,6S)-2-[(3S,5R)-1-allyloxycarbonyl-5-(imidazo[5,1-b]thiazol-5-yl)methylpyrrolidin-3-yl]thio-6-((1R)-1-hydroxyethyl)-1-methylcarbapen-2-em-3-carboxylate A 2 N aqueous sodium hydroxide solution (0.145 ml) is added to a solution of 115 mg of (3S,5R)-1-allyloxycarbonyl-3-benzoylthio-5-(imidazo[5,1-b]thiazol-5-ylmethyl)pyrrolidine in 0.8 ml of methanol under ice cooling, and the mixture is stirred for 20 min. Saturated saline (10 ml) is added thereto, the mixture is extracted twice with 10 ml of dichloromethane, and the extract is then dried over anhydrous magnesium sulfate, followed by filtration and the removal of the solvent by evaporation to give 120 mg of a mercaptan compound as a yellow oil. N,N-Diisopropylethylamine (0.061 ml) added dropwise to a solution of this mercaptan and 148 mg of allyl(1R,5R,6S)-2-(diphenylphosphono)oxy-6-((1R)-1-hydroxyethyl)-1-methylcarbapen-2-em-3-carboxylate in 2.0 ml of dry acetonitrile under ice cooling in an argon atmosphere, and the mixture is stirred as it is for 150 min. Saturated saline (10 ml) is added thereto, the mixture is extracted twice with 20 ml of ethyl acetate, and the combined organic layers are dried over anhydrous magnesium sulfate, followed by filtration and the removal of the solvent by evaporation to give 245 mg of yellow oil. The oil is successively purified by column chromatography on silica gel (ethyl acetate:methanol=95:5) and on Sephadex LH-20 (dichloromethane:methanol=1:1) to give 93.2 mg of allyl (1R,5S,6S)-2-[(3S,5R)-1-allyloxycarbonyl-5-(imidazo[5,1-b]thiazol-5-yl)methylpyrrolidin-3-yl]thio-6-((1R)-1-hydroxyethyl)-1-methylcarbapen-2-em-3-carboxylate as a colorless amorphous material.

NMR ($CDCl_3$) δ: 1.24 (3H, d, J=7.1 Hz), 1.35 (3H, d, J=6.3 Hz), 1.92 (1H, br.s), 2.14 (1H, br.s), 2.54 (1H, m), 3.15–3.35 (4H, dd+m, J1=6.9 Hz, J2=2.5 Hz), 3.45–3.67 (2H, m), 3.87–4.47 (4H, m), 4.55–4.72 (2+1H, br+m), 4.83 (1H, m), 5.23–5.48 (4H, m), 5.85–6.03 (1+1H, br+m), 6.77 (1H, br.s), 6.98 (1H, br.s), 7.37 & 7.55 (total 1H, br.s each).

MS ($FAB^+$): 573 ($M^+$+H)

b) (1R,5S,6S)-6-((1R)-1-hydroxyethyl)-2-[(3S,5R)-5-(imidazo[5,1-b]thiazol-5-yl)methylpyrrolidin-3-yl]thio-1-methylcarbapen-2-em-3-carboxylic acid Tetrakis(triphenylphosphine)palladium(0) (7.0 mg) is added to a solution of 34.5 mg of allyl(1R,5S,6S)-2-[(3S, 5R)-1-allyloxycarbonyl-5-(imidazo[5,1-b]thiazol-5-yl)methylpyrrolidin-3-yl]thio-6-((1R)-1-hydroxyethyl)-1-methylcarbapen-2-em-3-carboxylate and 0.040 ml of N-methylaniline in 1.2 ml of dry dichloromethane in an argon atmosphere at room temperature for 60 min. Distilled water (3 ml) is added thereto, the mixture is washed three times with 6 ml of ethyl acetate, and the aqueous layer is filtered, followed by concentration under reduced pressure and freeze drying to give 16.7 mg of a colorless flocculent material. The colorless flocculent material is purified by column chromatography on Cosmosil 40C18-PREP (water-methanol) to give 9.8 mg of the title compound as a colorless flocculent material.

NMR ($D_2O$) δ (HOD=4.80 ppm): 1.20 (3H, d, J=7.1 Hz), 1.28 (3H, d, J 6.0 Hz), 1.77 (1H, m), 2.77 (1H, m), 3.31–3.50 (5H, m), 3.65–3.70 (1H, m), 4.01 (1H, m), 4.10–4.26 (3H, m), 7.04 (1H, s), 7.11 (1H, d, J=4.2 Hz), 7.66 (1H, d, J=4.2 Hz).

MS ($FAB^+$): 449 ($M^+$+H)

Example 11

(1R,5S,6S)-6-((1R)-1-Hydroxyethyl)-1-methyl-2-[(3S,5R)-5-(6-methylimidazo[5,1-b]thiazolium-5-yl)methylpyrrolidin-3-yl]thiocarbapen-2-em-3-carboxylic acid iodide a) Allyl(1R,5S,6S)-2-[(3S,5R)-1-allyloxycarbonyl-5-(6-methyl-imidazo[5,1-b]thiazolium-5-yl)methylpyrrolidin-3-yl]thio-6-((1R)-1-hydroxyethyl)-1-methylcarbapen-2-em-3-carboxylate iodide Iodomethane (0.71 g) is added to 57.2 mg of allyl(1R, 5S,6S)-2-[(3S,5R)-1-allyloxycarbonyl-5-(imidazo[5,1-b]thiazol-5-yl)methylpyrrolidin-3-yl]thio-6-((1R)-1-hydroxyethyl)-1-methylcarbapen-2-em-3-carboxylate, and the mixture is stirred in an argon atmosphere in a light-shielded state at room temperature for 3 days. The excess reagent is removed by evaporation under reduced pressure, and the residue is purified by column chromatography on Sephadex LH-20 (dichloromethane methanol=1:1) to give 66.6 mg of allyl(1R,5S,6S)-2-[(3S,5R)-1-allyloxycarbonyl-5-(6-methylimidazo[5,1-b]thiazolium-5-yl)methylpyrrolidin-3-yl]thio-6-((1R)-1-hydroxyethyl)-1-methylcarbapen-2-em-3-carboxylate iodide as a yellow brown powder.

NMR ($CD_3OD$) δ: 1.28 (3H, d, J=7.2 Hz), 1.29 (3H, J=6.2 Hz), 1.40 (1H, m), 1.95–2.15 (1H, m), 2.60–3.00 (1H, br.s), 3.40–3.95 (6H, m), 3.98–4.2 (3H, m), 4.35 (3H, br), 4.72–4.87 (total 4H, m+br), 5.13–5.47 (4H, m), 5.70–6.15 (2H, br), 7.62 (1H, br.s), 7.67 (1H, br.d), 8.10 (1H, br.d).

MS ($FAB^+$): 587 ($M^+$) (excluding $I^-$)

b) (1R,5S,6S)-6-((1R)-1-hydroxyethyl)-1-methyl-2-[(3S,5R)-5-(6-methylimidazo[5,1-b]thiazolium-5-yl)methylpyrrolidin-3-yl]thiocarbapen-2-em-3-carboxylic acid iodide Tetrakis(triphenylphosphine)palladium(0) (10.7 mg) is added to a solution of 66 mg of allyl(1R,5S,6S)-2-[(3S,5R)-1-allyloxycarbonyl-5-(6-methylimidazo[5,1-b]thiazolium-5-yl)methylpyrrolidin-3-yl]thio-6-((1R)-1-hydroxyethyl)-1-methylcarbapen-2-em-3-carboxylate iodide and 0.060 ml of N-methylaniline in 1.5 ml of dry DMF, and the mixture is stirred in an argon atmosphere at room temperature for 30 min. Distilled water (4 ml) is added thereto, and the mixture is washed with three times with a mixed solution composed of 3 ml of ethyl acetate and 1 ml of dichloromethane. The aqueous layer is filtered, followed by concentration under reduced pressure and freeze drying to give 54 mg of a light orange flocculent material. The light orange flocculent material is purified by column chromatography on Cosmosil 40C18-PREP (water:methanol=20:1) to give 6.7 mg of the title compound as a colorless flocculent material.

NMR (D$_2$O) δ (HOD=4.80 ppm): 1.20 (3H, d, J=6.9 Hz), 1.28 (3H, d, J=6.3 Hz), 1.80 (1H, m), 2.74 (1H, m), 3.34 (1H, m), 3.43–3.49 (2H, m), 3.67 (1H, m), 3.88 (2H, m), 4.03–4.15 (5H, m), 4.22 (2H, m), 7.60 (1H, d, J=4.2 Hz), 7.66 (1H, s), 8.04 (1H, d, J=4.2 Hz).

Example 12

(1R,5S,6S)-6-((1R)-1-Hydroxyethyl)-2-[(3S,5S)-5-[1-hydroxy-1-(imidazo[5,1-b]thiazol-5-yl)methyl] pyrrolidin-3-yl]thio-1-methylcarbapen-2-em-3-carboxylic acid (stereoisomer A)

a) Allyl(1R,5S,6S)-2-[(3S,5S)-1-allyloxycarbonyl-5-(hydroxymethyl)pyrrolidin-3-yl]thio-6-[(1R)-1-(t-butyldimethylsilyloxy)ethyl]-1-methylcarbapen-2-em-3-carboxylate A 2 N aqueous sodium hydroxide solution (6.3 ml) is added to a solution of 3.122 g of (3S,5S)-3-acetylthio-1-allyloxycarbonyl-5-(hydroxymethyl)pyrrolidine in 36 ml of methanol under ice cooling, and the mixture is stirred for 15 min. Semi-saturated saline (100 ml) and 2 N hydrochloric acid are added thereto to adjust the pH value to 7, and the mixture is extracted twice 150 ml of ethyl acetate, and the extract was dried over anhydrous magnesium sulfate, followed by filtration and the removal of the solvent by evaporation to give 2.820 g of a mercaptan compound as a bright yellow liquid. N,N-Diisopropylethylamine (2.3 ml) is added dropwise to a solution of this mercaptan and 6.137 g of allyl(1R,5R,6S)-6-[(1R)-1-(t-butyldimethylsilyloxy) ethyl]-2-(diphenylphosphono)oxy-1-methylcarbapen-2-em-3-carboxylate in 20 ml of dry acetonitrile under ice cooling in an argon atmosphere, and the mixture is stirred at 4 to 6C for 110 min. The mixture is diluted with 300 ml of ethyl acetate, and the diluted solution is washed with 100 ml of semi-saturated saline and dried over anhydrous magnesium sulfate, followed by filtration and the removal of the solvent by evaporation to give a yellow oil. The oil is successively purified by column chromatography on silica gel (n-hexane:ethyl acetate=1:1) and on Sephadex LH-20 (dichloromethane:methanol=1:1) to give 5.277 g of allyl (1R,5S,6S)-2-[(3S,5S)-1-allyloxycarbonyl-5-(hydroxymethyl)pyrrolidin-3-yl]thio-6-[(1R)-1-(t-butyldimethylsilyloxy)ethyl]-1-methylcarbapen-2-em-3-carboxylate as a colorless oil.

NMR (CDCl$_3$) δ: 0.08 (3H, s), 0.09 (3H, s), 0.89 (9H, s), 1.23–1.27 (6H, m), 1.80–2.10 (1H, m), 2.49 (1H, m), 3.20–3.45 (3H, m), 3.59 (1H, m), 3.73 (2H, br.s+m), 3.95–4.40 (5H, m), 4.62 (2H, m), 4.68 (1H, m), 4.78 (1H, m), 5.18–5.47 (4H, m), 5, 95 (2H, m).

MS (ESI): 581 (M$^+$+H)

b) Allyl(1R,5S,6S)-2-((3S,5S)-1-allyloxycarbonyl-5-formylpyrrolidin-3-yl)thio-6-[(1R)-1-(t-butyldimethylsilyloxy)ethyl]-1-methylcarbapen-2-em-3-carboxylate Tetrakis(n-propylammonium) perruthenate (VII) (45 mg) is added a solution of 871 mg of allyl(1R,5S,6S)-2-[(3S, 5S)-1-allyloxycarbonyl-5-(hydroxymethyl)pyrrolidin-3-yl] thio-6-[(1R)-1-(t-butyldimethylsilyloxy)ethyl]-1-methylcarbapen-2-em-3-carboxylate, 272 mg of N-methylmorpholine N-oxide, and 750 mg of 4A active molecular sieves (powder) in 3 ml of dry dichloromethane, and the mixture is stirred in an argon atmosphere at room temperature for 10 min. The reaction solution as such is purified by column chromatography on silica gel (n-hexane:ethyl acetate=1:1) to give 719 mg of allyl(1R,5S, 6S)-2-((3S,5S)-1-allyloxycarbonyl-5-formylpyrrolidin-3-yl)thio-6-[(1R)-1-(t-butyldimethylsilyloxy)ethyl]-1-methylcarbapen-2-em-3-carboxylate as a colorless viscous material.

NMR (CDCl$_3$) δ: 0.09 (6H, s), 0.89 (9H, s), 1.22–1.25 (6H, m), 2.10 (1H, m), 2.59 (1H, m), 3.13–3.26 (2H, m), 3.52 (1H, m), 3.91 (2H, m), 4.20–4.32 (3H, m), 4.60–4.83 (4H, m), 5.20 (4H, m), 5.82–6.02 (2H, m), 9.64 (1H, m).

MS (FAB$^+$): 579 (M$^+$+H)

c) Allyl(1R,5S,6S)-2-[(3S,5S)-1-allyloxycarbonyl-5-[1-hydroxy-1-(imidazo[5,1-b]thiazol-5-yl)methyl] pyrrolidin-3-yl]thio-6-[(1R)-1-(t-butyldimethylsilyloxy)ethyl]-1-methylcarbapen-2-em-3-carboxylate A solution of 214 mg of 5-bromoimidazo[5,1-b]thiazole in 4.2 ml of anhydrous THF is added dropwise to a solution, prepared by diluting 1.05 ml of a 1.0 M ethylmagnesium bromide/THF solution with 4.2 ml of anhydrous THF, under ice cooling in an argon atmosphere over a period of 5 min and the mixture is stirred in this state at 4 to 7° C. for 15 min. After the internal temperature is cooled to −3° C., the solution is added dropwise to a solution of 609 mg of allyl(1R,5S,6S)-2-((3S,5S)-1-allyloxycarbonyl-5-formylpyrrolidin-3-ylthio)-6-[(1R)-1-(t-butyldimethylsilyloxy)ethyl]-1-methylcarbapen-2-em-3-carboxylate in 4.2 ml of anhydrous THF over a period of 7 min. The mixture is stirred in this state at −3 to +5° C. for additional 53 min. An aqueous semi-saturated ammonium chloride solution (20 ml) is added thereto, the mixture is extracted twice with 40 ml of ethyl acetate, and the combined organic layers are dried over anhydrous magnesium sulfate, followed by filtration and the removal of the solvent by evaporation to give a yellow oil. This oil is successively purified by column chromatography on silica gel (n-hexane:ethyl acetate=1:1 to 1:2) and on Sephadex LH-20 (dichloromethane:methanol=1:1) to give 158 mg of a high polar component (stereoisomer A), as a yellow amorphous material, and 37 mg of a low polar component (stereoisomer B), as a yellow oil, of allyl(1R,5S,6S)-2-[(3S,5S)-1-allyloxycarbonyl-5-[1-hydroxy-1-(imidazo[5,1-b]thiazol-5-yl)methyl]pyrrolidin-3-yl]thio-6-[(1R)-1-(t-butyldimethylsilyloxy)ethyl]-1-methylcarbapen-2-em-3-carboxylate Stereoisomer A NMR (CDCl$_3$) δ: 0.08 (6H, s), 0.88 (9H, s), 1.20 (3H, d, J=7.2 Hz), 1.24 (3H, d, J=6.3 Hz), 1.91 (1H, m), 2.28 (1H, br.s), 3.17–3.35 (1+2H, dd+br, J1=5.9 Hz, J2=2.7 Hz), 3.56 (1H, m), 4.08 (1H, br.s), 4.17–4.27 (2H, m), 4.45–4.82 (5H, m+br), 5.13–5.47 (5H, m), 5.75 & 5.94 (total 3H, br.s+m), 6.80 (1H, d, J=4.1 Hz), 7.01 (1H, s), 7.74 (1H, br.s).

MS (FAB$^+$): 703 (M$^+$+H)

Stereoisomer B

NMR (CDCl$_3$) δ: 0.08 (6H, s), 0.89 (9H, s), 1.22–1.26 (6H, m), 1.60 (1H, br.s), 2, 42 (2H, br.s), 3.20 (1H, dd, J1=5.8 Hz, J2=2.6 Hz), 3.27 (2H, m), 3.52 (1H, m), 3.95–4.30 (3H, m), 4.40–4.82 (5H, m), 5.20–5.50 (5H, m), 5.80–6.02 (2H, m), 6.77 (1H, br.d), 6.99 (1H, s), 7.68 (1H, d, J=4.2 Hz).

MS (FAB$^+$): 703 (M$^+$+H)

d) Allyl(1R,5S,6S)-2-[(3S,5S)-1-allyloxycarbonyl-5-[1-hydroxy-1-(imidazo[5,1-b]thiazol-5-yl)methyl]pyrrolidin-3-yl]thio-6-((1R)-1-hydroxyethyl)-1-methylcarbapen-2-em-3-carboxylate (stereoisomer A)

Acetic acid (0.19 ml) and 1.1 ml of a 1 M tetra-n-butylammonium fluoride/THF are added to a solution of 155 mg of the high polar component (stereoisomer A) of allyl (1R,5S,6S)-2-[(3S,5S)-1-allyloxycarbonyl-5-[1-hydroxy-1-(imidazo[5,1-b]thiazol-5-yl)methyl]pyrrolidin-3-yl]thio-6-[(1R)-1-(t-butyldimethylsilyloxy)ethyl]-1-methylcarbapen-2-em-3-carboxylate in 3.3 ml of anhydrous THF, and the mixture is stirred in an argon atmosphere at room temperature for 39 hr. The reaction solution is diluted with 30 ml of ethyl acetate, and the diluted solution is washed with semi-saturated saline and dried over anhydrous magnesium sulfate, followed by filtration and the removal of the solvent by evaporation to give a slightly yellow oil. This oil is successively purified by column chromatography on silica gel (ethyl acetate:methanol=95:5) and on Sephadex LH-20 (dichloromethane:methanol=1:1) to give 117 mg of allyl (1R,5S,6S)-2-[(3S,5S)-1-allyloxycarbonyl-5-[1-hydroxy-1-(imidazo[5,1-b]thiazol- 5-yl)methyl]pyrrolidin-3-yl]thio-6-((1R)-1-hydroxyethyl)-1-methylcarbapen-2-em-3-carboxylate (stereoisomer A) as a yellow viscous material.

Stereoisomer A

NMR (CDCl$_3$) δ: 1.22 (3H, d, J=7.2 Hz), 1.35 (3H, d, J=6.3 Hz), 1.60–2.00 (3H, br+m), 2.28 (1H, br.s), 3.17–3.35 (1+2H, dd+br, J1=7.0 Hz, J2=2.6 Hz), 3.54 (1H, br.t), 4.08 (1H, br.s), 4.18–4.27 (2H, m), 4.45–4.72 (4H, m+br), 4.82 (1H, m), 5.15–5.48 (5H, m), 5.95 (2H, m), 6.80 (1H, d, J=4.2 Hz), 7.01 (1H, s), 7.73 (1H, br.s).

MS (TS): 589 (M$^+$+H)

e) (1R,5S,6S)-6-((1R)-1-Hydroxyethyl)-2-[(3S,5S)-5-[1-hydroxy-1-(imidazo[5,1-b]thiazol-5-yl)methyl]pyrrolidin-3-yl]thio-1-methylcarbapen-2-em-3-carboxylic acid (stereoisomer A)

Morpholine (0.026 ml) and 6.5 mg of tetrakis(triphenylphosphine)palladium(0) are added to a solution of 65.6 mg of allyl(1R,5S,6S)-2-[(3S,5S)-1-allyloxycarbonyl-5-[1-hydroxy-1-(imidazo[5,1-b]thiazol-5-yl)methyl]pyrrolidin-3-yl]thio-6-((1R)-1-hydroxyethyl)-1-methylcarbapen-2-em-3-carboxylate (stereoisomer A) and 12 mg of triphenylphosphine in a mixture of 0.55 ml of anhydrous THF with 0.55 ml of dry methanol, and the mixture is stirred in an argon atmosphere at room temperature for 30 min. Ethyl acetate (5 ml) and 1 ml of dichloromethane are added thereof, and the resultant precipitate is further washed with 5 ml of ethyl acetate and 1 ml of dichloromethane, followed by drying in vacuo to give 48.4 mg of a colorless powder. The colorless powder is successively purified by column chromatography on Cosmosil 40C18-PREP (water:methanol=5:1 to 3:1) and on Cosmosil 5C18-MS (water:methanol=3:1) to give 3.3 mg of the title compound as a colorless flocculent material.

Stereoisomer A

NMR (D$_2$O) δ (HOD=4.80 ppm): 1.19 (3H, d, J=7.1 Hz), 1.28 (3H, d, J=6.3 Hz), 1.70 (1H, m), 2.59 (1H, m), 3.37 (1H, br.t), 3.44–3.50 (2H, m), 3.73 (1H, m), 4.05 (1H, m), 4.20–4.40 (3H, m), 5.34 (1H, d, J=8.3 Hz), 7.09 (1H, s), 7.17 (1H, d, J=4.1 Hz), 7.84 (1H, d, J=4.1 Hz).

Example 13

(1R,5S,6S)-6-((1R)-1-hydroxyethyl)-2-[(3S,5S)-5-[1-hydroxy-1-(6-methylimidazo[5,1-b]thiazolium-5-yl)methyl]pyrrolidin-3-yl]thio-1-methyl-carbapen-2-em-3-carboxylic acid iodide (stereoisomer A)

a) Allyl(1R,5S,6S)-2-[(3S,5S)-1-allyloxycarbonyl-5-[1-hydroxy-1-(6-methylimidazo[5,1-b]thiazolium-5-yl)methyl]pyrrolidin-3-yl]thio-6-((1R)-1-hydroxyethyl)-1-methylcarbapen-2-em-3-carboxylate iodide (stereoisomer A)

Iodomethane (0.76 g) is added to 62.8 mg of allyl(1R,5S,6S)-2-[(3S,5S)-1-allyloxycarbonyl-5-[1-hydroxy-1-(imidazo[5,1-b]thiazol-5-yl)methyl]pyrrolidin-3-yl]thio-6-((1R)-1-hydroxyethyl)-1-methylcarbapen-2-em-3-carboxylate (stereoisomer A) described in Example 12-d), and the mixture is stirred in an argon atmosphere in a light-shielded state at room temperature for 19.5 hr. The excess reagent is removed by evaporation under reduced pressure, and the residue is purified by column chromatography on Sephadex LH-20 (dichloromethane:methanol=1:1) to give 65 mg of allyl(1R,5S,6S)-2-[(3S,5S)-1-allyloxycarbonyl-5-[1-hydroxy-1-(6-methylimidazo[5,1-b]thiazolium-5-yl)methyl]pyrrolidin-3-yl]thio-6-((1R)-1-hydroxyethyl)-1-methylcarbapen-2-em-3-carboxylate iodide (sterecisomer A) as a milky white, glass-like solid.

NMR (CD$_3$COCD$_3$) δ: 1.20–1.24 (6H, m), 1.77–2.31 (total 2H, m), 2.70–3.95 (8H, m+br+dd, J1=7.0 Hz, J2=2.5 Hz), 4.00–4.30 (6H, m+s), 4.40–4.80 (3H, m+br), 5.05–5.30 (3H, m), 5.40–5.50 (1H, m), 5.55–5.80 (1H, br), 5.95 & 6.30 (total 2H, m+br.s), 7.59 (1H, br.s), 7.85 (1H, br.s), 8.14 (br.d, J=4.2 Hz).

MS (TS): 603 (M$^+$) (excluding I$^-$)

b) (1R,5S,6S)-6-((1R)-1-Hydroxyethyl)-2-[(3S,5S)-5-[1-hydroxy-1-(6-methylimidazo[5,1-b]thiazolium-5-yl)methyl]pyrrolidin-3-yl]thio-1-methyl-carbapen-2-em-3-carboxylic acid iodide (stereoisomer A)

Morpholine (0.018 ml) and 4.5 mg of tetrakis(triphenylphosphine)palladium(0) are successively added to a solution of 56 mg of allyl(1R,5S,6S)-1-allyloxycarbonyl-5-[1-hydroxy-1-(6-methylimidazo[5,1-b]thiazolium-5-yl)methyl]pyrrolidin-3-yl]thio-6-((1R)-1-hydroxyethyl)-1-methylcarbapen-2-em-3-carboxylate iodide (stereoisomer A) and 8 mg of triphenylphosphine in a mixture of 0.38 ml of anhydrous THF and 0.38 ml of dry methanol, and the mixture is stirred in an argon atmosphere at room temperature for 30 min. Ethyl acetate (5 ml) and 1 ml of dichloromethane are added thereto, and the resultant precipitate is washed with 5 ml of ethyl acetate and 1 ml of dichloromethane, followed by drying in vacuo to give 53.5 mg of a colorless powder. This powder is purified by column chromatography on Cosmosil 40C18-PREP (water:methanol=20:1) to give 1.9 mg of the title compound as a colorless flocculent material.

NMR (D$_2$O) δ (HOD=4.80 ppm): 1.20 (3H, d, J=7.4 Hz), 1.28 (3H, d, J=6.4 Hz), 1.79 (1H, m), 2.62 (1H, m), 3.37 (1H, m), 3.48 (1H, dd, J1=6.4 Hz, J2=2.8 Hz), 3.55 (1H, dd, J1=12.6 Hz, J2=3.2 Hz), 3.75 (1H, dd, J1=12.6 Hz, J2=6.5 Hz), 4.11 (1H, m), 4.17 (3H, s), 4.25 (2H, m), 4.36 (1H, dd), 5.80 (1H, d, J=8.8H), 7.64 (1H, d, J=4.3 Hz), 7.73 (1H, s), 8.21 (1H, d, J=4.3 Hz).

Example 14

(1R,5S,6S)-6-((1R)-1-Hydroxyethyl)-2-[(3S,5S)-5-[1-hydroxy-1-(imidazo[5,1-b]thiazol-7-yl)methyl]pyrrolidin-3-yl]thio-1-methylcarbapen-2-em- 3-carboxylic acid a) Allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-[(1R)-1-(t-butyldimethylsilyloxy)ethyl]-1-methylcarbapen-2-em-3-carboxylate (diastereomer mixture)

A 2 M methylmagnesium iodide/diethyl ether solution (1.30 ml) is diluted with 10 ml of anhydrous THF, and a solution of 650 mg of 7-iodoimidazo[5,1-b]thiazole in 10 ml of anhydrous THF is added dropwise to the diluted solution in an argon atmosphere over a period of 4 min. The mixture is stirred in this state at room temperature for additional 30 min. The internal temperature is lowered to −48° C., and the solution is added dropwise to a solution of 1.003 g of allyl(1R,5S,6S)-2-((3S,5S)-1-allyloxycarbonyl-5-formylpyrrolidin-3-yl)thio-6-[(1R)-1-(t-butyldimethylsilyloxy)ethyl]-1-methylcarbapen-2-em-3-carboxylate in 10 ml of anhydrous THF over a period of 5 min. The mixture is stirred in this state at −48 to −40° C. for 40 min, and the temperature is then raised to −25° C. over a period of 50 min. Semi-saturated aqueous ammonium chloride (50 ml) is added thereto, the mixture is extracted with 90 ml of ethyl acetate, and the organic layer is dried over anhydrous magnesium sulfate, followed by filtration and the removal of the solvent by evaporation to give a yellow viscous material. This viscous material is successively purified by column chromatography on Sephadex LH-20 (dichloromethane:methanol=1:1) and on silica gel (toluene:ethyl acetate=1:9) to give 491.3 mg of allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-[(1R)-1-(t-butyldimethylsilyloxy)ethyl]-1-methylcarbapen-2-em-3-carboxylate (a diastereomer mixture) as a yellow amorphous material.

NMR (CDCl$_3$) (diastereomer mixture) δ: 0.08 (6H, s), 0.88 (9H, s), 1.20–1.25 (6H, m), 1.62 (1H, br.s), 1.95–3.00 (4H, br), 3.17–3.35 (1+1H, dd+m, J1=5.8 Hz, J2=2.4 Hz), 3.47 (1H, m), 3.90–4.53 (4H, m+br), 4.57–5.10 (4H, m+br), 5.18–5.46 (4H, m), 5.57 & 5.94 (total 2H, br.s+m), 6.82 (1H, d, J=4.1 Hz), 7.36 & 7.37 (total 1H, d each, J=4.1 Hz), 7.92 & 7.94 (total 1H, br.s each).

MS (FAB$^+$): 703 (M$^+$+H)

b) Allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-((1R)-1-hydroxyethyl)-1-methylcarbapen-2-em-3-carboxylate (diastereomer mixture)

Acetic acid (0.60 ml) and 3.5 ml of a 1 M tetra-n-butylammonium fluoride/THF solution are added to a solution of 491 mg of allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-[(1R)-1-(t-butyldimethylsilyloxy)ethyl]-1-methylcarbapen-2-em-3-carboxylate (a diastereomer mixture) in 10.5 ml of anhydrous THF, and the mixture is stirred in an argon atmosphere at room temperature for 16 hr. The reaction solution is diluted with 100 ml of ethyl acetate, and the diluted solution is successively washed with a 5% aqueous sodium hydrogencarbonate solution and saturated saline and dried over anhydrous magnesium sulfate, followed by filtration and the removal of the solvent by evaporation to give a dark yellow oil. This oil is purified by column chromatography on silica gel (ethyl acetate:methanol=95:5) to give 353 mg of allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-((1R)-1-hydroxyethyl)-1-methylcarbapen-2-em-3-carboxylate (a diastereomer mixture) as a light yellow amorphous material.

NMR (CDCl$_3$) (diastereomer mixture) δ: 1.22 (3H, d, J=7.2 Hz), 1.35 (3H, d, J=6.3 Hz), 1.85 (3H, br), 2.35 (1H, br), 2.95 (1H, br), 3.22 (1H, dd, J1=7.4 Hz, J2=2.2 Hz), 3.40 (2H, m), 3.90–4.30 (3H, m), 4.32–4.75 (4H, m), 4.81 (1H, m), 4.90–5.48 (5H, br+m), 5.60 & 5.95 (total 2H, br+m), 6.82 (1H, d, J=4.2 Hz), 7.37 & 7.38 (total 1H, d each, J=4.2 Hz), 7.93 & 7.95 (total 1H, br.s each).

MS (FAB$^+$): 589 (M$^+$+H)

c) (1R,5S,6S)-6-((1R)-1-Hydroxyethyl)-2-[(3S,5S)-5-[1-hydroxy-1-(imidazo[5,1-b]thiazol-7-yl)methyl]pyrrolidin-3-yl]thio-1-methylcarbapen-2-em-3-carboxylic acid (diastereomer mixture)

Aniline (0.15 ml) and 31.4 mg of tetrakis(triphenylphosphine)palladium(0) are successively added to a solution of 160 mg of allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-((1R)-1-hydroxyethyl)-1-methylcarbapen-2-em-3-carboxylate (a diastereomer mixture) in 2.7 ml of dry dichloromethane, and the mixture is stirred in an argon atmosphere at room temperature for 45 min. Ethyl acetate (20 ml) is added, and the resultant precipitate is further washed with 20 ml of ethyl acetate and dried in vacuo to give 126 mg of a milky white powder. This powder (46.8 mg) is dissolved in methanol-water, and the solution is then purified by column chromatography on Cosmosil 5C18-MS (water:methanol=5:1) to give 15.0 mg of the title compound as a milky white flocculent material.

NMR (D$_2$O) (diastereomer mixture) δ (HOD=4.80 ppm): 1.17 (3H, d, J=7.1 Hz), 1.27 (3H, d, J=6.5 Hz), 1.76 & 1.90 (0.5+0.5H, m each), 2.57 (1H, m), 3.27–3.46 (3H, m), 3.70 (1H, m), 4.00 (1H, m), 4.21 (3H, m), 5.12 (0.5H, d, J=8.0 Hz), 5.23 (0.5H, d, J=4.9 Hz), 7.08 (1H, d, J=4.2 Hz), 7.68 (1H, d, J=4.2 Hz), 8.17 & 8.18 (0.5+0.5H, s each).

MS (FAB$^+$): 465 (M$^+$+H)

Example 15

(1R,5S,6S)-6-((1R)-1-Hydroxyethyl)-2-[(3S,5S)-5-[1-hydroxy-1-(6-methylimidazo[5,1-b]thiazolium-7-yl)methyl]pyrrolidin-3-yl]thio-1-methyl-carbapen-2-em-3-carboxylic acid iodide (stereoisomer A) and ditto (stereoisomer B)

a) Allyl(1R,5S,6S)-2-[(3S,5S)-1-allyloxycarbonyl-5-[1-hydroxy-1-(6-methylimidazo[5,1-b]thiazolium-7-yl)methyl]pyrrolidin-3-yl]thio-6-((1R)-1-hydroxyethyl)-1-methylcarbapen-2-em-3-carboxylate iodide (diastereomer mixture)

Iodomethane (2.13 g) is added to 177 mg of allyl(1R,5S,6S)-2-[(3S,5S)-1-allyloxycarbonyl-5-[1-hydroxy-1-(imidazo[5,1-b]thiazol-7-yl)methyl]pyrrolidin-3-yl]thio-6-((1R)-1-hydroxyethyl)-1-methylcarbapen-2-em-3-carboxylate prepared in Example 14-b), and the mixture is stirred in an argon atmosphere in a light-shielded state at room temperature for 12 hr. The excess reagent is removed by evaporation under reduced pressure. The residue is purified by column chromatography on Sephadex LH-20 (dichloromethane:methanol=1:1) to give 206 mg of allyl (1R,5S,6S)-2-[(3S,5S)-1-allyloxycarbonyl-5-[1-hydroxy-1-(6-methylimidazo[5,1-b]thiazolium-7-yl)methyl]pyrrolidin-3-yl]thio-6-((1R)-1-hydroxyethyl)-1-methylcarbapen-2-em-3-carboxylate iodide (a diastereomer mixture) as a light yellow amorphous material.

NMR (CD$_3$COCD$_3$) (diastereomer mixture) δ: 1.21–1.28 (6H, m), 1.42 (1H, m), 1.88 & 2.10 (0.5+0.5H, m each), 2,27 & 2.50 (0.5+0.5H, m each), 2.87 (1H, br shoulder), 3.15–3.35 (2H, m), 3.48–3.70 (1H, m), 3.90 (1H, br.t), 4.14 & 4.28 (total 3H, s each), 4.10–4.87 (7H, m+br), 5.10–5.35 (3H, m), 5.43–5.53 (1H, m), 5.63–6.07 (4H, br.s+m), 7.70 (0.5H, d, J=4.2 Hz), 7.76 (0.5H, d, J=4.2 Hz), 8.26 (0.5H, d, J=4.2 Hz), 8.32 (0.5H, d, J=4.2 Hz), 9.68 (0.5H, br.s), 9.77 (0.5H, br.s).

MS (FAB$^+$): 603 (M$^+$) (excluding I$^-$)

b) (1R,5S,6S)-6-((1R)-1-Hydroxyethyl)-2-[(3S,5S)-5-[1-hydroxy-1-(6-methylimidazo[5,1-b]thiazolium-7-yl)methyl]pyrrolidin-3-yl]thio-1-methyl-carbapen-2-em-3-carboxylic acid iodide (stereoisomer A) and ditto (stereoisomer B)

Aniline (0.15 ml) and 31.6 mg of tetrakis(triphenylphosphine)palladium(0) are successively added to a solution of 200 mg of allyl(1R,5S,6S)-2-[(3S,5S)-1-allyloxycarbonyl-5-[1-hydroxy-1-(6-methylimidazo[5,1-b]thiazolium-7-yl)methyl]pyrrolidin-3-yl]thio-6-((1R)-1-hydroxyethyl)-1-methylcarbapen-2-em-3-carboxylate iodide in a mixture of 2.7 ml of dry dichloromethane with 0.3 ml of dry ethanol, and the mixture is stirred in an argon atmosphere at room temperature for 60 min. Ethyl acetate (30 ml) is added, and the resultant precipitate is further washed with 30 ml of ethyl acetate and dried in vacuo to give 151 mg of a milky white powder. This powder (21.1 mg) is dissolved in methanol-water, and the solution is then purified by column chromatography on Cosmosil 5C18-MS (water:methanol=5:1) to give 3.6 mg of the title compound (1R,5S,6S)-6-((1R)-1-hydroxyethyl)-2-[(3S,5S)-5-[1-hydroxy-1-(6-methylimidazo[5,1-b]thiazolium-7-yl)methyl]pyrrolidin-3-yl]thio-1-methyl-carbapen-2-em-3-carboxylic acid iodide (stereoisomer A: high polar component) as a colorless flocculent material and 2.8 mg of the title compound (stereoisomer B: low polar component) as a milky white flocculent mate.

Stereoisomer A: High Polar Component

NMR (D$_2$O) δ (HOD=4.80 ppm): 1.19 (3H, d, J=7.4 Hz), 1.28 (3H, d, J=6.4 Hz), 1.75 (1H, m), 2.68 (1H, m), 3.31–3.48 (3H, m), 3.64 (1H, m), 4.03 (1H, br.s), 4.12 (3H, s), 4.10–4.27 (3H, m), 5.38 (1H, d, J=7.5 Hz), 7.56 (1H, d, J=4.2 Hz), 7.95 (1H, d, J=4.2 Hz), 9.31 (1H, br.s, gradually exchanged with D$_2$O).

Stereoisomer B: Low Polar Component

NMR (D$_2$O) δ (HOD=4.80 ppm): 1.19 (3H, d, J=7.2 Hz), 1.28 (3H, d, J=6.5 Hz), 2.06 (1H, m), 2.44 (1H, m), 3.36 (2H, m), 3.44 (1H, dd), 3.71 (1H, m), 3.94 (1H, m), 4.06 (3H, s), 4.13–4.27 (3H, m), 5.53 (1H, d, J=3.5 Hz), 7.55 (1H, d, J=4.3 Hz), 7.93 (1H, d, J=4.3 Hz), 9.27 (1H, br.s, gradually exchanged with D$_2$O).

Example 16

(1R,5S,6S)-6-((1R)-1-Hydroxyethyl)-2-[(3S,5S)-5-[1-hydroxy-1-(imidazo[5,1-b]thiazol-2-yl)methyl]pyrrolidin-3-yl]thio-1-methylcarbapen-2-em-3-carboxylic acid (stereoisomer A)

a) Allyl(1R,5S,6S)-2-[(3S,5S)-1-allyloxycarbonyl-5-[1-hydroxy-1-(imidazo[5,1-b]thiazol-2-yl)methyl]pyrrolidin-3-yl]thio-6-((1R)-1-hydroxyethyl)-1-methylcarbapen-2-em-3-carboxylate (stereoisomers A and B)

A 1 N aqueous sodium hydroxide solution (0.55 ml) is added to a solution of 191 mg of (3S,5S)-3-acetylthio-1-allyloxycarbonyl-5-[1-hydroxy-1-(imidazo[5,1-b]thiazol-2-yl)methyl]pyrrolidine (a diastereomer mixture) described in Synthesis Example 7 in 4 ml of methanol under ice cooling, and the mixture is stirred for 15 min. The mixture is adjusted to pH 7 by addition of 1 N hydrochloric acid, and methanol is removed by evaporation under reduced pressure. Semi-saturated saline (10 ml) is added to the residue, and the mixture is extracted three times with 10 ml of dichloromethane, followed by drying over anhydrous magnesium sulfate, filtration and the removal of the solvent by evaporation to give 159 mg of a mercaptan compound as a brown viscous material. N,N-Diisopropylethylamine (0.12 ml) is added dropwise to a solution of a mixture of this mercaptan and 263 mg of allyl (1R,5R,6S)-2-(diphenylphosphono)oxy-6-((1R)-1-hydroxyethyl)-1-methylcarbapen-2-em-3-carboxylate in 1.5 ml of dry acetonitrile under ice cooling in an argon atmosphere, and the mixture is stirred in this state for one hr. Water (10 ml) is added thereto, and the mixture is extracted three times with 5 ml of dichloromethane and washed with saturated saline, and the organic layer is dried over anhydrous magnesium sulfate, followed by filtration and the removal of the solvent by evaporation to give a brown oil. This oil is then purified four times by column chromatography on silica gel (ethyl acetate:methanol=95:5) to give 94.6 mg of allyl(1R,5S,6S)-2-[(3S,5S)-1-allyloxycarbonyl-5-[1-hydroxy-1-(imidazo[5,1-b]thiazol-2-yl)methyl]pyrrolidin-3-yl]thio-6-((1R)-1-hydroxyethyl)-1-methylcarbapen-2-em-3-carboxylate (a high polar component; stereoisomer A) and 59.7 mg of allyl(1R,5S,6S)-2-[(3S,5S)-1-allyloxycarbonyl-5-[1-hydroxy-1-(imidazo[5,1-b]thiazo1-2-yl)methyl]pyrrolidin-3-yl]thio-6-((1R)-1-hydroxyethyl)-1-methylcarbapen-2-em-3-carboxylate (a low polar component; stereoisomer B) both as a colorless amorphous material.

Stereoisomer A

NMR (CDCl$_3$) δ: 1.20 (3H, d, J=7.1 Hz), 1.28 (3H, d, J=6.1 Hz), 1.62–1.73 (1H, m), 2.30–2.43 (1H, m), 3.10–3.31 (3H, m), 3.40–3.52 (1H, m), 3.95–4.28 (5H, m), 4.50–4.80 (4H, m), 5.12–5.42 (5H, m), 5.83–5.96 (2H, m), 6.97 (1H, s), 7.33 (1H, s), 7.90 (1H, s).

MS (FAB$^+$): 589 (M$^+$+H)

Stereoisomer B

NMR (CDCl$_3$) δ: 1.20 (3H, d, J=7.2 Hz), 1.29 (3H, d, J=6.2 Hz), 1.64–1.75 (1H, m), 2.30–2.41 (1H, m), 3.16–3.31 (3H, m), 3.48–3.59 (1H, m), 3.98–4.24 (5H, m), 4.57–4.80 (4H, m), 4.96–5.01 (1H, m), 5.19–5.40 (4H, m), 5.81–5.97 (2H, m), 6.99 (1H, s), 7.38 (1H, s), 7.89 (1H, s).

MS (FAB$^+$): 589 (M$^+$+H)

b) (1R,5S,6S)-6-((1R)-1-Hydroxyethyl)-2-[(3S,5S)-5-[1-hydroxy-1-(imidazo[5,1-b]thiazol-2-yl)methyl]pyrrolidin- 3-yl]thio-1-methylcarbapen-2-em-3-carboxylic acid (stereoisomer A)

Tetrakis(triphenylphosphine)palladium(0) (8.4 mg) is added to a solution of 40.6 mg of allyl(1R,5S,6S)-2-[(3S,5S)-1-allyloxycarbonyl-5-[1-hydroxy-1-(imidazo[5,1-b]thiazol-2-yl)methyl]pyrrolidin-3-yl]thio-6-((1R)-1-hydroxyethyl)-1-methylcarbapen-2-em-3-carboxylate (stereoisomer A) and 0.045 ml of N-methylaniline in 1.0 ml of DMF, and the mixture is stirred in an argon atmosphere at room temperature for 35 min. DMF is removed by evaporation under reduced pressure, 3 ml of distilled water is added to the residue, and the mixture is extracted three times with 5 ml of ethyl acetate while removing insolubles. The aqueous layer is concentrated under reduced pressure to distil-off ethyl acetate, and the concentrate is then purified by column chromatography on Cosmosil 40C18-PREP (water-methanol) to give 3.5 mg of the title compound as a colorless flocculent material.

NMR (D$_2$O) δ (HOD=4.80 ppm): 1.21 (3H, d, J=7.1 Hz), 1.28 (3H, d, J=6.3 Hz), 1.96–2.06 (1H, m), 2.65–2.74 (1H, m), 3.31–3.48 (3H, m), 3.62–3.70 (1H, m), 3.97–4.05 (2H, m), 4.19–4.28 (2H, m), 5.23 (1H, d, J=6.6 Hz), 7.09 (1H, s), 7.83 (1H, s), 8.20 (1H, s).

Example 17

(1R,5S,6S)-6-((1R)-1-Hydroxyethyl)-2-[(3S,5S)-5-[1-hydroxy-1-(imidazo[5,1-b]thiazol-2-yl)methyl]pyrrolidin-3-yl]thio-1-methylcarbapen-2-em-3-carboxylic acid (stereoisomer B)

Tetrakis(triphenylphosphine)palladium(0) (30.7 mg) is added to a solution of 51.6 mg of allyl(1R,5S,6S)-2-[(3S,5S)-1-allyloxycarbonyl-5-[1-hydroxy-1-(imidazo[5,1-b]thiazol-2-yl)methyl]pyrrolidin-3-yl]thio-6-((1R)-1-hydroxyethyl)-1-methylcarbapen-2-em-3-carboxylate (stereoisomer B) described in Example 16-a) and 0.057 ml of N-methylaniline in a mixture of 2.0 ml of dry dichloromethane and 0.5 ml of DMF, and the mixture is stirred in an argon atmosphere at room temperature for 1.5 hr. Ethyl acetate (10 ml) is added thereto, and the resultant precipitate is further washed twice with 5 ml of ethyl acetate and dried in vacuo to give a yellow powder. This powder is then purified by column chromatography on Cosmosil 40C18-PREP (water-methanol) to give 0.83 mg of the title compound as a colorless flocculent material.

NMR (D$_2$O) δ (HOD=4.80 ppm): 1.18 (3H, d, J=7.4 Hz), 1.27 (3H, d, J=6.2 Hz), 1.61–1.73 (1H, m), 2.48–2.57 (1H, m), 3.33–3.43 (3H, m), 3.45–4.02 (1H, m), 3.75–3.93 (2H, m), 4.17–4.25 (2H, m), 5.04 (1H, d, J=9.0 Hz), 7.01 (1H, s), 7.82 (1H, s), 8.15 (1H, s).

Example 18

(1R,5S,6S)-6-((1R)-1-Hydroxyethyl)-2-[(3S,5S)-5-[1-hydroxy-1-(6-methylimidazo[5,1-b]thiazolium-2-yl)methyl]pyrrolidin-3-yl]thio-1-methylcarbapen-2-em-3-carboxylic acid iodide (stereoisomer A)

a) Allyl(1R,5S,6S)-6-((1R)-1-hydroxyethyl)-2-[(3S,5S)-1-allyloxycarbonyl-5-[1-hydroxy-1-(6-methylimidazo[5,1-b]thiazolium-2-yl)methyl]pyrrolidin-3-yl]thio-1-methylcarbapen-2-em-3-carboxylate iodide (stereoisomer A)

Iodomethane (0.6 ml) is added to 54.0 mg of allyl (1R,5S,6S)-2-[(3S,5S)-1-allyloxycarbonyl-5-[1-hydroxy-1-(imidazo[5,1-b]thiazol-2-yl)methyl]pyrrolidin-3-yl]thio-6-((1R)-1-hydroxyethyl)-1-methylcarbapen-2-em-3-carboxylate (stereoisomer A) described in Example 16-a), and the mixture is stirred in an argon atmosphere in a light-shielded state at room temperature for 5 hr. The excess reagent is removed by evaporation under reduced pressure to give 68.9 mg of allyl(1R,5S,6S)-6-((1R)-1-hydroxyethyl)-2-[(3S,5S)-1-allyloxycarbonyl-5-[1-hydroxy-1-(6-methylimidazo[5,1-b]thiazolium-2-yl)methyl]pyrrolidin-3-yl]thio- 1-methylcarbapen-2-em-3-carboxylate iodide (stereoisomer A) as a slightly yellow amorphous material.

NMR (CD$_3$OD) δ: 1.23 (3H, d, J=7.2 Hz), 1.28 (3H, d, J=6.3 Hz), 2.02–2.15 (1H, m), 2.35–2.46 (1H, m), 3.18–3.31 (4H, m), 3.53–3.60 (1H, m), 3.77–3.98 (1H, m), 4.10–4.33 (2H, m), 4.13 (3H, s), 4.57–4.75 (5H, m), 5.21–5.50 (5H, m), 5.90–6.01 (2H, m), 7.74 (1H, s), 8.03 (1H, s), 9.33 (1H, s).

MS (FAB$^+$): 603 (M$^+$)

b) (1R,5S,6S)-6-((1R)-1-Hydroxyethyl)-2-[(3S,5S)-5-[1-hydroxy-1-(6-methylimidazo[5,1-b]thiazolium-2-yl)methyl]pyrrolidin-3-yl]thio-1-methylcarbapen-2-em-3-carboxylic acid iodide (stereoisomer A)

Tetrakis(triphenylphosphine)palladium(0) (21.9 mg) is added to a solution of 68.9 mg of allyl(1R,5S,6S)-2-[(3S,5S)-1-allyloxycarbonyl-5-[1-hydroxy-1-(6-methylimidazo[5,1-b]thiazolium-2-yl)methyl]pyrrolidin-3-yl]thio-6-((1R)-1-hydroxyethyl)-1-methylcarbapen-2-em-3-carboxylate iodide (stereoisomer A) and 0.061 ml of N-methylaniline in 1.5 ml of DMF, and the mixture is stirred in an argon atmosphere at room temperature for 40 min. DMF is removed by evaporation under reduced pressure, 5 ml of distilled water is added to the residue, and the mixture is washed three times with 5 ml of ethyl acetate. The aqueous layer is concentrated under reduced pressure, and the concentrate is then purified by column chromatography on Cosmosil 40C18-PREP (water-methanol) to give 11.9 mg of the title compound as a white powder.

NMR (D$_2$O) δ (HOD=4.80 ppm): 1.20 (3H, d, J=7.2 Hz), 1.28 (3H, d, J=6.5 Hz), 2.01–2.11 (1H, m), 2.58–2.68 (1H, m), 3.35–3.48 (3H, m), 3.74–3.81 (1H, m), 3.99–4.10 (2H, m), 4.08 (1H, s), 4.15–4.28 (2H, m), 5.48 (1H, d, J=4.8 Hz), 7.62 (1H, s), 8.05 (1H, s), 9.20 (1H, s).

Example 19

(1R,5S,6S)-6-((1R)-1-Hydroxyethyl)-2-[(3S,5S)-5-[1-hydroxy- 1-(6-methylimidazo[5,1-b]thiazolium-2-yl)methyl]pyrrolidin-3-yl]thio-1-methylcarbapen-2-em-3-carboxylic acid iodide (stereoisomer B)

a) Allyl(1R,5S,6S)-2-[(3S,5S)-1-allyloxycarbonyl-5-[1-hydroxy-1-(6-methylimidazo[5,1-b]thiazolium-2-yl)methyl]pyrrolidin-3-yl]thio-6-((1R)-1-hydroxyethyl)-1-methylcarbapen-2-em-3-carboxylate iodide (stereoisomer B)

Iodomethane (0.65 ml) is added to 57.9 mg of allyl(1R,5S,6S)-2-[(3S,5S)-1-allyloxycarbonyl-5-[1-hydroxy-1-(imidazo[5,1-b]thiazol-2-yl)methyl]pyrrolidin-3-yl]thio-6-((1R)-1-hydroxyethyl)-1-methylcarbapen-2-em-3-carboxylate (stereoisomer B) described in Example 16-a), and the mixture is stirred in an argon atmosphere in a light-shielded state at room temperature for 8 hr. The excess reagent is removed by evaporation under reduced pressure, and the residue is then purified by column chromatography on Sephadex LH-20 (dichloromethane:methanol=1:1) to give 51.9 mg of allyl(1R,5S,6S)-2-[(3S,5S)-1-allyoxycarbonyl-5-[1-hydroxy-1-(6-methylimidazo[5,1-b]thiazolium-2-yl)methyl]pyrrolidin-3-yl]thio-6-((1R)-1-hydroxyethyl)-1-methylcarbapen-2-em-3-carboxylate iodide (stereoisomer B) as a slightly yellow amorphous material.

NMR (CD$_3$OD) δ: 1.21 (3H, d, J=7.1 Hz), 1.27 (3H, d, J=6.3 Hz), 1.88–1.98 (1H, m), 2.65–2.74 (1H, m), 3.22–3.35 (4H, m), 3.45–3.53 (1H, m), 3.79–3.87 (1H, m), 4.08–4.23 (2H, m), 4.13 (3H, s), 4.58–4.72 (5H, m), 5.20–5.50 (5H, m), 5.89–6.05 (2H, m), 7.72 (1H, s), 7.93 (1H, s), 9.33 (1H, s).

MS (FAB$^+$): 603 (M$^+$)

b) (1R,5S,6S)-6-((1R)-1-Hydroxyethyl)-2-[(3S,5S)-5-[1-hydroxy-1-(6-methylimidazo[5,1-b]thiazolium-2-yl)methyl]pyrrolidin-3-yl]thio-1-methylcarbapen-2-em-3-carboxylic acid iodide (stereoisomer B)

Tetrakis(triphenylphosphine)palladium(0) (8.2 mg) is added to a solution of 51.9 mg of allyl(1R,5S,6S)-2-[(3S, 5S)-1-allyloxycarbonyl-5-[1-hydroxy-1-(6-methylimidazo[5,1-b]thiazolium-2-yl)methyl]pyrrolidin-3-yl]thio-6-((1R)-1-hydroxyethyl)-1-methylcarbapen-2-em-3-carboxylate iodide (stereoisomer B) and 0.046 ml of N-methylaniline in 1.0 ml of DMF, and the mixture is stirred in an argon atmosphere at room temperature for 45 min. DMF is removed by evaporation under reduced pressure, 5 ml of distilled water is added thereto, and the mixture is washed three times with 5 ml of ethyl acetate. The aqueous layer is concentrated under reduced pressure, and the concentrate is successively purified by column chromatography on Cosmosil 40C18-PREP (water-methanol) and on Sephadex LH-20 (dichloromethane:methanol=1:1) to give 1.7 mg of the title compound as a white powder.

NMR ($D_2O$) δ (HOD=4.80 ppm): 1.20 (3H, d, J=6.9 Hz), 1.32 (3H, d, J=6.7 Hz), 1.82–1.90 (1H, m), 2.58–2.70 (1H, m), 3.33–3.49 (3H, m), 3.69–3.78 (1H, m), 4.06–4.21 (2H, m), 4.19 (3H, s), 4.22–4.27 (2H, m), 5.30 (1H, d, J=9.0 Hz), 7.63 (1H, s), 8.10 (1H, s), 9.20 (1H, s).

Example 20

(1R,5S,6S)-6-((1R)-1-Hydroxyethyl)-2-[(3S,5R)-5-(imidazo[5,1-b]thiazol-3-yl)methylpyrrolidin-3-yl]thio-1-methylcarbapen-2-em-3-carboxylic acid a) Allyl(1R,5S,6S)-2-[(3S,5R)-1-allyloxycarbonyl-5-(imidazo[5,1-b]thiazol-3-yl)methylpyrrolidin-3-yl]thio-6-[(1R)-1-(t-butyldimethylsilyloxy)ethyl]-1-methylcarbapen-2-em-3-carboxylate A 1 N aqueous sodium hydroxide solution (0.75 ml) is added to 249 mg of (3S,5R)-3-acetylthio-1-allyloxycarbonyl-5-(imidazo[5,1-b]thiazol-3-yl)methylpyrrolidine described in Synthesis Example 8 in 5 ml of methanol under ice cooling, and the mixture is stirred for 15 min. The mixture is adjusted to pH 7 by addition of 1 N hydrochloric acid, and methanol is removed by evaporation under reduced pressure. Semi-saturated saline (10 ml) is added to the residue, and the mixture is extracted three times with 10 ml of dichloromethane, followed by drying over anhydrous magnesium sulfate, filtration and the removal of the solvent by evaporation to give 215 mg of a mercaptan as a brown viscous material. N,N-Diisopropylethylamine (0.18 ml) is added dropwise to a solution of this mercaptan and 517 mg of allyl(1R,5R,6S)-6-[(1R)-1-(t-butyldimethysilyloxy)ethyl]-2-(diphenylphosphono)oxy-1-methylcarbapen-2-em-3-carboxylate in 3 ml of dry acetonitrile under ice cooling in an argon atmosphere, and the mixture is stirred in this state for 2 hr. Water (10 ml) is added thereto, and the mixture is extracted three times with 5 ml of dichloromethane and washed with saturated saline. The organic layer is dried over anhydrous magnesium sulfate and filtered, and the solvent is removed by evaporation to give a red viscous material. This viscous material is purified by column chromatography on silica gel (n-hexane:ethyl acetate=2:1) to give 332 mg of allyl(1R,5S,6S)-2-[(3S,5R)-1-allyloxycarbonyl-5-[1-(imidazo[5,1-b]thiazol-3-yl)methyl]pyrrolidin-3-yl]thio-6-[(1R)-1-(t-butyldimethylsilyloxy)ethyl]-1-methylcarbapen-2-em-3-carboxylate as a colorless amorphous material.

NMR ($CDCl_3$) δ: 0.02 (6H, s), 0.80 (9H, s), 1.12–1.20 (6H, m), 1.48–1.62 (1H, m), 1.66–1.80 (1H, m), 2.34–2.48 (1H, m), 2.85–3.00 (1H, m), 3.10–3.18 (2H, m), 3.27–3.41 (1H, m), 3.52–3.68 (1H, m), 3.85–4.30 (4H, m), 4.55–4.74 (4H, m), 5.17–5.40 (4H, m), 5.82–5.97 (2H, m), 6.45 (1H, br.s), 7.01 (1H, s), 7.94 (1H, s), 8.20 (1H, s).

MS (ES): ($M^++H$)

b) Allyl(1R,5S,6S)-2-[(3S,5R)-1-allyloxycarbonyl-5-(imidazo[5,1-b]thiazol-3-yl)methylpyrrolidin-3-yl]thio-6-((1R)-1-hydroxyethyl)-1-methylcarbapen-2-em-3-carboxylate Acetic acid (0.30 ml) and 1.7 ml of a 1 M tetra-n-butylammonium fluoride/THF solution are added to a solution of 239 mg of allyl(1R,5S,6S)-2-[(3S,5R)-1-allyloxycarbonyl-5-(imidazo[5,1-b]thiazol-3-yl)methylpyrrolidin-3-yl]thio-6-[(1R)-1-(t-butyldimethylsilyloxy)ethyl]-1-methylcarbapen-2-em-3-carboxylate anhydride in 5.2 ml of THF, and the mixture is stirred in an argon atmosphere at room temperature for 21 hr. The reaction solution is diluted with 50 ml of ethyl acetate, and 20 ml of water is added thereto. The mixture is extracted three times with ethyl acetate and washed out with 20 ml of saturated saline, followed by drying over anhydrous magnesium sulfate, filtration and the removal of the solvent by evaporation to give 87 mg of a crude product as an oil. This oil is purified by column chromatography on silica gel (ethyl acetate:methanol=95:5) to give 189 mg of allyl(1R,5S,6S)-2-[(3S,5R)-1-allyloxycarbonyl-5-(imidazo[5,1-b]thiazol-3-yl)methylpyrrolidin-3-yl]thio-6-((1R)-1-hydroxyethyl)-1-methylcarbapen-2-em-3-carboxylate as a colorless amorphous material.

NMR ($CDCl_3$) δ: 1.25 (3H, d, J 7.1 Hz), 1.36 (3H, d, J=6.3 Hz), 1.79–1.88 (1H, m), 2.45–2.58 (1H, m), 2.95–3.08 (1H, m), 3.25–3.49 (3H, m), 3.60–3.76 (1H, m), 3.95–4.40 (5H, m), 4.61–4.73 (3H, m), 4.81–4.88 (1H, m), 5.25–5.49 (4H, m), 5.90–6.04 (2H, m), 6.54 (1H, br.s), 7.10 (1H, s), 8.03 (1H, s), 8.31 (1H, s).

MS (ES): 573 ($M^++H$)

c) (1R,5S,6S)-6-((1R)-1-Hydroxyethyl)-2-[(3S,5R)-5-(imidazo[5,1-b]thiazol-3-yl)methylpyrrolidin-3-yl]thio-1-methylcarbapen-2-em-3-carboxylic acid Tetrakis(triphenylphosphine)palladium(0) (14.3 mg) is added to a solution of 71 mg of allyl(1R,5S,6S)-2-[(3S,5R)-1-allyloxycarbonyl-5-(imidazo[5,1-b]thiazol-3-yl)methylpyrrolidin-3-yl]thio-6-((1R)-1-hydroxyethyl)-1-methylcarbapen-2-em-3-carboxylate and 0.08 ml of N-methylaniline in 1.0 ml of dry dichloromethane, and the mixture is stirred in an argon atmosphere at room temperature for 40 min. Distilled water (3 ml) and 5 ml of ethyl acetate are added thereto to remove insolubles, followed by washing twice with 5 ml of ethyl acetate and concentration under reduced pressure. The concentrate is then freeze dried to give a colorless flocculent material. This material is then purified by column chromatography on Cosmosil 40C18-PREP (water:methanol) to give 6.12 mg of the title compound as a colorless flocculent material.

NMR ($D_2O$) δ (HOD=4.80 ppm): 1.21 (3H, d, J=7.4 Hz), 1.28 (3H, d, J=6.4 Hz), 1.80–1.90 (1H, m), 2.80–2.90 (1H, m), 3.33–3.47 (5H, m), 3.62–3.68 (1H, m), 4.01–4.26 (4H, m), 7.01 (1H, s), 7.13 (1H, s), 8.26 (1H, s).

Example 21

(1R,5S,6S)-6-((1R)-1-Hydroxyethyl)-1-methyl-2-[(3S,5R)-5-(6-methylimidazo[5,1-b]thiazolium-3-yl)methylpyrrolidin-3-yl]thiocarbapen-2-em-3-carboxylic acid iodide a) Allyl(1R,5S,6S)-2-[(3S,5R)-1-allyloxycarbonyl-5-(6-methylimidazo[5,1-b]thiazolium-3-yl)methylpyrrolidin-3-yl]thio-6-((1R)-1-hydroxyethyl)-1-methylcarbapen-2-em-3-carboxylate iodide Iodomethane (2.13 g) is added to 85.0 mg of allyl(1R,5S,6S)-2-[(3S,5R)-1-allyloxycarbonyl-5-(imidazo[5,1-b]

thiazol-3-yl)methylpyrrolidin-3-yl]thio-6-((1R)-1-hydroxyethyl)-1-methylcarbapen-2-em-3-carboxylate described in Example 20-b), and the mixture is stirred in an argon atmosphere in a light-shielded state at room temperature for 16 hr. The excess reagent is removed by evaporation under reduced pressure, and the residue is purified by column chromatography on Sephadex LH-20 (dichloromethane:methanol=1:1) to give 91.7 mg of allyl (1R,5S,6S)-2-[(3S,5R)-1-allyloxycarbonyl-5-(6-methylimidazo[5,1-b]thiazolium-3-yl)methylpyrrolidin-3-yl]thio-6-((1R)-1-hydroxyethyl)-1-methylcarbapen-2-em-3-carboxylate iodide as a slightly yellow solid.

NMR (CDCl$_3$) δ: 1.27 (3H, d, J=7.5 Hz), 1.36 (3H, d, J=6.4 Hz), 1.69–1.81 (1H, m), 2.89–2.99 (1H, m), 3.28–3.61 (3H, m), 3.71–3.88 (1H, m), 3.97–4.08 (1H, m), 4.24–4.38 (4H, m), 4.51–4.60 (1H, m), 4.65–4.88 (2H, m), 5.24–5.52 (6H, m), 5.87–6.07 (2H, m), 6.99 (1H, s), 7.59 (1H, s), 10.39 (1H, s).

MS (ES): 587 (M$^+$+H)

b) (1R,5S,6S)-6-((1R)-1-Hydroxyethyl)-1-methyl-2-[(3S,5R)-5-(6-methylimidazo[5,1-b]thiazolium-3-yl)methylpyrrolidin-3-yl]thiocarbapen-2-em-3-carboxylic acid iodide Tetrakis(triphenylphosphine)palladium(0) (14.3 mg) is added to a solution of 89.8 mg of allyl(1R,5S,6S)-2-[(3S,5R)-1-allyloxycarbonyl-5-(6-methylimidazo[5,1-b]thiazolium-3-yl)methylpyrrolidin-3-yl]thio-6-((1R)-1-hydroxyethyl)-1-methylcarbapen-2-em-3-carboxylate iodide and 0.084 ml of N-methylaniline in 1.0 ml of dry dichloromethane, and the mixture is stirred in an argon atmosphere at room temperature for 75 min. Distilled water (2 ml) is added thereto, and the mixture is washed three times with 5 ml of ethyl acetate. The aqueous layer is concentrated under reduced pressure, and the concentrate is then freeze dried to give a milky white flocculent material which is then purified by column chromatography on Cosmosil 40C18-PREP (water-methanol) to give 8.5 mg of the title compound as a slightly yellow powder.

NMR (D$_2$O) δ (HOD=4.80 ppm): 1.23 (3H, d, J=7.2 Hz), 1.28 (3H, d, J=6.4 Hz), 1.87–1.97 (1H, m), 2.86–2.97 (1H, m), 3.37–3.60 (5H, m), 3.73–3.80 (1H, m), 4.11 (3H, s), 4.20–4.32 (4H, m), 7.44 (1H, s), 7.67 (1H, s), 9.40 (1H, s).

Example 22

(1R,5S,6S)-6-((1R)-1-Hydroxyethyl)-2-[(3S,5R)-5-[6-(2-hydroxyethyl)imidazo[5,1-b]thiazolium-3-yl]methylpyrrolidin-3-yl]thio-1-methylcarbapen-2-em-3-carboxylic acid chloride 2-(t-Butyldimethylsilyloxy)ethyl trifluoromethanesulfonate (63.5 mg) is added to a solution of 98.3 mg of allyl(1R,5S,6S)-2-[(3S,5R)-1-allyloxycarbonyl-5-(imidazo[5,1-b]thiazol-3-yl)methylpyrrolidin-3-yl]thio-6-((1R)-1-hydroxyethyl)-1-methylcarbapen-2-em-3-carboxylate described in Example 20-b) in 1.0 ml of dry dichloroethane, and the mixture is stirred in an argon atmosphere at room temperature for 1.5 hr. The excess reagent is removed by evaporation under reduced pressure to give allyl(1R,5S,6S)-2-[(3S,5R)-1-allyloxycarbonyl-5-[6-(2-t-butyldimethylsilyloxyethyl)imidazo[5,1-b]thiazolium-3-yl]methylpyrrolidin-3-yl]thio-6-((1R)-1-hydroxyethyl)-1-methylcarbapen-2-em-3-carboxylate trifluoromethane sulfonate as a brown viscous material. Acetic acid (0.01 ml) and 0.18 ml of a 1 M tetra-n-butylammonium fluoride/THF solution are added to a solution of this compound in 1 ml of anhydrous THF, and the mixture is stirred in an argon atmosphere at room temperature for 1.5 hr. Dry ethanol (1 ml) is added thereto. Thereafter, 9.3 mg of triphenylphosphine, 0.038 ml of morpholine, and 11.3 mg of tetrakis(triphenylphosphine)palladium(0) are successively added to the mixture, and the mixture is then stirred in an argon atmosphere at room temperature for one hr. THF (10 ml) is added thereto, and the resultant precipitate is further washed twice with 5 ml of THF and dried in vacuo to give a yellow powder. The yellow powder is then purified by column chromatography on Cosmosil 40C18-PREP (water-methanol) and then passed through an anion exchange resin Amberlyst A-26 (Cl$^-$ form) to give 13.3 mg of the title compound as a colorless flocculent material.

NMR (D$_2$O) δ (HOD=4.80 ppm): 1.19 (3H, d, J=7.1 Hz), 1.27 (3H, d, J=6.3 Hz), 1.48–1.58 (1H, m), 2.59–2.69 (1H, m), 3.03–3.07 (1H, m), 3.22–3.42 (5H, m), 3.72 (1H, d, J=14.7 Hz), 3.84 (1H, br, m), 4.00 (2H, t, J=3.6 Hz), 4.18–4.26 (2H, m), 4.51 (2H, t, J=3.6 Hz), 7.31 (1H, s), 7.73 (1H, s).

Example 23

(1R,5S,6S)-6-((1R)-1-Hydroxyethyl)-2-[(3S,5S)-5-(imidazo[5,1-b]thiazol-2-yl)methylpyrrolidin-3-yl]thio-1-methylcarbapen-2-em-3-carboxylic acid a) Allyl(1R,5S,6S)-2-[(3S,5S)-1-allyloxycarbonyl-5-(imidazo[5,1-b]thiazol-2-yl)methylpyrrolidin-3-yl]thio-6-((1R)-1-hydroxyethyl)-1-methylcarbapen-2-em-3-carboxylate A 1 N aqueous sodium hydroxide solution (0.87 ml) is added to a solution of 289 mg of (3S,5S)-3-acetylthio-1-allyloxycarbonyl-5-(imidazo[5,1-b]thiazol-2-yl)methylpyrrolidine described in Synthesis Example 9 in 5 ml of methanol under ice cooling, and the mixture is stirred for 15 min. A 1 N aqueous sodium hydroxide solution (0.75 ml) is added thereto under ice cooling, and the mixture is stirred for 15 min. The mixture is adjusted to pH 7 by addition of 1 N hydrochloric acid, methanol is removed by evaporation under reduced pressure, 10 ml of semi-saturated saline is added thereto, and the mixture is extracted three times with 10 ml of dichloromethane, followed by drying over anhydrous magnesium sulfate, filtration and the removal of the solvent to give 244 mg of a mercaptan compound as a yellow oil. N,N-diisopropylethylamine (0.115 ml) is added dropwise to a solution of 143 mg of this mercaptan and 247 mg of allyl(1,R,5R,6S)-2-(diphenylphosphono)oxy-6-((1R)-1-hydroxyethyl)-1-methylcarbapen-2-em-3-carboxylate in 1.5 ml of dry acetonitrile, and the mixture is stirred for 2 hr under ice cooling in an argon atmosphere. Water (10 ml) is added thereto, the mixture is extracted three times with 10 ml of chloroform, and the combined organic layers are dried over anhydrous magnesium sulfate, followed by filtration and the removal of the solvent by evaporation to give 423 mg of a yellow oil. This oil is then purified by column chromatography on silica gel (ethyl acetate:methanol=95:5) to give 153.4 mg of allyl(1R,5S,6S)-2-[(3S,5S)-1-allyloxycarbonyl-5-(imidazo[5,1-b]thiazol-2-yl)methylpyrrolidin-3-yl]thio-6-((1R)-1-hydroxyethyl)-1-methylcarbapen-2-em-3-carboxylate as a colorless amorphous material.

NMR (CDCl$_3$) δ: 1.25 (3H, d, J=7.2 Hz), 1.36 (3H, d, J=6.3 Hz), 1.80–1.88 (1H, m), 2.45–2.56 (1H, m), 3.21–3.75 (5H, m), 3.60–3.68 (1H, m), 3.99–4.26 (4H, m), 4.62–4.72 (4H, m), 5.24–5.48 (4H, m), 5.90–6.15 (2H, m), 7.03 (1H, s), 7.27 (1H, s), 7.94 (1H, s).

MS (ES): 573 (M$^+$+H)

b) (1R,5S,6S)-6-((1R)-1-Hydroxyethyl)-2-[(3S,5S)-5-(imidazo[5,1-b]thiazol-2-yl)methylpyrrolidin-3-yl]thio-1-methylcarbapen-2-em-3-carboxylic acid Tetrakis(triphenylphosphine)palladium(0) (16.4 mg) is added to a solution of 81.1 mg of allyl(1R,5S,6S)-2-[(3S,5S)-1-allyloxycarbonyl-5-(imidazo[5,1-b]thiazol-2-yl)methylpyrrolidin-3-yl]thio-6-((1R)-1-hydroxyethyl)-1-methylcarbapen-2-em-3-carboxylate and 0.092 ml of N-methylaniline in 1.0 ml of dry dichloromethane, and the mixture is stirred in an argon atmosphere at room temperature for 45 min. Distilled water (3 ml) and 10 ml of ethyl acetate are added thereto remove insolubles. The aqueous layer is washed twice with 3 ml of ethyl acetate and concentrated under reduced pressure, and the concentrate is freeze dried to give a yellow flocculent material which is then purified by column chromatography on Cosmosil 40C18-PREP (water-methanol) to give 10.3 mg of the title compound as a colorless flocculent material.

NMR (D$_2$O) δ (HOD=4.80 ppm): 1.20 (3H, d, J=7.3 Hz), 1.28 (3H, d, J=6.4 Hz), 1.72–1.82 (1H, m), 2.74–2.83 (1H, m), 3.23–3.27 (2H, m), 3.33–3.39 (2H, m), 3.44–3.47 (1H, m), 3.59–3.65 (1H, m), 3.92–4.04 (2H, m), 4.20–4.28 (2H, m), 7.04 (1H, s), 7.68 (1H, s), 8.13 (1H, s).

Example 24

(1R,5S,6S)-6-((1R)-1-Hydroxyethyl)-1-methyl-2-[(3S,5S)-5-(6-methylimidazo[5,1-b]thiazolium-2-yl)methylpyrrolidin-3-yl]thiocarbapen-2-em-3-carboxylic acid iodide a) Allyl(1R,5S,6S)-2-[(3S,5S)-1-allyloxycarbonyl-5-(6-methylimidazo[5,1-b]thiazolium-2-yl)methylpyrrolidin-3-yl]thio-6-((1R)-1-hydroxyethyl)-1-methylcarbapen-2-em-3-carboxylate iodide Iodomethane (1.2 ml) is added to 113.3 mg of allyl(1R,5S,6S)-2-[(3S,5S)-1-allyloxycarbonyl-5-(imidazo[5,1-b]thiazol-2-yl)methylpyrrolidin-3-yl]thio-6-((1R)-1-hydroxyethyl)-1-methylcarbapen-2-em-3-carboxylate described in Example 23-a), and the mixture is stirred in an argon atmosphere in a light-shielded state at room temperature overnight. The excess reagent is removed by evaporation under reduced pressure, and the residue is purified by column chromatography on Sephadex LH-20 (dichloromethane:methanol=1:1) to give 84.6 mg of allyl(1R,5S,6S)-2-[(3S,5S)-1-allyloxycarbonyl-5-(6-methylimidazo[5,1-b]thiazolium-2-yl)methylpyrrolidin-3-yl]thio-6-((1R)-1-hydroxyethyl)-1-methylcarbapen-2-em-3-carboxylate iodide as a yellow viscous material.

NMR (CDCl$_3$) δ: 1.28 (3H, d, J=7.1 Hz), 1.39 (3H, d, J=6.1 Hz), 1.73–1.83 (1H, m), 2.62–2.72 (1H, m), 3.29–3.41 (6H, m), 4.24–4.35 (1H, m), 4.25 (3H, s), 4.65–4.85 (4H, m), 5.26–5.49 (6H, m), 5.90–6.02 (2H, m), 7.42 (1H, s), 8.41 (1H, s).

MS (ES): 587 (M$^+$)

b) (1R,5S,6S)-6-((1R)-1-Hydroxyethyl)-1-methyl-2-[(3S,5S)-5-(6-methylimidazo[5,1-b]thiazolium-2-yl)methylpyrrolidin-3-yl]thiocarbapen-2-em-3-carboxylic acid iodide Tetrakis(triphenylphosphine)palladium(0) (13.6 mg) is added to a solution of 84.6 mg of allyl(1R,5S,6S)-2-[(3S,5S)-1-allyloxycarbonyl-5-(6-methylimidazo[5,1-b]thiazolium-2-yl)methylpyrrolidin-3-yl]thio-6-((1R)-1-hydroxyethyl)-1-methylcarbapen-2-em-3-carboxylate iodide and 0.077 ml of N-methylaniline in 1.2 ml of anhydrous DMF, and the mixture is stirred in an argon atmosphere at room temperature for 40 min. DMF is removed by evaporation in vacuo, 5 ml of distilled water is added thereto, the mixture is washed three times with 5 ml of ethyl acetate and concentrated under reduced pressure, and the concentrate is freeze dried to give 74.7 mg of a yellow flocculent material. The yellow flocculent material is purified by column chromatography on Cosmosil 40C18-PREP (water-methanol) to give 21.2 mg of the title compound as a colorless flocculent material.

NMR (D$_2$O) δ (HOD=4.80 ppm): 1.21 (3H, d, J=7.2 Hz), 1.28 (3H, d, J=6.3 Hz), 1.81–1.91 (1H, m), 2.80–2.90 (1H, m), 3.38–3.50 (5H, m), 3.70–3.77 (1H, m), 4.05–4.11 (2H, m), 4.07 (3H, s), 4.21–4.26 (2H, m), 7.60 (1H, s), 7.95 (1H, s), 9.71 (1H, s).

Example 25

(1R,5S,6S)-6-((1R)-1-Hydroxyethyl)-2-[(3S,5S)-5-[6-(2-hydroxyethyl)imidazo[5,1-b]thiazolium-2-yl]methylpyrrolidin-3-yl]thio-1-methylcarbapen-2-em-3-carboxylic acid chloride 2-(t-Butyldimethylsilyloxy)ethyl trifluoromethanesulfonate (20.9 mg) is added to a solution of 32.3 mg of allyl(1R,5S,6S)-2-[(3S,5S)-1-allyloxycarbonyl-5-(imidazo[5,1-b]thiazol-2-yl)methylpyrrolidin-3-yl]thio-6-((1R)-1-hydroxyethyl)-1-methylcarbapen-2-em-3-carboxylate described in Example 23-a) in 0.5 ml of dry dichloroethane, and the mixture is stirred in an argon atmosphere at room temperature for 2 hr. The excess reagent is removed by evaporation under reduced pressure to give allyl(1R,5S,6S)-2-[(3S,5S)-1-allyloxycarbonyl-5-[6-(2-t-butyldimethylsilyloxyethyl)imidazo[5,1-b]thiazolium-2-yl]methylpyrrolidin-3-yl]thio-6-((1R)-1-hydroxyethyl)-1-methylcarbapen-2-em-3-carboxylate trifluoromethanesulfonate as a brown viscous material.

Acetic acid (0.0034 ml) and 0.057 ml of a 1 M tetra-n-butylammonium fluoride/THF solution are added to a solution of this compound in 0.5 ml of anhydrous THF, and the mixture is stirred in an argon atmosphere at room temperature for 2 hr. Dry ethanol (0. 5 ml) is added to this solution, and 5.9 mg of triphenylphosphine, 0.012 ml of morpholine, and 3.6 mg of tetrakis(triphenylphosphine)palladium(0) are successively added thereto, and the mixture is stirred in an argon atmosphere at room temperature for one hr. THF (10 ml) is added thereto, and the resultant precipitate is further washed twice with 3 ml of THF and dried in vacuo to prepare a yellow powder which is purified by column chromatography on Cosmosil 40C18-PREP (water-methanol) and then passed through an anion exchange resin Amberlyst A-26 (Cl$^-$ form) to give 4.4 mg of the title compound as a colorless flocculent material.

NMR (D$_2$O) δ (HOD=4.80 ppm): 1.21 (3H, d, J=7.1 Hz), 1.28 (3H, d, J=6.3 Hz), 1.81–1.91 (1H, m), 2.69–2.84 (1H, m), 3.31–3.48 (5H, m), 3.66–3.74 (1H, m), 3.98–4.12 (4H, m), 4.21–4.60 (2H, m), 4.49 (2H, t, J=4.5 Hz), 7.70 (1H, s), 7.97 (1H, s), 9.27 (1H, s).

Example 26

(1R,5S,6S)-2-[(3S,5S)-5-[6-(Carbamoylmethyl)imidazo[5,1-b]thiazolium-2-yl]methylpyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-[6-(carbamoylmethyl)imidazo[5,1-b]thiazolium-2-yl]methylpyrrolidin-3-yl]thio-6-((1R)-1-hydroxyethyl)-1-methylcarbapen-2-em-3-carboxylate iodide 2-Iodoacetamide (96.1 mg) is added to a solution of 33.9 mg of allyl(1R,5S,6S)-2-[(3S,5S)-1-allyloxycarbonyl-5-

(imidazo[5,1-b]thiazol-2-yl)methylpyrrolidin-3-yl]thio-6-((1R)-1-hydroxyethyl)-1-methylcarbapen-2-em-3-carboxylate described in Example 23-a) in 0.5 ml of dry acetone, and the mixture is stirred in an argon atmosphere at room temperature for 20 hr. The solvent is removed by evaporation under reduced pressure, and the residue is purified by column chromatography on Sephadex LH-20 (dichloromethane:methanol=1:1) to give 34.5 mg of allyl (1R,5S,6S)-2-[(3S,5S)-1-allyloxycarbonyl-5-[6-(carbamoylmethyl)imidazo[5,1-b]thiazolium-2-yl] methylpyrrolidin-3-yl]thio-6-((1R)-1-hydroxyethyl)-1-methylcarbapen- 2-em-3-carboxylate iodide as a slightly yellow solid.

NMR (CD$_3$OD) δ: 0.85–0.98 (1H, m), 1.23 (3H, d, J=7.4 Hz), 1.28 (3H, d, J=6.3 Hz), 1.76–1.87 (1H, m), 2.60–2.70 (1H, m), 3.23–3.56 (4H, m), 3.85–3.93 (1H, m), 4.09–4.38 (4H, m), 4.58–4.78 (5H, m), 5.20–5.41 (5H, m), 5.89–6.04 (2H, m), 7.20–7.42 (1H, m), 7.76 (1H, s), 8.00 (1H, s).

MS (FAB$^+$): 630 (M$^+$)

b) (1R,5S,6S)-2-[(3S,5S)-5-[6-(Carbamoylmethyl) imidazo[5,1-b]thiazolium-2-yl]methylpyrrolidin-3-yl]thio-6-((1R)-1-hydroxyethyl)-1-methylcarbapen-2-em-3-carboxylic acid iodide Acetic acid (0.01 ml) and 0.18 ml of a 1 M tetra-n-butylammonium fluoride/THF solution are added to a solution of 34.5 mg of allyl(1R,5S,6S)-2-[(3S,5S)-1-allyloxycarbonyl-5-[6-(carbamoylmethyl)imidazo[5,1-b] thiazolium-2-yl]methylpyrrolidin-3-yl]thio-1-methylcarbapen-2-em-3-carboxylate iodide and this compound in 1 ml of anhydrous THF, and the mixture is stirred in an argon atmosphere at room temperature for 1.5 hr. Dry ethanol (1 ml) is added thereto, and 9.3 mg of triphenylphosphine, 0.038 ml of morpholine, and 11.3 mg of tetrakis(triphenylphosphine)palladium(0) are successively added thereto, and the mixture is stirred in an argon atmosphere at room temperature for 1 hr. THF (10 ml) is added thereto, and the resultant precipitate is further washed twice with 5 ml of THF and dried in vacuo to give a yellow powder which is then purified by column chromatography on Cosmosil 40C18-PREP (water-methanol) to give 3.5 mg of the title compound as a colorless flocculent material.

NMR (D$_2$O) δ (HOD=4.80 ppm): 1.22 (3H, d, J=7.5 Hz), 1.28 (3H, d, J=6.2 Hz), 1.82–1.93 (1H, m), 2.80–2.90 (1H, m), 3.30–3.50 (5H, m), 3.65–3.68 (1H, m), 3.96–4.27 (4H, m), 5.27 (2H, s), 7.68 (1H, s), 8.00 (1H, s), 9.31 (1H, s).

Example 27

(1R,5S,6S)-2-[(3S,5S)-5-[6-(2-Fluoroethyl)imidazo [5,1-b]thiazolium-2-yl]methylpyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-5-[6-(2-fluoroethyl)imidazo[5,1-b]thiazolium-2-yl] methylpyrrolidin-3-yl]thio-6-((1R)-1-hydroxyethyl)-1-methylcarbapen-2-em-3-carboxylate trifluoromethanesulfonate 2-Fluoroethyl trifluoromethanesulfonate (76.4 mg) is added to 41.1 mg of allyl(1R,5S,6S)-2-[(3S,5S)-1-allyloxycarbonyl-5-(imidazo[5,1-b]thiazol-2-yl) methylpyrrolidin-3-yl]thio-6-((1R)-1-hydroxyethyl)-1-methylcarbapen-2-em-3-carboxylate described in Example 23-a), and the mixture is stirred in an argon atmosphere at room temperature for 2 hr. The solvent is removed by evaporation under reduced pressure, and the residue is purified by column chromatography on Sephadex LH-20 (dichloromethane:methanol 1:1) to give 54.1 mg of allyl (1R,5S,6S)-2-[(3S,5S)-1-allyloxycarbonyl-5-[6-(2-fluoroethyl)imidazo[5,1-b]thiazolium-2-yl] methylpyrrolidin-3-yl]thio-6-((1R)-1-hydroxyethyl)-1-methylcarbapen-2-em-3-carboxylate trifluoromethanesulfonate as a yellow viscous material.

NMR (CDCl$_3$) δ: 1.22–1.40 (6H, m), 1.82–1.95 (2H, m), 2.05–2.08 (1H, m), 2.52–2.55 (1H, m), 3.20–3.35 (5H, m), 3.62–3.70 (1H, m), 4.20–4.30 (4H, m), 4.63–4.98 (6H, m), 5.33–5.48 (4H, m), 5.89–6.00 (2H, m), 7.48 (1H, s), 7.95 (1H, s), 9.78 (1H, s).

MS (FAB$^+$): 619 (M$^+$)

b) (1R,5S,6S)-2-[(3S,5S)-5-[6-(2-Fluoroethyl) imidazo[5,1-b]thiazolium-2-yl]methylpyrrolidin-3-yl]thio-6-((1R)-1-hydroxyethyl)-1-methylcarbapen-2-em-3-carboxylic acid chloride Anhydrous THF (0.7 ml) and 0.7 ml of dry ethanol are added to 54.1 mg of allyl(1R,5S,6S)-2-[(3S,5S)-1-allyloxycarbonyl-5-[6-(2-fluoroethyl)imidazo[5,1-b] thiazol-2-yl]methylpyrrolidin-3-yl]thio-6-((1R)-1-hydroxyethyl)-1-methylcarbapen-2-em-3-carboxylate, and 7.9 mg of triphenylphosphine, 0.016 ml of morpholine, and 4.2 mg of tetrakis(triphenylphosphine)palladium(0) are successively added thereto, and the mixture is stirred in an argon atmosphere at room temperature for 55 min. THF (10 ml) is added thereto, and the resultant precipitate is further washed twice with 3 ml of THF and dried in vacuo to give a yellow powder which is then purified by column chromatography on Cosmosil 40C18-PREP (water-methanol) and passed through an anion exchange resin Amberlyst A-26 (Cl$^-$ form) to give 4.1 mg of the title compound as a colorless flocculent material.

NMR (D$_2$O) δ (HOD=4.80 ppm): 1.21 (3H, d, J=7.3 Hz), 1.28 (3H, d, J=6.3 Hz), 1.82–1.92 (1H, m), 2.79–2.80 (1H, m), 3.33–3.49 (5H, m), 3.68–3.75 (1H, m), 4.04–4.28 (4H, m), 4.70–4.98 (4H, m), 7.72 (1H, s), 7.98 (1H, s), 9.31 (1H, s).

Example 28

(1R,5S,6S)-6-((1R)-1-Hydroxyethyl)-1-methyl-2-[(3S,5S)-5-(3-methylimidazo[5,1-b]thiazol-2-yl) methylpyrrolidin-3-yl]thiocarbapen-2-em-3-carboxylic acid a) Allyl(1R,5S,6S)-2-[(3S,5S)-1-allyloxycarbonyl-5-(3-methylimidazo[5,1-b]thiazol-2-yl) methylpyrrolidin-3-yl]thio-6-((1R)-1-hydroxyethyl)-1-methylcarbapen-2-em-3-carboxylate The procedure of Example 23-a) is repeated to prepare 362.4 mg of a mercaptan compound as a yellow oil from 474.5 mg of (3S,5S)-3-acetylthio-1-allyloxycarbonyl-5-(3-methylimidazo[5,1-b]thiazol-2-yl)methylpyrrolidine described in Synthesis Example 10. Allyl(1R,5S,6S)-2-[(3S,5S)-1-allyloxycarbonyl-5-(3-methylimidazo[5,1-b]thiazol-2-yl)methylpyrrolidin- 3-yl]thio-6-((1R)-1-hydroxyethyl)-1-methylcarbapen-2-em-3-carboxylate (255.4 mg) is prepared as a colorless amorphous material from this mercaptan compound and 544.2 mg of allyl(1R,5R,6S)-2-(diphenylphosphono)oxy-6-((1R)-1-hydroxyethyl)-1-methylcarbapen-2-em-3-carboxylate.

NMR (CDCl$_3$) δ: 1.27 (3H, d, J=7.1 Hz), 1.36 (3H, d, J=6.2 Hz), 1.65–1.82 (1H, m), 2.40 (3H, s), 2.45–2.58 (1H, m), 2.90–3.01 (1H, m), 3.25–3.40 (5H, m), 3.60–3.67 (1H, m), 4.15–4.28 (3H, m), 4.62–4.88 (4H, m), 5.23–5.48 (4H, m), 5.91–6.03 (2H, m), 7.06 (1H, s), 7.86 (1H, s).

MS (FAB$^+$): 587 (M$^+$)

b) (1R,5S,6S)-6-((1R)-1-Hydroxyethyl)-1-methyl-2-[(3S,5S)-5-(3-methylimidazo[5,1-b]thiazol-2-yl)methylpyrrolidin-3-yl]thiocarbapen-2-em-3-carboxylic acid The procedure of Example 23-b) is repeated to prepare 53.2 mg of allyl(1R,5S,6S)-2-[(3S,5S)-1-allyloxycarbonyl-5-(3-methylimidazo[5,1-b]thiazol-2-yl)methylpyrrolidin-3-yl]thio-6-((1R)-1-hydroxyethyl)-1-methylcarbapen-2-em-3-carboxylate to give 5.8 mg of the title compound as a colorless flocculent material.

NMR (D$_2$O) δ (HOD=4.80 ppm): 1.19 (3H, d, J=7.4 Hz), 1.27 (3H, d, J=6.2 Hz), 1.72–1.82 (1H, m), 2.41 (3H, s), 2.71–2.81 (1H, m), 3.18–3.46 (5H, m), 3.62–3.68 (1H, m), 3.89–4.04 (1H, m), 4.18–4.26 (2H, m), 7.06 (1H, s), 8.12 (1H, s).

Example 29

(1R,5S,6S)-2-[(3S,5S)-5-(3,6-Dimethylimidazo[5,1-b]thiazolium-2-yl)methylpyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-(3,6-dimethylimidazo[5,1-b]thiazolium-2-yl)methylpyrrolidin-3-yl]thio-6-((1R)-1-hydroxyethyl)-1-methylcarbapen-2-em-3-carboxylate iodide The procedure of Example 24-a) is repeated to prepare 66.7 mg of allyl(1R,5S,6S)-2-[(3S,5S)-1-allyloxycarbonyl-5-(3,6-dimethylimidazo[5,1-b]thiazolium-2-yl)methylpyrrolidin-3-yl]thio-6-((1R)-1-hydroxyethyl)-1-methylcarbapen-2-em-3-carboxylate iodide as a yellow viscous material from 53.7 mg of allyl(1R,5S,6S)-2-[(3S,5S)-1-allyloxycarbonyl-5-(3-methylimidazo[5,1-b]thiazol-2-yl)methylpyrrolidin-3-yl]thio-6-(1R)-1-hydroxyethyl)-1-methylcarbapen-2-em-3-carboxylate described in Example 28-a).

NMR (CD$_3$COCD$_3$) δ: 1.10–1.15 (6H, m), 1.59–1.68 (1H, m), 2.45–2.63 (1H, m), 2.50 (3H, s), 3.12–3.54 (5H, m), 3.83–3.71 (5H, m), 4.35–4.65 (4H, m), 5.01–5.33 (4H, m), 5.72–5.88 (2H, m), 7.89 (1H, s), 9.48 (1H, s).

MS (FAB$^+$): 601 (M$^+$)

b) (1R,5S,6S)-2-[(3S,5S)-5-(3, 6-Dimethylimidazo[5,1-b]thiazolium-2-yl)methylpyrrolidin-3-yl]thio-6-((1R)-1-hydroxyethyl)-1-methylcarbapen-2-em-3-carboxylic acid iodide The procedure of Example 24-b) is repeated to prepare 5.9 mg of the title compound as a colorless flocculent material from 66.7 mg of allyl(1R,5S,6S)-2-[(3S,5S)-1-allyloxycarbonyl-5-(3,6-dimethylimidazo[5,1-b]thiazolium-2-yl)methylpyrrolidin-3-yl]thio-6-((1R)-1-hydroxyethyl)-1-methylcarbapen-2-em-3-carboxylate iodide.

NMR (D$_2$O) δ (HOD=4.80 ppm): 1.20 (3H, d, J=7.1 Hz), 1.27 (3H, d, J=6.3 Hz), 1.76–1.86 (1H, m), 2.50 (3H, s), 2.73–2.84 (1H, m), 3.30–3.48 (5H, m), 3.66–3.74 (1H, m), 3.98–4.07 (2H, m), 4.08 (3H, s), 4.20–4.26 (2H, m), 7.59 (1H, s), 9.21 (1H, s).

Example 30

(1R,5S,6S)-2-[(3S,5S)-5-(6-Carbamoyl-methyl-3-methylimidazo[5,1-b]thiazolium-2-yl)methylpyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-(6 -carbamoylmethyl-3-methylimidazo[5,1-b]thiazolium-2-yl)methylpyrrolidin-3-yl]thio-6-((1R)-1-hydroxyethyl)-1-methylcarbapen-2-em-3-carboxylate iodide The procedure of Example 26-a) is repeated to prepare 70.9 mg of allyl(1R,5S,6S)-2-[(3S,5S)-1-allyloxycarbonyl-5-(6-carbamoylmethyl-3-methylimidazo[5,1-b]thiazolium-2-yl)methylpyrrolidin-3-yl]thio-6-((1R)-1-hydroxyethyl)-1-methylcarbapen-2-em-3-carboxylate iodide as a yellow viscous material from 57.6 mg of allyl(1R,5S,6S)-2-[(3S,5S)-1-allyloxycarbonyl-5-(3-methylimidazo[5,1-b]thiazol-2-yl)methylpyrrolidin-3-yl]thio-6-((1R)-1-hydroxyethyl)-1-methylcarbapen-2-em-3-carboxylate described in Example 28-a).

NMR (CD$_3$COCD$_3$) δ: 1.14–1.22 (6H, m), 1.72–1.86 (1H, m), 2.57–2.62 (3H, m), 2.62 (3H, s), 3.10–3.60 (5H, m), 3.80–4.32 (5H, m), 4.52–4.78 (4H, m), 5.12–5.45 (6H, m), 5.87–5.98 (2H, m), 6.89 (1H, br.s), 7.70 (1H, br.s), 7.95 (1H, s), 9.70 (1H, s).

MS (FAB$^+$): 644 (M$^+$)

b) (1R,5S,6S)-2-[(3S,5S)-5-(6-Carbamoylmethyl-3-methylimidazo[5,1-b]thiazolium-2-yl)methylpyrrolidin-3-yl]thio-6-((1R)-1-hydroxyethyl)-1-methylcarbapen-2-em-3-carboxylic acid iodide The procedure of Example 26-b) is repeated to prepare 11.6 mg of the title compound as a colorless flocculent material from 70.9 mg of allyl(1R,5S,6S)-2-[(3S,5S)-1-allyloxycarbonyl-5-(6-carbamoylmethyl-3-methylimidazo[5,1-b]thiazolium-2-yl)methylpyrrolidin-3-yl]thio-6-((1R)-1-hydroxyethyl)-1-methylcarbapen-2-em-3-carboxylate iodide.

NMR (D$_2$O) δ (HOD=4.80 ppm): 1.20 (3H, d, J=7.1 Hz), 1.27 (3H, d, J=6.9 Hz), 1.62–1.71 (1H, m), 2.51 (3H, s), 2.65–2.73 (1H, m), 3.27–3.40 (5H, m), 3.44–3.56 (1H, m), 3.77–3.98 (2H, m), 4.20–4.28 (2H, m), 5.26 (2H, s), 7.64 (1H, s).

Example 31

(1R,5S,6S)-6-((1R)-1-Hydroxyethyl)-1-methyl-2-[(3S,5S)-5-(5-methylimidazo[5,1-b]thiazol-2-yl)methylpyrrolidin-3-yl]thiocarbapen-2-em-3-carboxylic acid a) Allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate The procedure of Example 23-a) is repeated to prepare 653.0 mg of a mercaptan compound as a yellow oil from 766.4 mg of (3S,5S)-3-acetylthio-1-allyloxycarbonyl-5-(5-methylimidazo[5,1-b]thiazol-2-yl)methylpyrrolidine described in Synthesis Example 11. Allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate (560.2 mg) is prepared as a colorless amorphous material from this mercaptan and 891.6 mg of allyl(1R,5R,6S)-2-(diphenylphosphono)oxy-6-((1R)-1-hydroxyethyl)-1-methylcarbapen-2-em-3-carboxylate.

NMR (CDCl$_3$) δ: 1.18 (3H, d, J=7.1 Hz), 1.29 (3H, d, J=6.3 Hz), 1.76–1.83 (1H, m), 2.40–2.50 (1H, m), 2.48 (3H, s), 2.96–3.08 (1H, m), 3.19–3.28 (4H, m), 3.52–3.58 (1H, m), 4.04–4.21 (4H, m), 4.57–4.68 (3H, m), 4.75–4.80 (1H, m), 5.18–5.42 (4H, m), 5.83–5.98 (2H, m), 6.81 (1H, s), 6.97 (1H, s).

MS (TS): 587 (M$^+$+H)

b) (1R,5S,6S)-6-((1R)-1-Hydroxyethyl)-1-methyl-2-[(3S,5S)-5-(5-methylimidazo[5,1-b]thiazol-2-yl)methylpyrrolidin-3-yl]thiocarbapen-2-em-3-carboxylic acid The procedure of Example 23-b) is repeated to prepare 12.4 mg of the title compound as a white powder from 77.3 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate.

NMR (D$_2$O) δ (HOD=4.80 ppm): 1.19 (3H, d, J=7.2 Hz), 1.27 (3H, d, J=6.3 Hz), 1.71–1.81 (1H, m), 2.52 (3H, s), 2.71–2.81 (1H, m), 3.24 (2H, d, J=7.2 Hz), 3.32–3.46 (3H, m), 3.60–3.67 (1H, m), 3.90–4.05 (2H, m), 4.20–4.28 (2H, m), 6.93 (1H, s), 7.54 (1H, s).

Example 32

(1R,5S,6S)-2-[(3S,5S)-5-(5,6-Dimethylimidazo[5,1-b]thiazolium-2-yl)methylpyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-(5, 6-dimethylimidazo[5,1-b]thiazolium-2-yl)methylpyrrolidin-3-yl]thio-6-((1R)-1-hydroxyethyl)-1-methylcarbapen-2-em-3-carboxylate iodide The procedure of Example 24-a) is repeated to prepare 88.4 mg of allyl(1R,5S,6S)-2-[(3S,5S)-1-allyloxycarbonyl-5-(5, 6-dimethylimidazo[5,1-b]thiazolium-2-yl)methylpyrrolidin-3-yl]thio-6-((1R)-1-hydroxyethyl)-1-methylcarbapen-2-em-3-carboxylate iodide as a yellow oil from 71.2 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate described in Example 31-a).

NMR (CDCl$_3$) δ: 1.18–1.33 (6H, m), 1.65–1.83 (1H, m), 2.63–2.74 (1H, m), 3.05 (3H, s), 3.20–3.35 (3H, m), 3.55–3.67 (1H, m), 4.05 (3H, s), 4.15–4.26 (2H, m), 4.55–4.64 (3H, m), 4.70–4.76 (1H, m), 5.19–5.43 (8H, m), 5.84–5.96 (2H, m), 7.55 (1H, s), 8.06 (1H, s).

MS (TS): 601 (M$^+$)

b) (1R,5S,6S)-2-[(3S,5S)-5-(5,6-Dimethylimidazo[5,1-b]thiazolium-2-yl)methylpyrrolidin-3-yl]thio-6-((1R)-1-hydroxyethyl)-1-methylcarbapen-2-em-3-carboxylic acid iodide The procedure of Example 24-b) is repeated to prepare 11.0 mg of the title compound as a colorless flocculent material from 88.4 mg of allyl(1R,5S,6S)-2-[(3S,5S)-1-allyloxycarbonyl-5-(5,6-dimethylimidazo[5,1-b]thiazolium-2-yl)methylpyrrolidin-3-yl]thio-6-((1R)-1-hydroxyethyl)-1-methylcarbapen-2-em-3-carboxylate iodide.

NMR (D$_2$O) δ (HOD 4.80 ppm): 1.21 (3H, d, J=7.1 Hz), 1.28 (3H, d, J=6.5 Hz), 1.80–1.85 (1H, m), 2.78 (3H, s), 2.79–2.89 (1H, m), 3.36–3.50 (5H, m), 3.70–3.77 (1H, m), 3.93 (3H, s), 4.02–4.11 (2H, m), 4.21–4.27 (2H, m), 7.47 (1H, s), 7.86 (1H, s).

Example 33

(1R,5S,6S)-2-[(3S,5S)-5-(6-Carbamoylmethyl-5-methylimidazo[5,1-b]thiazolium-2-yl)methylpyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-(6-carbamoylmethyl-5-methyl imidazo[5,1-b]thiazolium-2-yl)methylpyrrolidin-3-yl]thio-6-((1R)-1-hydroxyethyl)-1-methylcarbapen-2-em-3-carboxylate iodide The procedure of Example 26-a) is repeated to prepare 83.4 mg of allyl(1R,5S,6S)-2-[(3S,5S)-1-allyloxycarbonyl-5-(6-carbamoylmethyl-5-methylimidazo[5,1-b]thiazolium-2-yl)methylpyrrolidin-3-yl]thio-6-((1R)-1-hydroxyethyl)-1-methylcarbapen-2-em-3-carboxylate iodide as a yellow oil from 45.2 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate described in Example 31-a).

NMR (CD$_3$OD) δ: 1.23 (3H, d, J=7.4 Hz), 1.28 (3H, d, J=6.3 Hz), 1.78–1.89 (1H, m), 2.62–2.75 (1H, m), 2.82 (3H, s), 3.20–3.40 (4H, m), 3.49–3.59 (1H, m), 3.83–3.93 (1H, m), 4.08–4.18 (2H, m), 4.21–4.38 (2H, m), 4.61–4.76 (4H, m), 5.17–5.42 (6H, m), 5.89–6.03 (2H, m), 7.65 (1H, s), 8.01 (1H, s).

MS (Ts-Pos): 644 (M$^+$)

b) (1R,5S,6S)-2-[(3S,5S)-5-(6-Carbamoylmethyl-5-methylimidazo[5,1-b]thiazolium-2-yl)methylpyrrolidin-3-yl]thio-6-((1R)-1-hydroxyethyl)-1-methylcarbapen-2-em-3-carboxylic acid iodide The procedure of Example 26-b) is repeated to prepare 6.3 mg of the title compound as a slightly yellow flocculent material from 83.4 mg of allyl(1R,5S,6S)-2-[(3S,5S)-1-allyloxycarbonyl-5-(6-carbamoylmethyl-5-methylimidazo[5,1-b]thiazolium-2-yl)methylpyrrolidin-3-yl]thio-6-((1R)b-1-hydroxyethyl)-1-methylcarbapen-2-em-3-carboxylate iodide.

NMR (D$_2$O) δ (HOD=4.80 ppm): 1.21 (3H, d, J=7.1 Hz), 1.27 (3H, d, J=6.3 Hz), 1.80–1.90 (1H, m), 2.77 (3H, s), 2.77–2.88 (1H, m), 3.31–3.49 (5H, m), 3.68–3.75 (1H, m), 4.02–4.13 (2H, m), 4.20–4.28 (2H, m), 5.19 (2H, s), 7.55 (1H, s), 7.92 (1H, s).

Example 34

(1R,5S,6S)-6-((1R)-1-Hydroxyethyl)-2-[(3S,5R)-5-(imidazo[5,1-b]thiazol-7-yl)methylpyrrolidin-3-yl]thio-1-methylcarbapen-2-em-3-carboxylic acid a) Allyl(1R,5S,6S)-2-[(3S,5R)-1-allyloxycarbonyl-5-(imidazo[5,1-b]thiazol-7-yl)methylpyrrolidin-3-yl]thio-6-((1R)-1-hydroxyethyl)-1-methylcarbapen-2-em-3-carboxylate The procedure of Example 10-a) is repeated to prepare 86.2 mg of allyl(1R,5S,6S)-2-[(3S,5R)-1-allyloxycarbonyl-5-(imidazo[5,1-b]thiazol-7-yl)methylpyrrolidin-3-yl]thio-6-

((1R)-1-hydroxyethyl)-1-methylcarbapen-2-em-3-carboxylate from 169 mg of (3S,5R)-1-allyloxycarbonyl-3-benzoylthio-5-(imidazo[5,1-b]thiazol-7-yl)methylpyrrolidine described in Synthesis Example 12 and 162 mg of allyl(1R,5R,6S)-2-(diphenylphosphono)oxy-6-((1R)-1-hydroxyethyl)-1-methylcarbapen-2-em-3-carboxylate.

NMR (CDCl$_3$) δ: 1.23 (3H, d, J=7.4 Hz), 1.34 (3H, d, J=6.3 Hz), 1.96 (1H, m), 2.45 (1H, m), 3.00–3.60 (6H, m), 3.90–4.35 (4H, m), 4.55–4.97 (4H, m), 5.20–5.48 (4H, m), 5.97 (2H, m), 6.80 (1H, d, J=4.1 Hz), 7.37 (1H, d, J=4.1 Hz), 7.95 (1H, s).

b) (1R,5S,6S)-6-((1R)-1-Hydroxyethyl)-2-[(3S,5R)-5-(imidazo[5,1-b]thiazol-7-yl)methylpyrrolidin-3-yl]thio-1-methylcarbapen-2-em-3-carboxylic acid The procedure of Example 10-b) is repeated to prepare 11.1 mg of the title compound from 43.2 mg of allyl(1R,5S,6S)-2-[(3S,5R)-1-allyloxycarbonyl-5-(imidazo[5,1-b]thiazol-7-yl)methylpyrrolidin-3-yl]thio-6-((1R)-1-hydroxyethyl)-1-methylcarbapen-2-em-3-carboxylate.

NMR (D$_2$O) δ (HOD=4.80 ppm): 1.17 (3H, d, J=7.2 Hz), 1.27 (3H, d, J=6.3 Hz), 1.75 (1H, m), 2.71 (1H, m), 3.19 (2H, d, J=7.1 Hz), 3.25–3.48 (3H, m), 4.03 (2H, m), 4.20 (2H, m), 7.05 (1H, d, J=4.1 Hz), 7.64 (1H, d, J=4.1 Hz), 8.15 (1H, s).

Example 35

(1R,5S,6S)-6-((1R)-1-Hydroxyethyl)-1-methyl-2-[(3S,5R)-5-(6-methylimidazo[5,1-b]thiazolium-7-yl)methylpyrrolidin-3-yl]thiocarbapen-2-em-3-carboxylic acid iodide Iodomethane (0.468 ml) is added to 43.0 mg of allyl (1R,5S,6S)-2-[(3S,5R)-1-allyloxycarbonyl-5-(imidazo[5,1-b]thiazol-7-yl)methylpyrrolidin-3-yl]thio-6-((1R)-1-hydroxyethyl)-1-methylcarbapen-2-em-3-carboxylate described in Example 34-a), and the mixture is stirred in an argon atmosphere in a light-shielded state at room temperature for 19 hr. The excess reagent is removed by evaporation under reduced pressure to give a crude product of allyl(1R,5S,6S)-2-[(3S,5R)-1-allyloxycarbonyl-5-(6-methylimidazo[5,1-b]thiazolium-7-yl)methylpyrrolidin-3-yl]thio-6-((1R)-1-hydroxyethyl)-1-methylcarbapen-2-em-3-carboxylate iodide. The procedure of Example 11-b) is repeated, except that the whole quantity of the crude product prepared just above is used. Thus, 3.2 mg of the title compound is obtained.

NMR (D$_2$O) δ (HOD=4.80 ppm): 1.22 (3H, d, J=6.92 Hz), 1.29 (3H, d, J=6.2 Hz), 1.86 (1H, m), 2.80 (1H, m), 3.39 (1H, m), 3.46–3.58 (4H, m), 3.78 (1H, m), 4.06 (3H, s), 4.05–4.28 (4H, m), 7.56 (1H, d, J=4.4 Hz), 7.94 (1H, d, J=4.4 Hz), 9.29 (1H, s).

Example 36

(1R,5S,6S)-6-((1R)-1-Hydroxyethyl)-1-methyl-2-[(3S)-5-(6-methylimidazo[5,1-b]thiazolium-5-yl)pyrrolidin-3-yl]thiocarbapen-2-em-3-carboxylic acid chloride (stereoisomer A)

a) Allyl(1R,5S,6S)-2-[(3S)-1-allyloxycarbonyl-5-(imidazo[5,1-b]thiazol-5-yl)pyrrolidin-3-yl]thio-6-((1R)-1-hydroxyethyl)-1-methylcarbapen-2-em-3-carboxylate (stereoisomer A)

A 1 N aqueous sodium hydroxide solution (0.78 ml) is added to a solution of 0.25 g of (3S)-3-acetylthio-1-allyloxycarbonyl-5-(imidazo[5,1-b]thiazol-5-yl)pyrrolidine (stereoisomer A), described in Synthesis Example 14, in 5 ml of methanol under ice cooling, and the mixture is stirred at that temperature for 15 min. The mixture is adjusted to pH 7 by addition of 1 N-aqueous hydrochloric acid solution, dichloromethane is added thereto, and the mixture is successively washed with water and saturated saline. The organic layer is dried over magnesium sulfate. The solvent is removed by evaporation to give a mercaptan compound. Diisopropylethylamine (0.14 ml) is added to a solution of 0.27 g of allyl (1R,5S,6S)-2-(diphenylphosphono)oxy-6-((1R)-1-hydroxyethyl)-1-methylcarbapen-2-em-3-carboxylate in 4 ml of acetonitrile under ice cooling for 30 min. Ethyl acetate is added to the reaction mixture, and the mixture is successively washed with a saturated aqueous sodium hydrogencarbonate solution and saturated saline and then dried over magnesium sulfate. The solvent is removed by evaporation. The residue is purified by column chromatography on silica gel to give 0.26 g of allyl( 1R,5S,6S)-2-[(3S)-1-allyloxycarbonyl-5-(imidazo[5,1-b]thiazol-5-yl)pyrrolidin-3-yl]thio-6-((1R)-1-hydroxyethyl)-1-methylcarbapen-2-em-3-carboxylate (stereoisomer A).

b) (1R,5S,6S)-6-((1R)-1-Hydroxyethyl)-1-methyl-2-[(3S)-5-(6-methylimidazo[5,1-b]thiazolium-5-yl)pyrrolidin-3-yl]thiocarbapen-2-em-3-carboxylic acid chloride (stereoisomer A)

Methyl triflate (0.022 ml) is added to a solution of 80 mg of allyl(1R,5S,6S)-2-[(3S)-1-allyloxycarbonyl-5-(imidazo[5,1-b]thiazol-5-yl)pyrrolidin-3-yl]thio-6-((1R)-1-hydroxyethyl)-1-methylcarbapen-2-em-3-carboxylate (stereoisomer A) in 1 ml of dichloromethane under ice cooling, and the mixture is stirred at that temperature for one hr. The reaction mixture is concentrated under reduced pressure. DMF (2 ml), 0.055 ml of N-methylaniline, and 40 mg of tetrakis(triphenylphosphine)palladium(0) are added to the concentrate, and the mixture is stirred in an argon atmosphere at room temperature for 30 min. The reaction mixture is concentrated under reduced pressure, and water is added to the concentrate. The mixture is washed with dichloromethane. The aqueous layer is purified by column chromatography on Cosmosil 40C18-PREP and Amberlyst A-26 (Cl⁻ form) to give 12.6 mg of the title compound.

Example 37

(1R,5S,6S)-6-((1R)-1-Hydroxyethyl)-2-[(3S)-5-[6-(2-hydroxyethyl)imidazo[5,1-b]thiazolium-5-yl]pyrrolidin-3-yl]thio-1-methylcarbapen-2-em-3-carboxylic acid chloride (stereoisomer A)

1-t-Butyldimethylsilyloxy-2-trifluoromethanesulfonyloxyethane (58 mg) is added to a solution of 87 mg of allyl(1R,5S,6S)-2-[(3S)-1-allyloxycarbonyl-5-(imidazo[5,1-b]thiazol-5-yl)pyrrolidin-3-yl]thio-6-((1R)-1-hydroxyethyl)-1-methylcarbapen-2-em-3-carboxylate (stereoisomer A), described in Example 36-a), in 1 ml of dichloromethane under ice cooling, and the mixture is stirred at that temperature for one hr. The reaction mixture is concentrated under reduced pressure, and 1.5 ml of THF, 0.0095 ml of acetic acid, and 0.156 ml of a 1 M tetrabutylammonium fluoride/THF solution are added thereto. The mixture is stirred at room temperature for 2 hr. Ethyl alcohol (1.5 ml), 16 mg of triphenylphosphine, 0.034 ml of morpholine, and 60 mg of tetrakis(triphenylphosphine)palladium(0) are added thereto. The mixture is stirred in an argon atmosphere at room temperature for 30 min. The reaction mixture is concentrated under reduced pressure, water is added to the concentrate, and the mixture is washed with dichloromethane. The aqueous layer is purified by column chromatography on Cosmosil 40C18-PREP and Amberlyst A-26 (Cl⁻ form) to give 22.5 mg of the title compound.

NMR (D$_2$O) δ (HOD=4.80 ppm): 1.22 (3H, d, J=7.1 Hz), 1.29 (3H, d, J 6.5 Hz), 1.90–2.00 (1H, m), 2.75–2.87 (1H, m), 3.40–3.55 (3H, m), 3.87–4.00 (3H, m), 4.20–4.28 (2H, m), 4.45–4.53 (2H, m), 5.00–5.08 (1H, m), 7.54 (1H, d, J=4.3 Hz), 7.66 (1H, s), 8.33 (1H, d, J=4.3 Hz).

Example 38

(1R,5S,6S)-6-((1R)-1-Hydroxyethyl)-2-[(3S,5S)-5-[2(Z)-(imidazo[5,1-b]thiazol-3-yl)ethenyl] pyrrolidin-3-yl]thio-1-methylcarbapen-2-em-3-carboxylic acid a) Allyl(1R,5S,6S)-2-[(3S,5S)-1-allyloxycarbonyl-5-[2(E)-(imidazo[5,1-b]thiazol-3-yl)ethenyl] pyrrolidin-3-yl]thio-6-((1R)-1-hydroxyethyl)-1-methylcarbapen-2-em-3-carboxylate and allyl(1R,5S,6S)-2-[(3S,5S)-1-allyloxycarbonyl-5-[2(Z)-(imidazo[5,1-b]thiazol-3-yl)ethenyl]pyrrolidin-3-yl] thio-6-((1R)-1-hydroxyethyl)-1-methylcarbapen-2-em-3-carboxylate A 1 N-aqueous sodium hydroxide solution (0.69 ml) is added to a solution of 0.24 g of (3S,5S)-3-acetylthio-1-allyloxycarbonyl-5-[2-(imidazo[5,1-b]thiazol-3-yl)ethenyl] pyrrolidine (a mixture of geometrical isomers), described in Synthesis Example 13, in 3 ml of methanol under ice cooling, and the mixture is stirred at that temperature for 15 min. The mixture is adjusted to pH 7 by addition of a 1 N aqueous hydrochloric acid solution, dichloromethane is added thereto, and the mixture is successively washed with water and saturated saline and dried over magnesium sulfate. The solvent is removed by evaporation to give a mercaptan compound. Diisopropylethylamine (0.105 ml) is added to a solution of this mercaptan compound and 0.27 g of allyl (1R,5S,6S)-2-(diphenylphosphono)oxy-6-((1R)-1-hydroxyethyl)-1-methylcarbapen-2-em-3-carboxylate in 4 ml of acetonitrile under ice cooling, and the mixture is stirred for 30 min. Ethyl acetate is added to the reaction mixture, and the mixture is successively washed with a saturated aqueous sodium hydrogencarbonate solution and saturated saline and dried over magnesium sulfate. The solvent is removed by evaporation, and the residue is purified by column chromatography on silica gel to give 78 mg of allyl(1R,5S,6S)-2-[(3S,5S)-1-allyloxycarbonyl-5-[2 (E)-(imidazo[5,1-b]thiazol-3-yl)ethenyl]pyrrolidin-3-yl] thio-6-((1R)-1-hydroxyethyl)-1-methylcarbapen-2-em-3-carboxylate and 147 mg of allyl(1R,5S,b6S)-2-[(3S,5S)-1-allyloxycarbonyl-5-[2(Z)-(imidazo[5,1-b]thiazol-3-yl) ethenyl]pyrrolidin-3-yl]thio-6-((1R)-1-hydroxyethyl)-1-methylcarbapen-2-em-3-carboxylate.

b) (1R,5S,6S)-6-((1R)-1-Hydroxyethyl)-2-[(3S,5S)-5-[2(Z)-(imidazo[5,1-b]thiazol-3-yl)ethenyl] pyrrolidin-3-yl]thio-1-methylcarbapen-2-em-3-carboxylic acid Allyl(1R,5S,6S)-2-[(3S,5S)-1-allyloxycarbonyl-5-[2 (Z)-(imidazo[5,1-b]thiazol-3-yl)ethenyl]pyrrolidin-3-yl]thio-6-((1R)-1-hydroxyethyl)-1-methylcarbapen-2-em-3-carboxylate (80 mg) is dissolved in 1 ml of dichloromethane and 1 ml of DMF. N-Methylaniline (0.060 ml) and 40 mg of tetrakis(triphenylphosphine)palladium(0) are added thereto, and the mixture is stirred in an argon atmosphere at room temperature for 30 min. The reaction mixture is concentrated under reduced pressure. Ethyl acetate is added to the concentrate, and the resultant precipitate is collected by filtration and then purified by column chromatography on Cosmosil 40C18-PREP and Amberlyst A-26 (Cl⁻ form) to give 11.9 mg of the title compound.

NMR (D$_2$O) δ (HOD=4.80 ppm): 1.22 (3H, d, J=7.1 Hz), 1.29 (3H, d, J=6.3 Hz), 1.86–2.00 (1H, m), 2.82–2.94 (1H, m), 3.30–3.48 (3H, m), 3.62–3.70 (1H, m), 4.00–4.10 (1H, m), 4.18–4.30 (2H, m), 6.22–6.30 (1H, m), 6.74 (1H, d, J=11.3 Hz), 7.06 (1H, s), 7.12 (1H, s), 8.17 (1H, s).

Example 39

(1R,5S,6S)-6-((1R)-1-Hydroxyethyl)-1-methyl-2-[(3S,5S)-5-[2(Z)-(6-methylimidazo[5,1-b] thiazolium-3-yl)ethenyl]pyrrolidin-3-yl] thiocarbapen-2-em-3-carboxylic acid chloride Methyl triflate (0.0155 ml) is added to a solution of 67 mg of allyl(1R,5S,6S)-2-[(3S,5S)-1-allyloxycarbonyl-5-[2(Z)-(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 1 ml of dichloromethane under ice cooling, and the mixture is stirred at that temperature for one hr. The reaction mixture is concentrated under reduced pressure. Dichloromethane (1 ml), 1 ml of DMF, 0.050 ml of N-methylaniline, and 40 mg of tetrakis(triphenylphosphine)palladium(0) are added to the concentrate, and the mixture is stirred in an argon atmosphere at room temperature for 30 min. The reaction mixture is concentrated under reduced pressure, water is added to the concentrate, and the mixture is washed with dichloromethane. The aqueous layer is purified by column chromatography on Cosmosil 40C18-PREP and Amberlyst A-26 (Cl⁻ form) to give 6.0 mg of the title compound.

NMR (D$_2$O) δ (HOD=4.80 ppm): 1.22 (3H, d, J=7.1 Hz), 1.29 (3H, d, J=6.5 Hz), 1.94–2.03 (1H, m), 2.87–3.03 (1H, m), 3.03–3.42 (1H, m), 3.45–3.53 (1H, m), 3.67–3.76 (1H, m), 4.10 (3H, s), 4.20–4.30 (1H, m), 6.40–6.48 (1H, m), 6.75 (1H, d, J=11.4 Hz), 7.50 (1H, s), 7.68 (1H, s), 9.29 (1H, s).

Example 40

(1R,5S,6S)-6-((1R)-1-Hydroxyethyl)-1-methyl-2-[(3S,5S)-5-[2(E)-(6-methylimidazo[5,1-b] thiazolium-3-yl)ethenyl]pyrrolidin-3-yl] thiocarbapen-2-em-3-carboxylic acid chloride Methyl triflate (0.0225 ml) is added to a solution of 78 mg of allyl(1R,5S,6S)-2-[(3S,5S)-1-allyloxycarbonyl-5-[2(E)-(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 1 ml of dichloromethane under ice cooling, and the mixture is stirred at that temperature for one hr. The reaction mixture is concentrated under reduced pressure. Dichloromethane (1 ml), 1 ml of DMF, 0.071 ml of N-methylaniline, and 60 mg of tetrakis(triphenylphosphine)palladium(0) are added to the concentrate, and the mixture is stirred in an argon atmosphere at room temperature for 30 min. The reaction mixture is concentrated under reduced pressure, water is added thereto, and the mixture is washed with dichloromethane. The aqueous layer is purified by column chromatography on Cosmosil 40C18-PREP and Amberlyst A-26 (Cl⁻ form) to give 5.7 mg of the title compound.

NMR (D$_2$O) δ (HOD=4.80 ppm): 1.22 (3H, d, J=7.1 Hz), 1.29 (3H, d, J=6.5 Hz), 1.96–2.06 (1H, m), 2.80–3.05 (2H, m), 3.35–3.52 (2H, m), 3.68–3.80 (2H, m), 4.10 (3H, s), 4.10–4.18 (4H, m), 4.20–4.28 (2H, m), 6.53–6.63 (1H, m), 6.95 (1H, d, J=15.9 Hz), 7.65–7.72 (2H, m), 9.45 (1H, s).

Example 41

(1R,5S,6S)-2-[(3S,5S)-5-[6-(2-Cyclopropylmethyl)-5-methylimidazo[5,1-b]thiazolium-2-yl]methylpyrrolidin-3-yl]thio-6-((1R)-1-hydroxyethyl)-1-methylcarbapen-2-em-3-carboxylate (internal salt)

a) Allyl(1R,5S,6S)-2-[(3S,5S)-1-allyloxycarbonyl-5-[6-(2-cyclopropylmethyl)-5-methylimidazo[5,1-b]thiazolium-2-yl]methylpyrrolidin-3-yl]thio- 6-((1R)-1-hydroxyethyl)-1-methylcarbapen-2-em-3-carboxylate trifluoromethanesulfonate Cyclopropylmethyl bromide (0.044 ml) and 56 mg of sodium iodide are added to a solution of 43.7 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate, described in Example 31-a), in 0.4 ml of anhydrous acetonitrile, and the mixture is stirred in an argon atmosphere at room temperature for 27 hr. The solvent is removed by evaporation under reduced pressure, and the residue is purified by column chromatography on Sephadex LH-20 (dichloromethane:methanol=1:1) to give 47.9 mg of allyl(1R,5S,6S)-2-[(3S,5S)-1-allyloxycarbonyl-5-[6-(2-cyclopropylmethyl)-5-methylimidazo[5,1-b]thiazolium-2-yl]methylpyrrolidin-3-yl]thio-6-((1R)-1-hydroxyethyl)-1-methylcarbapen-2-em-3-carboxylate trifluoromethanesulfonate as a yellow oil.

NMR (CDCl$_3$) δ: 0.50–0.56 (2H, m), 0.71–0.76 (2H, m), 1.18 (3H, d, J=6.0 Hz), 1.27 (3H, d, J=6.1 Hz), 1.68–1.80 (1H, m), 2.58–2.71 (2H, m), 3.04 (3H, s), 3.10–3.26 (4H, m), 3.40 (s, 3H), 3.53–3.68 (1H, m), 3.89–4.06 (1H, m), 4.10–4.28 (4H, m), 4.54–4.78 (4H, m), 5.15–5.40 (4H, m), 5.80–5.95 (2H, m), 7.59 (1H, br.s), 8.19, 8.34 (total 1H, each s).

MS (ES): 641 (M$^+$)

b) (1R,5S,6S)-2-[(3S,5S)-5-[6-(2-Cyclopropylmethyl)-5-methylimidazo[5,1-b]thiazolium-2-yl]methylpyrrolidin-3-yl]thio-6-((1R)-1-hydroxyethyl)-1-methylcarbapen-2-em-3-carboxylate (internal salt)

Anhydrous THF (0.7 ml) and 0.7 ml of dry ethanol are added to 47.9 mg of allyl(1R,5S,6S)-2-[(3S,5S)-1-allyloxycarbonyl-5-[6-(2-cyclopropylmethyl)-5-methylimidazo[5,1 -b]thiazolium-2-yl]methylpyrrolidin-3-yl]thio-6-((1R)-1-hydroxyethyl)-1-methylcarbapen-2-em-3-carboxylate trifluoromethanesulfonate. Triphenylphosphine (7.8 mg), 0.016 ml of morpholine, and 4.3 mg of tetrakis(triphenylphosphine)palladium(0) are successively added thereto, and the mixture is stirred in an argon atmosphere at room temperature for one hr. THF (10 ml) is added thereto, and the resultant precipitate is further washed twice with 3 ml of THF and dried in vacuo to give a yellow powder which is then purified by column chromatography on Cosmosil 40C18-PREP (water-methanol) to give 2.0 mg of the title compound as a slightly yellow powder.

NMR (D$_2$O) δ (HOD=4.80 ppm): 0.46–0.48 (2H, m), 0.70–0.76 (2H, m), 1.21 (3H, d, J=7.1 Hz), 1.28 (3H, d, J=6.4 Hz), 1.46–1.55 (1H, m), 2.54–2.66 (1H, m), 2.79 (3H, s), 3.05–3.20 (3H, m), 3.26–3.44 (3H, m), 3.54–3.63 (1H, m), 4.80–4.89 (1H, m), 4.11 (2H, d, J=7.4 Hz), 4.17–4.26 (2H, m), 7.59 (1H, s), 7.75 (1H, s).

Example 42

(1R,5S,6S)-2-[(3S,5S)-5-[6-(2-Fluoroethyl)-5-methylimidazo[5,1-b]thiazolium-2-yl]methylpyrrolidin-3-yl]thio-6-((1R)-1-hydroxyethyl)-1-methylcarbapen-2-em-3-carboxylic acid trifluoromethanesulfonate a) Allyl(1R,5S,6S)-2-[(3S,5S)-1-allyloxycarbonyl-5-[6-(2-fluoroethyl)-5-methylimidazo[5,1-b]thiazolium-2-yl]methylpyrrolidin-3-yl]thio-6-((1R)-1-hydroxyethyl)-1-methylcarbapen-2-em-3-carboxylate trifluoromethanesulfonate 2-Fluoroethyl trifluoromethanesulfonate (40.6 mg) is added to 30.6 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate described in Example 31-a), and the mixture is stirred in an argon atmosphere at room temperature for 3.5 hr. The solvent is removed by evaporation under reduced pressure. The residue is purified by column chromatography on Sephadex LH-20 (dichloromethane:methanol=1:1) to give 36.4 mg of allyl(1R,5S,6S)-2-[(3S,5S)-1-allyloxycarbonyl-5-[6-(2-fluoroethyl)-5-methylimidazo[5,1-b]thiazolium-2-yl]methylpyrrolidin-3-yl]thio-6-((1R)-1-hydroxyethyl)-1-methylcarbapen-2-em-3-carboxylate trifluoromethanesulfonate as a yellow oil.

NMR (CD$_3$OD) δ: 1.23 (3H, d, J=7.2 Hz), 1.28 (3H, d, J=6.3 Hz), 1.77–1.90 (1H, m), 2.60–2.73 (1H, m), 2.87 (3H, s), 3.20–3.41 (4H, m), 3.43–3.56 (1H, m), 3.82–3.91 (1H, m), 4.06–4.38 (4H, m), 4.62–4.80 (4H, m), 4.81–4.91 (4H, m), 5.20–5.42 (4H, m), 5.89–6.03 (2H, m), 7.68 (1H, s), 7.97 (1H, s).

MS (ES): 633 (M$^+$)

b) (1R,5S,6S)-2-[(3S,5S)-5-[6-(2-Fluoroethyl)-5-methylimidazo[5,1-b]thiazolium-2-yl)]methylpyrrolidin-3-yl]thio-6-((1R)-1-hydroxyethyl)-1-methylcarbapen-2-em-3-carboxylic acid trifluoromethanesulfonate Anhydrous THF (0.5 ml) and 0.5 ml of dry ethanol are added to 36.4 mg of allyl(1R,5S,6S)-2-[(3S,5S)-1-allyloxycarbonyl-5-[6-(2-fluoroethyl)-5-methylimidazo[5,1-b]thiazol-2-yl]methylpyrrolidin-3-yl]thio-6-((1R)-1-hydroxyethyl)-1-methylcarbapen-2-em-3-carboxylate. Triphenylphosphine (5.5 mg), 0.011 ml of morpholine, and 3.0 mg of tetrakis(triphenylphosphine)palladium(0) are successively added thereto, and the mixture is stirred in an argon atmosphere at room temperature for one hr. THF (10 ml) is added thereto, and the resultant precipitate is further washed twice with 3 ml of THF and dried in vacuo to give a yellow powder which is then purified by column chromatography on Cosmosil 40C18-PREP (water-methanol) to give 3.1 mg of the title compound as a colorless flocculent material.

NMR (D$_2$O) δ (HOD=4.80 ppm): 1.21 (3H, d, J=7.1 Hz), 1.28 (3H, d, J=6.4 Hz), 1.81–1.92 (1H, m), 2.79–2.89 (1H, m), 2.82 (3H, s), 3.33–3.49 (4H, m), 3.69–3.85 (2H, m), 4.05–4.28 (3H, m), 4.09–4.93 (4H, m), 7.59 (1H, s), 7.89 (1H, s).

Example 43

(1R,5S,6S)-6-((1R)-1-hydroxyethyl)-2-[(3S,5S)-5-[6-(2-hydroxyethyl)-5-methylimidazo[5,1-b]thiazolium-2-yl]methylpyrrolidin-3-yl]thio-1-methylcarbapen-2-em-3-carboxylic acid trifluoromethanesulfonate 2-(t-Butyldimethylsilyloxy)ethyl trifluoromethanesulfonate (20.4 mg) is added to a solution of 32.4 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate, described in Example 31-a), in 0.5 ml of dry dichloroethane, and the mixture is stirred in an argon atmosphere at room temperature for 2 hr. The excess reagent is removed by evaporation under reduced pressure to give allyl(1R,5S,6S)-2-[(3S,5S)-1-allyloxycarbonyl-5-[6-[2-(t-butyldimethylsilyloxy)ethyl]-5-methylimidazo[5,1-b]thiazolium-2-yl]methylpyrrolidin-3-yl]thio-6-((1R)-1-hydroxyethyl)-1-methylcarbapen-2-em-3-carboxylate trifluoromethanesulfonate as a brown oil. Acetic acid (0.0033 ml) and 0.056 ml of a 1 M tetra-n-butylammonium fluoride/THF solution are added to a solution of this compound in 0.5 ml of anhydrous THF, and the mixture is stirred in an argon atmosphere at room temperature for one hr. Dry ethanol (0.5 ml) is added thereto. Triphenylphosphine (5.8 mg), 0.012 ml of morpholine, and 3.2 mg of tetrakis(triphenylphosphine)palladium(0) are successively added to the mixture, and the mixture is stirred in an argon atmosphere at room temperature for one hr. THF (10 ml) is added thereto, and the resultant precipitate is further washed twice with 3 ml of THF and dried in vacuo to give a yellow powder which is then purified by column chromatography on Cosmosil 40C18-PREP (water-methanol) to give 4.62 mg of the title compound as a colorless flocculent material.

NMR (D$_2$O) δ (HOD=4.80 ppm): 1.21 (3H, d, J=7.2 Hz), 1.28 (3H, d, J=6.3 Hz), 1.81–1.91 (1H, m), 2.79–2.90 (1H, m), 2.82 (3H, s), 3.31–3.49 (5H, m), 3.68–3.76 (1H, m), 3.98 (2H, t, J=4.5 Hz), 4.02–4.12 (2H, m), 4.21–4.28 (1H, m), 4.41 (2H, t, J=4.5 Hz), 7.57 (1H, s), 7.89 (1H, s).

MS (ES): 507 (M$^+$)

Example 44

(1R,5S,6S)-2-[(3S,5S)-5-[6-N,N-Dimethylcarbamoylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate (internal salt)

a) Allyl(1R,5S,6S)-2-[(3S,5S)-1-allyloxycarbonyl-5-[6-N,N-dimethylcarbamoylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate iodide N,N-Dimethylchloroacetamide (0.03 ml) and 41.5 mg of sodium iodide are added to a solution of 32.5 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate, described in Example 31-a), in 0.5 ml of dry DMF, and the mixture is stirred in an argon atmosphere at room temperature for 27 hr. The solvent is removed by evaporation under reduced pressure. The residue is purified by column chromatography on Sephadex LH-20 (dichloromethane:methanol=1:1) to give 42.1 mg of allyl(1R,5S,6S)-2-[(3S,5S)-1-allyloxycarbonyl-5-[6-N,N-dimethylcarbamoylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate iodide as a yellow oil.

NMR (CDCl$_3$) δ: 1.16 (3H, d, J=7.4 Hz), 1.23 (3H, d, J=6.1 Hz), 1.63–1.76 (1H, m), 2.46–2.59 (1H, m), 2.83 (3H, s), 2.90 (3H, s), 3.15 (3H, s), 3.12–3.41 (4H, m), 3.58–3.68 (1H, m), 3.91–4.02 (1H, m), 4.08–4.27 (4H, m), 4.53–4.65 (3H, m), 4.61–4.78 (1H, m), 5.16–5.40 (4H, m), 5.70 (1H, br.s), 5.80–5.95 (2H, m), 7.72 (1H, br.s), 8.78 (1H, s).

MS (TS): 672 (M$^+$)

b) (1R,5S,6S)-2-[(3S,5S)-5-[6-N,N-Dimethylcarbamoylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate (internal salt)

Anhydrous THF (0.5 ml) and 0.5 ml of dry ethanol are added to 42.1 mg of allyl(1R,5S,6S)-2-[(3S,5S)1-allyloxycarbonyl-5-[6-N,N-dimethylcarbamoylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate iodide. Triphenylphosphine (5.8 mg), 0.012 ml of morpholine, and 3.1 mg of tetrakis-(triphenylphosphine)palladium(0) are successively added thereto, and the mixture is stirred in an argon atmosphere at room temperature for one hr. THF (10 ml) is added thereto, and the resultant precipitate is further washed twice with 3 ml of THF and dried in vacuo to give a yellow powder which is then purified by column chromatography on Cosmosil 40C18-PREP (water-methanol) to give 10.4 mg of the title compound as a white powder.

NMR (D$_2$O) δ (HOD=4.80 ppm): 1.20 (3H, d, J=7.1 Hz), 1.28 (3H, d, J=6.3 Hz), 1.42–1.51 (1H, m), 2.51–2.66 (1H, m), 2.71 (3H, s), 3.00 (3H, m), 3.03–3.44 (6H, m), 3.15 (3H, s), 3.50–3.60 (1H, m), 3.77–3.86 (1H, m), 4.18–4.28 (2H, m), 5.37 (2H, s), 7.43 (1H, s), 7.79 (1H, s).

Example 45

(1R,5S,6S)-6-((1R)-1-Hydroxyethyl)-2-[(3S,5S)-5-[6-methoxymethyl-5-methylimidazo[5,1-b]thiazolium-2-yl]methylpyrrolidin-3-yl]thio-1-methylcarbapen-2-em- 3-carboxylate (internal salt)

a) Allyl(1R,5S,6S)-2-[(3S,5S)-1-allyloxycarbonyl-5-[6-methoxymethyl)-5-methylimidazo[5,1-b]thiazolium-2-yl]methylpyrrolidin-3-yl]thio-6-((1R)-1-hydroxyethyl)-1-methylcarbapen-2-em-3-carboxylate iodide Iodomethyl methyl ether (0.01 ml) is added to a solution of 34.0 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate, described in Example 31-a), in 0.5 ml of dry acetone, and the mixture is stirred in an argon atmosphere at room temperature for 10 min. The solvent is removed by evaporation under reduced pressure. The residue is purified by column chromatography on Sephadex LH-20 (dichloromethane:methanol=1:1) to give 42.3 mg of allyl(1R,5S,6S)-2-[(3S,5S)-1-allyloxycarbonyl-5-[6-methoxymethyl-5-methylimidazo[5,1-b]thiazolium-2-yl]methylpyrrolidin-3-yl]thio-6-((1R)-1-hydroxyethyl)-1-methylcarbapen-2-em-3-carboxylate iodide as a yellow oil.

NMR (CDCl$_3$) δ: 1.18–1.32 (6H, m), 1.68–1.80 (1H, m), 2.58–2.70 (1H, m), 3.03 (3H, s), 3.12–3.28 (2H, m), 3.45 (3H, s), 3.91–4.02 (1H, m), 4.08–4.27 (4H, m), 3.90–4.36 (3H, m), 4.52–4.72 (4H, m), 5.17–5.49 (4H, m), 5.71 (1H, br.s), 5.80–5.97 (2H, m), 7.88 (1H, s), 8.10 (1H, br.s).

MS (TS): 631 (M$^+$)

b) (1R,5S,6S)-6-((1R)-1-Hydroxyethyl)-2-[(3S,5S)-5-[6-methoxymethyl-5-methylimidazo[5,1-b]thiazolium-2-yl]methylpyrrolidin-3-yl]thio-1-methylcarbapen-2-em-3-carboxylate (internal salt)

Anhydrous THF (0.5 ml) and 0.5 ml of dry ethanol are added to 47.9 mg of allyl(1R,5S,6S)-2-[(3S,5S)-1- allyloxycarbonyl-5-[6-methoxymethyl-5-methylimidazo[5,1-b]thiazolium-2-yl]methylpyrrolidin-3-yl]thio- 6-((1R)-1-hydroxyethyl)-1-methylcarbapen-2-em-3-carboxylate iodide. Triphenylphosphine (5.8 mg), 0.012 ml of morpholine, and 3.2 mg of tetrakis(triphenylphosphine) palladium(0) are successively added in an argon atmosphere at room temperature for 75 min. THF (10 ml) is added thereto, and the resultant precipitate is further washed twice with 3 ml of THF and dried in vacuo to give a yellow powder which is then purified by column chromatography on Cosmosil 40C18-PREP (water-methanol) to give 2.2 mg of the title compound as a colorless flocculent material.

NMR (D$_2$O) δ (HOD=4.80 ppm): 1.21 (3H, d, J=7.1 Hz), 1.29 (3H, d, J=6.3 Hz), 1.42–1.55 (1H, m), 2.54–2.66 (1H, m), 2.85 (3H, m), 3.03–3.43 (6H, m), 3.42 (3H, s), 3.54–3.61 (1H, m), 3.79–3.87 (1H, m), 4.19–4.28 (2H, m), 5.64 (2H, s), 7.65 (1H, s), 7.80 (1H, s).

Example 46

(1R,5S,6S)-2-[(3S,5S)-5-[6-Ethoxycarbonylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate (internal salt)

a) Allyl(1R,5S,6S)-2-[(3S,5S)-1-allyloxycarbonyl-5-[6-ethoxycarbonylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate bromide Bromoethyl acetate (0.04 ml) is added to a solution of 42.6 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate, described in Example 31-a), in 0.7 ml of dry acetone, and the mixture is stirred in an argon atmosphere at room temperature for one hr. The solvent is removed by evaporation under reduced pressure. The residue is purified by column chromatography on Sephadex LH-20 (dichloromethane:methanol=1:1) to give 49.7 mg of allyl (1R,5S,6S)-2-[(3S,5S)-1-allyloxycarbonyl-5-[6-ethoxycarbonylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate bromide as a brown oil.

NMR (CDCl$_3$) δ: 1.18 (3H, d, J=7.1 Hz), 1.27 (3H, d, J=6.0 Hz), 1.28 (3H, t, J=7.1 Hz), 1.66–1.76 (1H, m), 2.40–2.68 (2H, m), 2.52 (3H, s), 3.10–3.45 (4H, m), 3.52–3.68 (1H, m), 3.90–4.02 (1H, m), 4.05–4.27 (5H, m), 4.53–4.67 (3H, m), 4.70–4.79 (1H, m), 5.16–5.45 (4H, m), 5.50 (1H, br.s), 5.81–5.96 (2H, m), 7.87 (1H, s), 8.00 (1H, br.s).

MS (TS): 673 (M$^+$)

b) (1R,5S,6S)-2-[(3S,5S)-5-[6-Ethoxycarbonylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate (internal salt)

Anhydrous THF (0.6 ml) and 0.6 ml of dry ethanol are added to 49.7 mg of allyl(1R,5S,6S)-2-[(3S,5S)-1-allyloxycarbonyl-5-[6-ethoxycarbonylmethyl-5-methylimidazo[5,1-b]thiazolium-2-yl]methylpyrrolidin-3-yl]thio-6-((1R)-1-hydroxyethyl)-1-methylcarbapen-2-em-3-carboxylate bromide. Triphenylphosphine (6.9 mg), 0.014 ml of morpholine, and 3.8 mg of tetrakis (triphenylphosphine)palladium(0) are successively added thereto, and the mixture is stirred in an argon atmosphere at room temperature for 55 min. THF (10 ml) is added, the resultant precipitate is further washed twice with 3 ml of THF and dried in vacuo to give a yellow powder which is then purified by column chromatography on Cosmosil 40C18-PREP (water-methanol) to give 1.6 mg of the title compound as a colorless flocculent material.

NMR (D$_2$O) δ (HOD=4.80 ppm): 1.21 (3H, d, J=7.1 Hz), 1.28 (3H, d, J=6.4 Hz), 1.29 (3H, t, J=7.1 Hz), 1.44–1.57 (1H, m), 2.50–2.67 (1H, m), 2.77 (3H, s), 3.01–3.47 (5H, m), 3.50–3.87 (3H, m), 4.19–4.27 (2H, m), 4.30 (2H, q, J=7.1 Hz), 5.24 (2H, s), 7.52 (1H, s), 7.79 (1H, s).

Example 47

(1R,5S,6S)-6-(1(R)-Hydroxyethyl)-2-[(3S,5S)-5-[2(Z)-(6-methylimidazo[5,1-b]thiazol-2-yl)vinyl]pyrrolidin-3-yl]thio-1-methylcarbapen-2-em-3-carboxylic acid chloride and (1R,5S,6S)-6-(1(R)-hydroxyethyl)-2-[(3S,5S)-5-[2(E)-(6-methylimidazo[5,1-b]thiazol-2-yl)vinyl]pyrrolidin-3-yl]thio-1-methylcarbapen-2-em-3-carboxylic acid chloride a) Allyl(1R,5S,6S)-2-[(3S,5S)-1-allyloxycarbonyl-5-[2-(imidazo[5,1-b]thiazol-2-yl)vinyl]pyrrolidin-3-yl]thio-6-(1(R)-hydroxyethyl)-1-methylcarbapen-2-em-3-carboxylate (mixture of geometrical isomers)

A 1 N aqueous sodium hydroxide solution (1.2 ml) is added to a solution of 0.42 g of (3S,5S)-3-acetylthio-1-allyloxycarbonyl-5-[2-(imidazo[5,1-b]thiazol-2-yl)vinyl]pyrrolidine, described in Synthesis Example 15 in 7 ml of methanol under ice cooling, and the mixture is stirred at that temperature for 15 min. The mixture is adjusted to pH 7 by addition of 1 N aqueous hydrochloric acid solution, dichloromethane is added thereto, and the mixture is successively washed with water and saturated saline and dried over magnesium sulfate. The solvent is removed by evaporation to give a mercaptan compound. Diisopropylethylamine (0.29 ml) is added to a solution of this mercaptan and 0.56 g of allyl(1R,5S,6S)-6-(1(R)-hydroxyethyl)-2-(diphenylphosphono)oxy-1-methylcarbapen-2-em-3-carboxylate in 4 ml of acetonitrile under ice cooling, and the mixture is stirred for 30 min. Ethyl acetate is added to the reaction mixture. The mixture is successively washed with a saturated aqueous sodium hydrogencarbonate solution and saturated saline and dried over magnesium sulfate. The solvent is removed by evaporation. The residue is purified by column chromatography on silica gel to give 0.47 g of allyl(1R,5S,6S)-2-[(3S,5S)-1-allyloxycarbonyl-5-[2-(imidazo[5,1-b]thiazol-2-yl)vinyl]pyrrolidin-3-yl]thio-6-(1(R)-hydroxyethyl)-1-methylcarbapen-2-em-3-carboxylate (a mixture of geometrical isomers).

b) (1R,5S,6S)-6-(1(R)-hydroxyethyl)-2-[(3S,5S)-5-[2(Z)-(6-methylimidazo[5,1-b]thiazol-2-yl)vinyl]pyrrolidin-3-yl]thio-1-methylcarbapen-2-em-3-carboxylic acid chloride and (1R,5S,6S)-6-(1(R)-hydroxyethyl)-2-[(3S,5S)-5-[2(E)-(6-methylimidazo[5,1-b]thiazol-2-yl)vinyl]pyrrolidin-3-yl]thio-1-methylcarbapen-2-em-3-carboxylic acid chloride Methyl triflate (0.017 ml) is added to a solution of 86 mg of allyl(1R,5S,6S)-2-[(3S,5S)-1-allyloxycarbonyl-5-[2-(imidazo[5,1-b]thiazol-2-yl)vinyl]pyrrolidin-3-yl]thio-6-(1(R)-hydroxyethyl)-1-methylcarbapen-2-em-3-carboxylate (a mixture of geometrical isomers) in 1 ml of dichloromethane under ice cooling, and the mixture is stirred at that temperature for one hr. The reaction mixture is concentrated under reduced pressure. Ethyl alcohol (1 ml), 1 ml of THF, 0.033 ml of N-methylmorpholine, 16 mg of triphenylphosphine, and 40 mg of tetrakis (triphenylphosphine)palladium(0) are added thereto, and the mixture is stirred in an argon atmosphere at room temperature for 30 min. The reaction mixture is concentrated under reduced pressure. Water is added to the residue, and the mixture is washed with dichloromethane. The aqueous layer is purified by column chromatography on Cosmosil 40C18-PREP and Amberlyst A-26 (Cl⁻ form) to give 12.0 mg of (1R,5S,6S)-6-(1(R)-hydroxyethyl)-2-[(3S,5S)-5-[2(Z)-(6-methylimidazo[5,1-b]thiazol-2-yl)vinyl]pyrrolidin-3-yl]thio-1-methylcarbapen-2-em-3-carboxylic acid chloride and 5.4 mg of (1R,5S,6S)-6-(1(R)-hydroxyethyl)-2-[(3S,5S)-5-[2(E)-(6-methylimidazo[5,1-b]thiazol-2-yl)vinyl]pyrrolidin-3-yl]thio-1-methylcarbapen-2-em-3-carboxylic acid chloride.

(Z) form

NMR (D₂O) δ: 1.19 (3H, d, J=7.1 Hz), 1.28 (3H, d, J=6.3 Hz), 1.55–1.65 (1H, m), 2.65–2.80 (1H, m), 3.10–3.15 (1H, m), 3.30–3.45 (3H, m), 3.80–3.95 (1H, m), 4.07 (3H, s), 4.15–4.30 (2H, m), 4.30–4.40 (1H, m), 6.08 (1H, dd, J=11.6, 9.7 Hz), 6.62 (1H, d, J=11.6 Hz), 7.60 (1H, s), 7.92 (1H, s).

(E) form

NMR (D₂O) δ: 1.22 (3H, d, J=7.1 Hz), 1.28 (3H, d, J=6.3 Hz), 1.70–1.80 (1H, m), 2.70–2.80 (1H, m), 3.20–3.30 (1H, m), 3.30–3.55 (3H, m), 3.95–4.05 (1H, m), 4.07 (3H, s), 4.15–4.30 (3H, m), 6.29 (1H, dd, J=15.7 Hz, 7.7 Hz), 6.92 (1H, d, J=15.7 Hz), 7.57 (1H, s), 7.95 (1H, s).

Example 48

(5S,6S)-6-(1(R)-Hydroxyethyl)-2-[(3S,5S)-5-[2(Z)-(6-methylimidazo[5,1-b]thiazol-2-yl)vinyl] pyrrolidin-3-yl]thiocarbapen-2-em-3-carboxylic acid chloride and (5S,6S)-6-(1(R)-hydroxyethyl)-2-[(3S, 5S)-5-[2(E)-(6-methylimidazo[5,1-b]thiazol-2-yl) vinyl]pyrrolidin-3-yl]thiocarbapen-2-em-3-carboxylic acid chloride a) Allyl(5S,6S)-2-[(3S,5S)-1-allyloxycarbonyl5-[2-(imidazo[5,1-b]thiazol-2-yl)vinyl]pyrrolidin-3-yl] thio-6-(1(R)-hydroxyethyl)carbapen-2-em-3-carboxylate (mixture of geometrical isomers)

A 1 N aqueous sodium hydroxide solution (0.67 ml) is added to a solution of 0.24 g of (3S,5S)-3-acetylthio-1-allyloxycarbonyl-5-[2-(imidazo[5,1-b]thiazol-2-yl)vinyl] pyrrolidine (a mixture of geometrical isomers), described in Synthesis Example 15, in 6.3 ml of methanol under ice cooling. The mixture is stirred at that temperature for 15 min. The mixture is adjusted to pH 7 by addition of a 1 N aqueous hydrochloric acid solution, dichloromethane is added thereto, and the mixture is successively washed with water and saturated saline and dried over magnesium sulfate. The solvent is removed by evaporation to a mercaptan compound. Diisopropylethylamine (0.16 ml) is added to a solution of this mercaptan compound and 0.29 g of (5S,6S)-6-(1(R)-hydroxyethyl)-2 -(diphenylphosphono) oxycarbapen-2-em-3-carboxylate in 2 ml of acetonitrile under ice cooling, and the mixture is stirred for 30 min. Ethyl acetate is added to the reaction mixture, and the mixture is successively washed with a saturated sodium hydrogencarbonate solution and saturated saline and dried over magnesium sulfate. The solvent is removed by evaporation. The residue is purified by column chromatography on silica gel to give 0.18 g of (5S,6S)-2-[(3S,5S)-1-allyloxycarbonyl-5-[2-(imidazo[5,1-b]thiazol-2-yl)vinyl] pyrrolidin-3-yl]thio-6-(1(R)-hydroxyethyl)carbapen-2-em-3-carboxylate (a mixture of geometrical isomers).

b) (5S,6S)-6-(1(R)-hydroxyethyl)-2-[(3S,5S)-5-[2 (Z)-(6-methylimidazo[5,1-b]thiazol-2-yl)vinyl] pyrrolidin-3-yl]thiocarbapen-2-em-3-carboxylic acid chloride and (5S,6S)-6-(1(R)-hydroxyethyl)-2-[(3S, 5S)-5-[2(E)-(6-methylimidazo[5,1-b]thiazol-2-yl) vinyl]pyrrolidin-3-yl]thiocarbapen-2-em-3-carboxylic acid chloride Methyl triflate (0.018 ml) is added to 91 mg of a solution of (5S,6S)-2-[(3S,5S)-1-allyloxycarbonyl-5-[2-(imidazo[5, 1-b]thiazol-2-yl)vinyl]pyrrolidin-3-yl]thio-6-(1(R)-hydroxyethyl)carbapen-2-em-3-carboxylate (a mixture of geometrical isomers) in 1 ml of dichloromethane under ice cooling, and the mixture is stirred at that temperature for one hr. The reaction mixture is concentrated under reduced pressure. Ethanol (1 ml), 1 ml of THF, 0.033 ml of N-methylmorpholine, 16 mg of triphenylphosphine, and 40 mg of tetrakis(triphenylphosphine)palladium(0) are added to the concentrate, and the mixture is stirred in an argon atmosphere at room temperature for 30 min. The reaction mixture is concentrated under reduced pressure, water is added to the residue, and the mixture is washed with dichloromethane. The aqueous layer is purified by column chromatography on Cosmosil 40C18-PREP and Amberlyst A-26 (Cl⁻ form) to give 6.7 mg of (5S,6S)-6-(1(R)-hydroxyethyl)-2-[(3S,5S)-5-[2 (Z)-(6-methylimidazo[5,1-b] thiazol-2-yl)vinyl]pyrrolidin-3-yl]thiocarbapen-2-em-3-carboxylic acid chloride and 7.1 mg of (5S,6S)-6-(1(R)-hydroxyethyl)-2-[(3S,5S)-5-[2(E)-(6-methylimidazo[5,1-b] thiazol-2-yl)vinyl]pyrrolidin-3-yl]thiocarbapen-2-em-3-carboxylic acid chloride.

(Z) form

NMR (D₂O) δ: 1.27 (3H, d, J=6.3 Hz), 1.55–1.75 (1H, m), 2.65–2.80 (1H, m), 3.10–3.30 (2H, m), 3.35–3.40 (1H, m), 3.45–3.55 (1H, m), 3.60–3.80 (1H, m), 3.85–3.95 (1H, m), 4.07 (3H, s), 4.15–4.25 (2H, m), 4.35–4.45 (1H, m), 6.08 (1H, dd, J=11.6 Hz, 9.7 Hz), 6.63 (1H, d, J=11.6 Hz), 7.60 (1H, s), 7.92 (1H, s).

(E) form

NMR (D₂O) δ: 1.27 (3H, d, J 6.4 Hz), 1.80–1.95 (1H, m), 2.65–2.85 (1H, m), 3.15–3.25 (2H, m), 3.25–3.35 (1H, m), 3.35–3.40 (1H, m), 3.60–3.80 (2H, m), 3.95–4.05 (1H, m), 4.07 (3H, s), 4.15–4.35 (2H, m), 6.08 (1H, dd, J=15.6 Hz, 7.5 Hz), 6.94 (1H, d, J=15.6 Hz), 7.57 (1H, s), 7.96 (1H, s).

Example 49

(1R,5S,6S)-2-[(3S,5S)-5-[Imidazo[5,1-b]thiazol-3-yl]pyrrolidin-3-yl]thio-6-((1R)-1-hydroxyethyl)-1-methylcarbapen-2-em-3-carboxylic acid a) Allyl(1R,5S,6S)-2-[(3S,5S)-1-allyloxycarbonyl-5-(imidazo[5,1-b]thiazol-3-yl)pyrrolidin-3-yl]thio-6-((1R)-hydroxyethyl)-1-methylcarbapen-2-em-3-carboxylate A 1 N aqueous sodium hydroxide solution (0.76 ml) is added to a solution of 0. 27 g of (3S,5S)-3-acetylthio-1-allyloxycarbonyl-5-(imidazo[5,1-b]thiazol-3-yl)pyrrolidine, described in Synthesis Example 16, in 3.5 ml of methanol under ice cooling, and the mixture is stirred at that temperature for 15 min. The mixture is neutralized with a 1 N hydrochloric acid solution, dichloromethane is added thereto, and the mixture is successively washed with water and saturated saline. The organic layer is dried over magnesium sulfate. The solvent is removed by evaporation to give a mercaptan compound. Diisopropylethylamine (0.14 ml) is added to a solution of this mercaptan and 0.38 g of allyl(1R,5S,6S)-2-(diphenylphosphino)oxy-6-((1R)-1-hydroxyethyl)-1-methylcarbapen-2-emcarboxylate in 2 ml of acetonitrile under ice cooling, and the mixture is stirred at that temperature for 30 min. Ethyl acetate is added to the reaction mixture, and the mixture is successively washed with a saturated sodium hydrogencarbonate solution and saturated saline and dried over magnesium sulfate. The solvent is removed by evaporation. The residue is purified by column chromatography on silica gel (methanol:ethyl acetate=12:88) to give 0.24 g of allyl(1R,5S,6S)-2-[(3S,5S)-1-allyloxycarbonyl-5-(imidazo[5,1-b]thiazol-3-yl)pyrrolidin-3-yl]thio-6-((1R)-1-hydroxyethyl)-1-methylcarbapen-2-em-3-carboxylate.

b) (1R,5S,6S)-2-[(3S,5S)-5-[Imidazo[5,1-b]thiazol-3-yl]pyrrolidin-3-yl]thio-6-((1R)-1-hydroxyethyl)-1-methylcarbapen-2-em-3-carboxylic acid Allyl(1R,5S,6S)-2-[(3S,5S)-1-allyloxycarbonyl-5-(imidazo[5,1-b]thiazol-3-yl)pyrrolidin-3-yl]thio-6-((1R)-1-hydroxyethyl-1-methylcarbapen-2-em-3-carboxylate (65 mg) is dissolved in 0.75 ml of ethanol and 0.75 ml of THF. Triphenylphosphine (12 mg) and 0.025 ml of morpholine are added thereto, and 40 mg of tetrakis(triphenylphosphine)palladium(0) is further added thereto, and the mixture is stirred in an argon atmosphere at room temperature for 30 min. The reaction mixture is brought into a powder using ethyl acetate, and the powder is then purified by column chromatography on Cosmosil 40C18-PREP (30% aqueous methanol solution) to give 10 mg of the title compound.

NMR (D$_2$O) δ (HOD=4.80 ppm): 1.24 (3H, d, J=7.3 Hz), 1.30 (3H, d, J=6.3 Hz), 2.00–2.10 (1H, m), 2.85–3.00 (1H, m), 3.05–3.10 (1H, m), 3.40–3.55 (2H, m), 3.65–3.85 (2H, m), 4.15–4.30 (2H, m), 4.65–4.70 (1H, m), 7.13 (1H, s), 7.15 (1H, s), 8.28 (1H, s).

Example 50

(1R,5S,6S)-6-((1R)-1-Hydroxyethyl)-1-methyl-2-[(3S,5S)-5-[(6-methylimidazo[5,1-b]thiazolium)-3-yl]pyrrolidin-3-yl]thiocarbapen-2-em-3-carboxylic acid chloride Methyl triflate (19 μl) is added to 80 mg of allyl(1R,5S,6S)-2-[(3S,5S)-1-allyloxycarbonyl-5-(imidazo[5,1-b]thiazol-3-yl)pyrrolidin-3-yl]thio-6-((1R)-1-hydroxyethyl)-1-methylcarbapen-2-em-3-carboxylate, described in Example 49a), in 1 ml of dichloromethane under ice cooling, and the mixture is stirred for one hr. The reaction mixture is concentrated under reduced pressure, and the residue is dissolved in 0.75 ml of ethanol and 0.75 ml of THF. Triphenylphosphine (12 mg) and 0.025 ml of morpholine are added to the solution, 40 mg of tetrakis(triphenylphosphine)palladium(0) is further added thereto, and the mixture is stirred in an argon atmosphere at room temperature for 30 min. The reaction mixture is brought into a powder using ethyl acetate, and the powder is purified by column chromatography on Cosmosil 40C18-PREP (30% aqueous methanol solution) and Amberlyst A-26 (Cl$^-$ form) (water) to give 8.9 mg of the title compound.

NMR (D$_2$O) δ (HOD=4.80 ppm): 1.24 (3H, d, J=7.3 Hz), 1.30 (3H, d, J=6.3 Hz), 1.90–2.00 (1H, m), 2.80–2.90 (1H, m), 2.98 (1H, dd, J=5.3, 11.9 Hz), 3.40–3.50 (3H, m), 3.85–3.95 (1H, m), 4.11 (3H, s), 4.20–4.30 (2H, m), 4.63 (1H, t, J=7.7 Hz), 7.48 (1H, s), 7.62 (1H, s), 9.35 (1H, s).

Example 51

(1R,5S,6S)-2-[(3S,5S)-5-[(6-Carbamoylmethylimidazo[5,1-b]thiazolium)-3-yl]pyrrolidin-3-yl]thio-6-((1R)-1-hydroxyethyl)-1-methylcarbapen-2-em-3-carboxylic acid iodide Iodoacetamide (258 mg) is added to a solution of 76 mg of allyl(1R,5S,6S)-2-[(3S,5S)-1-allyloxycarbonyl-5-(imidazo[5,1-b]thiazol-3-yl)pyrrolidin-3-yl]thio-6-((1R)-1-hydroxyethyl)-1-methylcarbapen-2-em-3-carboxylate, described in Example 49-a), in 1 ml of acetone, and the mixture is stirred in an argon atmosphere in a light-shielded state at room temperature for 20 hr. The mixture is subjected to evaporation under reduced pressure. The residue is purified by column chromatography on Sephadex LH-20 (dichloromethane:methanol=1:1) and dissolved in 0.75 ml of ethanol and 0.75 ml of THF. Triphenylphosphine (12 mg) and 0.025 ml of morpholine are added to the solution, 40 mg of tetrakis(triphenylphosphine)palladium(0) is further added thereto, and the mixture is stirred in an argon atmosphere at room temperature for 30 min. The reaction mixture is brought into a powder using ethyl acetate, and the powder is purified by column chromatography on Cosmosil 40C18-PREP (15% aqueous methanol solution) to give 17.9 mg of the title compound.

NMR (D$_2$O) δ (HOD=4.80 ppm): 1.24 (3H, d, J=7.3 Hz), 1.30 (3H, d, J=6.3 Hz), 1.90–2.00 (1H, m), 2.80–2.90 (1H, m), 2.97 (1H, dd, J=5.2, 11.8 Hz), 3.35–3.50 (3H, m), 3.85–3.90 (1H, m), 4.20–4.30 (2H, m), 4.64 (1H, t, J=7.7 Hz), 5.30 (2H, s), 7.51 (1H, s), 7.73 (1H, s).

Example 52

(1R,5S,6S)-2-[(3S,5S)-5-[2-(Imidazo[5,1-b]thiazol-2-yl)ethenyl]pyrrolidin-3-yl]thio-6-((1R)-1-hydroxyethyl)-1-methylcarbapen-2-em-3-carboxylic acid a) Allyl(1R,5S,6S)-2-[(3S,5S)-1-allyloxycarbonyl-5-[2-(imidazo[5,1-b]thiazol-2-yl)ethenyl]pyrrolidin-3-yl]thio-6-((1R)-1-hydroxyethyl)-1-methylcarbapen-2-em-3-carboxylate The procedure of Example 49-a) is repeated, except that 0.42 g of (3S,5S)-3-acetylthio-1-allyloxycarbonyl-5-[2-(imidazo[5,1-b]thiazol-3-yl)ethenyl]pyrrolidine (a mixture of geometrical isomers) described in Synthesis Example 15 is used. Thus, 0.27 g of allyl(1R,5S,6S)-2-[(3S,5S)-1-allyloxycarbonyl-5-[[2-(imidazo[5,1 -b]thiazol-2-yl)ethenyl]pyrrolidin-3-yl]thio-6-((1R)-1-hydroxyethyl)-1-methylcarbapen-2-em-3-carboxylate (mixture of geometrical isomers) is prepared.

b) (1R,5S,6S)-2-[(3S,5S)-5-[[2-[Imidazo[5,1-b]thiazol-2-yl]ethenyl]pyrrolidin-3-yl]thio-6-((1R)-1-hydroxyethyl)-1-methylcarbapen-2-em-3-carboxylic acid The procedure of Example 49-b) is repeated, except that 86 mg of allyl(1R,5S,6S)-2-[(3S,5S)-1-allyloxycarbonyl-5-[[2-(imidazo[5,1-b]thiazol-2-yl)ethenyl]pyrrolidin-3-yl]thio-6-((1R)-1-hydroxyethyl)-1-methylcarbapen-2-em-3-carboxylate (a mixture of geometrical isomers) is used. Thus, 86 mg of the title compound (a mixture of geometrical isomers) is prepared.

NMR (D₂O) δ (HOD=4.80 ppm): 1.24 (3H, d, J=7.3 Hz), 1.30 (3H, d, J=6.3 Hz), 1.90–2.00 (1H, m), 2.80–2.90 (1H, m), 3.35–3.50 (3H, m), 3.65–3.80 (1H, m), 4.00–4.10 (1H, m), 4.20–4.45 (3H, m), 5.94 (0.5H, t, J=11.2 Hz), 6.94 (0.5H, d, J=15.9 Hz), 7.03, 7.07 (1H, s, each), 7.76 (1H, s), 8.14, 8.18 (1H, s, each).

Example 53

1R,5S,6S)-2-[(3S,5S)-5-[2(E)-(6-(Carbamoylmethyl) imidazo[5,1-b]thiazolium-2-yl)ethenyl]pyrrolidin-3-yl]thio-6-((1R)-1-hydroxyethyl)-1-methylcarbapen-2-em-3-carboxylic acid iodide (E form) (CP0742) and (1R,5S,6S)-2-[(3S,5S)-5-[2(Z)-(6-(carbamoylmethyl)imidazo[5,1-b]thiazolium-2-yl) ethenyl]pyrrolidin-3-yl]thio-6-((1R)-1-hydroxyethyl)-1-methylcarbapen-2-em-3-carboxylic acid iodide (Z form)

The procedure of Example 51 is repeated, except that 86 mg of allyl(1R,5S,6S)-2-[(3S,5S)-1-allyloxycarbonyl-5-[[2-(imidazo[5,1-b]thiazol-2-yl)ethenyl]pyrrolidin-3-yl]thio-6-((1R)-1-hydroxyethyl)-1-methylcarbapen-2-em-3-carboxylate (a mixture of geometrical isomers) described in Example 52-a) is used. Thus, the title compound (E form 11.0 mg; Z form 9.2 mg) is prepared.

(E form)

NMR (D₂O) δ (HOD=4.80 ppm): 1.24 (3H, d, J=7.3 Hz), 1.30 (3H, d, J=6.3 Hz), 1.50–1.60 (1H, m), 2.55–2.70 (1H, m), 3.03 (1H, dd, J=3.6, 11.9 Hz), 3.25–3.45 (3H, m), 3.80–3.95 (2H, m), 4.15–4.30 (2H, m), 5.25 (2H, s), 6.30 (1H, dd, J=7.1, 15.9 Hz), 6.80 (1H, d, J=15.9 Hz), 7.62 (1H, s), 7.94 (1H, s).

(Z form)

NMR (D₂O) δ (HOD=4.80 ppm): 1.24 (3H, d, J=7.3 Hz), 1.30 (3H, d, J=6.3 Hz), 1.90–2.00 (1H, m), 2.80–2.90 (1H, m), 3.05 (1H, dd, J=3.6, 11.9 Hz), 3.31 (1H, dd, J=6.1, 11.9 Hz), 3.35–3.45 (2H, m), 3.85–3.95 (1H, m), 4.20–4.35 (3H, m), 5.28 (2H, s), 6.11 (1H, t, J=11.4 Hz), 6.58 (1H, d, J=11.4 Hz), 7.67 (1H, s), 7.95 (1H, s).

Example 54

(1R,5S,6S)-2-[(3S,5S)-5-[[2(Z)-(6-(Carbamoylmethyl)imidazo[5,1-b]thiazolium-3-yl) ethenyl]pyrrolidin-3-yl]thio-6-((1R)-1-hydroxyethyl)-1-methylcarbapen-2-em-3-carboxylic acid iodide The procedure of Example 51 is repeated, except that 57 mg of allyl(1R,5S,6S)-2-[(3S,5S)-1-allyloxycarbonyl-5-[[2 (Z)-(imidazo[5,1-b]thiazol-3-yl)ethenyl]pyrrolidin-3-yl] thio-6-((1R)-1-hydroxyethyl)-1-methylcarbapen-2-em-3-carboxylate described in Example 38-a) is used. Thus, 2.3 mg of the title compound is prepared.

NMR (D₂O) δ (HOD=4.80 ppm): 1.24 (3H, d, J=7.3 Hz), 1.30 (3H, d, J=6.3 Hz), 1.50–1.60 (1H, m), 2.55–2.70 (1H, m), 3.03 (1H, dd, J=3.6, 12.1 Hz), 3.26 (1H, dd, J=6.3, 12.1 Hz), 3.30–3.45 (2H, m)3.75–3.85 (1H, m), 4.15–4.30 (3H, m), 5.28 (2H, s), 6.31 (1H, t, J=11.5 Hz), 6.50 (1H, d, J=11.5 Hz), 7.43 (1H, s), 7.70 (1H, s).

Example 55

(1R,5S,6S)-2-[(3S,5S)-5-[2(E)-(6-(Carbamoylmethyl)imidazo[5,1-b]thiazol-3-yl) ethenyl]pyrrolidin-3-yl]thio-6-((1R)-1-hydroxyethyl)-1-methylcarbapen-2-em-3-carboxylic acid chloride Iodoacetamide (703 mg) is added to a solution of 218 mg of allyl(1R,5S,6S)-2-[(3S,5S)-1-allyloxycarbonyl-5-[[2(E)-(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 2 ml of acetone, and the mixture is stirred in an argon atmosphere in a light-shielded state at room temperature for 20 hr. The mixture is subjected to evaporation under reduced pressure. The residue is purified by column chromatography on Sephadex LH-20 (dichloromethane:methanol=1:1) and Amberlyst A-26 (Cl⁻ form) (water). The procedure of Example 49-b) is repeated, except that the purification product prepared just above is used. Thus, 40.5 mg of the title compound is prepared.

NMR (D₂O) δ (HOD=4.80 ppm): 1.24 (3H, d, J=7.3 Hz), 1.30 (3H, d, J=6.3 Hz), 1.50–1.60 (1H, m), 2.55–2.70 (1H, m), 3.22 (1H, dd, J=3.6, 12.1 Hz), 3.35–3.50 (3H, m), 3.90–4.00 (1H, m), 5.32 (2H, s), 6.55 (1H, dd, J=7.5, 16.2 Hz), 6.80 (1H, d, J=16.2 Hz), 7.62 (1H, s), 7.74 (1H, s).

Example 56

(1R,5S,6S)-2-[(3S,5S)-5-[2(E)-(6-(Carbamoylethyl) imidazo[5,1-b]thiazol-3-yl)ethenyl]pyrrolidin-3-yl] thio-6-((1R)-1-hydroxyethyl)-1-methylcarbapen-2-em-3-carboxylic acid iodide Sodium iodide (70 mg) and 71 mg of propionamide bromide are added to a solution of 55 mg of allyl(1R,5S, 6S)-2-[(3S,5S)-1-allyloxycarbonyl-5-[2(E)-(imidazo[5,1-b] thiazol-3-yl)ethenyl]pyrrolidin-3-yl]thio-6-((1R)-1-hydroxyethyl)-1-methylcarbapen-2-em-3-carboxylate, described in Example 38-a) in 1 ml of acetone and 0.5 ml of DMF, and the mixture is stirred in a light-shielded state at room temperature for 36 hr. The solvent is removed under reduced pressure, and the residue is purified by column chromatography on Sephadex LH-20 (dichloromethane:methanol=1:1). The procedure of Example 49-a) is repeated, except that the purification product prepared just above is used. Thus, 2 mg of the title compound is prepared.

NMR (D₂O) δ (HOD=4.80 ppm): 1.24 (3H, d, J=7.3 Hz), 1.30 (3H, d, J=6.3 Hz), 1.50–1.60 (1H, m), 2.55–2.70 (1H, m), 3.00 (2H, t, J=6.3 Hz), 3.07 (1H, dd, J=6.4, 11.6 Hz), 3.25–3.45 (2H, m), 3.85–4.00 (2H, m), 4.20–4.30 (2H, m), 4.70 (2H, t, J=6.3 Hz), 6.54 (1H, d, J=15.9 Hz), 6.70 (1H, dd, J=7.4, 15.9 Hz), 7.51 (1H, s), 7.72 (1H, s).

Example 57

(1R,5S,6S)-2-[(3S,5S)-5-[2(Z)-(6-(Carbamoylmethyl)imidazo[5,1-b]thiazolium-5-yl) ethenyl]pyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-Allyloxycarbonyl-5-[2-(imidazo[5,1-b]thiazol-2-yl)ethenyl]pyrrolidin-5-yl]thio-6-((1R)-1-hydroxyethyl)-1-methylcarbapen-2-em-3-carboxylate The procedure of Example 49-a) is repeated, except that 0.25 g of (3S,5S)-3-acetylthio-1-allyloxycarbonyl-5-(imidazo[5,1-b]thiazol-5-yl)pyrrolidine (a mixture of geometrical isomers) described in Synthesis Example 17 is used. Thus, 0.24 g of allyl(1R,5S,6S)-2-[(3S,5S)-1-allyloxycarbonyl-5-[2-(imidazo[5,1-b]thiazol-2-yl)ethenyl] pyrrolidin-5-yl]thio-6-((1R)-1-hydroxyethyl)-1-methylcarbapen-2-em-3-carboxylate (a mixture of geometrical isomers) is prepared.

b) (1R,5S,6S)-2-[(3S,5S)-5-[2(Z)-(6-
(Carbamoylmethyl)imidazo[5,1-b]thiazolium-3-yl)
ethenyl]pyrrolidin-5-yl]thio-6-((1R)-1-
hydroxyethyl)-1-methylcarbapen-2-em-3-carboxylic
acid iodide The procedure of Example 51 is prepared, except that 135 mg of allyl(1R,5S,6S)-2-[(3S,5S)-1-allyloxycarbonyl-5-[2-(imidazo[5,1-b]thiazol-2-yl)ethenyl]pyrrolidin- 5-yl]thio-6-((1R)-1-hydroxyethyl)-1-methylcarbapen-2-em-3-carboxylate is used. Thus, 12.3 mg of the title compound is prepared.

NMR (D$_2$O) δ (HOD=4.80 ppm): 1.24 (3H, d, J=7.3 Hz), 1.30 (3H, d, J=6.3 Hz), 1.50–1.60 (1H, m), 2.55–2.70 (1H, m), 3.20 (1H, dd, J=3.1, 11.8 Hz), 3.35–3.55 (3H, m), 3.90–4.00 (1H, m), 4.20–4.30 (3H, m), 5.28 (2H, s), 6.83 (2H, m), 7.68 (1H, d, J=4.4 Hz), 7.73 (1H, s), 8.10 (1H, d, J=4.4 Hz).

Example 58

(1R,5S,6S)-2-[(3S,5S)-5-[2(E)-(6-
(Carbamoylmethyl)imidazo[5,1-b]thiazolium-7-yl)
ethenyl]pyrrolidin-3-yl]thio-6-((1R)-1-
hydroxyethyl)-1-methylcarbapen-2-em-3-carboxylic
acid iodide a) Allyl(1R,5S,6S)-2-[(3S,5S)-1-allyloxycarbonyl-5-
[[2-(imidazo[5,1-b]thiazol-2-yl)ethenyl]pyrrolidin-5-
yl]thio-6-((1R)-1-hydroxyethyl)-1-methylcarbapen-
2-em-3-carboxylate The procedure of Example 49-a) is repeated, except that 0.26 g of (3S,5S)-3-acetylthio-1-allyloxycarbonyl-5-(imidazo[5,1-b]thiazol-7-yl)pyrrolidine (a mixture of geometrical isomers) described in Synthesis Example 18 is used. Thus, 0.23 g of allyl(1R,5S,6S)-2-[(3S,5S)-1-allyloxycarbonyl-5-[[2-(imidazo[5,1-b]thiazol-2-yl)ethenyl]pyrrolidin-5-yl]thio-6-((1R)-1-hydroxyethyl)-1-methylcarbapen-2-em-3-carboxylate (a mixture of geometrical isomers) is prepared.

b) (1R,5S,6S)-2-[(3S,5S)-5-[2(E)-(6-
(Carbamoylmethyl)imidazo[5,1-b]thiazolium-3-yl)
ethenyl]pyrrolidin-5-yl]thio-6-((1R)-1-
hydroxyethyl)-1-methylcarbapen-2-em-3-carboxylic
acid iodide The procedure of Example 51 is repeated, except that 211 mg of allyl(1R,5S,6S)-2-[(3S,5S)-1-allyloxycarbonyl-5-[[2-(imidazo[5,1-b]thiazol-2-yl)ethenyl]pyrrolidin-7-yl]thio-6-((1R)-1-hydroxyethyl)-1-methylcarbapen-2-em-3-carboxylate is used. Thus, 28.6 mg of the title compound is prepared.

NMR (D$_2$O) δ (HOD=4.80 ppm): 1.24 (3H, d, J=7.3 Hz), 1.30 (3H, d, J=6.3 Hz), 1.50–1.60 (1H, m), 2.55–2.70 (1H, m), 3.00–3.10 (1H, m), 3.35–3.45 (3H, m), 3.75–4.00 (3H, m), 4.15–4.30 (2H, m), 5.30 (2H, s), 6.29 (1H, dd, J=7.2, 16.0 Hz), 6.60 (1H, d, J=16.0 Hz), 7.68 (1H, d, J=4.4 Hz), 8.00 (1H, d, J=4.4 Hz).

Example 59

(1R,5S,6 )-2–3S,5S)-5-[2(E)-(6-(Carbamoylmethyl)-
3-methylimidazo[5,1-b]thiazolium-2-yl)ethenyl]
pyrrolidin-3-yl]thio-6-((1R)-1-hydroxyethyl)-1-
methylcarbapen-2-em-3-carboxylic acid iodide (E
form) and (1R,5S,6S)-2-[(3S,5S)-5-[2(Z)-(6-
(carbamoylmethyl)-3-methylimidazo[5,1-b]
thiazolium-2-yl)ethenyl]pyrrolidin-3-yl]thio-6-((1R)-
1-hydroxyethyl)-1-methylcarbapen-2-em-3-
carboxylic acid iodide (Z form)

a) Allyl(1R,5S,6S)-2-[(3S,5S)-1-allyloxycarbonyl-5-
[[2-(3-methylimidazo[5,1-b]thiazol-2-yl)ethenyl]
pyrrolidin-3-yl]thio-6-((1R)-1-hydroxyethyl)-1-
methylcarbapen-2-em-3-carboxylate The procedure of Example 49-a) is repeated, except that 0.20 g of (3S,5S)-3-acetylthio-1-allyloxycarbonyl-5-(3-methylimidazo[5,1-b]thiazol-2-yl)pyrrolidine (a mixture of geometrical isomers) described in Synthesis Example 19 is used. Thus, 0.20 g of allyl(1R,5S,6S)-2-[(3S,5S)-1-allyloxycarbonyl-5-[[2-(3-methylimidazo[5,1-b]thiazol-2-yl)ethenyl]pyrrolidin-3-yl]thio-6-((1R)-1-hydroxyethyl)-1-methylcarbapen-2-em-3-carboxylate (a mixture of geometrical isomers) is prepared.

b) (1R,5S,6S)-2-[(3S,5S)-5-[2(E)-(6-
(Carbamoylmethyl)-3-methylimidazo[5,1-b]
thiazolium-2-yl)ethenyl]pyrrolidin-3-yl]thio-6-((1R)-
1-hydroxyethyl)-1-methylcarbapen-2-em-3-
carboxylic acid iodide (E form) and (1R,5S,6S)-2-
[(3S,5S)-5-[2(Z)-(6-(carbamoylmethyl)-3-
methylimidazo[5,1-b]thiazolium-2-yl)ethenyl]
pyrrolidin-3-yl]thio-6-((1R)-1-hydroxyethyl)-1-
methylcarbapen-2-em-3-carboxylic acid iodide (Z
form)

The procedure of Example 51 is repeated, except that 0.20 g of allyl(1R,5S,6S)-2-[(3S,5S)-1-allyloxycarbonyl-5-[2-(3-methylimidazo[5,1-b]thiazol-2-yl)ethenyl]pyrrolidin-3-yl]thio-6-((1R)-1-hydroxyethyl)-1-methylcarbapen-2-em-3-carboxylate (a mixture of geometrical isomers) is used. Thus, the title compound (E form 10.5 mg, Z form 6.2 mg) is prepared.

(E form)

NMR (D$_2$O) δ (HOD=4.80 ppm): 1.24 (3H, d, J=7.3 Hz), 1.30 (3H, d, J=6.3 Hz), 1.50–1.60 (1H, m), 2.51 (3H, s), 2.55–2.70 (1H, m), 3.03 (1H, dd, J=3.6, 12.1 Hz), 3.25–3.45 (3H, m), 3.80–3.95 (2H, m), 4.20–4.30 (2H, m), 5.25 (2H, m), 6.22 (1H, dd, 3=7.4, 15.1 Hz), 6.82 (1H, d, J=15.1 Hz), 7.60 (1H, s).

(Z form)

NMR (D$_2$O) δ (HOD=4.80 ppm): 1.22 (3H, d, J=7.3 Hz), 1.25–1.30 (3H, m), 1.45–1.55 (1H, m), 2.45 (3H, s), 2.95–3.05 (1H, m), 3.20–3.45 (2H, m), 3.65–3.90 (3H, m), 4.10–4.25 (3H, m), 5.27 (2H, s), 6.10 (1H, t, J=11.1 Hz), 6.55 (1H, d, J=11.1 Hz), 7.65 (1H, s).

Example 60

(1R,5S,6S)-2-[(3S,5S)-5-[2(E)-(6-
(Carbamoylmethyl)-2-methylimidazo[5,1-b]
thiazolium-3-yl)ethenyl]pyrrolidin-3-yl]thio-6-((1R)-
1-hydroxyethyl)-1-methylcarbapen-2-em-3-
carboxylic acid iodide (E form) and (1R,5S,6S)-2-
[(3S,5S)-5-[2(Z)-(6-(carbamoylmethyl)-2-
methylimidazo[5,1-b]thiazolium-3-yl)ethenyl]
pyrrolidin-3-yl]thio-6-((1R)-1-hydroxyethyl)-1-
methylcarbapen-2-em-3-carboxylic acid iodide (Z
form)

a) Allyl(1R,5S,6S)-2-[(3S,5S)-1-allyloxycarbonyl-5-
[2-(2-methylimidazo[5,1-b]thiazol-3-yl)ethenyl]
pyrrolidin-3-yl]thio-6-((1R)-1-hydroxyethyl)-1-
methylcarbapen-2-em-3-carboxylate The procedure
of Example 49-a) is repeated, except that 0.20 g of
(3S,5S)-3-acetylthio-1-allyloxycarbonyl-5-(2-
methylimidazo[5,1-b]thiazol- 3-yl)pyrrolidine (a
mixture of geometrical isomers) described in
Synthesis Example 20 is used. Thus, 0.15 g of allyl
(1R,5S,6S)-2-[(3S,5S)-1-allyloxycarbonyl-5-[2-(2-
methylimidazo[5,1-b]thiazol-3-yl)ethenyl]
pyrrolidin-3-yl]thio-6-((1R)-1-hydroxyethyl)-1-
methylcarbapen-2-em-3-carboxylate (a mixture of
geometrical isomers) is prepared.

b) (1R,5S,6S)-2-[(3S,5S)-5-[2(E)-(6-
(Carbamoylmethyl)-2-methylimidazo[5,1-b]
thiazolium-3-yl)ethenyl]pyrrolidin-3-yl]thio-6-((1R)-
1-hydroxyethyl)-1-methylcarbapen-2-em-3-
carboxylic acid iodide (E form) and (1R,5S,6S)-2-
[(3S,5S)-5-[2(Z)-(6-(carbamoylmethyl)-2-
methylimidazo[5,1-b]thiazolium-3-yl)ethenyl]
pyrrolidin-3-yl]thio-6-((1R)-1-hydroxyethyl)-1-
methylcarbapen-2-em-3-carboxylic acid iodide (Z
form)

The procedure of Example 51 is repeated, except that 0.15 g of allyl(1R,5S,6S)-2-[(3S,5S)-1-allyloxycarbonyl-5-[[2-

(2-methylimidazo[5,1-b]thiazol-3-yl)ethenyl]pyrrolidin-3-yl]thio-6-((1R)-1-hydroxyethyl)-1-methylcarbapen-2-em-3-carboxylate (a mixture of geometrical isomers). Thus, the title compound (E form 10.2 mg, Z form 7.4 mg) is prepared.

(E form)

NMR (D$_2$O) δ (HOD=4.80 ppm): 1.24 (3H, d, J=7.3 Hz), 1.30 (3H, d, J=6.3 Hz), 1.50–1.60 (1H, m), 2.48 (3H, s), 2.55–2.70 (1H, m), 3.03 (1H, dd, J=3.3, 11.9 Hz), 3.25–3.45 (3H, m), 3.80–3.40 (2H, m), 4.15–4.30 (2H, m), 5.29 (2H, s), 6.40 (1H, dd, J=7.4, 16.4 Hz), 6.66 (1H, d, J=16.4 Hz), 7.63 (1H, s).

(Z form)

NMR (D$_2$O) δ (HOD=4.80 ppm): 1.18 (3H, d, J=7.3 Hz), 1.25 (3H, d, J=6.4 Hz), 1.45–1.55 (1H, m), 2.40 (3H, s), 2.40–2.50 (1H, m), 2.92 (1H, dd, J=3.5, 11.8 Hz), 3.13 (1H, dd, J=6.2, 11.9 Hz), 3.40–3.50 (2H, m), 3.65–3.85 (3H, m), 4.15–4.30 (2H, m), 5.22 (2H, s), 6.29 (1H, d, J=10.7 Hz), 6.38 (1H, t, J=10.7 Hz), 7.60 (1H, s).

Example 61

(1R,5S,6S)-6-((1R)-1-Hydroxyethyl)-1-methyl-2-[(3S,5S)-5-(5-methylthioimidazo[5,1-b]thiazol-2-yl)methylpyrrolidin-3-yl]thiocarbapen-2-em-3-carboxylic acid a) Allyl(1R,5S,6S)-2-[(3S,5S)-1-allyloxycarbonyl-5-(5-methylthioimidazo[5,1-b]thiazol-2-yl)methylpyrrolidin-3-yl]thio-6-((1R)-1-hydroxyethyl)-1-methylcarbapen-2-em-3-carboxylate The procedure of Example 23-a) is repeated, except that 671.9 mg of (3S,5S)-1-allyloxycarbonyl-3-benzoylthio-5-5-methylthioimidazo[5,1-b]thiazol-2-yl)methylpyrrolidine described in Synthesis Example 21 is used. Thus, 677.3 mg of a mercaptan compound is prepared as a yellow oil. Allyl(1R,5S,6S)-2-[(3S,5S)-1-allyloxycarbonyl-5-(5-methylthioimidazo[5,1-b]thiazol-2-yl)methylpyrrolidin-3-yl]thio-6-((1R)-1-hydroxyethyl)-1-methylcarbapen-2-em-3-carboxylate (344.2 mg) is prepared as a colorless amorphous material from this mercaptan and 589.0 mg of allyl(1R,5R,6S)-2-(diphenylphosphono)oxy-6-((1R)-1-hydroxyethyl)-1-methylcarbapen-2-em-3-carboxylate.

NMR (CDCl$_3$) δ: 1.19 (3H, d, J=7.0 Hz), 1.29 (3H, d, J=6.2 Hz), 1.71–1.82 (1H, m), 2.40–2.54 (1H, m), 2.46 (3H, s), 2.99–3.60 (6H, m), 4.05–4.22 (4H, m), 4.55–4.80 (4H, m), 5.18–5.41 (4H, m), 5.84–5.96 (2H, m), 7.01 (1H, s), 7.17 (1H, s).

b) 1R,5S,6S)-6-((1R)-1-Hydroxyethyl)-1-methyl-2-[(3S,5S)-5-(5-methylthioimidazo[5,1-b]thiazol-2-yl)methylpyrrolidin-3-yl]thiocarbapen-2-em-3-carboxylic acid The procedure of Example 23-b) is repeated, except that 44.0 mg of allyl(1R,5S,6S)-2-[(3S,5S)-1-allyloxycarbonyl-5-(5-methylthioimidazo[5,1-b]thiazol-2-yl)methylpyrrolidin-3-yl]thio-6-((1R)-1-hydroxyethyl)-1-methylcarbapen-2-em-3-carboxylate is used. Thus, 5.7 mg of the title compound is prepared as a white powder.

NMR (D$_2$O) δ (HOD=4.80 ppm): 1.21 (3H, d, J=6.9 Hz), 1.28 (3H, d, J=6.5 Hz), 1.74–1.89 (1H, m), 2.45 (3H, s), 2.75–2.86 (1H, m), 3.27–3.98 (5H, m), 3.62–3.74 (1H, m), 3.91–4.09 (2H, m), 4.20–4.28 (2H, m), 7.12 (1H, s), 7.73 (1H, s).

Example 62

(1R,5S,6S)-6-((1R)-1-Hydroxyethyl)-1-methyl-2-[(3S,5S)-5-(6-methyl-5-methylthioimidazo[5,1-b]thiazolium-2-yl)methylpyrrolidin-3-yl]thiocarbapen-2-em-3-carboxylate (internal salt)

a) Allyl(1R,5S,6S)-2-[(3S,5S)-1-allyloxycarbonyl-5-(6-methyl-5-methylthioimidazo[5,1-b]thiazolium-2-yl)methylpyrrolidin-3-yl]thio-6-((1R)-1-hydroxyethyl)-1-methylcarbapen-2-em-3-carboxylate iodide The procedure of Example 24-a) is repeated, except that 47.4 mg of allyl(1R,5S,6S)-2-[(3S,5S)-1-allyloxycarbonyl-5-(5-methylthioimidazo[5,1-b]thiazol-2-yl)methylpyrrolidin-3-yl]thio-6-((1R)-1-hydroxyethyl)-1-methylcarbapen-2-em-3-carboxylate described in Example 61-a) is used. Thus, 53.4 mg of allyl(1R,5S,6S)-2-[(3S,5S)-1-allyloxycarbonyl-5-(6-methyl-5-methylthioimidazo[5,1-b]thiazolium-2-yl)methylpyrrolidin-3-yl]thio-6-((R)-1-hydroxyethyl)-1-methylcarbapen-2-em-3-carboxylate iodide as a yellow oil.

NMR (CDCl$_3$) δ: 1.21 (3H, d, J=7.2 Hz), 1.27 (3H, d, J=6.3 Hz), 1.82–1.97 (1H, m), 2.61 (3H, s), 2.70–2.81 (1H, m), 3.26–3.41 (5H, m), 3.86–4.22 (5H, m), 4.15 (3H, s), 4.52–4.75 (4H, m), 5.20–5.43 (4H, m), 5.89–6.06 (2H, m), 7.91 (1H, s), 8.18 (1H, s).

MS (FAB$^+$): 633 (M$^+$)

b) (1R,5S,6S)-6-((1R)-1-Hydroxyethyl)-1-methyl-2-[(3S,5S)-5-(6-methyl-5-methylthioimidazo[5,1-b]thiazolium-2-yl)methylpyrrolidin-3-yl]thiocarbapen-2-em-3-carboxylate (internal salt)

The procedure of Example 24-b) is repeated, except that 53.4 mg of allyl(1R,5S,6S)-2-[(3S,5S)-1-allyloxycarbonyl-5-(6-methyl-5-methylthioimidazo[5,1-b]thiazolium-2-yl)methylpyrrolidin-3-yl]thio-6-((1R)-1-hydroxyethyl)-1-methylcarbapen-2-em-3-carboxylate iodide is used. Thus, 10.0 mg of the title compound is prepared as a colorless flocculent material.

NMR (D$_2$O) δ (HOD=4.80 ppm): 1.20 (3H, d, J=7.1 Hz), 1.28 (3H, d, J=6.3 Hz), 1.43–1.53 (1H, m), 2.52 (3H, s), 2.50–2.64 (1H, m), 3.00–3.46 (6H, m), 3.50–3.61 (1H, m), 3.75–3.88 (1H, m), 4.10 (3H, s), 4.13–4.28 (2H, m), 7.74 (1H, s), 7.99 (1H, s).

Example 63

(1R,5S,6S)-2-[(3S,5S)-5-(6-Carbamoylmethyl-5-methylthioimidazo[5,1-b]thiazolium-2-yl)methylpyrrolidin-3-yl]thio-6-((1R)-1-hydroxyethyl)-1-methylcarbapen-2-em-3-carboxylic acid iodide a) Allyl(1R,5S,6S)-2-[(3S,5S)-1-allyloxycarbonyl-5-(6-carbamoylmethyl-5-methylthioimidazo[5,1-b]thiazolium-2-yl)methylpyrrolidin-3-yl]thio-6-((1R)-1-hydroxyethyl)-1-methylcarbapen-2-em-3-carboxylate iodide The procedure of Example 26-a) is repeated, except that 55.8 mg of allyl(1R,5S,6S)-2-[(3S,5S)-1-allyloxycarbonyl-5-(5-methylthioimidazo[5,1-b]thiazol-2-yl)methylpyrrolidin-3-yl]thio-6-((1R)-1-hydroxyethyl)-1-methylcarbapen-2-em-3-carboxylate described in Example 61-a) is used. Thus, 73.1 mg of allyl(1R,5S,6S)-2-[(3S,5S)-1-allyloxycarbonyl-5-(6-carbamoylmethyl-5-methylthioimidazo[5,1-b]thiazolium-2-yl)methylpyrrolidin- 3-yl]thio-6-((1R)-1-hydroxyethyl)-1-methylcarbapen-2-em-3-carboxylate iodide is prepared as a yellow oil.

NMR (CD₃OD) δ: 1.22 (3H, d, J=7.3 Hz), 1.28 (3H, d, J=6.2 Hz), 1.81–1.97 (1H, m), 2.59 (3H, s), 2.60–2.79 (1H, m), 3.27–3.54 (5H, m), 3.86–4.48 (5H, m), 4.50–4.71 (4H, m), 5.20–5.43 (4H, m), 5.32 (2H, s), 5.89–6.06 (2H, m), 7.96 (1H, s), 8.24 (1H, s).

MS (TS): 676 (M⁺)

b) (1R,5S,6S)-2-[(3S,5S)-5-(6-Carbamoylmethyl-5-methylthioimidazo[5,1-b]thiazolium-2-yl) methylpyrrolidin-3-yl]thio-6-((1R)-1-hydroxyethyl)-1-methylcarbapen-2-em-3-carboxylic acid iodide The procedure of Example 26-b) is repeated, except that 73.1 mg of allyl(1R,5S,6S)-2-[(3S,5S)-1-allyloxycarbonyl-5-(6-carbamoylmethyl-5-methylthioimidazo[5,1-b]thiazolium-2-yl)methylpyrrolidin-3-yl]thio-6-((1R)-1-hydroxyethyl)-1-methylcarbapen-2-em-3-carboxylate iodide is used. Thus, 9.3 mg of the title compound is prepared as a white flocculent material.

NMR (D₂O) δ (HOD=4.80 ppm): 1.20 (3H, d, J=6.1 Hz), 1.28 (3H, d, J=6.3 Hz), 1.45–1.57 (1H, m), 2.51 (3H, s), 2.52–2.69 (1H, m), 3.02–3.10 (1H, m), 3.19–3.42 (5H, m), 3.51–3.68 (1H, m), 3.79–3.89 (1H, m), 4.17–4.28 (2H, m), 5.34 (2H, s), 7.83 (1H, s), 8.07 (1H, s).

Example 64

(1R,5S,6S)-2-[(3S,5S)-5-(5-Chloroimidazo[5,1-b]thiazol-2-yl)methylpyrrolidin-3-yl]thio-6-((1R)-1-hydroxyethyl)-1-methylcarbapen-2-em-3-carboxylic acid a) Allyl(1R,5S,6S)-2-[(3S,5S)-1-allyloxycarbonyl-5-(5-chloroimidazo[5,1-b]thiazol-2-yl) methylpyrrolidin-3-yl]thio-6-((1R)-1-hydroxyethyl)-1-methylcarbapen-2-em-3-carboxylate The procedure of Example 23-a) is repeated, except that 303.0 mg of (3S,5S)-1-allyloxycarbonyl-3-benzoylthio-5-(5-chloroimidazo[5,1-b]thiazol-2-yl)methylpyrrolidine described in Synthesis Example 23 is used. Thus, 261.0 mg of a mercaptan compound is prepared as a yellow oil. Allyl(1R,5S,6S)-2-[(3S,5S)-1-allyloxycarbonyl-5-(5-chloroimidazo[5,1-b]thiazol-2-yl)methylpyrrolidin-3-yl]thio-6-((1R)-1-hydroxyethyl)-1-methylcarbapen-2-em-3-carboxylate (186.7 mg) is prepared as a colorless amorphous material from this mercaptan and 260.9 mg of allyl(1R,5R,6S)-2-(diphenylphosphono)oxy-6-((1R)-1-hydroxyethyl)-1-methylcarbapen-2-em-3-carboxylate.

NMR (CDCl₃) δ: 1.21–1.38 (6H, m), 1.77–1.87 (1H, m), 2.45–2.57 (1H, m), 3.03–3.40 (4H, m), 3.58–3.67 (1H, m), 3.95–4.25 (5H, m), 4.10–4.84 (4H, m), 5.22–5.47 (4H, m), 5.88–6.02 (2H, m), 6.93 (1H, s), 7.11 (1H, s).

MS (FAB⁺): 607 (M⁺)

b) (1R,5S,6S)-2-[(3S,5S)-5-(5-Chloroimidazo[5,1-b]thiazol-2-yl)methylpyrrolidin-3-yl]thio-6-((1R)-1-hydroxyethyl)-1-methylcarbapen-2-em-3-carboxylic acid The procedure of Example 23-b) is repeated, except that 45.2 mg of allyl(1R,5S,6S)-2-[(3S,5S)-1-allyloxycarbonyl-5-(5-chloroimidazo[5,1-b]thiazol-2-yl)methylpyrrolidin-3-yl]thio-6-((1R)-1-hydroxyethyl)-1-methylcarbapen-2-em-3-carboxylate is prepared. Thus, 2.2 mg of the title compound is prepared as a white powder.

NMR (D₂O) δ (HOD=4.80 ppm): 1.21 (3H, d, J=6.8 Hz), 1.28 (3H, d, J=6.1 Hz), 1.63–1.76 (1H, m), 2.69–2.80 (1H, m), 3.19–3.40 (5H, m), 3.42–3.60 (2H, m), 3.80–4.02 (2H, m), 4.20–4.28 (1H, m), 7.00 (1H, s), 7.55 (1H, s).

Example 65

(1R,5S,6S)-2-[(3S,5S)-5-(5-Chloro-6-methylimidazo[5,1-b]thiazolium-2-yl)methylpyrrolidin-3-yl]thio-6-((1R)-1-hydroxyethyl)-1-methylcarbapen-2-em-3-carboxylic acid a) Allyl(1R,5S,6S)-2-[(3S,5S)-1-allyloxycarbonyl-5-(5-chloro-6-methylimidazo[5,1-b]thiazolium-2-yl) methylpyrrolidin-3-yl]thio-6-((1R)-1-hydroxyethyl)-1-methylcarbapen-2-em-3-carboxylate iodide The procedure of Example 24-a) is prepared, except that 46.6 mg of allyl(1R,5S,6S)-2-[(3S,5S)-1-allyloxycarbonyl-5-(5-chloroimidazo[5,1-b]thiazol-2-yl)methylpyrrolidin-3-yl]thio-6-((1R)-1 -hydroxyethyl)-1-methylcarbapen-2-em-3-carboxylate described in Example 64-a) is used. Thus, 57.9 mg of allyl(1R,5S,6S)-2-[(3S,5S)-1-allyloxycarbonyl-5-(6-methyl-5-chloroimidazo[5,1-b]thiazolium-2-yl) methylpyrrolidin-3-yl]thio-6-((1R)-1-hydroxyethyl)-1-methylcarbapen-2-em-3-carboxylate iodide is prepared as a yellow oil.

NMR (CDCl₃) δ: 1.20–1.30 (6H, m), 1.55–1.65 (1H, m), 2.52–2.62 (1H, m), 3.20–3.50 (5H, m), 3.60–3.71 (1H, m), 4.06–4.25 (4H, m), 4.12 (3H, s), 4.50–4.77 (4H, m), 5.18–5.40 (4H, m), 5.82–5.98 (2H, m), 7.55 (1H, s), 8.30 (1H, s).

MS (FAB⁺): 623 (M⁺+H)

b) (1R,5S,6S)-2-[(3S,5S)-5-(5-Chloro-6-methylimidazo[5,1-b]thiazolium-2-yl) methylpyrrolidin-3-yl]thio-6-((1R)-1-hydroxyethyl)-1-methylcarbapen-2-em-3-carboxylic acid iodide The procedure of Example 24-b) is repeated, except that 57.9 mg of allyl(1R,5S,6S)-2-[(3S,5S)-1-allyloxycarbonyl-5-(5-chloro-6-methylimidazo[5,1-b]thiazolium-2-yl) methylpyrrolidin-3-yl]thio-6-((1R)-1-hydroxyethyl)-1-methylcarbapen-2-em-3-carboxylate iodide was used. Thus, 4.4 mg of the title compound is prepared as a colorless flocculent material.

NMR (D₂O) δ (HOD=4.80 ppm): 1.22 (3H, d, J=7.4 Hz), 1.28 (3H, d, J=6.3 Hz), 1.81–1.91 (1H, m), 2.80–2.90 (1H, m), 3.30–3.50 (6H, m), 3.69–3.75 (1H, m), 4.01 (3H, s), 4.02–4.15 (2H, m), 4.21–4.28 (1H, m), 7.74 (1H, s), 7.94 (1H, s).

Example 66

(1R,5S,6S)-2-[(3S,5S)-5-(6-Carbamoylmethyl-5-chloroimidazo[5,1-b]thiazolium-2-yl) methylpyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-5-(6-carbamoylmethyl-5-chloroimidazo[5,1-b] thiazolium-2-yl)methylpyrrolidin- 3-yl]thio-6-((1R)-1-hydroxyethyl)-1-methylcarbapen-2-em-3-carboxylate chloride 2-Iodoacetamide (198.0 mg) and 221.9 mg of aluminum perchlorate are added to a solution of 42.6 mg of allyl (1R,5S,6S)-2-[(3S,5S)-1-allyloxycarbonyl-5-(5-chloroimidazo[5,1-b]thiazol-2-yl)methylpyrrolidin-3-yl]

thio-6-((1R)-1-hydroxyethyl)-1-methylcarbapen-2-em-3-carboxylate, described in Example 64-a), in 1.0 ml of dry acetonitrile. The mixture is stirred in an argon atmosphere at room temperature for 48 hr. The mixture is then filtered to remove insolubles, and the filtrate is subjected to evaporation. The residue is purified by column chromatography on Sephadex LH-20 (dichloromethane:methanol=1:1) and then ion-exchanged using Amberlyst A-26 (Cl⁻ form) (water) to give 48.3 mg of allyl(1R,5S,6S)-2-[(3S,5S)-1-allyloxycarbonyl-5-(6-carbamoylmethyl-5-chloroimidazo[5,1-b]thiazolium-2-yl)methylpyrrolidin-3-yl]thio-6-((1R)-1-hydroxyethyl)-1-methylcarbapen-2-em-3-carboxylate chloride as a yellow oil.

NMR (CD$_3$OD) δ: 1.30–1.45 (6H, m), 1.86–1.95 (1H, m), 2.58–2.65 (1H, m), 3.35–3.45 (4H, m), 3.60–3.70 (5H, m), 4.40–4.65 (6H, m), 5.20–5.35 (5H, m), 5.90–6.05 (2H, m), 7.89 (1H, s), 7.97 (1H, s).

MS (ES): 665 (M⁺)

b) (1R,5S,6S)-2-[(3S,5S)-5-(6-Carbamoylmethyl-5-chloroimidazo[5,1-b]thiazolium-2-yl)methylpyrrolidin-3-yl]thio-6-((1R)-1-hydroxyethyl)-1-methylcarbapen-2-em-3-carboxylic acid chloride The procedure of Example 26-b) is repeated, except that 48.3 mg of allyl(1R,5S,6S)-2-[(3S,5S)-1-allyloxycarbonyl-5-(6-carbamoylmethyl-5-chloroimidazo[5,1-b]thiazolium-2-yl)methylpyrrolidin-3-yl]thio-6-((1R)-1-hydroxyethyl)-1-methylcarbapen-2-em-3-carboxylate chloride is used. Thus, 1.0 mg of the title compound is prepared as a white flocculent material.

NMR (D$_2$O) δ (HOD=4.80 ppm): 1.27 (3H, d, J=7.1 Hz), 1.35 (3H, d, J=6.4 Hz), 1.70–1.85 (1H, m), 2.55–2.70 (1H, m), 3.20–3.50 (5H, m), 3.82–3.92 (3H, m), 4.20–4.40 (2H, m), 5.10 (2H, s), 7.46 (1H, s), 7.96 (1H, s).

Example 67

(1R,5S,6S)-2-[(3S,5S)-5-(6-(2-Carbamoylethyl)-5-methylimidazo[5,1-b]thiazolium-2-yl)methylpyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-5-(6-(2-carbamoylethyl)-5-methylimidazo[5,1-b]thiazolium-2-yl)methylpyrrolidin-3-yl]thio-6-((1R)-1-hydroxyethyl)-1-methylcarbapen-2-em-3-carboxylate chloride 3-Bromopropionamide (409.6 mg) and 403.8 mg of sodium iodide are added to a solution of 43.1 mg of allyl(1R,5S,6S)-2-[(3S,5S)-1-allyloxycarbonyl-5-(5-methylimidazo[5,1-b]thiazol-2-yl)methylpyrrolidin-3-yl]thio-6-((1R)-1-hydroxyethyl)-1-methylcarbapen-2-em-3-carboxylate, described in Example 31-a), in 0.3 ml of dry DMF, and the mixture is stirred in an argon atmosphere at room temperature for four days. The mixture is then subjected to evaporation under reduced pressure, and the residue is purified by column chromatography on Sephadex LH-20 (dichloromethane:methanol=1:1) and then ion-exchanged using Amberlyst A-26 (Cl⁻ form) (water) to give 47.5 mg of allyl(1R,5S,6S)-2-[(3S,5S)-1-allyloxycarbonyl-5-(6-(2-carbamoylethyl)-5-methylimidazo[5,1-b]thiazolium-2-yl)methylpyrrolidin-3-yl]thio-6-((1R)-1-hydroxyethyl)-1-methylcarbapen-2-em-3-carboxylate chloride as a yellow oil.

NMR (CD$_3$OD) δ: 1.23 (3H, d, J=7.1 Hz), 1.28 (3H, d, J=6.3 Hz), 1.78–1.85 (1H, m), 2.52–2.70 (2H, m), 2.90 (3H, s), 2.91–3.00 (1H, m), 3.20–3.52 (5H, m), 3.83–3.90 (1H, m), 4.08–4.25 (5H, m), 4.52–4.70 (5H, m), 5.20–5.42 (4H, m), 5.87–6.02 (2H, m), 7.66 (1H, s), 7.97 (1H, s).

b) (1R,5S,6S)-2-[(3S,5S)-5-(6-(2-Carbamoylethyl)-5-methylimidazo[5,1-b]thiazolium-2-yl)methylpyrrolidin-3-yl]thio-6-((1R)-1-hydroxyethyl)-1-methylcarbapen-2-em-3-carboxylic acid chloride The procedure of Example 26-b) is repeated, except that 47.5 mg of allyl(1R,5S,6S)-2-[(3S,5S)-1-allyloxycarbonyl-5-(6-(2-carbamoylethyl)-5-methylimidazo[5,1-b]thiazolium-2-yl)methylpyrrolidin-3-yl]thio-6-((1R)-1-hydroxyethyl)-1-methylcarbapen-2-em-3-carboxylate chloride is used. Thus, 7.9 mg of the title compound is prepared as a slightly yellow flocculent material.

NMR (D$_2$O) δ (HOD=4.80 ppm): 1.19 (3H, d, J=7.1 Hz), 1.28 (3H, d, J=6.3 Hz), 1.40–1.50 (1H, m), 2.52–2.60 (1H, m), 2.80 (3H, s), 2.90 (2H, t, J=6.4 Hz), 3.00–3.05 (1H, m), 3.10–3.15 (2H, m), 3.22–3.28 (1H, m), 3.32–3.42 (2H, m), 3.48–3.57 (1H, m), 4.17–4.28 (2H, m), 4.54 (2H, t, J=6.3 Hz), 7.50 (1H, s), 7.74 (1H, s).

Example 68

(1R,5S,6S)-2-[(3S,5S)-5-[2(Z)-(6-Carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-6-((1R)-1-hydroxyethyl)-5-[2(E)-(5-methylimidazo[5,1-b]thiazol-3-yl)ethenyl]pyrrolidin-3-yl]thio-1-methylcarbapen-2-em-3-carboxylate and allyl(1R,5S,6S)-2-[(3S,5S)-1-allyloxycarbonyl-6-((1R)-1-hydroxyethyl)-5-[2(Z)-(5-methylimidazo[5,1-b]thiazol-3-yl)ethenyl]pyrrolidin-3-yl]thio-1-methylcarbapen-2-em-3-carboxylate A 1 N aqueous sodium hydroxide solution (1.83 ml) is added to a solution of 0.65 g of (3S,5S)-3-acetylthio-1-allyloxycarbonyl-5-[2-(5-methylimidazo[5,1-b]thiazol-3-yl)ethenyl]pyrrolidine, described in Synthesis Example 22, in 5 ml of methanol under ice cooling, and the mixture is stirred at that temperature for 40 min. The mixture is adjusted to pH 7 by addition of a 1 N aqueous hydrochloric acid solution, dichloromethane is added thereto, followed by extraction three times. The extract is washed with saturated saline and dried over magnesium sulfate. The solvent is removed by evaporation to give a mercaptan compound. Diisopropylethylamine (0.43 ml) is added to a solution of this mercaptan compound and 0.83 g of allyl (1R,5S,6S)-2-(diphenylphosphono)oxy-6-((1R)-1-hydroxyethyl)-1-methylcarbapen-2-em-3-carboxylate in 6 ml of acetonitrile under ice cooling, and the mixture is stirred for 3.6 hr. Dichloromethane is added to the reaction mixture, followed by extraction three times. The extract is washed with saturated saline and then dried over magnesium sulfate. The solvent is removed by evaporation. The residue is purified by column chromatography on silica gel (ethyl acetate:methanol=95:5) to give 389.1 mg of allyl(1R,5S,6S)-2-[(3S,5S)-1-allyloxycarbonyl-6-((1R)-1-hydroxyethyl)-5-[2(E)-(5-methylimidazo[5,1-b]thiazol-3-yl)ethenyl]pyrrolidin-3-yl]thio-1-methylcarbapen-2-em-3-carboxylate and 188.8 mg of allyl(1R,5S,6S)-2-[(3S,5S)-1-allyloxycarbonyl-6-((1R)-1-hydroxyethyl)-5-[2(Z)-(5-methylimidazo[5,1-b]thiazol-3-yl)ethenyl]pyrrolidin-3-yl]thio-1-methylcarbapen-2-em-3-carboxylate.

(E) form

NMR (CDCl₃) δ: 1.29 (3H, d, J=7.1 Hz), 1.37 (3H, d, J=6.3 Hz), 1.84–1.96 (1H, m), 2.63–2.74 (2H, m), 2.67 (3H, s), 3.23–3.46 (4H, m), 3.68–3.78 (1H, m), 4.20–4.28 (2H, m), 4.10–4.35 (5H, m), 5.20–5.64 (4H, m), 5.88–6.01 (2H, m), 6.18–6.27 (1H, m), 6.69 (1H, s), 6.89 (1H, s).

MS (TS): 599 (M⁺+H)

(Z) form

NMR (CDCl₃) δ: 1.27 (3H, d, J=7.2 Hz), 1.36 (3H, d, J=6.3 Hz), 1.75–1.90 (1H, m), 2.64 (3H, s), 2.58–2.70 (1H, m), 3.25–3.48 (3H, m), 3.63–3.70 (1H, m), 4.20–4.28 (2H, m), 4.55–4.95 (6H, m), 5.28–5.50 (4H, m), 5.93–6.08 (2H, m), 6.45 (1H, s), 6.49 (1H, s), 6.90 (1H, s).

MS (TS): 599 (M⁺+H)

b) Allyl(1R,5S,6S)-2-[(3S,5S)-1-allyloxycarbonyl-5-[2(Z)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylate chloride 2-Iodoacetamide (246.4 mg) is added to a solution of 79.8 mg of allyl(1R,5S,6S)-2-[(3S,5S)-1-allyloxycarbonyl-6-((1R)-1-hydroxyethyl)-5-[2(Z)-(5-methylimidazo[5,1-b]thiazol-3-yl)ethenyl]pyrrolidin-3-yl]thio-1-methylcarbapen-2-em-3-carboxylate in 0.7 ml of dry acetone, and the mixture is stirred in an argon atmosphere at room temperature for 18 hr. The mixture is then subjected to evaporation under reduced pressure. The residue is purified by column chromatography on Sephadex LH-20 (dichloromethane:methanol=1:1) and then ion-exchanged using Amberlyst A-26 (Cl⁻ ⁻ form) (water) to give 104.2 mg of allyl(1R,5S,6S)-2-[(3S,5S)-1-allyloxycarbonyl-5-[2(Z)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylate chloride as a yellow oil.

NMR (CD₃OD) δ: 1.23–1.35 (6H, m), 1.84–1.98 (1H, m), 2.18 (3H, s), 2.60–2.90 (3H, m), 3.38–3.57 (3H, m), 3.90–4.15 (3H, m), 4.20–4.24 (1H, m), 4.50–4.85 (4H, m), 5.18–5.28 (4H, m), 5.40 & 5.46 (total 1H, s, each), 5.90–6.02 (2H, m), 6.20–6.32 (1H, m), 6.63 (1H, d, J=11.0 Hz), 7.22 & 7.40 (total 1H, s, each), 7.55 & 7.71 (total 1H, s, each).

MS (TS): 656 (M⁺+H)

c) (1R,5S,6S)-2-[(3S,5S)-5-[2(Z)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylic acid chloride Triphenylphosphine (14.2 mg), 0.029 ml of morpholine, and 8.8 mg of tetrakis(triphenylphosphine)palladium(0) are successively added to a solution of 104.2 mg of allyl(1R,5S,6S)-2-[(3S,5S)-1-allyloxycarbonyl-5-[2(Z )-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylate chloride in 0.8 ml of THF and 0.8 ml of dry ethanol, and the mixture is stirred in an argon atmosphere at room temperature for one hr. THF (10 ml) is added, and the resultant precipitate is further washed twice with 5 ml of THF and dried in vacuo to prepare a yellow powder which is then purified by column chromatography on Cosmosil 40C18-PREP (aqueous methanol solution) to give 5.7 mg of the title compound as a colorless flocculent material.

NMR (D₂O) δ (HOD=4.80 ppm): 1.20 (3H, d, J=7.4 Hz), 1.28 (3H, d, J=6.6 Hz), 1.54–1.64 (1H, m), 2.53–2.62 (1H, m), 2.83 (3H, s), 3.01–3.06 (1H, m), 3.20–3.28 (1H, m), 3.35–3.45 (2H, m), 3.76–3.74 (1H, m), 4.10–4.28 (3H, m), 5.20 (2H, s), 6.31 (1H, t, J=10.4 Hz), 6.65 (1H, d, J=11.0 Hz), 7.27 (1H, s), 7.56 (1H, s).

Example 69

(1R,5S,6S)-2-[(3S,5S)-5-[2(E)-(6-Carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-5-[2(E)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylate chloride The procedure of Example 68-b) is repeated, except that 67.1 mg of allyl(1R,5S,6S)-2-[(3S,5S)-1-allyloxycarbonyl-5-[2(E)-(5-methylimidazo[5,1-b]thiazol-3-yl)ethenyl]pyrrolidin-3-yl]thio-6-((1R)-1-hydroxyethyl)-1-methylcarbapen-2-em-3-carboxylate described in Example 68-a) is used. Thus, 90.9 mg of allyl(1R,5S,6S)-1-allyloxycarbonyl-5-[2(E)-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylate chloride is prepared as a yellow oil.

NMR (CD₃OD) δ: 1.25–1.31 (6H, m), 1.95–2.04 (1H, m), 2.18 (3H, s), 2.60–2.67 (2H, m), 2.75–2.92 (1H, m), 3.43–3.54 (2H, m), 3.97–4.25 (3H, m), 4.60–4.75 (4H, m), 4.85–4.90 (3H, m), 5.15–5.40 (4H, m), 5.85–6.00 (2H, m), 6.45–6.55 (1H, m), 6.72 & 6.77 (total 1H, s, each), 7.50 (1H, s), 7.69 (1H, s).

MS (TS): 656 (M⁺+H)

b) (1R,5S,6S)-2-[(3S,5S)-5-[2(E)-(6-Carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylic acid chloride The procedure of Example 68-c) is repeated, except that 90.9 mg of allyl(1R,5S,6S)-2-[(3S,5S)-1-allyloxycarbonyl-5-[2 (Z )-(6-carbamoylmethyl-5-methylimidazo[5,1-b]thiazolium-3-yl)ethenyl]pyrrolidin-3-yl]thio-6-((1R)-1-hydroxyethyl)-1-methylcarbapen-2-em-3-carboxylate chloride is used. Thus, 6.9 mg of the title compound is prepared as a colorless flocculent material.

NMR (D₂O) δ (HOD=4.80 ppm): 1.23 (3H, d, J=7.1 Hz), 1.29 (3H, d, J=6.3 Hz), 1.98–2.09 (1H, m), 2.87 (3H, s), 2.88–2.97 (1H, m), 3.36–3.50 (3H, m), 3.75–3.81 (1H, m), 4.10–4.28 (3H, m), 4.57 (1H, d, J=7.5 Hz), 5.22 (2H, s), 6.58 (1H, dd, J1=15.5 Hz, J2=8.0 Hz), 7.06 (1H, d, J=15.7 Hz), 7.54 (1H, s), 7.59 (1H, s).

Example 70

(1R,5S,6S)-2-[(3S,5S)-5-[2(Z)-(6-Ethylimidazo[5,1-b]thiazolium-3-yl)ethenyl]pyrrolidin-3-yl]thio-6-((1R)-1-hydroxyethyl)-1-methylcarbapen-2-em-3-carboxylate (internal salt)

a) Allyl(1R,5S,6S)-2-[(3S,5S)-1-allyloxycarbonyl-5-[2(Z)-(6-ethylimidazo[5,1-b]thiazolium-3-yl)ethenyl]pyrrolidin-3-yl]thio-6-((1R)-1-hydroxyethyl)-1-methylcarbapen-2-em-3-carboxylate 1-Iodoethane (1.1 ml) is added to a solution of 78.2 mg of allyl(1R,5S,6S)-2-[(3S,5S)-1-allyloxycarbonyl-5-[2(Z)-

(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 0.4 ml of dry acetone, and the mixture is stirred in an argon atmosphere at room temperature for 24 hr. The mixture is subjected to evaporation under reduced pressure. The residue is purified by column chromatography on Sephadex LH-20 (dichloromethane:methanol=1:1) and then ion-exchanged using Amberlyst A-26 (Cl⁻⁻ form) (water) to give 90.4 mg of allyl(1R,5S,6S)-2-[(3S,5S)-1-allyloxycarbonyl-5-[2(Z)-(6-ethylimidazo[5,1-b]thiazolium-3-yl)ethenyl]pyrrolidin-3-yl]thio-6-((1R)-1-hydroxyethyl)-1-methylcarbapen-2-em-3-carboxylate chloride as a yellow oil.

NMR (CD$_3$OD) δ: 1.22–1.30 (6H, m), 1.64 (3H, t, J=7.1 Hz), 1.80–1.98 (1H, m), 2.15–2.18 (3H, m), 2.60–2.62 (2H, m), 2.80–3.05 (1H, m), 3.40–3.65 (3H, m), 3.82–4.28 (3H, m), 4.62–4.80 (4H, m), 5.18–5.48 (2H, m), 5.86–6.02 (1H, m), 6.30–6.58 (2H, m), 7.56 & 7.70 (total 1H, s, each), 7.89 & 7.91 (total 1H, s, each), 7.85–7.92 (1H, m), 9.60 & 9.70 (total 1H, s, each).

MS (FAB$^+$): 613 (M$^+$+H)

b) (1R,5S,6S)-2-[(3S,5S)-5-[2(Z)-(6-ethylimidazo[5,1-b]thiazolium-3-yl)ethenyl]pyrrolidin-3-yl]thio-6-((1R)-1-hydroxyethyl)-1-methylcarbapen-2-em-3-carboxylate (internal salt)

The procedure of Example 68-c) is repeated, except that 90.4 mg of allyl(1R,5S,6S)-2-[(3S,5S)-1-allyloxycarbonyl-5-[2(z)-(6-ethylimidazo[5,1-b]thiazolium-3-yl)ethenyl]pyrrolidin-3-yl]thio-6-((1R)-1-hydroxyethyl)-1-methylcarbapen-2-em-3-carboxylate chloride is used. Thus, 10.4 mg of the title compound is prepared as a colorless flocculent material.

NMR (D$_2$O) δ (HOD=4.80 ppm): 1.19 (3H, d, J=7.1 Hz), 1.28 (3H, d, J=6.4 Hz), 1.57 (3H, t, J=7.4 Hz), 1.55–1.60 (1H, m), 2.58–2.60 (1H, m), 3.00–3.05 (1H, m), 3.22–3.30 (1H, m), 3.33–3.42 (3H, m), 3.78–3.85 (2H, m), 4.15–4.28 (2H, m), 4.38–4.44 (2H, q, J=7.4 Hz), 6.29 (1H, t, J=9.4 Hz), 6.47 (1H, d, J=11.3 Hz), 7.37 (1H, s), 7.69 (1H, s).

Example 71

(1R,5S,6S)-6-((1R)-1-Hydroxyethyl)-2-[(3S,5S)-5-[2(Z)-(6-(2-hydroxyethyl)imidazo[5,1-b]thiazolium-3-yl)ethenyl]pyrrolidin-3-yl]thio-1-methylcarbapen-2-em-3-carboxylic acid trifluoromethanesulfonate 2-(t-Butyldimethylsilyloxy)ethyl trifluoromethanesulfonate (42.2 mg) is added to a solution of 51.8 mg of allyl(1R,5S,6S)-2-[(3S,5S)-1-allyloxycarbonyl-5-[2(Z)-(imidazo[5,1-b]thiazol-3-yl)ethenylpyrroidin-3-yl]thio-6-((1R)-1-hydroxyethyl)-1-methylcarbapen-2-em-3-carboxylate, described in Example 38-a), in 0.5 ml of dry dichloroethane, and the mixture is stirred in an argon atmosphere at room temperature for 1.5 hr. The excess reagent is removed by evaporation under reduced pressure to give allyl(1R,5S,6S)-2-[(3S,5S)-1-allyloxycarbonyl-5-[2(Z)-(6-(2-t-butyldimethylsilyloxyethyl)imidazo[5,1-b]thiazolium-3-yl)ethenyl]pyrrolidin-3-yl]thio-6-((1R)-1-hydroxyethyl)-1-methylcarbapen-2-em-3-carboxylate trifluoromethanesulfonate as a brown viscous material. Acetic acid (0.0054 ml) and 0.09 ml of 1 M tetra-n-butylammonium fluoride/THF solution are added to a solution of this compound in 0.5 ml of anhydrous THF, and the mixture is stirred in an argon atmosphere at room temperature for 2.5 hr. Dry ethanol (0.5 ml) is added to this solution. Triphenylphosphine (10.4 mg), 0.02 ml of morpholine, and 5.2 mg of tetrakis(triphenylphosphine)palladium(0) are successively added thereto, and the mixture is stirred in an argon atmosphere at room temperature for one hr. THF (10 ml) is added, and the resultant precipitate is further washed twice with 3 ml of THF and dried in vacuo to give a yellow powder which is then purified by column chromatography on Cosmosil 40C18-PREP (aqueous methanol solution) to give 0.9 mg of the title compound as a colorless flocculent material.

NMR (D$_2$O) δ (HOD=4.80 ppm): 1.21 (3H, d, J=7.1 Hz), 1.28 (3H, d, J=6.3 Hz), 1.94–2.06 (1H, m), 2.88–2.98 (1H, m), 3.33–3.54 (3H, m), 3.70–3.80 (1H, m), 4.00–4.04 (2H, m), 4.08–4.19 (1H, m), 4.22–4.30 (1H, m), 4.48–4.54 (2H, m), 6.44 (1H, t, J=10.7 Hz), 6.76 (1H, d, J=11.0 Hz), 7.52 (1H, s), 7.77 (1H, s), 9.40 (1H, s).

Example 72

(1R,5S,6S)-2-[(3S,5S)-5-[2(Z)-(6-(2-Carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate (internal salt)

a) Allyl(1R,5S,6S)-2-[(3S,5S)-1-allyloxycarbonyl-5-[2(Z)-(6-(2-carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate chloride 3-Bromopropionamide (273.4 mg) and 274.8 mg of sodium iodide are added to a solution of 51.8 mg of allyl(1R,5S,6S)-2-[(3S,5S)-1-allyloxycarbonyl-5-[2(Z)-(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 0.7 ml of dry acetonitrile, and the mixture is stirred in an argon atmosphere at room temperature for five days. The mixture is subjected to evaporation under reduced pressure. The residue is purified by column chromatography on Sephadex LH-20 (dichloromethane:methanol=1:1) and ion-exchanged using Amberlyst A-26 (Cl⁻ form) (water) to give 51.0 mg of allyl(1R,5S,6S)-2-[(3S,5S)-1-allyloxycarbonyl- 5-[2(Z)-(6-(2-carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate chloride as a yellow oil.

NMR (CD$_3$OD) δ: 1.24–1.30 (6H, m), 1.80–1.95 (1H, m), 2.85–2.90 (4H, m), 2.95–3.00 (6H, m), 3.40–3.58 (1H, m), 3.94–4.15 (2H, m), 4.23–4.26 (1H, m), 4.55–4.80 (4H, m), 5.20–5.27 (2H, m), 5.40–5.48 (2H, m), 5.90–6.02 (2H, m), 6.30–6.54 (1H, m), 7.08–7.10 (1H, m), 7.70 (1H, s), 7.90 (1H, s), 7.98 (1H, s).

MS (TSP): 656 (M$^+$+H)

b) (1R,5S,6S)-2-[(3S,5S)-5-[2(Z)-(6-(2-carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate (internal salt)

The same procedure of Example 68-c) is repeated, except that 51.0 mg of allyl(1R,5S,6S)-2-[(3S,5S)-1-allyloxycarbonyl-5-[2(Z)-(6-(2-carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate chloride is used. Thus, 9.2 mg of the title compound is prepared as a colorless flocculent material.

NMR (D₂O) δ (HOD=4.80 ppm): 1.19 (3H, d, J=7.1 Hz), 1.28 (3H, d, J=6.3 Hz), 1.52–1.62 (1H, m), 2.58–2.68 (1H, m), 2.95–3.06 (3H, m), 3.22–3.45 (3H, m), 3.80–3.88 (1H, m), 4.63–4.72 (3H, m), 6.30 (1H, t, J=9.4 Hz), 6.48 (1H, d, J=11.5 Hz), 7.40 (1H, s), 7.71 (1H, s).

Example 73

(1R,5S,6S)-2-[(3S,5S)-5-[2(Z)-(6-(2-Fluoroethyl)imidazo[5,1-b]thiazolium-3-yl)ethenyl]pyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-5-[2(Z)-(6-(2-fluoroethyl)imidazo[5,1-b]thiazolium-3-yl)ethenyl]pyrrolidin-3-yl]thio-6-((1R)-1-hydroxyethyl)-1-methylcarbapen-2-em-3-carboxylate chloride 2-Fluoroethyl trifluoromethanesulfonate (198.9 mg) is added to a solution of 53.1 mg of allyl(1R,5S,6S)-2-[(3S,5S)-1-allyloxycarbonyl-5-[2(Z)-(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 0.8 ml of dry dichloroethane, and the mixture is stirred in an argon atmosphere at room temperature for 24 hr. The solvent is removed by evaporation under reduced pressure, and the residue is purified by column chromatography on Sephadex LH-20 (dichloromethane:methanol=1:1) and ion-exchanged using Amberlyst A-26 (Cl⁻ form) (water) to give 63.7 mg of allyl(1R,5S,6S)-2-[(3S,5S)-1-allyloxycarbonyl-5-[2(Z)-(6-(2-fluoroethyl)imidazo[5,1-b]thiazolium-3-yl)ethenyl]pyrrolidin-3-yl]thio-6-((1R)-1-hydroxyethyl)-1-methylcarbapen-2-em-3-carboxylate chloride as a yellow oil.

NMR (CD₃OD) δ: 1.51–1.35 (6H, m), 1.88–1.95 (1H, m), 2.70–2.85 (1H, m), 3.30–3.60 (2H, m), 3.95–4.15 (4H, m), 4.38–4.60 (4H, m), 4.70–5.05 (7H, m), 5.20–5.45 (4H, m), 5.88–6.05 (2H, m), 6.63–6.68 (1H, m), 7.60 & 7.75 (total 1H, s, each), 7.86 & 7.94 (total 1H, s, each), 9.65 & 9.72 (total 1H, s, each).

MS (TSP): 631 (M⁺+H)

b) (1R,5S,6S)-2-[(3S,5S)-5-[2(Z)-(6-(2-fluoroethyl)imidazo[5,1-b]thiazolium-3-yl)ethenyl]pyrrolidin-3-yl]thio-6-((1R)-1-hydroxyethyl)-1-methylcarbapen-2-em-3-carboxylic acid chloride The same procedure of Example 68-c) is repeated, except that 63.7 mg of allyl(1R,5S,6S)-2-[(3S 5S)-1-allyloxycarbonyl-5-[2 (Z)-(6-(2-fluoroethyl)imidazo[5,1-b]thiazolium-3-yl)ethenyl]pyrrolidin-3-yl]thio-6-((1R)-1-hydroxyethyl)-1-methylcarbapen-2-em-3-carboxylate chloride is used. Thus, 5.1 mg of the title compound is prepared as a colorless flocculent material.

NMR (D₂O) δ (HOD=4.80 ppm): 1.22 (3H, d, J=7.2 Hz), 1.28 (3H, d, J=6.3 Hz), 1.96–2.04 (1H, m), 2.88–2.98 (1H, m), 3.32–3.40 (1H, m), 3.48–3.54 (2H, m), 3.70–3.76 (2H, m), 4.08–4.15 (1H, m), 4.21–4.28 (2H, m), 4.70–4.75 (1H, m), 4.90–4.98 (3H, m), 6.44 (1H, t, J=9.9 Hz), 6.76 (1H, d, J=11.1 Hz), 7.54 (1H, s), 7.79 (1H, s), 9.44 (1H, s).

Example 74

(1R,5S,6S)-2-[(3S,5S)-5-[2(Z)-(6-(2-Carbamoylethyl)imidazo[5,1-b]thiazolium-3-yl)ethenyl]pyrrolidin-3-yl]thio-6-((1R)-1-hydroxyethyl)-1-methylcarbapen-2-em-3-carboxylate (internal salt)

a) Allyl(1R,5S,6S)-2-[(3S,5S)-1-allyloxycarbonyl-5-[2(Z)-6-cyclopropylmethylimidazo[5,1-b]thiazolium-3-yl)ethenyl]pyrrolidin-3-yl]thio-6-((1R)-1-hydroxyethyl)-1-methylcarbapen-2-em-3-carboxylate chloride Cyclopropylmethyl bromide (124.2 mg) and 63.9 mg of sodium iodide are added to a solution of 49.9 mg of allyl(1R,5S,6S)-2-[(3S,5S)-1-allyloxycarbonyl-5-[2(Z)-(imidazo[5,1-b]thiazol-3-yl)ethenyl]pyrrolidin-3-yl]thio-6-((1R)-1-hydroxyethyl)-1-methylcarbapen-2-em-3-carboxylate, described in Example 38-a), in 0.4 ml of dry acetonitrile, and the mixture is stirred in an argon atmosphere at room temperature for four days. The mixture is subjected to evaporation under reduced pressure, and the residue is purified by column chromatography on Sephadex LH-20 (dichloromethane:methanol=1:1) and then ion-exchanged using Amberlyst A-26 (Cl⁻ form) (water) to give 52.3 mg of allyl(1R,5S,6S)-2-[(3S,5S)-1-allyloxycarbonyl-5-[2(Z)-6-cyclopropylmethylimidazo[5,1-b]thiazolium-3-yl)ethenyl]pyrrolidin-3-yl]thio-6-((1R)-1-hydroxyethyl)-1-methylcarbapen-2-em-3-carboxylate chloride as a yellow oil.

NMR (CD₃OD) δ: 0.57 (2H, d, J=4.5 Hz), 0.77 (2H, d, J=7.4 Hz), 1.24–1.35 (6H, m), 1.38–1.40 (1H, m), 1.80–1.98 (1H, m), 2.76–2.95 (1H, m), 3.32–3.34 (2H, m), 3.40–3.59 (2H, m), 3.92–4.17 (2H, m), 4.21–4.30 (2H, m), 4.62–4.80 (2H, m), 4.90–5.08 (4H, m), 5.10–5.32 (3H, m), 5.40–5.50 (2H, m), 5.88–6.02 (2H, m), 6.12–6.58 (1H, m), 7.60 & 7.70 (total 1H, s, each), 7.90 & 8.22 (total 1H, s, each), 9.62 & 9.70 (total 1H, s, each).

b) (1R,5S,6S)-2-[(3S,5S)-5-[2(Z)-6-Cyclopropylmethylimidazo[5,1-b]thiazolium-3-yl)ethenyl]pyrrolidin-3-yl]thio-6-((1R)-1-hydroxyethyl)-1-methylcarbapen-2-em-3-carboxylate (internal salt)

The same procedure of Example 68-c) is repeated, except that 52.3 mg of allyl(1R,5S,6S)-2-[(3S,5S)-1-allyloxycarbonyl-5-[2(Z)-6-cyclopropylmethylimidazo[5,1-b]thiazolium-3-yl)ethenyl]pyrrolidin-3-yl]thio-6-((1R)-1-hydroxyethyl)-1-methylcarbapen-2-em-3-carboxylate chloride is used. Thus, 8.4 mg of the title compound is prepared as a colorless flocculent material.

NMR (D₂O) δ (HOD=4.80 ppm): 0.50 (2H, d, J=4.7 Hz), 0.75 (2H, d, J=7.9 Hz), 1.20 (3H, d, J=6.9 Hz), 1.28 (3H, d, J=6.3 Hz), 1.33–1.44 (1H, m), 1.53–1.63 (1H, m), 2.59–2.70 (1H, m), 3.00–3.07 (1H, m), 3.22–3.30 (1H, m), 3.35–3.42 (2H, m), 3.78–3.86 (1H, m), 4.18–4.28 (6H, m), 6.49 (1H, t, J=11.3 Hz), 6.80 (1H, t, J=10.5 Hz), 7.38 (1H, s), 7.74 (1H, s).

Example 75

(1R,5S,6S)-6-((1R)-1-Hydroxyethyl)-2-[(3S,5S)-5-[2(Z)-(6-(2-hydroxyethyl)imidazo[5,1-b]thiazolium-2-yl)ethenyl]pyrrolidin-3-yl]thio-1-methylcarbapen-2-em-3-carboxylate (internal salt)

The procedure of Example 71 is repeated, except that 101.8 mg of allyl(1R,5S,6S)-2-[(3S,5S)-1-allyloxycarbonyl-5-[2-(imidazo[5,1-b]thiazol-2-yl)ethenyl]pyrrolidin-3-yl]thio-6-((1R)-1-hydroxyethyl)-1-methylcarbapen-2-em-3-carboxylate (a mixture of geometrical isomers) described in Example 47-a) is used. The resultant yellow powder is purified by column chromatography on Cosmosil 40C18-PREP (an aqueous methanol solution) to isolate geometrical isomers. Thus, 6.8 mg of the title compound is prepared as a colorless flocculent material.

NMR (D₂O) δ (HOD=4.80 ppm): 1.21 (3H, d, J=7.1 Hz), 1.28 (3H, d, J=6.3 Hz), 1.10–1.18 (1H, m), 2.68–2.78 (1H, m), 3.11–3.14 (1H, m), 3.36–3.45 (1H, m), 4.20–4.40 (3H, m), 4.08–4.19 (1H, m), 4.22–4.30 (1H, m), 4.42–4.52 (3H, m), 4.75–4.85 (2H, m), 6.10 (1H, t, J=10.2 Hz), 6.61 (1H, d, J=11.5 Hz), 7.70 (1H, s), 7.83 (1H, s).

Example 76

(1R,5S,6S)-2-[(3S,5S)-5-[2(Z)-(6-(2-Carbamoylethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid chloride a) Allyl(1R,5S,6S)-2-[(3S,5S)-1-allyloxycarbonyl-5-[2-(6-(2-carbamoylethyl)imidazo[5,1-b]thiazolium-2-yl)ethenyl]pyrrolidin-3-yl]thio-6-((1R)-1-hydroxyethyl)-1-methylcarbapen-2-em-3-carboxylate chloride (a mixture of geometrical isomers)

3-Bromopropionamide (523.7 mg) and 574.8 mg of sodium iodide are added to a solution of 100.1 mg of allyl(1R,5S,6S)-2-[(3S,5S)-1-allyloxycarbonyl-5-[2-(imidazo[5,1-b]thiazol-2-yl)ethenyl]pyrrolidin-3-yl]thio-6-((1R)-1-hydroxyethyl)-1-methylcarbapen-2-em-3-carboxylate (a mixture of geometrical isomers), described in Example 47-a), in 0.6 ml of DMF, and the mixture is stirred in an argon atmosphere at room temperature for one day. The solvent is removed by evaporation under reduced pressure, and the residue is purified by column chromatography on Sephadex LH-20 (dichloromethane:methanol=1:1) and then ion-exchanged using Amberlyst A-26 (Cl⁻ form) (water) to give 112.1 mg of allyl(1R,5S,6S)-2-[(3S,5S)-1-allyloxycarbonyl-5-[2-(6-(2-carbamoylethyl)imidazo[5,1-b]thiazolium-2-yl)ethenyl]pyrrolidin-3-yl]thio-6-((1R)-1-hydroxyethyl)-1-methylcarbapen-2-em-3-carboxylate chloride (a mixture of geometrical isomers) as a yellow oil.

NMR (CD$_3$OD) δ: 1.25–1.30 (6H, m), 1.80–1.95 (1H, m), 2.85–3.00 (5H, m), 3.30–3.60 (3H, m), 3.95–4.15 (3H, m), 4.22–4.28 (1H, m), 4.50–4.75 (5H, m), 5.15–5.45 (4H, m), 5.87–6.00 (2H, m), 6.42–6.50 (1H, m), 6.77 (1H, d, J=18 Hz), 7.79 & 7.82 (total 1H, s, each), 7.98 & 8.03 (total 1H, s, each), 9.40 & 9.44 (total 1H, s, each).

MS (TSP): 656 (M⁺)

b) (1R,5S,6S)-2-[(3S,5S)-5-[2(Z)-(6-(2-carbamoylethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid chloride The procedure of Example 68-c) is repeated, except that 112.1 mg of allyl(1R,5S,6S)-2-(3S,5S)-1-allyloxycarbonyl-5-[2-(6-(2-carbamoylethyl)imidazo[5,1-b]thiazolium-2-yl)ethenyl]pyrrolidin-3-yl]thio-6-((1R)-1-hydroxyethyl)-1-methylcarbapen-2-em-3-carboxylate chloride (a mixture of geometrical isomers). The resultant yellow powder is purified by column chromatography on Cosmosil 40C18-PREP (aqueous methanol solution) to isolate geometrical isomers. Thus, 6.9 mg of the title compound is prepared as a colorless flocculent material.

NMR (D$_2$O) δ (HOD=4.80 ppm): 1.23 (3H, d, J=7.1 Hz), 1.28 (3H, d, J=6.4 Hz), 1.92–2.04 (1H, m), 2.90–3.02 (4H, m), 3.37–3.40 (1H, m), 3.46–4.05 (2H, m), 3.72–3.80 (1H, m), 4.10–4.18 (1H, m), 4.22–4.29 (2H, m), 4.67–4.72 (2H, m), 6.21 (1H, t, J=11.8 Hz), 6.80 (1H, d, J=11.3 Hz), 7.71 (1H, s), 7.99 (1H, s), 9.32 (1H, s).

Example 77

(1R,5S,6S)-2-[(3S,5S)-5-[2(Z)-(6-(2-Fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid chloride (Z form) and (1R,5S,6S)-2-[(3S,5S)-5-[2(E)-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylate (internal salt) (E form)

a) Allyl(1R,5S,6S)-2-[(3S,5S)-1-allyloxycarbonyl-5-[2-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylate chloride (mixture of geometrical isomers)

The same procedure of Example 73-a) is repeated, except that 100.5 mg of allyl(1R,5S,6S)-2-[(3S,5S)-1-allyloxycarbonyl-5-[2-(imidazo[5,1-b]thiazol-3-yl)ethenyl]pyrrolidin-3-yl]thio-6-((1R)-1-hydroxyethyl)-1-methylcarbapen-2-em-3-carboxylate (a mixture of geometrical isomers) described in Example 47-a) is used. Thus, 108.6 mg of allyl(1R,5S,6S)-2-[(3S,5S)-1-allyloxycarbonyl-5-[2-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylate chloride (a mixture of geometrical isomers) as a yellow oil.

NMR (CD$_3$OD) δ: 1.04–1.15 (6H, m), 1.60–1.75 (1H, m), 2.50–2.71 (1H, m), 3.10–3.27 (5H, m), 3.74–3.98 (2H, m), 4.02–4.08 (1H, m), 4.40–4.80 (8H, m), 4.95–5.25 (4H, m), 5.70–5.80 (1H, m), 6.08–6.30 (1H, m), 6.59 (1H, d, J=10.5 Hz), 7.61 & 7.65 (total 1H, s, each), 7.85–8.00 (1H, m), 9.24 & 9.28 (total 1H, s, each).

MS (FAB⁺): 631 (M⁺)

b) (1R,5S,6S)-2-[(3S,5S)-5-[2(Z)-(6-(2-Fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylic acid chloride and (1R,5S,6S)-2-[(3S,5S)-5-[2(E)-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylate (internal salt)

The procedure of Example 68-c) is repeated, except that 108.6 mg of allyl(1R,5S,6S)-2-[(3S,5S)-1-allyloxycarbonyl-5-[2-(6-(2-fluoroethyl)imidazo[5,1-b]thiazolium-2-yl)ethenyl]pyrrolidin-3-yl]thio-6-((1R)-1-hydroxyethyl)-1-methylcarbapen-2-em-3-carboxylate chloride (a mixture of geometrical isomers). The resultant yellow powder is purified by column chromatography on Cosmosil 40C18-PREP (aqueous methanol solution) to isolate geometrical isomers. Thus, the title compound (7.9 mg of (Z) form and 3.2 mg of (E) form both as a colorless flocculent material) is prepared.

(Z) form

NMR (D$_2$O) δ (HOD=4.80 ppm): 1.22 (3H, d, J=7.1 Hz), 1.28 (3H, d, J=6.4 Hz), 1.90–2.01 (1H, m), 2.89–2.98 (1H, m), 3.34–3.50 (3H, m), 3.70–3.85 (2H, m), 4.08–4.12 (1H, m), 4.21–4.30 (2H, m), 4.70–4.85 (3H, m), 4.93–4.98 (1H, m), 6.22 (1H, t, J=11.3 Hz), 6.80 (1H, d, J=11.6 Hz), 7.75 (1H, s), 8.01 (1H, s), 9.36 (1H, s).

(E) form

NMR (D$_2$O) δ (HOD=4.80 ppm): 1.21 (3H, d, J=7.1 Hz), 1.29 (3H, d, J=6.3 Hz), 1.53–1.61 (1H, m), 2.59–2.68 (1H, m), 3.03–3.09 (1H, m), 3.06 (1H, dd, J1=11.9 Hz, J2=3.4

Hz), 3.29–3.43 (3H, m), 3.82–3.98 (2H, m), 4.20–4.28 (2H, m), 4.67–4.69 (1H, m), 4.72–4.81 (3H, m), 4.94–4.97 (1H, m), 6.30 (1H, dd, J1=15.6 Hz, J2=7.3 Hz), 6.82 (1H, d, J=16.1 Hz), 7.67 (1H, s), 7.91 (1H, s).

Synthesis Example 1

(3S,5S)-3-Acetylthio-1-allyloxycarbonyl-5-[(imidazo[5,1-b]thiazol-5-yl)methylamino-carbonyl]pyrrolidine A 1.1 M Vilsmeier reagent/dichloromethane solution (1.5 ml) prepared from DMF and phosphorus oxychloride by a conventional method is added at 0° C. to a solution of 416 mg of (3S,5S)-3-acetylthio-1-oxycarbonylpyrrolidin-5-carboxylic acid in 1.5 ml of dry dichloromethane, and the mixture is stirred in this state at 3 to 8° C. for 75 min. A solution of 265 mg of 5-aminomethylimidazo[5,1-b]thiazole in dry dichloromethane is added dropwise to the mixture over a period of 5 min, and the mixture is stirred at 5 to 8° C. for additional 85 min. The mixture is neutralized with dilute aqueous sodium hydroxide solution, adjusted to pH 9 by addition of a 5% aqueous sodium hydrogencarbonate solution, and subjected to salting out, followed by extraction twice with 50 ml of ethyl acetate. The combined organic layers are dried over magnesium sulfate+potassium carbonate and filtered, and the solvent is removed by evaporation under reduced pressure to give 514 mg of a yellow oil. This oil is successively purified by column chromatography on Sephadex LH-20 (chloroform:methanol=1:1) and silica gel (ethyl acetate:methanol=95:5) to give 293 mg of the title compound as a slightly yellow oil.

NMR (CDCl$_3$) δ: 2.22 (3H, s), 2.3 (1H, br.s), 2.6 (1H, br.s), 3.33–3.37 (1H, m), 3.91–4.05 (2H, m), 4.4 (1H, br.s), 4.55 (2H, br.s), 4.66 (1H, dd, J1=15.3 Hz, J2=5.9 Hz), 4.84 (1H, dd, J1=15.3 Hz, J2=6.6 Hz), 5.2 (1H, br.s), 5.85 (1H, br.s), 6.77 (1H, d, J=4.2 Hz), 6.98 (1H, s), 7.2 (1H, br.s), 7.74 (1H, d, J=4.2 Hz).

MS (EI): 408 (M$^+$)

Synthesis Example 2

(3S,5S)-3-Acetylthio-1-allyloxycarbonyl-5-[N-(imidazo[5,1-b]thiazol-5-yl)methyl-N-methylaminocarbonyl]pyrrolidine The procedure of Synthesis Example 1 is repeated, except that 260 mg of (3S,5S)-3-acetylthio-1-allyloxycarbonylpyrrolidin-5-carboxylic acid, 0.95 ml of a 1.1 M Vilsmeier reagent/dichloromethane solution, and 159 mg of 5-(N-methylaminomethyl)imidazo[5,1-b]thiazole. Thus, 190.6 mg of the title compound is prepared as a slightly yellow amorphous material.

NMR (CDCl$_3$) (approximately 3:2 conformer mixture) δ: 1.78–1.88 (1H, m), 2.31 (3H, s), 2.66–2.81 (1H, m), 3.07 (1H×3/5, s), 3.10 (1H×2/5, s), 3.46 (1H, dd, J1=10.2 Hz, J2=8.7 Hz), 3.99 (1H, quintet, J=8.1 Hz), 4.07–4.15 (1H, m), 4.22 (1H×2/5, dd, J1=13.3 Hz, J2=5.4 Hz), 4.47 (1H×2/5, dd, J1=13.3 Hz, J2=5.7 Hz), 4.57–4.60 (2H×3/5, m), 4.69 (1H, dd, J1=15.4 Hz, J2=7.4 Hz), 4.82 (1H×3/5, d, J=15.0 Hz), 4.96 (1H×3/5, d, J=15.0 Hz), 4.97–5.03 (2H×2/5, m), 5.09–5.36 (2H, m), 5.50 (1H×2/5, m), 5.93 (1H×3/5, m), 6.73 (1H, d, J=4.3 Hz), 6.98 (1H×3/5, s), 7.00 (1H×2/5, s), 7.72 (1H×3/5, d, J=4.3 Hz), 7.81 (1H×2/5, d, J=4.3 Hz).

MS (EI): 422 (M$^+$)

Synthesis Example 3

(3S,5S)-3-Acetylthio-1-allyloxycarbonyl-5-[N-[5-(allyloxycarbonylaminomethyl)imidazo[5,1-b]thiazol-3-yl]methyl-N-methylaminocarbonyl]pyrrolidine The procedure of Synthesis Example 1 is repeated, except that 255 mg of (3S,5S)-3-acetylthio-1-allyloxycarbonylpyrrolidin-5-carboxylic acid, 0.93 ml of a 1.1 M Vilsmeier reagent/dichloromethane solution, and 262 mg of 5-allyloxycarbonylaminomethyl-3-(N-methylaminomethyl)imidazo[5,1-b]thiazole are used and 0.145 ml of triethylamine is finally added at 4° C. followed by stirring at room temperature for additional 50 min. Thus, 327.5 mg of the title compound is prepared as a colorless amorphous material.

NMR (CDCl$_3$) (conformer mixture) δ: 1.9–2.0 (1H, m), 2.32 (3H×1/3, s), 2.37 (3H×2/3, s), 2.65–2.95 (total 1H, m), 3.12 & 3.18 & 3.27 (total 3H, s, 3:1:6 each), 3.37–3.40 (1H, m), 3.90–4.15 (2H, m), 4.50–4.95 (total 9H, m), 5.15–5.35 (4H, m), 5.8–6.1 (2+1H, m+br.s), 6.77 (1H, d, J=4.2 Hz), 6.82 & 6.95 (total 1H, s, 3:1 each), 6.95 & 7.02 (total 1H, s, 3:1 each).

MS (EI): 535 (M$^+$)

Synthesis Example 4

(3S,5S)-3-Acetylthio-1-allyloxycarbonyl-5-[1-hydroxy-1-(imidazot 5,1-b]thiazol-3-yl)methyl]pyrrolidine (stereoisomer A)

a) (3R,5S)-1-Allyloxycarbonyl-3-t-butyldimethylsilyloxy-5-[1-hydroxy-1-(imidazo[5,1-b]thiazol-3-yl)methyl]pyrrolidine (stereoisomer A) and ditto (stereoisomer B)

(3R,5S)-1-Allyloxycarbonyl-3-t-butyldimethylsilyloxy-5-[1-hydroxy-1-(imidazo[5,1-b]thiazol-3-yl)methyl]pyrrolidine (diastereomer mixture) (1.80 g) described in Synthesis Example 7-a) is purified by flash column chromatography on silica gel (Silica Gel 60, No. 9385, 360 g, manufactured by Merck; dichloromethane:ethanol=2 0:1) to give 650 mg of (3R,5S)-1-allyloxycarbonyl-3-t-butyldimethylsilyloxy-5-[1-hydroxy-1-(imidazo[5,1-b]thiazol-3-yl)methyl]pyrrolidine (stereoisomer A, a high polar component) as a yellowish white powder and 586 mg of (3R,5S)-1-allyloxycarbonyl-3-t-butyldimethylsilyloxy-5-[1-hydroxy-1-(imidazo[5,1-b]thiazol-3-yl)methyl]pyrrolidine (stereoisomer B, a low polar component) as a milky white amorphous material and 429 mg of a mixture of both the isomers as a milky white amorphous material.

Stereoisomer A

NMR (CD$_3$COCD$_3$) δ: 0.07 (3H, s), 0.08 (3H, s), 0.86 (9H, s), 1.70–1.90 (1H, m), 2.33–2.45 (1H, m), 3.47 (1H, dt, J1=10.7 Hz, J2=3.9 Hz), 3.57 (1H, dt, J1=10.7 Hz, J2=5.0 Hz), 4.35–4.51 (1H, m), 4.55–4.70 (3H, m), 5.15–5.50 (4H, m, 1H is exchangeable with D$_2$O), 5.90–6.05 (1H, m), 6.96 (1H, s), 7.03 (1H, s), 8.10 & 8.37 (total 1H, s, 1:3 each).

MS (FAB+): 438 (M$^+$+H)

Stereoisomer B

NMR (CDCl$_3$) δ: −0.01 (3H, s), 0.01 (3H, s), 0.82 (9H, s), 1.66–1.73 (1H, m), 3.40 (1H, dd, J1=11.6 Hz, J2=3.8 Hz), 3.64 (1H, dd, J1=11.6 Hz, J2=1.7 Hz), 4.21–4.24 (1H, m), 4.55–4.79 (4H, m), 5.25–5.37 (2H, m), 5.90–6.02 (1H, m), 6.25 (1H, br.s), 6.63 (1H, s), 7.08 (1H, s), 8.26 (1H, s).

MS (FAB$^+$): 438 (M$^+$+H)

b) (3R,5S)-1-Allyloxycarbonyl-3-hydroxy-5-[1-hydroxy-1-(imidazo[5,1-b]thiazol-3-yl)methyl]pyrrolidine (stereoisomer A)

Concentrated hydrochloric acid (2.0 ml) is added dropwise to a solution of 525 mg of (3R,5S)-1-allyloxycarbonyl-3-t-butyldimethylsilyloxy-5-[1-hydroxy-1-(imidazo[5,1-b]thiazol-3-yl)methyl]pyrrolidine (stereoisomer A) in 50 ml of dry acetonitrile under ice cooling (internal temperature 7° C.). The mixture is stirred in this state for 5 min, and the temperature is then raised to 15° C. over a period of 20 min. The reaction solution is concentrated to about 20 ml under reduced pressure, and the concentrate is adjusted to pH 8.5 by addition of 40 ml of a 5% aqueous sodium hydrogencarbonate solution. The mixture is then extracted three times with 100 ml of ethyl acetate. The combined organic layers are dried over magnesium sulfate, and the solvent is removed by evaporation under reduced pressure to give 457 mg of crude (3R,5S)-1-allyloxycarbonyl-3-hydroxy-5-[1-hydroxy-1-(imidazo[5,1-b]thiazol-3-yl)methyl]pyrrolidine (stereoisomer A) as a milky white amorphous material.

Stereoisomer A

NMR (CD$_3$COCD$_3$) δ: 1.73–1.88 (1H, m), 2.36–2.45 (1H, m), 3.42–3.65 (2H, m), 4.18 (1H, br.s+shoulder), 4.35–4.65 (3H, m), 5.17–5.55 (4H, m), 5.90–6.05 (1H, m), 6.96 (1H, s), 7.03 (1H, s), 8.10 & 8.37 (total 1H, s, 1:2 each).

MS (EI): 323 (M$^+$)

c) (3R,5S)-1-Allyloxycarbonyl-5-[1-hydroxy-1-(imidazo[5,1-b]thiazol-3-yl)methyl]-3-methanesulfonyloxypyrrolidine (stereoisomer A)

Triethylamine (0.25 ml) and 0.12 ml of methanesulfonyl chloride are successively added to a solution of 457 mg of crude (3R,5S)-1-allyloxycarbonyl-3-hydroxy-5-[1-hydroxy-1-(imidazo[5,1-b]thiazol-3-yl)methyl]pyrrolidine (stereoisomer A) in 12 ml of dry THF in an argon atmosphere at 3° C., and the mixture is stirred in this state for 30 min. A 5% aqueous sodium hydrogencarbonate solution (30 ml) is added thereto, and the mixture is extracted with 100 ml of ethyl acetate. The organic layer is washed with saturated saline, dried over magnesium sulfate, and filtered, and the solvent is removed by evaporation under reduced pressure to give a slightly cloudy orange brown oil. This oil is purified by flash column chromatography on silica gel (ethyl acetate:methanol=92:8) to give 344 mg of crude (3R,5S)-1-allyloxycarbonyl-5-[1-hydroxy-1-(imidazo[5,1-b]thiazol-3-yl)methyl]-3-methanesulfonyloxypyrrolidine (stereoisomer A) as a milky white amorphous material.

Stereoisomer A

NMR (CD$_3$COCD$_3$) δ: 2.12–2.30 (1H, m), 2.62–2.71 (1H, m), 3.14 (3H, s), 3.67–3.97 (2H, m), 4.44–4.67 (3H, m), 5.19–5.57 (5H, m, 1H is exchangeable with D$_2$O), 5.92–6.07 (1H, m), 7.01 (1H, s), 7.04 (1H, s), 8.09 & 8.34 (total 1H, s, 1:2 each).

MS (EI): 401 (M$^+$)

d) (3S,5S)-3-Acetylthio-1-allyloxycarbonyl-5-[1-hydroxy-1-(imidazo[5,1-b]thiazol-3-yl)methyl] pyrrolidine (stereoisomer A)

Potassium thioacetate (134 mg) is added to a solution of 314 mg of (3R,5S)-1-allyloxycarbonyl-5-[1-hydroxy-1-(imidazo[5,1-b]thiazol-3-yl)methyl]-3-methanesulfonyloxypyrrolidine (stereoisomer A) in a mixture of 4 ml of dry DMF and 2 ml of dry toluene, and the mixture is stirred in an argon atmosphere at a bath temperature of 70° C. for 22 hr. The mixture is diluted with 60 ml of ethyl acetate and washed twice with semi-saturated saline, and the organic layer is dried over magnesium sulfate and filtered. The solvent is removed by evaporation under reduced pressure, and the residue is dried under reduced pressure by means of a vacuum pump. The dark red oil is purified by flash column chromatography on silica gel (ethyl acetate) to give 217 mg of the title compound as a slightly red amorphous material.

Stereoisomer A

NMR (CDCl$_3$) δ: 2.17–2.35 (3H, br+m), 2.33 (3H, s), 3.20 (1H, br.t), 3.84 (2H, quintet, J=8.4 Hz), 4.19 (1H, br.t), 4.32 (1H, dt, J1=7.8 Hz, J2=2.6 Hz), 4.4–4.6 (2H, m), 5.19–5.35 (2H, m), 5.54 & 5.75 (total 1H, br.s each), 5.85–5.95 (1H, m), 6.71 (1H, s), 6.99 (1H, s), 8.06 & 8.24 (total 1H, br.s, 1:2 each).

MS (EI): 381 (M$^+$)

Synthesis Example 5

(3S,5S)-3-Acetylthio-1-allyloxycarbonyl-5-[1-hydroxy-1-(imidazo[5,1-b]thiazol-3-yl)methyl] pyrrolidine (stereoisomer B)

a) (3R,5S)-1-Allyloxycarbonyl-3-hydroxy-5-[1-hydroxy-1-(imidazo[5,1-b]thiazol-3-yl)methyl] pyrrolidine (stereoisomer B)

Concentrated hydrochloric acid (0.34 ml) is added dropwise to a solution of 372 mg of (3R,5S)-1-allyloxycarbonyl-3-t-butyldimethylsilyloxy-5-[1-hydroxy-1-(imidazo[5,1-b]thiazol-3-yl)methyl]pyrrolidine (stereoisomer B), described in Synthesis Example 4-a), in 8.5 ml of dry acetonitrile under ice cooling (internal temperature 3° C.). The mixture is stirred in this state for 20 min and diluted with 50 ml of ethyl acetate, and the diluted solution is adjusted to pH 9.2 by addition of a 5% aqueous sodium hydrogencarbonate solution, followed by shaking. The organic layer is separated. The aqueous layer is extracted twice with 50 ml of ethyl acetate while adjusting the pH value to 9.2 by addition of a 5% aqueous sodium hydrogencarbonate solution. The organic layer is combined with the above organic layer, and the combined organic layers are dried over magnesium sulfate, followed by filtration and the removal of the solvent by evaporation under reduced pressure to give 313 mg of crude (3R,5S)-1-allyloxycarbonyl-3-hydroxy-5-[1-hydroxy-1-(imidazo[5,1-b]thiazol-3-yl)methyl]pyrrolidine (stereoisomer B) as a slight yellow viscous material.

Stereoisomer B

NMR (CDCl$_3$) δ: 1.65–1.85 (3H, m), 3.42–3.50 (1H, m), 3.79 (1H, br.d, J=12.1 Hz), 4.33 (1H, br.s), 4.60–4.70 (3H, m), 4.80 (1H, br.d, J=7.9 Hz), 5.25–5.38 (2H, m), 5.88–6.02 (1H, m), 6.62 (1H, s), 6.65 (1H, br.s), 6.97 (1H, s), 8.21 (1H, br.s).

MS (EI): 323 (M$^+$)

b) (3R 5S)-1-Allyloxycarbonyl-5-[1-hydroxy-1-(imidazo[5,1-b]thiazol-3-yl)methyl]-3-methanesulfonyloxypyrrolidine (stereoisomer B)

Triethylamine (0.165 ml) and 0.080 ml of methanesulfonyl chloride are successively added to 313 mg of crude (3R,5S)-1-allyloxycarbonyl-3-hydroxy-5-[1-hydroxy-1-(imidazo[5,1-b]thiazol-3-yl)methyl]pyrrolidine (stereoisomer B) in 8.5 ml of THF in an argon atmosphere at −14° C., and the mixture is stirred in this state for 40 min. Further, 0.008 ml of methanesulfonyl chloride is added thereto, and the mixture is stirred for 20 min. A 5% aqueous sodium hydrogencarbonate solution (20 ml) is added thereto, and the mixture is extracted wit 50 ml of ethyl acetate. The organic layer is dried over magnesium sulfate and filtered. The solvent is removed by evaporation under reduced pressure to give 355 mg of crude (3R,5S)-1-allyloxycarbonyl-5-[1-hydroxy-(imidazo[5,1-b]thiazol-3-yl)methyl]-3-methanesulfonyloxypyrrolidine (stereoisomer B) as a slight yellow amorphous material.

Stereoisomer B

NMR (CDCl$_3$) δ: 1.75 (1H, br.s), 1.90–2.15 (2H, m), 3.01 (3H, s), 3.60 (1H, dd, J1=13.4 Hz, J2=3.8 Hz), 4.10–4.16 (1H, m), 4.60–4.72 (3H, m), 4.85 (1H, br.d, J=7.5 Hz), 5.15 (1H, br.s), 5.25–5.40 (2H, m), 5.88–6.02 (1H, m), 6.69 (1H, s), 7.09 (1H, s), 8.26 (1H, br.s).

MS (EI): 401 (M$^+$)

c) (3S,5S)-3-Acetylthio-1-allyloxycarbonyl- 5-[1-hydroxy-1-(imidazo[5,1-b]thiazol-3-yl)methyl] pyrrolidine (stereoisomer B)

Potassium thioacetate (149 mg) is added to a solution of 355 mg of crude (3R,5S)-1-allyloxycarbonyl-5-[1-hydroxy-1-(imidazo[5,1-b]thiazol-3-yl)methyl]-3-methanesulfonyloxypyrrolidine (stereoisomer B) in a mixture of 3 ml of dry DMF and 1.5 ml of dry toluene, and the mixture is stirred in an argon atmosphere at a bath temperature of 80° C. for 12 hr. The mixture is diluted with 100 ml of ethyl acetate and washed twice with 40 ml of a 5% aqueous sodium hydrogencarbonate solution. The organic layer is dried over magnesium sulfate and filtered, and the solvent is removed by evaporation under reduced pressure. The residue is dried under reduced pressure by means of a vacuum pump for 2 hr. The resultant brown oil is successively purified by column chromatography on silica gel (ethyl acetate) and on Sephadex LH-20 (chloroform:methanol=1:1) to give 139.1 mg of the title compound as a slightly red amorphous material.

Stereoisomer B

NMR (CDCl$_3$) δ: 1.70 (1H, m), 2.29 (1H, m), 2.33 (3H, s), 3.22 (1H, br.t), 3.84 (1H, quintet, J=7.7 Hz), 4.17 (1H, br.t), 4.53 (1H, dd, J1=14.5 Hz, J2=7.7 Hz), 4.60–4.80 (2H, m), 4.92 (1H, d, J=8.0 Hz), 5.22–5.42 (2H, m), 5.85–6.00 (1H, m), 6.50 (1H, br.s), 6.68 (1H, s), 7.04 (1H, s), 8.23 (1H, br.s).

MS (EI): 381 (M$^+$)

Synthesis Example 6

(3S,5R)-1-Allyloxycarbonyl-3-benzoylthio-5-(imidazo[5,1-b]thiazol-5-yl)methylpyrrolidine a) 5-Bromoimidazo[5,1-b]thiazole,7-bromoimidazo [5,1-b]thiazole, and 5,7-dibromoimidazo[5,1-b] thiazole N-Bromosuccinimide (8.900 g) is added to a solution of 6.208 g of imidazo[5,1-b]thiazole in 250 ml of dry dichloroethane, and the mixture is stirred at −7 to −4° C. for 40 min. The reaction solution is concentrated to about 50 ml under reduced pressure, the concentrate is diluted with 500 ml of ethyl acetate, the diluted solution is successively washed twice with 250 ml of distilled water and twice with 250 ml of semi-saturated saline. The organic layer is dried over magnesium sulfate and filtered, and the solvent is removed by evaporation under reduced pressure to give an oil which is then purified by flash column chromatography on silica gel (n-hexane:ethyl acetate=2:1 to 1:1) to give 3.245 g of 5-bromoimidazo[5,1-b]thiazole as a milky white powder, 4.443 g of 7-bromoimidazo[5,1-b]thiazole as a milky white powder, and 1.174 g of 5,7-dibromoimidazo[5,1-b]thiazole as a colorless crystallite.

5-Bromoimidazo[5,1-b]thiazole

NMR (CDCl$_3$) δ: 6.89 (1H, d, J=4.3 Hz), 7.09 (1H, s), 7.29 (1H, d, J=4.3 Hz).

MS (TSP): 205 (M$^+$+H+2), 203 (M$^+$+H)

7-Bromoimidazo[5,1-b]thiazole

NMR (CDCl$_3$) δ: 6.88 (1H, d, J=4.2 Hz), 7.43 (1H, d, J=4.2 Hz), 7.91 (1H, s).

MS (TSP): 205 (M$^+$+H+2), 203 (M$^+$+H)

5,7-Dibromoimidazo[5,1-b]thiazole

NMR (CDCl$_3$) δ: 6.94 (1H, d, J=4.3 Hz), 7.31 (1H, d, J=4.3 Hz).

MS (TSP): 285 (M$^+$+H+4), 283 (M$^+$+H+2), 281 (M$^+$+H)

b) (3R,5S)-1-Allyloxycarbonyl-3-t-butyldimethylsilyloxy-5-[1-hydroxy-1-(imidazo[5,1-b]thiazol-5-yl)methyl]pyrrolidine (stereoisomer A) and ditto (stereoisomer B)

A 0.99 M ethylmagnesium bromide/THF solution (15.2 ml) is diluted with 60 ml of anhydrous THF. A solution of 3.046 g of 5-bromoimidazo[5,1-b]thiazole in 60 ml of anhydrous THF is added dropwise to the diluted solution in an argon atmosphere over a period of 15 min (4 to 8° C.), and the mixture is stirred in this state for 5 min. The mixture is then cooled to −3° C. over a period of 10 min. Thereafter, a solution of 4.702 g of (3R,5S)-1-allyloxycarbonyl-3-t-butyldimethylsilyloxy-5-formylpyrrolidine in 60 ml of anhydrous THF is added dropwise thereto over a period of 20 min (−3 to −1° C.). The mixture is stirred in this state at −1 to +1° C. for 80 min. An aqueous semi-saturated ammonium chloride solution (180 ml) is added thereto, and the mixture is extracted twice with 360 ml of ethyl acetate. The organic layer is dried over magnesium sulfate and filtered, and the solvent is removed by evaporation under reduced pressure to give a yellow oil which is then purified by flash column chromatography on silica gel (n-hexane:ethyl acetate=1:1 to 1:2) to give 4.934 g of 3R,5S)-1-allyloxycarbonyl-3-t-butyldimethylsilyloxy-5-[1-hydroxy-1-(imidazo[5,1-b]thiazol-5-yl)methyl]pyrrolidine (stereoisomer A, a high polar component) as a colorless amorphous material and 605.5 mg of (3R,5S)-1-allyloxycarbonyl-3-t-butyldimethylsilyloxy-5-[1-hydroxy-1-(imidazo[5,1-b]thiazol-5-yl)methyl]pyrrolidine (stereoisomer B, a low polar component) as a slightly yellow, high viscous material.

Stereoisomer A

NMR (CDCl$_3$) δ: −0.02 (3H, s), 0.01 (3H, s), 0.81 (9H, s), 1.53–1.63 (1H, m), 1.94–2.15 (1H, m), 3.37 (1H, dd, J1=11.5 Hz, J2=3.9 Hz), 3.60 (1H, br.d, J=11.5 Hz), 4.18 (1H, br.s), 4.44 (1H, q, J=7.7 Hz), 4.60–4.73 (2H, m), 5.00 (1H, d, J=7.7 Hz), 5.23–5.37 (2H, m), 5.89–6.02 (1H, m), 6.05 (1H, br.s), 6.77 (1H, d, J=4.3 Hz), 6.97 (1H, s), 7.80 (1H, d, J=4.3 Hz).

MS (TSP): 438 (M$^+$+H)

Stereoisomer B

NMR (CDCl$_3$) δ: 0.00 (3H, s), 0.02 (3H, s), 0.83 (9H, s), 1.87–1.97 (1H, m), 2.09 (1H, s), 2.33–2.43 (1H, m), 3.12 (1H, dd, J1=11.3 Hz, J2=5.0 Hz), 3.35 (1H, dd, J1=11.3 Hz, J2=3.2 Hz), 4.04 (1H, quintet, J=4.5 Hz), 4.49 (1H, br.t, J=7.5 Hz), 4.62–4.65 (2H, m), 5.20–5.37 (3H, br+m), 5.88–5.99 (1H, m), 6.74 (1H, d, J=4.1 Hz), 6.98 (1H, s), 7.71 (1H, d, J=4.1 Hz).

MS (ES): 438 (M$^+$+H)

c) (3R,5R)-1-Allyloxycarbonyl-3-hydroxy-5-(imidazo[5,1-b]thiazol-5-yl)methylpyrrolidine Thionyl chloride (0.39 ml) is added to a solution of 774 mg of (3R,5S)-1-allyloxycarbonyl-3-t-butyldimethyl-silyloxy-5-[1-hydroxy-1-(imidazo[5,1-b]thiazol-5-yl)methyl]pyrrolidine (stereoisomer A) in 0.014 ml of dry DMF and 5.3 ml of dry dichloromethane under ice cooling, and the mixture is stirred in this state for 25 min. The solvent and the excess reagent are removed by evaporation under reduced pressure, and the residue is dried under reduced pressure by means of a vacuum pump to give a bright yellow amorphous material which is then dissolved in 17.7 ml of 90% acetic acid. Zinc (1.156 g) is added to the solution under ice cooling, and the mixture is stirred in this state for 20 min. Further, the ice bath is removed, and stirring is continued for additional 10 min. Distilled water and ethyl acetate are added, and the mixture adjusted to pH 6 under stirring by addition of sodium hydrogencarbonate. The organic layer is separated, and the residual aqueous layer is adjusted to pH 8 by addition of sodium hydrogencarbonate, followed by extraction with ethyl acetate. The combined organic layers are washed twice with an 5% aqueous sodium hydrogencarbonate solution, dried over magnesium sulfate and potassium carbonate and filtered. The solvent is removed by evaporation under reduced pressure. The residue, together with acetonitrile, is once subjected to azeotropic evaporation, the residue is redissolved in 17.7 ml of acetonitrile, 0.70 ml of concentrated hydrochloric acid is added thereto under ice cooling, and the mixture is stirred in this state for 15 min. The mixture is diluted with 200 ml of ethyl acetate, the diluted solution is washed with 50 ml of a 5% aqueous sodium hydrogencarbonate solution, the organic layer is dried over magnesium sulfate, filtered, and the solvent is removed by evaporation under reduced pressure to give a yellowish orange amorphous material. The amorphous material is successively purified by column chromatography on silica gel (first, ethyl acetate:methanol= 9:1; second, chloroform:methanol 9:1) and on Sephadex LH-20 (chloroform:methanol=1:1) to give 138 mg of (3R, 5R)-1-allyloxycarbonyl-3-hydroxy-5-(imidazo[5,1-b] thiazol-5-yl)methylpyrrolidine as a colorless amorphous material.

NMR (CDCl$_3$) δ: 1.96–2.10 (1H, m), 2.15–2.30 (1H, m), 3.08–3.16 (1H, m), 3.25–3.60 (3H, m), 4.00 (1H, br.s), 4.17–4.40 (2H, m), 4.45–4.66 (2H, m), 5.20–5.40 (2H, m), 5.86–6.00 (1H, m), 6.77 (1H, d, J=4.1 Hz), 6.90 (1H, s), 7.22 (1H, br.s), 7.62 (1H, d, J 4.1 Hz).

MS (ES): 308 (M$^+$+H)

d) (3S,5R)-1-Allyloxycarbonyl-3-benzoylthio-5-(imidazo[5,1-b]thiazol-5-yl)methylpyrrolidine Diethyl azodicarboxylate (0.105 ml) is added to a solution of 102 mg of (3R,5R)-1-allyloxycarbonyl-3-hydroxy-5-(imidazo[5,1-b]thiazol-5-yl)methylpyrrolidine and 174 mg of triphenylphosphine in 1.7 ml of anhydrous THF at −11 to −10° C., the mixture is stirred in this state for 15 min, 0.130 ml of thiobenzoic acid (90%) is added thereto, and the mixture is stirred for 14 hr while raising the temperature this state to room temperature. The solvent and the excess reagent are removed by evaporation under reduced pressure to give a yellow oil which is then successively purified by column chromatography on Sephadex LH-20 (chloroform:methanol=1:1) and on silica gel (first, n-hexane:ethyl acetate=1:1) to give 87 mg of the title compound as a yellow oil.

NMR (CDCl$_3$) δ: 2.13–2.35 (1H, m), 2.50–2.65 (1H, m), 3.17–3.30 (2H, m), 3.45–3.62 (1H, m), 4.15–4.35 (3H, m), 4.62–4.65 (2H, m), 5.22–5.36 (2H, m), 5.88–6.02 (1H, m), 6.76 (1H, d, J=4.2 Hz), 6.97 (1H, s), 7.42–7.48 (2H, m), 7.56–7.61 (2H, m), 7.91–7.94 (2H, m).

MS (EI): 427 (M$^+$)

Synthesis Example 7

(3S,5S)-3-Acetylthio-1-allyloxycarbonyl-5-[1-hydroxy-1-(imidazo[5,1-b]thiazol-2-yl)methyl] pyrrolidine (diastereomer mixture)

a) (3R,5S)-1-Allyloxycarbonyl-3-t-butyldimethylsilyloxy-5-[1-hydroxy-1-(imidazo[5,1-b]thiazol-2-yl)methyl]pyrrolidine (diastereomer mixture) and (3R,5S)-1-allyloxycarbonyl-3-t-butyldimethylsilyloxy-5-[1-hydroxy-1-(imidazo[5,1-b]thiazol-3-yl)methyl]pyrrolidine (diastereomer mixture)

A 1.69 M n-butyllithium-hexane solution (7.2 ml) is added dropwise to a solution of 2.09 g of imidazo[5,1-b] thiazole in 40 ml of dry THF over a period of 10 min while maintaining the temperature at −70° C. or below, and the mixture is stirred at that temperature for 2 hr. A solution of 5.32 g of (3R,5S)-1-allyloxycarbonyl-3-t-butyldimethylsilyloxy-5-formylpyrrolidine in 20 ml of THF is gradually added dropwise to the mixed solution, and the mixture is stirred at −70° C. for 1.5 hr. The temperature is raised to 0° C. over a period of one hr, and the mixture is stirred at 0° C. for one hr and further at room temperature for 1.5 hr. Water is added to the reaction solution, and the mixture is extracted three times with ethyl acetate. The organic layer is washed twice with saturated saline, dried over anhydrous magnesium sulfate, and filtered, and the solvent is removed by evaporation under reduced pressure. The resultant crude product is successively purified by column chromatography on Sephadex LH-20 (dichloromethane:methanol=1:1) and on silica gel (hexane:ethyl acetate=1:1) to give 0.92 g of (3R,5S)-1-allyloxycarbonyl-3-t-butyldimethylsilyloxy-5-[1-hydroxy-1-(imidazo[5,1-b]thiazol-2-yl)methyl]pyrrolidine (a diastereomer mixture) and 1.85 g of (3R,5S)-1-allyloxycarbonyl-3-t-butyldimethylsilyloxy-5 -[1-hydroxy-1-(imidazo[5,1-b] thiazol-3-yl)methyl]pyrrolidine (a diastereomer mixture) as a yellow amorphous material.

(3R,5S)-1-Allyloxycarbonyl-3-t-butyldimethylsilyloxy-5-[1-hydroxy-1-(imidazo[5,1-b]thiazol-2-yl)methyl]pyrrolidine (diastereomer mixture)

NMR (CDCl$_3$) δ: 0.01, 0.02 (total 6H, s, each), 0.82, 0.83 (total 9H, s, each), 1.66–1.75 (1H, m), 1.83–1.95 (1H, m), 3.30–3.41 (1H, m), 4.20–4.35 (2H, m), 4.36–4.81 (3H, m), 4.79–4.83, 5.02 (total 1H, m+s), 5.31–5.46 (2H, m), 5.87–6.00 (1H, m), 7.01, 7.03 (total 1H, s, each), 7.34 (1H, s), 7.90 (1H, s) MS (ES): 437 (M$^+$).

(3R,5S)1-allyloxycarbonyl-3-t-butyldimethylsilyloxy-5-[1-hydroxy-1-(imidazo[5,1-b]thiazol-3-yl)methyl] pyrrolidine (diastereomer mixture)

NMR (CDCl$_3$) δ: 0.02, 0.03 (total 6H, s, each), 0.82, 0.84 (total 9H, s, each), 1.63–1.76 (2H, m), 3.36–3.51 (1H, m), 3.65–3.69 (1H, m), 4.22–4.46 (1H, m), 4.50–4.80 (4H, m), 5.27–5.39 (2H, m), 5.91–6.03 (1H, m), 6.64, 6.66 (total 1H, s, each), 7.08 (1H, s), 8.26, 8.29 (total 1H, s, each).

MS (ES): 437 (M$^+$)

b) (3R,5S)-1-Allyloxycarbonyl-5-[1-hydroxy-1-(imidazo[5,1-b]thiazol-2-yl)methyl]-3-methanesulfonyloxypyrrolidine (diastereomer mixture)

Concentrated hydrochloric acid (0.85 ml) is added dropwise to a solution of 899 mg of (3R,5S)-1-allyloxycarbonyl- 3-t-butyldimethylsilyloxy-5-[1-hydroxy-1-(imidazo[5,1-b]thiazol-2-yl)methyl]pyrrolidine in 20 ml of dry acetonitrile under ice cooling, and the mixture is stirred at that temperature for 20 min. The reaction solution is diluted with 50 ml of ethyl acetate, water is added thereto, and the mixture is rendered weakly alkaline by addition of a saturated aqueous sodium hydrogencarbonate solution. The mixture is then extracted three times with ethyl acetate, and the organic layer is washed twice with saturated saline, dried over anhydrous magnesium sulfate and filtered. The solvent is removed by evaporation under reduced pressure to give a crude product of (3R,5S)-1-allyloxycarbonyl-3-hydroxy-5-[1-hydroxy-1-(imidazo[5,1-b]thiazol-2-yl)methyl]pyrrolidine. Triethylamine (0.46 ml) and 0.24 ml of methanesulfonyl chloride are successively added to a solution of this compound in 20 ml of THF, and the mixture is stirred under an argon stream at −14° C. for 50 min. Water is added to the reaction solution, and the mixture is extracted four times with ethyl acetate. The organic layer is washed once with saturated saline, dried over anhydrous magnesium sulfate and filtered, and the solvent is removed by evaporation under reduced pressure to give a crude product which is then purified by column chromatography on silica gel (ethyl acetate:methanol=9:1) to give 472.6 mg of (3R,5S)-1-allyloxycarbonyl-5-[1-hydroxy-1-(imidazo[5,1-b]thiazol-2-yl)methyl]-3-methanesulfonyloxypyrrolidine (a diastereomer mixture) as a yellow viscous material.

NMR (CDCl$_3$) δ: 1.53–1.72 (2H, m), 2.25–2.45 (1H, m), 2.50–2.75 (1H, m), 3.02, 3.03 (total 3H, s, each), 3.57–3.67 (1H, m), 4.00–4.15 (1H, m), 4.38–4.48 (1H, m), 4.65–4.75 (2H, m), 5.15–5.36 (3H, m), 5.90–6.02 (1H, m), 7.05 (1H, s), 7.39 (1H, s), 7.93 (1H, s).

MS (FAB$^+$): 402 (M$^+$+H)

c) (3S,5S)-3-Acetylthio-1-allyloxycarbonyl-5-[1-hydroxy-1-(imidazo[5,1-b]thiazol-2-yl)methyl]pyrrolidine (diastereomer mixture)

Potassium thioacetate (204 mg) is added to a solution of 236.9 mg of (3R,5S)-1-allyloxycarbonyl-3-methanesulfonyloxy-5-[1-hydroxy-1-(imidazo[5,1-b]thiazol-2-yl)methyl]pyrrolidine (a diastereomer mixture) in 10 ml of DMF, and the mixture is stirred under an argon stream a 70° C. for 5 hr. The reaction solution is cooled, water is added thereto, and the mixture is extracted three times with ethyl acetate. The organic layer is washed once with saturated saline, dried over anhydrous magnesium sulfate and filtered, and the solvent is removed by evaporation under reduced pressure. The resultant crude product is purified by column chromatography on silica gel (hexane:acetone=1:1) to give 136.4 mg of the title compound (a diastereomer mixture) as a brown oil.

NMR (CDCl$_3$) δ: 1.60–1.69 (1H, m), 1.72–1.88 (1H, m), 2.25, 2.26 (total 3H, s, each), 2.95–3.05 (1H, m), 3.13–3.21 (1H, m), 3.69–3.81 (1H, m), 4.09–4.28 (2H, m), 4.54–4.60 (2H, m), 4.86–4.90 (1H, m), 5.16–5.30 (2H, m), 5.81–5.92 (1H, m), 6.97, 6.98 (total 1H, s, each), 7.31 (1H, s), 7.86 (1H, s).

MS (FAB$^+$): 382 (M$^+$+H)

Synthesis Example 8

(3S,5R)-3-Acetylthio-1-allyloxycarbonyl-5-(imidazo[5,1-b]thiazol-3-yl)methylpyrrolidine a) (3R,5S)-1-Allyoxycarbonyl-3-t-butyldimethylsilyloxy-5-[1-(imidazo[5,1-b]thiazol-3-yl)-1-(methylthiocarbonyloxy)methyl]pyrrolidine (diastereomer mixture)

Imidazole (2.7 mg), 0.53 ml of carbon disulfide, and 128 mg of sodium hydride are successively added to a solution of 1.28 g of (3R,5S)-1-allyloxycarbonyl-3-t-butyldimethylsilyloxy-5-[1-hydroxy-1-(imidazo[5,1-b]thiazol-3-yl)methyl]pyrrolidine (a diastereomer mixture), described in Synthesis Example 7-a), in 20 ml of dry THF under ice cooling, and the mixture is stirred at that temperature for 20 min. Methyl iodide (0.19 ml) is added dropwise to the mixed solution, and the temperature of the mixture is gradually raised and stirred at room temperature overnight. Water is added to the reaction solution, and the mixture is extracted three times with ethyl acetate. The organic layer is washed twice with saturated saline, dried over anhydrous magnesium sulfate, and filtered. The solvent is removed by evaporation under reduced pressure, and the resultant crude product is purified by column chromatography on silica gel (hexane:ethyl acetate=1:1) to give 1.31 g of (3R,5R)-1-allyloxycarbonyl-3-t-butyldimethylsilyloxy-5-[1-(imidazo[5,1-b]thiazol-3-yl)-1-(methylthiocarbonyloxy)methyl]pyrrolidine (a diastereomer mixture) as a colorless oil.

NMR (CDCl$_3$) δ: 0.02, 0.03 (total 6H, s, each), 0.85 (9H, s), 2.07–2.11 (2H, m), 2.60 (3H, s), 3.20–3.60 (2H, m), 4.20–4.45 (2H, m), 4.58–4.78 (3H, m), 5.21–5.31 (2H, m), 5, 79–5.98 (1H, m), 6.72 (1H, s), 7.10 (1H, s), 8.12, 8.19 (total 1H, s, each).

MS (FAB$^+$): 528 (M$^+$+H)

b) (3R,5R)-1-Allyloxycarbonyl-3-t-butyldimethylsilyloxy-5-(imidazo[5,1-b]thiazol-3-yl)methylpyrrolidine Tri-n-butyltin hydride (1.34 ml) and 143 mg of 2,2'-azobisisobutyronitrile are added to a solution of 1.31 g of (3R,5S)-1-allyloxycarbonyl-3-t-butyldimethylsilyloxy-5-[1-imidazo[5,1-b]thiazo-3)-1-(methylthiocarbonyloxy)methyl]pyrrolidine (a diastereomer mixture) in 15 ml of dry toluene, and the mixture is deaerated under an argon stream for 20 min and heated under reflux for 5 hr. The solvent in the reaction solution is removed by evaporation under reduced pressure to give a crude product which is then successively purified by column chromatography on silica gel (dichloromethane:methanol=50:1) and on Sephadex LH-20 (chloroform:methanol=1:1) to give 732 mg of (3R, 5R)-1-allyloxycarbonyl-3-t-butyldimethylsilyloxy-5-(imidazo[5,1-b]thiazol-3-yl)methylpyrrolidine as a slightly yellow amorphous material.

NMR (CDCl$_3$) δ: 0.01 (6H, s), 0.82 (9H, s), 1.75–1.86 (1H, m), 1.91–2.04 (1H, m), 2.72–2.91 (1H, m), 3.25–3.53 (3H, m), 4.22–4.38 (2H, m), 4.58–4.69 (2H, m), 5.20–5.33 (2H, m), 5.86–6.00 (1H, m), 6.41 (1H, s), 7.07 (1H, s), 8.00, 8.17 (total 1H, s, each).

MS (FAB$^+$): 422 (M$^+$+H)

c) (3R,5R)-1-Allyloxycarbonyl-5-(imidazo[5,1-b]thiazol-3-yl)methyl-3-methanesulfonyloxypyrrolidine Concentrated hydrochloric acid (0.75 ml) is added dropwise to a solution of 732 mg of (3R,5R)-1-allyloxycarbonyl-3-t-butyldimethylsilyloxy-5-(imidazo[5,1-b]thiazol-3-yl)methylpyrrolidine in 15 ml of dry acetonitrile under ice cooling, and the mixture is stirred at that temperature for 30 min. The reaction solution is diluted wit 50 ml of ethyl acetate, water is added thereto, and the mixture is rendered weakly alkaline by addition of a saturated aqueous sodium hydrogencarbonate solution and extracted three times with ethyl acetate. The organic layer is washed once with saturated saline, dried over anhydrous magnesium sulfate, and filtered, and the solvent is removed by evaporation under reduced pressure to give a crude product of (3R,5R)-1- allyloxycarbonyl-3-hydroxy-5-(imidazo[5,1-b]thiazol-3-yl)methylpyrrolidine. Triethylamine (0.41 ml) and 0.23 ml of methanesulfonyl chloride are successively added to a solution of this compound in 3 ml of dichloromethane under an argon stream under ice cooling, and the mixture is stirred at that temperature for 2 hr. Water is added to the reaction solution, and the mixture is extracted three times with dichloromethane. The organic layer is washed twice with saturated saline, dried over anhydrous magnesium sulfate, and filtered, and the solvent is removed by evaporation under reduced pressure to give a crude product which is then purified by column chromatography on silica gel (ethyl acetate) to give 428.2 mg of (3R,5R)-1-allyloxycarbonyl-5-(imidazo[5,1-b]thiazol-3-yl)methyl-3-methanesulfonyloxypyrrolidine as a colorless oil.

NMR (CDCl$_3$) δ: 1.85–2.08 (1H, m), 2.31–2.50 (1H, m), 2.71–2.93 (1H, m), 2.95 (3H, s), 3.31–3.63 (2H, m), 3.83–4.12 (1H, m), 4.29–4.41 (1H, m), 4.56–4.65 (1H, m), 5.09–5.36 (3H, m), 5.82–5.98 (1H, m), 6.42 (1H, s), 7.04 (1H, s), 7.94, 8.14 (total 1H, s, each).

MS (EI): 385 (M$^+$)

d) (3S,5R)-3-Acetylthio-1-allyloxycarbonyl-5-(imidazo[5,1-b]thiazol-3-yl)methylpyrrolidine Potassium thioacetate (365 mg) is added to a solution of 427.7 mg of (3R,5R)-1-allyloxycarbonyl-5-(imidazo[5,1-b]thiazol-3-yl)methyl-3-methanesulfonyloxypyrrolidine in 4.5 ml of DMF, and the mixture is stirred under an argon stream at 70° C. for 8.5 hr. The reaction solution is cooled, water is added thereto, and the mixture is extracted four times with ethyl acetate. The organic layer is washed once with saturated saline, dried over anhydrous magnesium sulfate, and filtered. The solvent is removed by evaporation under reduced pressure to give a crude product which is then purified by column chromatography on silica gel (hexane:ethyl acetate=1:1) to give 374.7 mg of the title compound as a brown viscous material.

NMR (CDCl$_3$) δ: 1.62–1.79 (1H, m), 2.30 (3H s), 2.35–2.53 (1H, m), 2.79–2.88 (1H, m), 3.22–3.56 (2H, m), 3.85–4.09 (2H, m), 4.18–4.28 (1H, m), 4.53–4.61 (2H, m), 5.16–5.33 (2H, m), 5.81–5.95 (1H, m), 6.40 (1H, s), 7.03 (1H, s), 7.95, 8.18 (total 1H, s, each).

MS (TSP): 366 (M$^+$+H)

Synthesis Example 9

(3S,5S)-3-Acetylthio-1-allyloxycarbonyl-5-(imidazo[5,1-b]thiazol-2-yl)methylpyrrolidine a) (3R,5S)-1-Allyloxycarbonyl-3-t-butyldimethylsilyloxy-5-[1-(imidazo[5,1-b]thiazol-2-yl)-1-(methylthiocarbonyloxy)methyl]pyrrolidine The procedure of Synthesis Example 8-a) is repeated, except that 1.16 g of (3R,5S)-1-allyloxycarbonyl-3-t-butyldimethylsilyloxy-5-[1-hydroxy-1-(imidazo[5,1-b]thiazol-2-yl)methyl]pyrrolidine (a diastereomer mixture) described in Synthesis Example 7-a) is used. Thus, 1.24 g of (3R,5S)-1-allyloxycarbonyl-3-t-butyldimethylsilyloxy-5-[1-(imidazo[5,1-b]thiazol-2-yl)-1-(methylthiocarbonyloxy)methyl]pyrrolidine (diastereomer mixture) as a yellow oil.

NMR (CDCl$_3$) δ: 0.01, 0.02 (total 6H, s, each), 0.82, 0.87 (total 9H, s, each), 1.71–1.79 (1H, m), 2.05–2.19 (1H, m), 2.61 (3H, s), 3.30–3.36 (1H, m), 3.42–3.62 (2H, m), 4.21–4.29 (1H, m), 4.50–4.70 (3H, m), 5.20–5.35 (2H, m), 5, 88–6.01 (1H, m), 7.04 (1H, s), 7.26 (1H, s), 7.93 (1H, s).

MS (FAB$^+$): 528 (M$^+$+H)

b) (3R,5S)-1-Allyloxycarbonyl-3-t-butyldimethylsilyloxy-5-(imidazo[5,1-b]thiazol-2-yl)methylpyrrolidine The procedure of Synthesis Example 8-b) is repeated, except that 1.24 g of (3R,5S)-1-allyloxycarbonyl-3-t-butyldimethylsilyloxy-5-[1-(imidazo[5,1-b]thiazol-2-yl)-1-(methylthiocarbonyloxy)methyl]pyrrolidine is used and purification is performed by column chromatography on silica gel (ethyl acetate:methanol=9:1). Thus, 656.2 mg of (3R,5S)-1-allyloxycarbonyl-3-t-butyldimethylsilyloxy-5-(imidazo[5,1-b]thiazol-2-yl)methylpyrrolidine is prepared as a colorless oil.

NMR (CDCl$_3$) δ: 0.02 (6H, s), 0.81 (9H, s), 1.87–1.98 (1H, m), 2.93–3.04 (1H, m), 3.00–3.18 (2H, m), 3.36–3.58 (2H, m), 4.21–4.30 (2H, m), 4.61–4.67 (2H, m), 5.20–5.34 (2H, m), 5.89–6.00 (1H, m), 7.00 (1H, s), 7.16 (1H, s), 7.89 (1H, s).

MS (FAB$^+$): 422 (M$^+$+H)

c) (3R,5S)-1-Allyloxycarbonyl-5-(imidazo[5,1-b]thiazol-2-yl)methyl-3-methanesulfonyloxypyrrolidine The procedure of Synthesis Example 8-c) is repeated, except that 656.2 mg of (3R,5S)-1-allyloxycarbonyl-3-t-butyldimethylsilyloxy-5-(imidazo[5,1-b]thiazol-2-yl)methylpyrrolidine is used and the methanesulfonation is performed under ice cooling. Thus, 349.1 mg of (3R,5S)-1-allyloxycarbonyl-3-mesyloxy-5-(imidazo[5,1-b]thiazol-2-yl)methylpyrrolidine as a colorless oil.

NMR (CDCl$_3$) δ: 1.90–2.06 (1H, m), 2.32–2.45 (1H, m), 2.95 (3H, s), 2.98–3.23 (2H, m), 3.40–3.52 (1H, m), 3.87–4.00 (1H, m), 4.21–4.30 (1H, m), 4.58–4.64 (2H, m), 5.07–5.11 (1H, m), 5.17–5.31 (2H, m), 5.83–5.98 (1H, m), 6.95 (1H, s), 7.14 (1H, s), 7.85 (1H, s).

MS (FAB$^+$: 386 (M$^+$+H)

d) (3S,5S)-3-Acetylthio-1-allyloxycarbonyl-5-(imidazo[5,1-b]thiazol-2-yl)methylpyrrolidine The procedure of Synthesis Example 8-d) is repeated, except that 326.8 mg of (3R,5S)-1-allyloxycarbonyl-3-mesyloxy-5-(imidazo[5,1-b]thiazol-2-yl)methylpyrrolidine is used. Thus, 289.4 mg of the title compound is prepared as a brown viscous material.

NMR (CDCl$_3$) δ: 1.66–1.78 (1H, m), 2.24 (3H, s), 2.34–2.50 (1H, m), 2.91–3.22 (3H, m), 3.76–3.87 (1H, m), 3.97–4.12 (2H, m), 4.54–4.59 (2H, m), 5.15–5.30 (2H, m), 5.81–5.95 (1H, m), 6.95 (1H, s), 7.14 (1H, s), 7.84 (1H, s).

MS (FAB$^+$: 366 (M$^+$+H)

Synthesis Example 10

(3S,5S)-3-Acetylthio-1-allyloxycarbonyl-5-(3-methylimidazo[5,1-b]thiazol-2-yl)methylpyrrolidine a) (3R,5S)-1-Allyloxycarbonyl-3-t-butyldimethylsilyloxy-5-[1-hydroxy-1-(3-methylimidazo[5,1-b]thiazol-2-yl)methyl]pyrrolidine (a diastereomer mixture)

A 1.69 M n-butyllithium/n-hexane solution (7.4 ml) is added dropwise to a solution of 1.56 g of 3-methylimidazo[5,1-b]thiazole in 25 ml of dry THF over a period of 10 min while maintaining the temperature at −70° C. or below, and the mixture is stirred at that temperature for 2 hr. A solution of 3.54 g of (3R,5S)-1-allyloxycarbonyl-3-t- butyldimethylsilyloxy-5-formylpyrrolidine in 15 ml of THF is gradually added dropwise to the mixed solution, the temperature is raised from −70° C. to 0° C. over a period of 3 hr, the mixture is stirred at 0° C. for 2 hr and at room temperature for 2 hr. Water is added to the reaction solution, and the mixture is extracted three times with ethyl acetate. The organic layer is washed twice with saturated saline, dried over anhydrous magnesium sulfate, and filtered, and the solvent is removed by evaporation under reduced pressure to give a crude product which is then successively purified by column chromatography on silica gel (ethyl acetate) and on Sephadex LH-20 (dichloromethane:methanol=1:1) to give 2.74 g of (3R,5S)-1-allyloxycarbonyl-3-t-butyldimethylsilyloxy-5-[1-hydroxy-1-(3-methylimidazo[5,1-b]thiazol-2-yl)methyl] pyrrolidine (a diastereomer mixture) as a colorless amorphous material.

NMR (CDCl$_3$) δ: 0.01, 0.02 (total 6H, s, each), 0.80, 0.81 (total 9H, s, each), 1.63–2.06 (3H, m), 2.32, 2.39 (total 3H, s, each), 3.35–3.61 (2H, m), 4.17–4.38 (2H, m), 4.58–4.88 (2H, m), 5.02–5.31 (2H, m), 5.81–5.99 (1H, m), 7.00, 7.03 (total 1H, s, each), 7.79 (1H, s).

MS (EI): 451 (M$^+$)

b) (3R,5S)-1-Allyloxycarbonyl-3-t-butyldimethylsilyloxy-5-[1-(3-methylimidazo[5,1-b]thiazol-2-yl)-1-(methylthiocarbonyloxy)methyl]pyrrolidine (diastereomer mixture)

The procedure of Synthesis Example 8-a) is repeated, except that 1.40 g of (3R,5S)-1-allyloxycarbonyl-3-t-butyldimethylsilyloxy-5-[1-hydroxy-1-(3-methylimidazo[5,1-b]thiazol-2-yl)methyl]pyrrolidine is used. Thus, 1.74 g of (3R,5S)-1-allyloxycarbonyl-3-t-butyldimethylsilyloxy-5-[1-(3-methylimidazo[5,1-b]thiazol-2-yl)-1-(methylthiocarbonyloxy)methyl]pyrrolidine (a diastereomer mixture) as a brown oil.

NMR (CDCl$_3$) δ: 0.07 (6H, s), 0.80, 0.88 (total 9H, s, each), 1.70–2.28 (3H, m), 2.35, 2.19 (total 3H, s, each), 2.65 (3H, s), 3.20–3.55 (2H, m), 4.20–4.66 (3H, m), 5.02–5.31 (2H, m), 5.81–5.99 (1H, m), 7.01–7.10 (1H, m), 7.81–7.91 (1H, m).

MS (ESI): 542 (M$^+$+H)

c) (3R,5S)-1-Allyloxycarbonyl-3-t-butyldimethylsilyloxy-5-[(3-methylimidazo[5,1-b]thiazol-2-yl)methyl]pyrrolidine The procedure of Synthesis Example 8-b) is repeated, except that 1.74 g of (3R,5S)-1-allyloxycarbonyl-3-t-butyldimethylsilyloxy-5-[1-(3-methylimidazo[5,1-b]thiazol-2-yl)-1-(methylthiocarbonyloxy)methyl]pyrrolidine is used. Thus, 660.9 mg of (3R,5S)-1-allyloxycarbonyl-3-t-butyldimethylsilyloxy-5-[(3-methylimidazo[5,1-b]thiazol-2-yl)methyl]pyrrolidine is prepared as a yellow oil.

NMR (CDCl$_3$) δ: 0.01 (6H, s), 0.82 (9H, s), 1.70–2.01 (2H, m), 2.36 (3H, s), 2.75–2.84 (1H, m), 3.03–3.22 (1H, m), 3.39–3.42 (2H, m), 4.14–4.27 (2H, m), 4.61–4.66 (2H, m), 5.19–5.34 (2H, m), 5.88–6.01 (1H, m), 7.03 (1H, s), 7.82 (1H, s).

MS (ESI): 436 (M$^+$+H)

d) (3R,5S)-1-Allyloxycarbonyl-3-methanesulfonyloxy-5-[(3-methylimidazo[5,1-b]thiazol-2-yl)methyl]pyrrolidine The procedure of Synthesis Example 9-c) is repeated, except that 660.9 mg of (3R,5S)-1-allyloxycarbonyl-3-t-butyldimethylsilyloxy-5-[(3-methylimidazo[5,1-b]thiazol-2-yl)methyl]pyrrolidine is used. Thus, 596.5 mg of (3R,5S)-1-allyloxycarbonyl-3-methanesulfonyloxy-5-[(3-methylimidazo[5,1-b]thiazol-2-yl)methyl]pyrrolidine is prepared as a colorless oil.

NMR (CDCl$_3$) δ: 1.91–2.18 (2H, m), 2.45 (3H, s), 2.45–2.60 (1H, m), 3.10 (3H, s), 3.30–3.39 (1H, m), 3.58–3.68 (1H, m), 3.99–4.17 (1H, m), 4.33–4.41 (1H, m), 4.72–4.79 (2H, m), 5.21–5.27 (1H, m), 5.33–5.46 (2H, m), 5.98–6.12 (1H, m), 7.12 (1H, s), 7.93 (1H, s).

MS (FAB$^+$: 400 (M$^+$+H)

e) (3S,5S)-3-Acetylthio-1-allyloxycarbonyl-5-[(3-methylimidazo[5,1-b]thiazol-2-yl)methyl]pyrrolidine The procedure of Synthesis Example 8-d) is repeated, except that 596.5 mg of (3R,5S)-1-allyloxycarbonyl-3-methanesulfonyloxy-5-[(3-methylimidazo[5,1-b]thiazol-2-yl)methyl]pyrrolidine is used. Thus, 474.5 mg of the title compound is prepared as a yellow oil.

NMR (CDCl$_3$) δ: 1.69–1.88 (1H, m), 2.34 (3H, s), 2.39 (3H, s), 2.40–2.60 (1H, m), 2.81–2.90 (1H, m), 3.20–3.41 (2H, m), 3.05–3.96 (1H, m), 4.01–4.18 (2H, m), 4.62–4.64 (2H, m), 5.22–5.38 (2H, m), 5.89–6.01 (1H, m), 7.05 (1H, s), 7.84 (1H, s).

MS (FAB$^+$: 380 (M$^+$)

Synthesis Example 11

(3S,5S)-3-Acetylthio-1-allyloxycarbonyl-5-(5-methylimidazo[5,1-b]thiazol-2-yl)methylpyrrolidine a) (3R,5S)-1-Allyloxycarbonyl-3-t-butyldimethylsilyloxy-5-[1-hydroxy-1-(5-methylimidazo[5,1-b]thiazol-2-yl)]methylpyrrolidine The procedure of Synthesis Example 10-a) is repeated, except that 1.53 g of 5-methylimidazo[5,1-b]thiazole and 3.46 g of (3R,5S)-1-allyloxycarbonyl-3-t-butyldimethylsilyloxy-5-formylpyrrolidine is used and the purification is successively performed by column chromatography on silica gel (ethyl acetate:methanol=9:1) and on Sephadex LH-20 (dichloromethane:methanol=1:1) to give 0.92 g of (3R,5S)-1-allyloxycarbonyl-3-t-butyldimethylsilyloxy-5-[1-hydroxy-1-(5-methylimidazo[5,1-b]thiazol-2-yl)methyl]pyrrolidine (a diastereomer mixture) as a slightly yellow amorphous material.

NMR (CDCl$_3$) δ: 0.00, 0.01 (total 6H, s, each), 0.81, 0.82 (total 9H, s, each), 1.60–2.04 (3H, m ), 2.51 (3H, s), 3.31–3.68 (2H, m), 4.20–4.48 (2H, m), 4.60–4.75 (2H, m), 4.98 (1H, m), 5.21–5.34 (2H, m), 5.88–6.00 (1H, m), 6.86, 6.88 (total 1H, s, each), 7.16, 7.17 (total 1H, s, each).

MS (FAB$^+$: 452 (M$^+$+H)

b) (3R,5S)-1-Allyloxycarbonyl-3-t-butyldimethylsilyloxy-5-[1-(5-methylimidazo[5,1-b]thiazol-2-yl)-1-(methylthiothiocarbonyloxy)methyl]pyrrolidine The procedure of Synthesis Example 8-a) is repeated, except that 1.79 g of (3R,5S)-1-allyloxycarbonyl-3-t-butyldimethylsilyloxy-5-[1-hydroxy-1-(5-methylimidazo[5,1-b]thiazol-2-yl)methyl]pyrrolidine is used. Thus, 2.19 g of (3R,5S)-1-allyloxycarbonyl-3-t-butyldimethylsilyloxy-5-[1-(5-methylimidazo[5,1-b]thiazol2-yl)-1-(methylthiothiocarbonyloxy)methyl]pyrrolidine (a diastereomer mixture) is prepared as a yellow oil.

NMR (CDCl$_3$) δ: 0.06 (6H, s), 0.81, 0.87 (total 9H, s, each), 1.69–1.88 (1H, m), 2.01–2.18 (1H, m), 2.31–2.38

(1H, m), 2.51 (3H, s), 2.60, 2.61 (total 3H, s, each), 3.30–3.55 (2H, m), 4.22–4.67 (4H, m), 5.19–5.33 (2H, m), 5.87–6.03 (1H, m), 6.88–6.93 (1H, m), 7.10–7.21 (1H, m).

MS (FAB$^+$: 542 (M$^+$+H)

c) (3R,5S)-1-Allyloxycarbonyl-3-t-butyldimethylsilyloxy-5-(5-methylimidazo[5,1-b]thiazol-2-yl)methylpyrrolidine The procedure of Synthesis Example 8-b) is repeated, except that 2.19 g of (3R,5S)-1-allyloxycarbonyl-3-t-butyldimethylsilyloxy-5-[1-(5-methylimidazo[5,1-b]thiazol-2-yl)-1-(methylthiothiocarbonyloxy)methyl]pyrrolidine is used. Thus, 1.10 g of (3R,5S)-1-allyloxycarbonyl-3-t-butyldimethylsilyloxy-5-(5-methylimidazo[5,1-b]thiazol-2-yl)methylpyrrolidine is prepared as a yellow oil.

NMR (CDCl$_3$) δ: 0.05 (6H, s), 0.81 (9H, s), 1.79–1.88 (1H, m), 1.93–2.05 (1H, m), 2.50 (3H, s), 2.98–3.12 (2H, m), 3.37–3.45 (2H, m), 4.19–4.28 (2H, m), 4.59–4.68 (2H, m), 5.19–5.33 (2H, m), 5.88–6.01 (1H, m), 6.84 (1H, s), 6.97 (1H, s).

MS (FAB$^+$): 436 (M$^+$+H)

d) (3R,5S)-1-Allyloxycarbonyl-3-methanesulfonyloxy-5-(5-methylimidazo[5,1-b]thiazol-2-yl)methylpyrrolidine The procedure of Synthesis Example 9-c) is repeated, except that 1.15 g of (3R,5S)-1-allyloxycarbonyl-3-t-butyldimethylsilyloxy-5-(5-methylimidazo[5,1-b]thiazol-2-yl)methylpyrrolidine is used. Thus, 1.04 g of (3R,5S)-1-allyloxycarbonyl-3-methanesulfonyloxy-5-(5-methylimidazo[5,1-b]thiazol-2-yl)methylpyrrolidine is prepared as a colorless oil.

NMR (CDCl$_3$) δ: 2.10–2.21 (1H, m), 2.48–2.62 (1H, m), 2.60 (3H, s), 3.10 (3H, s), 3.11–3.38 (2H, m), 3.58–3.69 (1H, m), 4.01–4.15 (1H, m), 4.34–4.43 (1H, m), 4.71–4.80 (2H, m), 5.20–5.25 (1H, m), 5.32–5.44 (2H, m), 5.98–6.10 (1H, m), 6.93 (1H, s), 7.10 (1H, s).

MS (TS): 400 (M$^+$+H)

e) (3S,5S)-3-Acetylthio-1-allyloxycarbonyl-5-(5-methylimidazo[5,1-b]thiazol-2-yl)methylpyrrolidine The procedure of Synthesis Example 8-d) is repeated, except that 1.04 g of (3R,5S)-1-allyloxycarbonyl-3-methanesulfonyloxy-5-(5-methylimidazo[5,1-b]thiazol-2-yl)methylpyrrolidine is used. Thus, 766.4 mg of the title compound is prepared as a brown oil.

NMR (CDCl$_3$) δ: 1.60–1.79 (2H, m), 2.27 (3H, s), 2.47 (3H, s), 2.40–2.51 (1H, m), 2.90–3.00 (1H, m), 3.02–3.23 (2H, m), 3.78–3.89 (1H, m), 3.99–4.11 (1H, m), 4.54–4.58 (2H, m), 5.15–5.30 (2H, m), 5.81–5.96 (1H, m), 6.80 (1H, s), 6.94 (1H, s).

MS (TS): 380 (M$^+$)

Synthesis Example 12

(3S,5R)-1-Allyloxycarbonyl-3-benzoylthio-5-(imidazo[5,1-b]thiazol-7-yl)methylpyrrolidine a) 5,7-Diiodoimidazo[5,1-b]thiazole,5-iodoimidazo[5,1-b]thiazole, and 7-iodoimidazo[5,1-b]thiazole A solution of 5.95 g of imidazo[5,1-b]thiazole and 150 ml in 1,2-dichloroethane is cooled to −38° C., 10.80 g of N-iodosuccinimide is added thereto, and the temperature of the mixture is raised to room temperature over a period of 3 hr. Further, the mixture is stirred for 5 hr, 250 ml of dichloromethane is added thereto, and the mixture is washed twice with 250 ml of water. The organic layer is dried over anhydrous magnesium sulfate and filtered, and the solvent is removed by evaporation. The residue is purified by column chromatography on silica gel (toluene:ethyl acetate= 10:1→3:1 1→ethyl acetate alone). Thus, 1.65 g of 5,7-diiodoimidazo[5,1-b]thiazole, 1.59 g of 5-iodoimidazo[5,1-b]thiazole, and 8.06 g of 7-iodoimidazo[5,1-b]thiazole are prepared.

5,7-Diiodoimidazo[5,1-b]thiazole

NMR (CDCl$_3$) δ: 6.97 (1H, d, J=4.3 Hz), 7.36 (1H, d, J=4.3 Hz).

MS (EI): 376 (M$^+$)

5-Iodoimidazo[5,1-b]thiazole

NMR (CDCl$_3$) δ: 6.91 (1H, d, J=4.3 Hz), 7.17 (1H, s), 7.28 (1H, d, J=4.3 Hz).

MS (EI): 250 (M$^+$)

7-Iodoimidazo[5,1-b]thiazole

NMR (CDCl$_3$) δ: 6.89 (1H, d, J=4.3 Hz), 7.50 (1H, d, J=4.3 Hz), 7.96 (1H, s).

MS (EI): 250 (M$^+$)

b) (3R,5S)-1-Allyloxycarbonyl-3-t-butyldimethylsilyloxy-5-[1-hydroxy-1-(imidazo[5,1-b]thiazol-7-yl)methyl]pyrrolidine (stereoisomer A) and ditto (stereoisomer B)

A 2 M methylmagnesium iodide/diethyl ether solution (4.6 ml) is diluted with 50 ml of anhydrous THF, and a solution of 2.0 g of 7-iodoimidazo[5,1-b]thiazole in 50 ml of THF is added dropwise to the diluted solution under ice cooling in an argon atmosphere. The mixture is stirred at that temperature for 10 min and then at room temperature for 1.5 hr and cooled to −50° C., and a solution of 1.735 g of (3R,5S)-1-allyloxycarbonyl-3-t-butyldimethylsilyloxy-5-formylpyrrolidine in 50 ml of THF is added dropwise thereto. A reaction is allowed to proceed while raising the temperature to 10° C. over a period of 3 hr, 200 ml of a semi-saturated aqueous ammonium chloride solution is added thereto, and the mixture is extracted twice with 250 ml of ethyl acetate. The organic layer is dried over anhydrous magnesium sulfate and filtered, and the solvent is removed by evaporation. The residue is purified by column chromatography on silica gel (ethyl acetate alone→ethyl acetate:methanol=20:1→10:1). Thus, 450 mg of (3R,5S)-1-allyloxycarbonyl-3-t-butyldimethylsilyloxy-5-[1-hydroxy-1-(imidazo[5,1-b]thiazol-7-yl)methyl]pyrrolidine (stereoisomer A: a high polar component) and 395 mg of (3R,5S)-1-allyloxycarbonyl-3-t-butyldimethylsilyloxy-5-[1-hydroxy-1-(imidazo[5,1-b]thiazol-7-yl)methyl]pyrrolidine (stereoisomer B: a low polar component) are prepared.

Stereoisomer A

NMR (CDCl$_3$) δ: 0.01 (6H, s), 0.82 (9H, s), 1.78 (1H, m), 2.18 (1H, m), 3.40 (1H, m), 3.60 (1H, m), 4.20 (1H, m), 4.34 (1H, m), 4.65 (2H, m), 4.87 (1H, m), 5.20–5.40 (2H, m), 5.30–6.05 (2H, m), 6.82 (1H, d, J=4.2 Hz), 7.36 (1H, d, J=4.2 Hz), 7.91 (1H, s).

Stereoisomer B

NMR (CDCl$_3$) δ: 0.02 (6H, s), 0.84 (9H, s), 1.70 (1H, m), 2.00 (1H, m), 2.46 (1H, m), 3.03 (1H, m), 3.40 (1H, m), 4.11 (1H, m), 4.45–4.70 (3H, m), 5.00–5.40 (2H, m), 5.60–6.00 (2H, m), 6.80 (1H, d, J=4.2 Hz), 7.35 (1H, d, J=4.2 Hz), 7.88 (1H, s).

c) (3R,5S)-1-Allyloxycarbonyl-3-t-butyldimethylsilyloxy-5-[1-(imidazo[5,1-b]thiazol-7-yl)-1-(methylthiothiocarbonyloxy)methyl]pyrrolidine (stereoisomer A)

The procedure of Synthesis Example 8-a) is repeated, except that 511 mg of (3R,5S)-1-allyloxycarbonyl-3-t-butyldimethylsilyloxy-5-[1-hydroxy-1-(imidazo[5,1-b]thiazol-7-yl)methyl]pyrrolidine (stereoisomer A) is used. Thus, 410 mg of (3R,5S)-1-allyloxycarbonyl-3-t-butyldimethylsilyloxy-5-[1-(imidazo[5,1-b]thiazol-7-yl)-1-(methylthiothiocarbonyloxy)methyl]pyrrolidine (stereoisomer A) is prepared.

NMR (CDCl$_3$) δ: 0.01 (6H, s), 0.85 (9H, s), 2.08 (1H, m), 2.43 (3H, s), 2.50 (1H, m), 2.98 (1H, m), 3.20–3.43 (1H, m), 3.80–4.02 (1H, m), 4.52 (1H, m), 4.57–4.76 (2H, m), 5.13–5.50 (2H, m), 5.50–5.78 (1H, m), 5.88–6.20 (1H, m), 6.82 (1H, d, J=4.3 Hz), 7.34 (1H, d, J=4.3 Hz), 7.92 (1H, s).

d) (3R,5R)-1-Allyloxycarbonyl-3-t-butyldimethylsilyloxy-5-(imidazo[5,1-b]thiazol-7-yl)methylpyrrolidine The procedure of Synthesis Example 8-b) is repeated, except that 410 mg of (3R,5S)-1-allyloxycarbonyl-3-(t-butyldimethylsilyloxy-5-[1-(imidazo[5,1-b]thiazol-7-yl)-1-(methylthiothiocarbonyloxy)methyl]pyrrolidine (stereoisomer A) is used. Thus, 206 mg of (3R,5R)-1-allyloxycarbonyl-3-t-butyldimethylsilyloxy-5-(imidazo[5,1-b]thiazol-7-yl)methylpyrrolidine is prepared.

NMR (CDCl$_3$) δ: 0.01 (6H, s), 0.83 (9H, s), 1.82–2.25 (2H, m), 3.00–3.45 (4H, m), 4.05 (1H, m), 4.30 (1H, m), 4.67 (2H, m), 5.18–5.40 (2H, m), 6.00 (1H, m), 6.79 (1H, d, J=4.3 Hz), 7.34 (1H, d, J=4.3 Hz), 7.92 (1H, s).

e) (3R,5R)-1-Allyloxycarbonyl-3-hydroxy-5-(imidazo[5,1-b]thiazol-7-yl)methylpyrrolidine Concentrated hydrochloric acid (0.204 ml) is added dropwise to a solution of 206 mg of (3R,5R)-1-allyloxycarbonyl-3-t-butyldimethylsilyloxy-5-(imidazo[5,1-b]thiazol-7-yl)methylpyrrolidine in 5 ml of dry acetonitrile under ice cooling, and the mixture is stirred at that temperature for 20 min. The reaction solution is diluted with 20 ml of ethyl acetate, saline is added to the diluted solution, the mixture is adjusted to pH 9 by addition of a saturated aqueous sodium hydrogencarbonate solution, and the mixture is extracted three times with ethyl acetate. The organic layer is dried over anhydrous magnesium sulfate and filtered, and the solvent is removed by evaporation under reduced pressure. The residue is purified by column chromatography on silica gel (chloroform:methanol=10:1) to give 162 mg of (3R,5R)-1-allyloxycarbonyl-3-hydroxy-5-(imidazo[5,1-b]thiazol-7-yl)methylpyrrolidine.

NMR (CDCl$_3$) δ: 1.90–2.40 (2H, m), 3.00–3.60 (5H, m), 4.25 (1H, m), 4.33 (1H, m), 4.64 (2H, m), 5.16–5.40 (2H, m), 5.98 (1H, m), 6.79 (1H, d, J=4.5 Hz), 7.34 (1H, d, J =4.5 Hz), 7.90 (1H, s).

f) (3S,5R)-1-Allyloxycarbonyl-3-benzoylthio-5-(imidazo[5,1-b]thiazol-7-yl)methylpyrrolidine A solution of 134 mg of (3R,5R)-1-allyloxycarbonyl-3-hydroxy-5-(imidazo[5,1-b]thiazol-7-yl)methylpyrrolidine in 8 ml of THF is ice-cooled. Triphenylphosphine (228 mg) and 0.139 ml of diethyl azodicarboxylate are added in an argon atmosphere. The mixture is stirred at that temperature for 1.5 hr, 0.104 ml of thiobenzoic acid is added thereto, and the mixture is stirred at that temperature for 20 min and then at room temperature for 3 hr. The reaction solution is diluted with 30 ml of ethyl acetate, saline is added thereto, the mixture is adjusted to pH 9 by addition of a saturated aqueous sodium hydrogencarbonate solution, and the organic layer is separated. The organic layer is dried over anhydrous magnesium sulfate and filtered, and the solvent is removed by evaporation under reduced pressure. The residue is purified by column chromatography on silica gel (toluene:ethyl acetate=1:1→chloroform:ethyl acetate 2:1) to give 147 mg of the title compound.

NMR (CDCl$_3$) δ: 2.10 (1H, m), 2.54 (1H, m), 3.00–3.35 (3H, m), 4.05 (1H, m), 4.18 (1H, m), 4.30 (1H, m), 4.65 (2H, m), 5.20–5.42 (2H, m), 6, 00 (1H, m), 6.77 (1H, d, J=4.2 Hz), 7.34 (1H, d, J=4.2 Hz), 7.40–7.60 (3H, m), 7.90 (1H, s), 7.93 (2H, m).

Synthesis Example 13

(3S,5S)-3-Acetylthio-1-allyloxycarbonyl-5-[2-(imidazo[5,1-b]thiazol-3-yl)ethenyl]pyrrolidine (a mixture of geometrical isomers) a)(Imidazo[5,1-b]thiazol-3-yl)methyltriphenylphosphonium chloride hydrochloride Thionyl chloride (12.7 ml) is added to 6.67 g of 3-hydroxymethylimidazo[5,1-b]thiazole hydrochloride, and the mixture is stirred at 60° C. for 30 min. The temperature is returned to room temperature, isopropyl ether is added thereto, the supernatant is decanted, and the residue is dried under reduced pressure to give 3-chloromethylimidazo[5,1-b]thiazole hydrochloride. This compound is dissolved in 35 ml of DMF, 10.11 g of triphenylphosphine is added thereto, and the mixture is stirred at 100° C. for 12 hr. The resultant precipitate is collected by filtration to give 8.86 g of (imidazo[5,1-b]thiazol-3-yl)methyltriphenylphosphonium chloride hydrochloride.

NMR (CDCl$_3$) δ: 5.99 (2H, d, 3=14.8 Hz), 7.41 (1H, s), 7.60–7.70 (6H, m), 7.80–7.90 (9H, m), 9.59 (1H, s).

b) (3R,5S)-1-Allyloxycarbonyl-3-hydroxy-5-[2-(imidazo[5,1-b]thiazol-3-yl)ethenyl]pyrrolidine (mixture of geometrical isomers)

Potassium-t-butoxide (1.95 g) is added to a solution of 4.09 g of (imidazo[5,1-b]thiazol-3-yl)methyltriphenylphosphonium chloride hydrochloride in 15 ml of THF and 15 ml of DMSO under ice cooling. The mixture is stirred for 2 hr, a solution of 2.9 g of (3R,5S)-1-allyloxycarbonyl-3-t-butyldimethylsilyloxy-5-formylpyrrolidine in 15 ml of THF is added thereto, and the mixture is stirred under ice cooling for 2 hr. Ethyl acetate is added to the reaction mixture, the mixture is successively washed with dilute hydrochloric acid and saturated saline, and dried over magnesium sulfate. The solvent is removed by evaporation, the residue is dissolved in 80 ml of methanol, 3.5 ml of a 5 N aqueous hydrochloric acid solution is added to the solution, and the mixture is stirred at room temperature for 12 hr. The mixture is neutralized with a 5 N aqueous sodium hydroxide solution, dichloromethane is added thereto, and the mixture is successively washed with water and saturated saline and dried over magnesium sulfate. The solvent is removed by evaporation, and the residue is purified by column chromatography on silica gel to give 1.48 g of (3R,5S)-1-allyloxycarbonyl-3-hydroxy-5-[2-(imidazo[5,1-b]thiazol-3-yl)ethenyl]pyrrolidine.

NMR (CDCl$_3$) δ: 1.75–2.00 (1H, m), 2.05–2.30 (1H, m), 3.40–3.55 (2H, m), 4.75–5.35 (3H, m), 5.80–6.00 (1H, m), 6.35–6.64 (2H, m), 7.05–7.15 (1H, m), 7.20–7.30 (1H, m), 8.20–8.50 (1H, m).

c) (3S,5S)-3-Acetylthio-1-allyloxycarbonyl-5-[2-(imidazo[5,1-b]thiazol-3-yl)ethenyl]pyrrolidine (mixture of geometrical isomers)

Triethylamine (0.84 g) and 0.43 ml of methanesulfonyl chloride are added to a solution of (3R,5S)-1-allyloxycarbonyl-3-hydroxy-5-[2-(imidazo[5,1-b]thiazol-3-yl)ethenyl]pyrrolidine in 20 ml of dichloromethane, and the mixture is stirred under ice cooling for 2 hr. Dichloromethane is added to the reaction mixture, and the mixture is successively washed with a saturated aqueous sodium hydrogencarbonate solution and saturated saline and dried over magnesium sulfate. The solvent is removed by evaporation to give a methanesulfonyloxy derivative. Potassium thioacetate (0.77 g) is added to a solution of this compound in 15 ml of DMF, and the mixture is stirred at 70° C. for 4 hr. Ethyl acetate is added to the reaction mixture, and the mixture is successively washed with water, a saturated aqueous sodium hydrogencarbonate solution and saturated saline and dried over magnesium sulfate. The solvent is removed by evaporation, and the residue is purified by column chromatography on silica gel to give 1.44 g of the title compound.

NMR (CDCl$_3$) δ: 1.75–1.95 (1H, m), 2.34 (3H, m), 2.56–2.80 (1H, m), 3.33–3.48 (1H, m), 3.90–4.15 (2H, m), 4.40–4.65 (2H, m), 4.85–5.35 (3H, m), 5.60–6.05 (2H, m), 6.20–6.35 (1H, m), 6.40–6.75 (1H, m), 7.11 (1H, m), 7.92–8.20 (1H, m).

Synthesis Example 14

(3S)-3-Acetylthio-1-allyloxycarbonyl-5-(imidazo[5,1-b]thiazol-5-yl)pyrrolidine (stereoisomer A) and ditto (stereoisomer B)

a) (3S,5S)-3-Acetylthio-1-allyloxycarbonyl-5-[(thiazol-2-yl)methylaminocarbonyl]pyrrolidine 1-Hydroxybenzotriazole (0.47 g) and 0.66 g of dicyclohexylcarbodiimide are added to a solution of 0.83 g of (3S,5S)-3-acetylthio-1-oxycarbonylpyrrolidin-5-carboxylic acid in 12 ml of THF, and the mixture is stirred at room temperature for 12 hr. The reaction mixture is ice-cooled, a solution of 0.37 g of 2-aminomethylthiazole in 1 ml of THF is added thereto, and the mixture is stirred for 12 hr. Insolubles are removed by filtration, and the solvent is removed by evaporation. The residue is purified by column chromatography on silica gel to give 1.00 g of (3S,5S)-3-acetylthio-1-allyloxycarbonyl-5-[(thiazol-2-yl)methylaminocarbonyl]pyrrolidine.

NMR (CDCl$_3$) δ: 2.30 (3H, s), 2.30–2.80 (2H, m), 3.30–3.40 (1H, m), 3.90–4.00 (1H, m), 4.10–4.15 (1H, m), 4.40–5.50 (1H, m), 4.45–4.55 (2H, m), 4, 78 (2H, d, J=5.8 Hz), 5.15–5.35 (2H, m), 5.80–5.95 (1H, m), 7.29 (1H, d, J=3.3 Hz), 7.55 (1H, s), 7.72 (1H, d, J=3.3 Hz).

b) (3S)-3-Acetylthio-1-allyloxycarbonyl-5-(imidazo[5,1-b]thiazol-5-yl)pyrrolidine (stereoisomer A) and ditto (stereoisomer B)

Phosphorus oxychloride (1.2 ml) is added to a solution of 1.00 g of (3S,5S)-3-acetylthio-1-allyloxycarbonyl-5-[(thiazol-2-yl)methylaminocarbonyl]pyrrolidine in 10 ml of toluene, and the mixture is stirred at 100° C. for one hr. The reaction mixture is concentrated under reduced pressure, dichloromethane is added to the residue, and the mixture is successively washed with an aqueous potassium carbonate solution and saturated saline and dried over magnesium sulfate. The solvent is removed by evaporation, and the residue is purified by column chromatography on silica gel to give 0.27 g of the title compound (stereoisomer A: a high polar component) and 0.07 g of the title compound (stereoisomer B: a low polar component).

Stereoisomer A

NMR (CDCl$_3$) δ: 2.32 (3H, s), 2.70–2.83 (2H, m), 3.30–3.40 (1H, m), 3.91–4.05 (1H, m), 4.19–4.26 (1H, m), 4.36–4.60 (2H, m), 4, 90–5.30 (3H, m), 5.80–5.95 (1H, m), 6.75–6.80 (1H, m), 7.05 (1H, s), 7.70–7.80 (1H, m).

Stereoisomer B

NMR (CDCl$_3$) δ: 2.22–2.40 (4H, m), 2.98–3.07 (1H, m), 3.55–3.63 (1H, m), 3.95–4.05 (1H, m), 4.44–5.62 (3H, m), 5.17–5.32 (3H, m), 5.82–5.96 (1H, m), 6.75–6.82 (1H, m), 7.03 (1H, s), 7.86 (1H, m).

Synthesis Example 15

(3S,5S)-3-Acetylthio-1-allyloxycarbonyl-5-[2-(imidazo[5,1-b]thiazol-2-yl)vinyl]pyrrolidine a) (Imidazo[5,1-b]thiazol-2-yl)methyltriphenylphosphonium chloride hydrochloride 2-Hydroxymethylimidazo[5,1-b]thiazole hydrochloride (1.40 g) is suspended in 15 ml of THF, 0.8 ml of thionyl chloride is added thereto, and the mixture is stirred at 60° C. for 1.5 hr. The solvent is removed by evaporation to give 2-chloromethylimidazo[5,1-b]thiazole hydrochloride. This compound is dissolved in 7 ml of DMF, 1.78 g of triphenylphosphine is added thereto, and the mixture is stirred at 100° C. for 12 hr. The resultant precipitate is collected by filtration to give 2.14 g of (imidazo[5,1-b]thiazol-2-yl)methyltriphenylphosphonium chloride hydrochloride.

NMR (CDCl$_3$) δ: 5.89 (2H, d, J=15.4 Hz), 7.57 (1H, s), 7.75–8.05 (16H, m), 9.40 (1H, s).

b) (3R,5S)-1-Allyloxycarbonyl-3-methanesulfonyloxy-5-[2-(imidazo[5,1-b]thiazol-2-yl)vinyl]pyrrolidine Potassium t-butoxide (1.06 g) is added to a solution of 2.24 g of (imidazo[5,1-b]thiazol-2-yl)methyltriphenylphosphonium chloride hydrochloride in a mixture of 5 ml of THF and 5 ml of dimethylsulfoxide under ice cooling. The mixture is stirred under ice cooling for 2 hr, a solution of 1.32 g of (3R,5S)-1-allyloxycarbonyl-3-methanesulfonyloxy-5-formylpyrrolidine in 5 ml of THF, and the mixture is stirred under ice cooling for 2 hr. Ethyl acetate is added to the reaction mixture, and the mixture is successively washed with dilute hydrochloric acid and saturated saline and dried over magnesium sulfate. The solvent is removed by evaporation. The residue is purified by column chromatography on silica gel to give 1.07 g of (3R,5S)-1-allyloxycarbonyl-3-methanesulfonyloxy-5-[2-(imidazo[5,1-b]thiazol-2-yl)vinyl]pyrrolidine (a mixture of geometrical isomers).

NMR (CDCl$_3$) δ: 1.90–2.15 (1H, m), 2.55–2.70 (1H, mn), 3.05–3.10 (3H, m), 3.65–3.75 (1H, m), 3.95–4.05 (1H, m), 4.05–4.70 (2H, m), 5.05–5.35 (4H, m), 5.65–6.00 (2H, m), 6.30–6.70 (1H, m), 7.00–7.05 (1H, m), 7.15 (1H, s), 7.84–7.95 (1H, m).

c) (3S,5S)-3-Acetylthio-1-allyloxycarbonyl-5-[2-(imidazo[5,1-b]thiazol-2-yl)vinyl]pyrrolidine (a mixture of geometrical isomers)

Potassium thioacetate (0.22 g) is added to a solution of 1.07 g of (3R,5S)-1-allyloxycarbonyl-3-methane sulfonyloxy-5-[2-(imidazo[5,1-b]thiazol-2-yl)vinyl]pyrrolidine (a mixture of geometrical isomers) in 5 ml of DMF, and the mixture is stirred at 70° C. for 4 hr. Ethyl acetate is added to the reaction mixture, and the mixture is successively washed with water and a saturated aqueous sodium hydrogencarbonate solution, and saturated saline and dried over magnesium sulfate. The solvent is removed by evaporation. The residue is purified by column chromatography on silica gel to give 0.42 g of the title compound.

NMR (CDCl$_3$) δ: 2.32–2.38 (3H, m), 2.55–2.80 (1H, m), 3.30–3.40 (1H, m), 3.90–4.15 (2H, m), 4.50–4.70 (3H, m), 4.90–5.35 (3H, m), 5.70–6.00 (2H, m), 6.25–6.60 (1H, m), 7.00–7.05 (1H, m), 7.15 (1H, s), 7.92–8.00 (1H, m).

Synthesis Example 16

(3S,5S)-3-Acetylthio-1-allyloxycarbonyl-5-(imidazo[5,1-b]thiazol-3-yl)pyrrolidine a) (3R,5S)-1-Allyloxycarbonyl-5-[2-(t-butoxyaminomethyl)thiazol-4-yl]-3-t-butyldimethyloxypyrrolidine A solution of 0.72 g of (3S,5R)-1-allyloxycarbonyl-3-t-butyldimethyloxyproline ethyl ester and 0.35 g of lithium bromide in 5 ml of dry THF, the mixture is cooled on a dry ice/acetone bath, and a 1.4 M methyllithium/diethyl ether is added dropwise thereto. The mixture is stirred at that temperature for 30 min, and the reaction is terminated by a saturated aqueous ammonium chloride solution. Ethyl acetate is added thereto, and the mixture is washed with saturated saline. The solvent is concentrated under reduced pressure. DMF (2 ml), 0.20 g of sodium bromide, 0.20 g of calcium carbonate, and 0.38 g of t-(butoxycarbonylamino)acetothioamide. The mixture is stirred at 45° C. for 2 hr. Ethyl acetate is added to the reaction mixture, and the mixture is washed with saline and dried over anhydrous magnesium sulfate. The solvent is concentrated under reduced pressure. The residue is purified by column chromatography on silica gel (hexane:ethyl acetate=3:1) to give 0.08 g of (3R,5S)-1-allyloxycarbonyl-3-t-butyldimethyloxy-5-[2-(t-butoxyaminomethyl)thiazol-4-yl]pyrrolidine.

NMR (CDCl$_3$) δ: 0.07 (6H, s), 0.88 (9H, s), 1.47 (9H, s), 2.20–2.30 (2H, m), 3.45–3.60 (1H, m), 3.65–3.75 (1H, m), 4.45–4.60 (5H, m), 5.05–5.30 (4H, m), 5.70–5.95 (1H, m), 6.95–7.05 (1H, m).

b) (3R,5S)-1-Allyloxycarbonyl-5-[2-(t-butoxyaminomethyl)thiazol-4-yl]-3-methanesulfonyloxypyrrolidine A 1 M tetrabutylammonium fluoride/THF solution (4 ml) is added to a solution of 1.85 g of (3R,5S)-1-allyloxycarbonyl-3-t-butyldimethyloxy-5-[2-(t-butoxyaminomethyl)thiazol-4-yl]pyrrolidine in 30 ml of THF at room temperature for 2 hr. Ethyl acetate is added to the reaction mixture, and the mixture is washed with saline. Dichloromethane (20 ml), 0.78 ml of triethylamine, and 0.39 ml of methanesulfonyl chloride are added thereto. The mixture is stirred at room temperature for one hr. The reaction mixture is successively washed with water, an aqueous sodium hydrogencarbonate solution and saline and dried over anhydrous magnesium sulfate. The solvent is removed by evaporation, and the residue is purified by column chromatography on silica gel (hexane:ethyl acetate=1:1) to give 1.26 g of (3R,5S)-1-allyloxycarbonyl-5-[2-(t-butoxyaminomethyl)thiazol-4-yl]-3-methanesulfonyloxypyrrolidine.

NMR (CDCl$_3$) δ: 1.45 (9H, s), 2.55–2.65 (2H, m), 3.05 (3H, m), 3.85–4.05 (2H, m), 4.45–4.60 (4H, m), 5.05–5.50 (5H, m), 5.70–5.95 (1H, m), 7.00–7.15 (1H, m).

c) (3R,5S)-1-Allyloxycarbonyl-5-(2-formylaminomethylthiazol-4-yl)-3-methanesulfonyloxypyrrolidine Trifluoroacetic acid (4 ml) is added to 1.26 g of (3R,5S)-1-allyloxycarbonyl-5-[2-(t-butoxyaminomethyl)thiazol-4-yl]-3-methanesulfonyloxypyrrolidine, and the mixture is stirred at room temperature for one hr. The reaction mixture is concentrated under reduced pressure. A saturated aqueous sodium hydrogencarbonate solution (30 ml) and 20 ml of dichloromethane are added to the residue, a mixed acid anhydride prepared from 1.0 ml of formic acid and 0.75 ml of acetic acid are added dropwise thereto, and the mixture is stirred at room temperature for one hr. The reaction mixture is subjected to separation, and the organic layer is washed with saturated saline and dried over anhydrous magnesium sulfate. The solvent is removed by evaporation under reduced pressure. The residue is purified by column chromatography on silica gel (methanol:ethyl acetate=5:95) to give 0.81 g of (3R,5S)-1-allyloxycarbonyl-5-(2-formylaminomethylthiazol-4-yl)-3-methanesulfonyloxypyrrolidine.

NMR (CDCl$_3$) δ: 2.50–2.70 (2H, m), 3.05 (3H, s), 3.85–4.00 (2H, m), 4.45–4.60 (2H, m), 4.75 (2H, dd, J=1.0, 5.8 Hz), 5.05–5.35 (3H, m), 5.40–5.50 (1H, m), 5.70–6.00 (1H, m), 6.35 (1H, br s), 7.05–7.15 (1H, m), 8.30 (1H, s).

d) (3R,5S)-1-Allyloxycarbonyl-5-(imidazo[5,1-b]thiazol-3-yl)-3-methanesulfonyloxypyrrolidine Toluene (20 ml) and 0.95 ml of phosphorus oxychloride are added to (3R,5S)-1-allyloxycarbonyl-5-(2-formylaminomethylthiazol-4-yl)-3-methanesulfonyloxypyrrolidine, and the mixture is heated under reflux at 120° C. for 45 min. The mixture is concentrated under reduced pressure. Dichloromethane is added to the residue, and the mixture is successively washed with water, an aqueous sodium hydrogencarbonate solution and saline and dried over anhydrous magnesium sulfate. The solvent is removed by evaporation. The residue is purified by column chromatography on silica gel (methanol:ethyl acetate=5:95) to give 0. 52 g of (3R,5S)-1-allyloxycarbonyl-5-(imidazo[5,1-b]thiazol-3-yl)-3-methanesulfonyloxypyrrolidine.

NMR (CDCl$_3$) δ: 2.40–2.50 (1H, m), 2.70–2.90 (1H, m), 3.10 (3H, s), 3.80–3.90 (1H, m), 4.10–4.25 (1H, m), 4.45–4.65 (2H, m), 5.05–5.35 (4H, m), 5.60–5.95 (1H, m), 6.63 (1H, s), 7.11 (1H, s), 7.84 (1H, s).

e) (3S,5S)-3-Acetylthio-1-allyloxycarbonyl-5-(imidazo[5,1-b]thiazol-3-yl)pyrrolidine Potassium thioacetate (0.24 g) is added to a solution of 0.52 g of (3R,5S)-1-allyloxycarbonyl-5-(imidazo[5,1-b]thiazol-4-yl)-3-methanesulfonyloxypyrrolidine in 5 ml of DMF, and the mixture is stirred at 70° C. for 2 hr. Ethyl acetate is added to the reaction mixture, and the mixture is successively washed with water, an aqueous sodium hydrogencarbonate solution and saline and dried over anhydrous magnesium sulfate. The solvent is removed by evaporation. The residue is purified by column chromatography on silica gel (methanol:ethyl acetate=2:98) to give 0.46 g of the title compound.

NMR (CDCl$_3$) δ: 2.33 (3H, s), 2.10–2.20 (1H, m), 2.80–2.90 (1H, m), 3.45–3.55 (1H, m), 4.05–4.15 (1H, m), 4.25–4.35 (1H, m), 4.45–4.55 (2H, m), 5.05–5.35 (3H, m), 5.70–5.95 (1H, m), 6.60 (1H, s), 7.11 (1H, s), 7.84 (1H, s).

Synthesis Example 17

(3S,5S)-3-Acetylthio-1-allyloxycarbonyl-5-[2-(imidazo[5,1-b]thiazol-5-yl)ethenyl]pyrrolidine (mixture of geometrical isomers)

a) (Imidazo[5,1-b]thiazol-5-yl)methyltriphenylphosphonium chloride

Triphenylphosphine (2.51 g) is added to a solution of 1.23 g of 5-hydroxymethylimidazo[5,1-b]thiazole hydrochloride in 20 ml of DMF, and the mixture is stirred at 100° C. for 12 hr. The solvent is removed by evaporation, and the residue is purified by column chromatography on silica gel (methanol:dichloromethane=5:95) to give 2.1 g of (imidazo[5,1-b]thiazol-5-yl)methyltriphenylphosphonium chloride.

NMR (DMSO-d6) δ: 5.73 (2H, d, J=14.8 Hz), 6.98 (1H, s), 7.12 (1H, d, J=4.3 Hz), 7.65–7.90 (16H, m).

b) (3R,5S)-1-Allyloxycarbonyl-5-[2-(imidazo[5,1-b]thiazol-5-yl)ethenyl]-3-methanesulfonyloxypyrrolidine Potassium t-butoxide (0.11 g) is added to a solution of 0.44 g of (imidazo[5,1-b]thiazol-5-yl)methyltriphenylphosphonium chloride in 2 ml of THF and 2 ml of dimethyl sulfoxide under ice cooling. The mixture is stirred at that temperature for one hr, and a solution of 0.28 g of (3R,5S)-1-allyloxycarbonyl-3-t-butyldimethylsilyloxy-5-formylpyrrolidine in 2 ml of THF, and the mixture is stirred at that temperature for 2 hr. Ethyl acetate is added to the reaction mixture, and the mixture is successively washed with dilute hydrochloric acid, a saturated aqueous sodium hydrogencarbonate solution and saturated saline and dried over anhydrous magnesium sulfate. The solvent is removed by evaporation, and the residue is purified by column chromatography on silica gel (methanol:ethyl acetate=5:95) to give 0.33 g of (3R,5S)-1-allyloxycarbonyl-5-[2-(imidazo[5,1-b]thiazol-5-yl)ethenyl]-3-methanesulfonyloxypyrrolidine (a mixture of geometrical isomers).

NMR (CDCl$_3$) δ: 2.15–2.25 (1H, m), 2.55–2.65 (1H, m), 3.06 (3H, s), 3.65–3.75 (1H, m), 3.95–4.10 (1H, m), 4.60 (2H, m), 4.75 (1H, m), 5.10–5.35 (3H, m), 5.85–6.00 (1H, m), 6.35–6.40 (1H, dd, J=7.3, 15.6 Hz), 6.50–6.70 (1H, m), 6.85–6.90 (1H, m), 7.10 (1H, s), 7.40–7.50 (1H, m).

c) (3S,5S)-3-Acetylthio-1-allyloxycarbonyl-5-[2-(imidazo[5,1-b]thiazol-5-yl)ethenyl]pyrrolidine The procedure of Synthesis Example 16-e) is repeated, except that 0.32 g of (3S,5S)-1-allyloxycarbonyl-5-[2-(imidazo[5,1-b]thiazol-5-yl)ethenyl]-3-methanesulfonyloxypyrrolidine is used. Thus, 0.25 g of the title compound is prepared.

NMR (CDCl$_3$) δ: 1.85–1.95 (1H, m), 2.32 (3H, s), 2.60–2.75 (1H, m), 3.30–3.40 (1H, m), 3.95–4.05 (1H, m), 4.05–4.15 (1H, m), 4.55–4.65 (3H, m), 5.10–5.35 (2H, m), 5.80–6.00 (1H, m), 6.40–6.65 (2H, m), 6.85–6.90 (1H, m), 7.10 (1H, s), 7.45 (1H, dd, J 4.1 Hz).

Synthesis Example 18

(3S,5S)-3-Acetylthio-1-allyloxycarbonyl-5-[2-(imidazo[5,1-b]thiazol-7-yl)ethenyl]pyrrolidine (mixture of geometrical isomers)

The procedure of Synthesis Example 15 is repeated, except that 0.44 g of 7-hydroxymethylimidazo[5,1-b]thiazole hydrochloride is used. Thus, 0.25 g of the title compound is prepared.

NMR (CDCl$_3$) δ: 1.85–1.95 (1H, m), 2.33, 2.35 (3H, s, each), 2.60–2.75 (1H, m), 3.30–3.40 (1H, m), 3.95–4.05 (1H, m), 4.10–4.15 (1H, m), 4.55–4.65 (3H, m), 5.10–5.30 (2H, m), 5.80–6.00 (2H, m), 6.50–6.60 (2H, m), 6.75–6.90 (1H, m), 7.30–7.40 (1H, m), 7.90, 9.95 (1H, s each).

Synthesis Example 19

(3S,5S)-3-Acetylthio-1-allyloxycarbonyl-5-[2-(3-methylimidazo[5,1-b]thiazol-2-yl)ethenyl]pyrrolidine (a mixture of geometrical isomers)

The procedure of Synthesis Example 15 is repeated, except that 1.0 g of 3-methyl-2-hydroxymethylimidazo[5,1-b]thiazole hydrochloride is used. Thus, 0.92 g of the title compound is prepared.

NMR (CDCl$_3$) δ: 2.05–2.20 (1H, m), 2.42 (3H, s), 2.55–2.70 (1H, m), 3.07 (3H, s), 3.65–3.75 (1H, m), 3.95–4.10 (1H, m), 4.55–4.70 (3H, m), 5.00–5.35 (3H, m), 5.60–5.75 (1H, m), 5.80–6.00 (1H, m), 6.35–6.70 (1H, m), 7.00–7.10 (1H, m), 7.85–7.90 (1H, m).

Synthesis Example 20

(3S,5S)-3-Acetylthio-1-allyloxycarbonyl-5-[2-(2-methylimidazo[5,1-b]thiazol-3-yl)ethenyl]pyrrolidine (mixture of geometrical isomers)

The procedure of Synthesis Example 15 is repeated, except that 0.80 g of 2-methyl-3-hydroxymethylimidazo[5,1-b]thiazole hydrochloride is used. Thus, 1.20 g of the title compound is prepared.

NMR (CDCl$_3$) δ: 1.85–2.00 (1H, m), 2.35–2.40 (6H, m), 2.70–2.85 (1H, m), 3.40–3.50 (1H, m), 4.00–4.15 (2H, m), 4.55–4.65 (3H, m), 5.15–5.35 (2H, m), 5.85–6.00 (1H, m), 6.15–6.25 (1H, m), 6.40–6.60 (1H, m), 7.00–7.10 (1H, m), 8.00 (1H, s).

Synthesis Example 21

(3S,5S)-1-Allyloxycarbonyl-3-benzoylthio-5-(5-methylthioimidazo[5,1-b]thiazol-2-yl)methylpyrrolidine a) (3R,5S)-1-Allyloxycarbonyl-3-t-butyldimethylsilyloxy-5-[1-hydroxy-1-(5-methylthioimidazo[5,1-b]thiazol-2-yl)]methylpyrrolidine (diastereomer mixture)

The procedure of Synthesis Example 10-a) is repeated, except that 1.60 g of 5-methylthioimidazo[5,1-b]thiazole and 2.97 g of (3R,5S)-1-allyloxycarbonyl-3-t-butyldimethylsilyloxy-5-formylpyrrolidine are used and the purification is successively performed by column chromatography on Sephadex LH-20 (dichloromethane:methanol=1:1) and on silica gel (hexane:ethyl acetate=1:2) to give 2.37 g of (3R,5S)-1-allyloxycarbonyl-3-t-butyldimethylsilyloxy-5-[1-hydroxy-1-(5-methylthioimidazo[5,1-b]thiazol-2-yl)methyl]pyrrolidine (a diastereomer mixture) as a yellow amorphous material.

NMR (CDCl$_3$) δ: 0.02 (6H, s), 0.83 (9H, s), 1.66–2.07 (2H, m), 2.51 (3H, s), 3.32–3.70 (3H, m), 4.24–4.37 (2H, m), 4.37–4.81 (2H, m), 5.24–5.38 (2H, m), 5.90–6.01 (1H, m), 6.19 (1H, s), 7.09 & 7.11 (total 1H, s, each).

MS (FAB$^+$): 484 (M$^+$+H)

b) (3R,5S)-1-Allyloxycarbonyl-3-t-butyldimethylsilyloxy-5-[1-(5-methylthioimidazo[5,1-b]thiazol-2-yl)-1-(methylthiocarbonyloxy)methyl]pyrrolidine (diastereomer mixture)

The procedure of Synthesis Example 8-a) is repeated, except that 2.10 g of (3R,5S)-1-allyloxycarbonyl-3-t- butyldimethylsilyloxy-5-[1-hydroxy-1-(5-methylthioimidazo[5,1-b]thiazol-2-yl)methyl]pyrrolidine (a diastereomer mixture). Thus, 2.84 g of (3R,5S)-1-allyloxycarbonyl-3-t-butyldimethylsilyloxy-5-[1-(5-methylthioimidazo[5,1-b]thiazol-2-yl)-1-(methylthiocarbonyloxy)methyl]pyrrolidine (diastereomer mixture) is prepared as a yellow oil.

NMR (CDCl$_3$) δ: 0.01 & 0.06 (total 6H, s, each), 0.80 & 0.84 (total 9H, s, each), 1.81–1.87 (1H, m), 2.02–2.12 (1H, m), 2.49 (3H, s), 2.59 (3H, s), 3.42–3.53 (1H, m), 3.70–3.75 (2H, m), 4.22–4.66 (4H, m), 5.18–5.32 (2H, m), 5.86–6.00 (1H, m), 7.08 (1H, s), 7.31 (1H, br, s).

MS (FAB$^+$: 574 (M$^+$+H)

c) (3R,5S)-1-Allyloxycarbonyl-3-t-butyldimethylsilyloxy-5-(5-methylthioimidazo[5,1-b]thiazol-2-yl)methylpyrrolidine The procedure of Synthesis Example 9-b) is repeated, except that 2.84 g of (3R,5S)-1-allyloxycarbonyl-3-t-butyldimethylsilyloxy-5-[1-(5-methylthioimidazo[5,1-b]thiazol-2-yl)-1-(methylthiothiocarbonyloxy)methyl]pyrrolidine (a diastereomer mixture) is used. Thus, 1.37 g of (3R,5S)-1-allyloxycarbonyl-3-t-butyldimethylsilyloxy-5-(5-methylthioimidazo[5,1-b]thiazol-2-yl)methylpyrrolidine is prepared as a yellow oil.

NMR (CDCl$_3$) δ: 0.03 (6H, s), 0.84 (9H, s), 1.78–1.91 (1H, m), 1.96–2.08 (1H, m), 2.51 (3H, s), 3.03–3.19 (2H, m), 3.38–3.58 (2H, m), 4.22–4.31 (2H, m), 4.64–4.68 (2H, m), 5.22–5.38 (2H, m), 5.90–6.02 (1H, m), 7.07 (1H, s), 7.20 (1H, br.s).

MS (TS): 468 (M$^+$+H)

d) (3S,5S)-1-Allyloxycarbonyl-3-benzoylthio-5-(5-methylthioimidazo[5,1-b]thiazol-2-yl)methylpyrrolidine Concentrated hydrochloric acid (1.3 ml) is added to a solution of 1.37 g of (3R,5S)-1-allyloxycarbonyl-3-t-butyldimethylsilyloxy-5-(5-methylthioimidazo[5,1-b]thiazol-2-yl)methylpyrrolidine in 15 ml of acetonitrile under ice cooling, and the mixture is stirred for 30 min. The reaction mixture is neutralized with a saturated sodium hydrogencarbonate solution, and ethyl acetate is added, followed by extraction three times. The extract is washed three times with semi-saturated saline and dried over magnesium sulfate. The solvent is removed by evaporation to give 1.03 g of (3R,5S)-1-allyloxycarbonyl-3-hydroxy-5-(5-methylthioimidazo[5,1-b]thiazol-2-yl)methylpyrrolidine. This compound is dissolved in 18 ml of THF, 1.53 g of triphenylphosphine and 0.92 ml of diethyl azodicarboxylate are added thereto at −17° C., and the mixture is stirred for 30 min. Further, 0.7 ml of thiobenzoic acid is added thereto, and the mixture is stirred at about −20° C. for 40 min. The solvent is removed by evaporation, and the residue is purified by column chromatography on Sephadex LH-20 (dichloromethane:methanol=1:1) to give 1.06 g of the title compound as a yellow oil.

NMR (CDCl$_3$) δ: 1.79–1.80 (1H, m), 1.91–2.10 (1H, m), 2.42 (3H, s), 2.49–2.61 (1H, m), 3.00–3.12 (1H, m), 3.19–3.30 (1H, m), 4.00–4.18 (3H, m), 5.15–5.30 (2H, m), 5.81–5.96 (1H, m), 7.01 (1H, s), 7.16 (1H, br.s), 7.35–7.41 (2H, m), 7.49–7.62 (1H, m), 7.80–7.83 (2H, m).

MS (TS): 474 (M$^+$+H)

Synthesis Example 22

(3S,5S)-3-Acetylthio-1-allyloxycarbonyl-5-[2-(5-methylimidazo[5,1-b]thiazol-3-yl)ethenyl]pyrrolidine a) (5-Methylimidazo[5,1-b]thiazol-3-yl)methyltriphenylphosphonium chloride hydrochloride 3-Hydroxymethyl-5-methylimidazo[5,1-b]thiazolehydrochloride (1.10 g) is suspended in 20 ml of THF, 0.7 ml of thionyl chloride is added thereto, and the mixture is stirred at 85° C. for 3.5 hr. The solvent is removed by evaporation to give 1.10 g of 3-chloromethyl-5-methylimidazo[5,1-b]thiazolehydrochloride. This compound is dissolved in 7 ml of DMF, 1.36 g of triphenylphosphine is added thereto, and the mixture is stirred at 83° C. for 15 hr and at 90° C. for 4 hr. The resultant precipitate is collected by filtration and washed with diethyl ether to give 1.87 g of (5-methylimidazo[5,1-b]thiazol-3-yl)methyltriphenylphosphonium chloride hydrochloride.

NMR (CD$_3$OD) δ: 2.68 (3H, s), 5.59 (2H, s), 7.16 (1H, s), 7.58 (1H, s), 7.75–8.05 (15H, m) MS (TS): 413 (M$^+$)

b) (3R,5S)-1-Allyloxycarbonyl-4-methanesulfonyloxy-2-[2-(5-methylimidazo[5,1-b]thiazol-3-yl)ethenyl]pyrrolidine Potassium t-butoxide (0.45 g) is added to a solution of 0.91 g of (5-methylimidazo[5,1-b]thiazol-3-yl)methyltriphenylphosphonium chloride hydrochloride in a mixture of 3 ml of THF with 3 ml of dimethyl sulfoxide under ice cooling. The mixture is stirred under ice cooling for 2 hr, a solution of 0.60 g of (3R,5S)-1-allyloxycarbonyl-5-formyl-3-methanesulfonyloxypyrrolidine in 2 ml of THF is added thereto, and the mixture is stirred under ice cooling for 1 hr. Ethyl acetate is added to the reaction mixture, and the mixture is successively washed with dilute hydrochloric acid and saturated saline and dried over magnesium sulfate. The solvent is removed by evaporation, and the residue is purified by column chromatography on silica gel (ethyl acetate:methanol=95:5) to give 0.49 g of (3R,5S)-1-allyloxycarbonyl-4-methanesulfonyloxy-2-[2-(5-methylimidazo[5,1-b]thiazol-3-yl)ethenyl]pyrrolidine (a mixture of geometrical isomers).

NMR (CD$_3$OD) δ: 2.38–2.50 (1H, m), 2.57 (3H, s), 2.98 (3H, s), 3.60–3.68 (1H, m), 3.89–3.98 (1H, m), 4.38–4.57 (2H, m), 4.94 (2H, d, J=7.4 Hz), 5.15–5.26 (2H, m), 5.69–5.78 (1H, m), 6.43 (1H, d, J=11.3 Hz), 6.80 (1H, s), 7.10 (1H, s).

MS (TS): 412 (M$^+$+H)

c) (3S,5S)-3-Acetylthio-1-allyloxycarbonyl-5-[2-(5-methylimidazo[5,1-b]thiazol-3-yl)ethenyl]pyrrolidine (mixture of geometrical isomers)

Potassium thioacetate (0.33 g) is added to a solution of 0.87 g of (3R,5S)-1-allyloxycarbonyl-4-methanesulfonyloxy-2-[2-(5-methylimidazo[5,1-b]thiazol-3-yl)ethenyl]pyrrolidine (a mixture of geometrical isomers) in 6 ml of DMF, and the mixture is stirred at 70° C. for 6.5 hr. Water and ethyl acetate are added to the reaction mixture, followed by extraction three times. The extract is washed with saturated saline and dried over magnesium sulfate. The solvent is removed by evaporation, and the residue is purified by column chromatography on silica gel (ethyl acetate) to give 0.65 g of the title compound.

NMR (CDCl$_3$) δ: 2.36 (3H, s), 2.58–2.73 (3H, m), 3.32–3.43 (1H, m), 3.89–4.10 (2H, m), 4.50–4.65 (2H, m), 4.83–5.35 (4H, m), 5.72–6.00 (2H, m), 6.15–6.21 (1H, m), 6.44 (1H, d, J=11.3 Hz), 6.63 (1H, s), 6.89 (1H, s).

MS (TS): 392 (M$^+$+H)

Synthesis Example 23

(3S,5S)-1-Allyloxycarbonyl-3-benzoylthio-5-(5-chloroimidazo[5,1-b]thiazol-2-yl)methylpyrrolidine a) (3R,5S)-1-Allyloxycarbonyl-3-t-butyldimethylsilyloxy-5-[1-(5-chloroimidazo[5,1-b]thiazol-2-yl)-1-hydroxymethyl]pyrrolidine (diastereomer mixture)

A 1.4 M methyllithium/diethyl ether solution (7.9 ml) is diluted with 20 ml of anhydrous THF, and the diluted solution is purged with argon and cooled to −69° C. A solution of 1.586 g of 5-chloroimidazo[5,1-b]thiazole in 20 ml of anhydrous THF is added dropwise to the solution with stirring over a period of 17 min while maintaining the solution at −65° C. or below, and the mixture is stirred in this state for additional 37 min. A solution of 3.135 g of (3R,5S)-1-allyloxycarbonyl-3-t-butyldimethylsilyloxy-5-formylpyrrolidine in 20 ml of anhydrous THF is added dropwise to the mixed solution over a period of 23 min while maintaining the temperature at −65° C. or below, and the mixture is stirred in this state for additional 52 min. Semi-saturated saline (100 ml) is added to the reaction solution, the mixture is extracted twice with 200 ml of ethyl acetate, and the combined organic layers are washed with saturated saline and dried over anhydrous magnesium sulfate, followed by filtration. The solvent is removed by evaporation under reduced pressure to give a crude product which is then purified by column chromatography on silica gel (hexane:ethyl acetate=2:1) to give 2.351 g of (3R,5s)-1-allyloxycarbonyl-3-t-butyldimethylsilyloxy-5-[1-(5-chloroimidazo[5,1-b]thiazol-2-yl)-1-hydroxymethyl]pyrrolidine (diastereomer mixture) as a light yellow amorphous material.

NMR (CDCl$_3$) δ: 0.02–0.04 (6H, m), 0.83 & 0.85 (total 9H, s, each), 1.67–2.07 (2H, m), 3.30–3.45 (1H, m), 3.55–3.70 (1H, m), 4.20–4.50 (2H, m), 4.60–4.75 (2H, m), 4.80 & 5.05 (total 1H, d, each), 5.22–5.37 (2H, m), 5.7 & 6.15 (total 1H, br.s, each), 5.88–6.02 (1H, m), 6.95 & 6.97 (total 1H, s, each), 7.24 (1H, s).

MS (FAB$^+$: 474 (M$^+$+3H), 472 (M$^+$+1H)

b) (3R,5S)-1-Allyloxycarbonyl-3-t-butyldimethylsilyloxy-5-[1-(5-chloroimidazo[5,1-b] thiazol-2-yl)-1-(methylthiothiocarbonyloxy)methyl] pyrrolidine (diastereomer mixture)

(3R,5S)-1-Allyloxycarbonyl-3-t-butyldimethylsilyloxy-5-[1-(5-chloroimidazo[5,1-b]thiazol-2-yl)-1-hydroxymethyl]pyrrolidine (a diastereomer mixture) (2.300 g) and 3.3 mg of imidazole are dissolved in 24.5 ml of anhydrous THF. Carbon disulfide (0.44 ml) and 292 mg of 60% sodium hydride are successively added to the solution in an argon atmosphere on ice bath, and the mixture is stirred in this state for 20 min. Methyl iodide (0.32 ml) is added dropwise thereto, and the mixture is stirred in this state for one hr. The reaction solution is diluted with 250 ml of ethyl acetate, washed with semi-saturated saline, and dried over anhydrous magnesium sulfate. The solvent is removed by evaporation under reduced pressure to give a crude product which is then purified by column chromatography on silica gel (hexane:ethyl acetate=3:1) to give 2.607 g of (3R,5S)-1-allyloxycarbonyl-3-t-butyldimethylsilyloxy-5-[1-(5-chloroimidazo[5,1-b]thiazol-2-yl)-1-(methylthiothiocarbonyloxy)methyl]pyrrolidine (a diastereomer mixture) as a yellow viscous material.

NMR (CDCl$_3$) δ: 0.02 & 0.03 & 0.08 (total 6H, s, each), 0.83 & 0.87 (total 9H, s, each), 1.62 (1H, s), 2.08 (1H, m), 2.61 & 2.62 (total 3H, s, each), 3.25–3.70 (total 3H, m), 4.25 (1H, m), 4.50–4.80 (3H, br), 5.20–5.35 (2H, m), 5.85–6.05 (1H, m), 6.96 & 6.98 (total 1H, s, each), 7.15–7.35 (1H, m).

MS (FAB$^+$: 564 (M$^+$+3H), 562 (M$^+$+1H)

c) (3R,5S)-1-Allyloxycarbonyl-3-t-butyldimethylsilyloxy-5-(5-chloroimidazo[5,1-b] thiazol-2-yl)methylpyrrolidine Tri-n-butyltin hydride (1.8 ml) and 147 mg of 2,2'-azobisisobutyronitrile are added to a solution of 2.520 g of (3R,5S)-1-allyloxycarbonyl-3-t-butyldimethylsilyloxy-5-[1-(5-chloroimidazo[5,1-b]thiazol-2-yl)-1-(methylthiothiocarbonyloxy)methyl]pyrrolidine (a diastereomer mixture) in 22.5 ml of dry toluene, and the mixture is stirred in an argon atmosphere at an external temperature of 80° C. for 90 min. The reaction solution is diluted with 200 ml of ethyl acetate, washed with semi-saturated saline and dried over anhydrous magnesium sulfate. The solvent is removed by evaporation under reduced pressure to give a crude product which is then purified by column chromatography on silica gel (hexane:ethyl acetate=2:1) to give 1.467 g of (3R,5s)-1-allyloxycarbonyl-3-t-butyldimethylsilyloxy-5-(5-chloroimidazo[5,1-b]thiazol-2-yl)methylpyrrolidine as a slightly yellow oil.

NMR (CDCl$_3$) δ: 0.01 & 0.06 & 0.07 (total 6H, s, each), 0.82 & 0.87 (total 9H, s, each), 1.75–1.88 (1H, m), 1.93–2.15 (1H, m), 2.97–3.25 (2H, m), 3.35–3.60 (2H, m), 4.24 (2H, br.s), 4.60–4.67 (2H, m), 5.19–5.35 (2H, m), 5.88–6.02 (1H, m), 6.92 (1H, s), 7.05 (1H, s).

MS (TSP): 458 (M$^+$+3H), 456 (M$^+$+1H)

d) (3R,5S)-1-Allyloxycarbonyl-5-(5-chloroimidazo [5,1-b]thiazol-2-yl)methyl-3-hydroxypyrrolidine A solution of 1.430 g of (3R,5S)-1-allyloxycarbonyl-3-t-butyldimethylsilyloxy-5-(5-chloroimidazo[5,1-b]thiazol-2-yl)methylpyrrolidine in 31.5 ml of dry acetonitrile is cooled to 3° C., 1.3 ml of concentrated hydrochloric acid is added dropwise thereto while maintaining the internal temperature at 4° C. or below, and the mixture is stirred in this state for 15 min. The reaction solution is diluted with 200 ml of ethyl acetate, washed with 40 ml of a 5% aqueous sodium hydrogencarbonate solution (aqueous layer pH 9) and dried over anhydrous magnesium sulfate. The solvent is removed by evaporation under reduced pressure to give a crude product which is then purified by column chromatography on silica gel (ethyl acetate) to give 1.020 g of (3R,5S)-allyloxycarbonyl- 5-(5-chloroimidazo[5,1-b]thiazol-2-yl) methyl-3-hydroxypyrrolidine as a slightly yellow viscous material.

NMR (CDCl$_3$) δ: 1.80–1.95 (1H, m), 2.06–2.25 (1H, m), 2.55–2.80 (1H, m), 3.05–3.25 (2H, m), 3.40–3.47 (1H, m), 3.60–3.75 (1H, m), 4.25–4.35 (1H, m), 4.38 (1H, br.s), 4.55–4.70 (2H, m), 5.22–5.36 (2H, m), 5.88–6.02 (1H, m), 6.92 (1H, s), 7.08 (1H, s).

MS (FAB$^+$: 344 (M$^+$+3H), 342 (M$^+$+1H)

e) (3S,5S)-1-Allyloxycarbonyl-3-benzoylthio-5-(5-chloroimidazo[5,1-b]thiazol-2-yl)methylpyrrolidine A solution of 438 mg of (3R,5S)-1-allyloxycarbonyl-5-(5-chloroimidazo[5,1-b]thiazol-2-yl)methyl-3-hydroxypyrrolidine and 672 mg of triphenylphosphine in 6.5 ml of anhydrous THF is cooled to −10° C. in an argon atmosphere. Diethyl azodicarboxylate (0.40 ml) is added dropwise to the mixture over a period of 7 min while maintaining the solution at −5° C. or below, and the mixture is stirred in this state for 23 min. Thiobenzoic acid (90%) (0.34 ml) is added dropwise to the mixed solution at −10° C. over a period of 5 min, and the mixture is stirred in this state for additional 25 min. The solvent is removed by evaporation under reduced pressure to give an oil which is then purified by column chromatography on silica gel (hexane:ethyl acetate=1:1) to give 505 mg of the title compound as a bright yellow viscous material.

NMR (CDCl$_3$) δ: 1.83–1.96 (1H, m), 2.55–2.70 (1H, m), 3.05–3.45 (3H, m), 4.15–4.35 (3H, m), 4.62–4.68 (2H, m), 5.22–5.38 (2H, m), 5.88–6.02 (1H, m), 6.93 & 6.95 (total 1H, s), 7.10 (1H, br.s), 7.40–7.50 (2H, m), 7.55–7.63 (1H, m), 7.89 & 8.15 (total 2H, d, each).

MS (FAB$^+$: 464 (M$^+$+3H), 462 (M$^+$+1H)

Structures of the compounds prepared in the above examples are summarized in Table 1.

TABLE 1

| Example No. | R$^1$ | R$^2$ | A | R$^3$ | R$^4$ | R$^5$ | R$^6$ | R$^7$ |
|---|---|---|---|---|---|---|---|---|
| 1 | CH$_3$ | H | —CONH—CH$_2$— | H | H | bond | H | — |
| 2 | CH$_3$ | H | —CONH—CH$_2$— | H | H | bond | H | Me |
| 3 | CH$_3$ | H | —CON(—CH$_3$)— | H | H | bond | H | — |
| 4 | CH$_3$ | H | —CON(—CH$_3$)— | H | H | bond | H | Me |
| 5 | CH$_3$ | H | —CON(—CH$_3$)— | H | bond | H | H | Me |
| 6 | CH$_3$ | H | —CH(OH)— | H | bond | H | H | — |
| 7 | CH$_3$ | H | —CH(OH)— | H | bond | H | H | Me |
| 8 | CH$_3$ | H | —CH(OH)— | H | bond | H | H | — |
| 9 | CH$_3$ | H | —CH(OH)— | H | bond | H | H | Me |
| 10 | CH$_3$ | H | —CH$_2$— | H | H | bond | H | — |
| 11 | CH$_3$ | H | —CH$_2$— | H | H | bond | H | Me |
| 12 | CH$_3$ | H | —CH(OH)— | H | H | bond | H | — |
| 13 | CH$_3$ | H | —CH(OH)— | H | H | bond | H | Me |
| 14 | CH$_3$ | H | —CH(OH)— | H | H | H | bond | — |
| 15 | CH$_3$ | H | —CH(OH)— | H | H | H | bond | Me |
| 16 | CH$_3$ | H | —CH(OH)— | bond | H | H | H | — |
| 17 | CH$_3$ | H | —CH(OH)— | bond | H | H | H | — |
| 18 | CH$_3$ | H | —CH(OH)— | bond | H | H | H | Me |
| 19 | CH$_3$ | H | —CH(OH)— | bond | H | H | H | Me |
| 20 | CH$_3$ | H | —CH$_2$— | H | bond | H | H | — |
| 21 | CH$_3$ | H | —CH$_2$— | H | bond | H | H | Me |
| 22 | CH$_3$ | H | —CH$_2$— | H | bond | H | H | —(CH$_2$)$_2$—OH |
| 23 | CH$_3$ | H | —CH$_2$— | bond | H | H | H | — |
| 24 | CH$_3$ | H | —CH$_2$— | bond | H | H | H | Me |
| 25 | CH$_3$ | H | —CH$_2$— | bond | H | H | H | —(CH$_2$)$_2$—OH |
| 26 | CH$_3$ | H | —CH$_2$— | bond | H | H | H | —CH$_2$—CONH$_2$ |
| 27 | CH$_3$ | H | —CH$_2$— | bond | H | H | H | —(CH$_2$)$_2$—F |
| 28 | CH$_3$ | H | —CH$_2$— | bond | Me | H | H | — |
| 29 | CH$_3$ | H | —CH$_2$— | bond | Me | H | H | Me |
| 30 | CH$_3$ | H | —CH$_2$— | bond | Me | H | H | —CH$_2$—CONH$_2$ |
| 31 | CH$_3$ | H | —CH$_2$— | bond | H | Me | H | — |
| 32 | CH$_3$ | H | —CH$_2$— | bond | H | Me | H | Me |
| 33 | CH$_3$ | H | —CH$_2$— | bond | H | Me | H | —CH$_2$—CONH$_2$ |
| 34 | CH$_3$ | H | —CH$_2$— | H | H | H | bond | — |
| 35 | CH$_3$ | H | —CH$_2$— | H | H | H | bond | Me |
| 36 | CH$_3$ | H | bond | H | H | bond | H | Me |
| 37 | CH$_3$ | H | bond | H | H | bond | H | —(CH$_2$)$_2$—OH |
| 38 | CH$_3$ | H | (Z)—CH=CH— | H | bond | H | H | — |
| 39 | CH$_3$ | H | (Z)—CH=CH— | H | bond | H | H | Me |
| 40 | CH$_3$ | H | (E)—CH=CH— | H | bond | H | H | Me |
| 41 | CH$_3$ | H | —CH$_2$— | bond | H | Me | H | 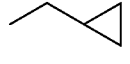 |
| 42 | CH$_3$ | H | —CH$_2$— | bond | H | Me | H | —(CH$_2$)$_2$—F |
| 43 | CH$_3$ | H | —CH$_2$— | bond | H | Me | H | —(CH$_2$)$_2$—OH |
| 44 | CH$_3$ | H | —CH$_2$— | bond | H | Me | H | —CH$_2$—CONMe$_2$ |
| 45 | CH$_3$ | H | —CH$_2$— | bond | H | Me | H | —CH$_2$O—Me |
| 46(1) | CH$_3$ | H | —CH$_2$— | bond | H | Me | H | —CH$_2$—COOEt |
| 46(2) | CH$_3$ | H | —CH$_2$— | bond | H | Me | H | —CH$_2$—COOH |
| 47(A) | CH$_3$ | H | (Z)—CH=CH— | bond | H | H | H | Me |
| 47(B) | CH$_3$ | H | (E)—CH=CH— | bond | H | H | H | Me |
| 48(A) | H | H | (Z)—CH=CH— | bond | H | H | H | Me |
| 48(B) | H | H | (E)—CH=CH— | bond | H | H | H | Me |
| 49 | CH$_3$ | H | bond | H | bond | H | H | — |
| 50 | CH$_3$ | H | bond | H | bond | H | H | Me |
| 51 | CH$_3$ | H | bond | H | bond | H | H | —CH$_2$—CONH$_2$ |
| 52 | CH$_3$ | H | (E)—CH=CH— | bond | H | H | H | — |
| 53(A) | CH$_3$ | H | (E)—CH=CH— | bond | H | H | H | —CH$_2$—CONH$_2$ |
| 53(B) | CH$_3$ | H | (Z)—CH=CH— | bond | H | H | H | —CH$_2$—CONH$_2$ |
| 54 | CH$_3$ | H | (Z)—CH=CH— | H | bond | H | H | —CH$_2$—CONH$_2$ |
| 55 | CH$_3$ | H | (E)—CH=CH— | H | bond | H | H | —CH$_2$—CONH$_2$ |
| 56 | CH$_3$ | H | (E)—CH=CH— | H | bond | H | H | —(CH$_2$)$_2$—CONH$_2$ |
| 57 | CH$_3$ | H | (Z)—CH=CH— | H | H | bond | H | —CH$_2$—CONH$_2$ |
| 58 | CH$_3$ | H | (E)—CH=CH— | H | H | H | bond | —CH$_2$—CONH$_2$ |
| 59(A) | CH$_3$ | H | (E)—CH=CH— | bond | Me | H | H | —CH$_2$—CONH$_2$ |
| 59(B) | CH$_3$ | H | (Z)—CH=CH— | bond | Me | H | H | —CH$_2$—CONH$_2$ |
| 60(A) | CH$_3$ | H | (E)—CH=CH— | Me | bond | H | H | —CH$_2$—CONH$_2$ |
| 60(B) | CH$_3$ | H | (Z)—CH=CH— | Me | bond | H | H | —CH$_2$—CONH$_2$ |
| 61 | CH$_3$ | H | —CH$_2$— | bond | H | —SMe | H | — |

TABLE 1-continued

| Example No. | R¹ | R² | A | R³ | R⁴ | R⁵ | R⁶ | R⁷ |
|---|---|---|---|---|---|---|---|---|
| 62 | CH₃ | H | —CH₂— | bond | H | —SMe | H | Me |
| 63 | CH₃ | H | —CH₂— | bond | H | —SMe | H | —CH₂—CONH₂ |
| 64 | CH₃ | H | —CH₂— | bond | H | Cl | H | — |
| 65 | CH₃ | H | —CH₂— | bond | H | Cl | H | Me |
| 66 | CH₃ | H | —CH₂— | bond | H | Cl | H | —CH₂—CONH₂ |
| 67 | CH₃ | H | —CH₂— | bond | H | Me | H | —(CH₂)₂—CONH₂ |
| 68 | CH₃ | H | (Z)—CH=CH— | H | bond | Me | H | —CH₂—CONH₂ |
| 69 | CH₃ | H | (E)—CH=CH— | H | bond | Me | H | —CH₂—CONH₂ |
| 70 | CH₃ | H | (Z)—CH=CH— | H | bond | H | H | —Et |
| 71 | CH₃ | H | (Z)—CH=CH— | H | bond | H | H | —(CH₂)₂—OH |
| 72 | CH₃ | H | (Z)—CH=CH— | H | bond | H | H | —(CH₂)₂—CONH₂ |
| 73 | CH₃ | H | (Z)—CH=CH— | H | bond | H | H | —(CH₂)₂—F |
| 74 | CH₃ | H | (Z)—CH=CH— | H | bond | H | H |  |
| 75 | CH₃ | H | (Z)—CH=CH— | bond | H | H | H | —(CH₂)₂—OH |
| 76 | CH₃ | H | (Z)—CH=CH— | bond | H | H | H | —(CH₂)₂—CONH₂ |
| 77(A) | CH₃ | H | (Z)—CH=CH— | bond | H | H | H | —(CH₂)₂—F |
| 77(B) | CH₃ | H | (E)—CH=CH— | bond | H | H | H | —(CH₂)₂—F |

Pharmacological Test Example 1

Antimicrobial Activity

For representative compounds among the novel carbapenem derivatives of the present invention, the minimum inhibitory concentration (MIC, μg/ml) against various pathogenic bacteria was measured in accordance with a method described in CHEMOTHERAPY, Vol. 16, No. 1, 99 (1968). The results are summarized in Tables 2 to 5.

TABLE 2

| Test strain | Compound of Ex. 38 | Compound of Ex. 39 | Compound of Ex. 50 | Compound of Ex. 53A |
|---|---|---|---|---|
| S. aureus 209P JC-1 | 0.10 | <0.025 | 0.05 | 0.05 |
| S. aureus M126* | 25 | 6.25 | 12.5 | 12.5 |
| E. coli NIHJ JC-2 | 0.10 | <0.025 | 0.05 | 0.05 |
| K. pneumoniae PCI602 | 0.20 | 0.05 | 0.10 | 0.10 |
| E. coli GN206 | 0.10 | <0.025 | 0.05 | 0.10 |
| P. vulgaris GN76 | 1.56 | 0.39 | 0.78 | 0.78 |
| M. morganii 1510 | 0.78 | 0.20 | 0.39 | 0.39 |
| C. freundii GN346 | 0.20 | 0.10 | 0.10 | 0.10 |
| E. cloacae G-0008 | 0.10 | 0.05 | 0.05 | 0.10 |
| S. marcescens No. 1 | 0.20 | 0.05 | 0.10 | 0.10 |
| Ps. aeruginosa GN10362 | 6.25 | 6.25 | 0.78 | 0.78 |

*: Highly Meticillin-resistant strain

TABLE 3

| Test strain | Compound of Ex. 2 | Compound of Ex. 6 | Compound of Ex. 18 | Compound of Ex. 26 |
|---|---|---|---|---|
| S. aureus 209P JC-1 | <0.025 | <0.025 | <0.025 | <0.025 |
| S. aureus M126* | 6.25 | 6.25 | 12.5 | 6.25 |
| E. coli NIHJ JC-2 | 0.10 | 0.05 | 0.05 | 0.05 |
| K. pneumoniae PCI602 | 0.10 | 0.10 | 0.10 | 0.10 |
| E. coli GN206 | 0.05 | 0.10 | 0.05 | 0.05 |
| P. vulgaris GN76 | 1.56 | 0.78 | 0.39 | 0.39 |
| M. morganii 1510 | 0.39 | 0.39 | 0.20 | 0.39 |
| C. freundii GN346 | 0.20 | 0.10 | 0.20 | 0.05 |
| E. cloacae G-0008 | 0.10 | 0.10 | 0.05 | 0.05 |
| S. marcescens No. 1 | 0.20 | 0.20 | 0.10 | 0.20 |
| Ps. aeruginosa GN10362 | 12.5 | 1.56 | 3.13 | 0.78 |

*: Highly Meticillin-resistant strain

TABLE 4

| Test strain | Compound of Ex. 53B | Compound of Ex. 54 | Compound of Ex. 67 | Compound of Ex. 72 |
|---|---|---|---|---|
| S. aureus 209P JC-1 | <0.025 | <0.025 | <0.025 | <0.025 |
| S. aureus M126* | 3.13 | 3.13 | 12.5 | 6.25 |
| E. coli NIHJ JC-2 | 0.05 | <0.025 | 0.05 | 0.05 |
| K. pneumoniae PCI602 | 0.05 | 0.05 | 0.10 | 0.10 |
| E. coli GN206 | 0.05 | 0.05 | 0.10 | 0.10 |
| P. vulgaris GN76 | 0.39 | 0.39 | 0.78 | 0.78 |
| M. morganii 1510 | 0.20 | 0.20 | 0.39 | 0.39 |
| C. freundii GN346 | 0.05 | 0.05 | 0.05 | 0.10 |
| E. cloacae G-0008 | 0.05 | <0.025 | 0.05 | 0.05 |
| S. marcescens No. 1 | 0.10 | 0.10 | 0.39 | 0.10 |

TABLE 4-continued

| Test strain | Compound of Ex. 53B | Compound of Ex. 54 | Compound of Ex. 67 | Compound of Ex. 72 |
|---|---|---|---|---|
| Ps. aeruginosa GN10362 | 0.78 | 1.56 | 0.78 | 1.56 |

*: Highly Meticillin-resistant strain

TABLE 5

| Test strain | Compound of Ex. 76 | Compound A | Compoound B |
|---|---|---|---|
| S. aureus 209P JC-1 | <0.025 | <0.025 | <0.025 |
| S. aureus M126* | 6.25 | 50 | 25 |
| E. coli NIHJ JC-2 | 0.05 | 0.10 | 0.10 |
| K. pneumoniae PCI602 | 0.10 | 0.39 | 0.20 |
| E. coli GN206 0.10 | 0.10 | 0.10 | 0.20 |
| P. vulgaris GN76 0.39 | 0.39 | 3.13 | 3.13 |
| M. morganii 1510 0.20 | 0.20 | 0.78 | 0.78 |
| C. freundii GN346 | 0.10 | 0.10 | 0.20 |
| E. cloacae G-0008 | 0.05 | 0.10 | 0.20 |
| S. marcescens No. 1 | 0.20 | 0.39 | 0.39 |
| Ps. aeruginosa GN10362 | 0.78 | 1.56 | 12.5 |

*: Highly Meticillin-resistant strain
Compound A: Imipenem
Compound B: Panipenem Pharmacological Test Example 2

Stability Against DHP-I

The stability of representative compounds, among the novel carbapenem derivatives of the present invention, against kidney dehydropeptidase-I (DHP-I) of a pig and a mouse was measured, and the residue (%) of the carbapenem derivatives three hr after the initiation of the test is summarized in Table 6.

The stability against DHP-I was measured according to the following method.

1. Preparation of DHP-I from kidney acetone powder of each animal.

1.5 g of a kidney acetone powder (manufactured by Sigma) Porcine Type II (Lot. 33H7225) was suspended in 100 ml of 50 mM Tris-HCl buffer (pH 7.0) containing 20% butanol, and the suspension was stirred at 5° C. for 48 hr. The suspension was then dialyzed against 50 mM Tris-HCl buffer (pH 7.0) (a cellulose tube 30/32 Viskase Sales Corp.) until the odor of butanol disappeared, thereby removing butanol. The dialyzate is centrifuged at 10000×g (KUBOTA 6800) for 20 min, and the supernatant was obtained as a partially purified DHP-I. This partially purified DHP-I was subdivided and stored at −80° C. The above procedure was repeated, except that 1.5 g of Mouse (Lot. 23F8105) was used. Thus, a partially purified DHP-I was prepared and stored.

2. Measurement of stability against each DHP-I.

For the carbapenem as the substrate agent, a solution (2000 μg (potency)/ml) was prepared using sterilized, purified water. For the sample solution, the carbapenem (2000 μg (potency)/ml) solution was added to the partially purified DHP-I of each animal to a final concentration of 100 μg (potency)/ml). For the blank, 50 mM Tris-HCl buffer (pH 7.0) was used instead of the partially purified DHP-I of each animal. The reaction was allowed to proceed at 37° C. for 3 hr, and a given amount of the reaction mixture was sampled. Methanol in the same amount as the sampled reaction mixture was added under ice cooling to terminate the reaction. The reaction mixture was filtered through a filter (Sanprep LCR 13-LH manufactured by MILLIPORE) and subjected to HPLC (column: CAPCELL PACK C18SG120, manufactured by Shiseido Co., Ltd.; detection: UV; mobile layer: acetonitrile/10 mM aqueous acetic acid solution) to determined the residue (%).

Residue (%)=(Sample Peak Area/Blank Peak Area)×100

TABLE 6

| DHP-1 (%) | Compound of Ex. 20 | Compound of Ex. 26 | Compound A | Compound B | Compound C |
|---|---|---|---|---|---|
| Pig | 100 | 95 | 24 | 19 | 71 |
| Mouse | 97 | 90 | 0.6 | 28 | 18 |

Compound A: Imipenem
Compound B: Panipenem
Compound C: Meropenem

Pharmacological Test Example 3

Acute Toxicity in Intravenous Administration

In a test using mice (ICR, male) (three mice for each group), the compound prepared in Example 53 was administered at a dose of 1,000 mg/kg. As a result, all the mice survived.

Preparation Example 1

Preparation for Injection

A pharmaceutical composition containing a compound according to the present invention is aseptically charged into vials so that each vial contains 1000 mg (potency) of the compound of the present invention.

Compound prepared in example 53 250 parts (potency)

| Milk sugar | 60 parts |
|---|---|
| Magnesium stearate | 5 parts |

Preparation Example 2

Soft Capsuled Preparation for Rectal Administration

| Olive oil | 160 parts |
|---|---|
| Polyoxyethylene lauryl ether | 10 parts |
| Sodium hexametaphosphate | 5 parts |

25 parts (potency) of the compound prepared in example 53 is added to and homogeneously mixed with a base comprising the above ingredients, and the mixture is charged into soft capsules for rectal administration so that each capsule contains 250 mg of the compound prepared in example 53.

What is claimed is:

1. A compound of formula (I) or a pharmacologically acceptable salt thereof:

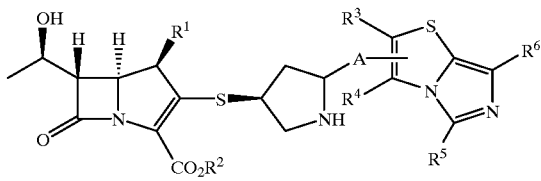

(I)

wherein

A represents a bond, —(CH$_2$)m—, —CHR$^8$—, —(CH$_2$)n—CH=CH—(CH$_2$)n'—, —C(=O)N(—R$^9$)CH$_2$— wherein R$^8$ represents hydroxyl, methoxy, halogen, or amino, R$^9$ represents hydrogen or —(CH$_2$)pCH$_3$ wherein p is an integer of 0 to 3, m is an integer of 1 to 3, and n and n' each represent an integer of 0 to 3;

R$^1$ represents hydrogen or lower alkyl;

R$^2$ represents hydrogen, sodium, or potassium; and any one of R$^3$, R$^4$, R$^5$, and R$^6$ represents a bond and is bonded to A, and the remaining three substituents, which may be the same or different, represent hydrogen, halogen, nitro, cyano, lower alkyl, lower cycloalkyl, lower alkylthio, C$_{2-4}$ alkenyl, formyl, lower alkylcarbonyl, arylcarbonyl, or aryl;

one or more hydrogen atoms in said lower alkyl, lower cycloalkyl, C$_{2-4}$ alkenyl, and aryl groups as a group or a portion of a group, which may be represented by R$^3$, R$^4$, R$^5$, and R$^6$, may be substituted by a group selected from the group consisting of halogen, nitro, cyano, lower alkylthio, lower alkoxy, hydroxyl, amino, lower cycloalkyl, N-lower alkylamino, formyl, lower alkylcarbonyl, arylcarbonyl, carboxyl, lower alkoxycarbonyl, formylamino, lower alkylcarbonylamino, carbamoyl, (N-lower alkylamino) carbonyl, aminosulfonyl, (N-lower alkylamino) sulfonyl, aminosulfonylamino, (N-lower alkylamino) sulfonylamino, and aryl, or any two of R$^3$, R$^4$, R$^5$, and R$^6$ may form together a five-membered heterocyclic saturated ring, containing one oxygen atom and one nitrogen atom, in which the ring may be substituted by oxo (=O), or any two of R$^3$, R$^4$, R$^5$, and R$^6$ may form together C$_{3-6}$ alkylene.

2. The compound according to claim 1, wherein R$^1$ is hydrogen or methyl and R$^2$ represents hydrogen.

3. The compound according to claim 1, wherein R$^3$, R$^4$, R$^5$, and R$^6$ except for at representing a bond, which may be the same or different, represent hydrogen, halogen, cyano, lower alkyl, lower cycloalkyl, lower alkylthio, C$_{2-4}$ alkenyl, formyl, lower alkylcarbonyl, or aryl, and one or more hydrogen atoms in said the lower alkyl, lower cycloalkyl, C$_{2-4}$ alkenyl, and aryl groups may be substituted.

4. The compound according to claim 1, wherein A represents a bond, —CH$_2$—, —CH(OH)—, —CH=CH—, —C(O)NHCH$_2$—, or —C(=O)N(—CH$_3$)CH$_2$—;

R$^1$ represents hydrogen or methyl;

R$^2$ represents hydrogen; and

R$^3$, R$^4$, R$^5$, and R$^6$ except for at representing a bond, which may be the same or different, represent hydrogen, or halogen, lower alkyl, lower cycloalkyl, or lower alkylthio, and said lower alkyl, lower cycloalkyl, and lower alkylthio groups may be substituted by a group selected from the group consisting of halogen, hydroxyl, amino, lower cycloalkyl, lower alkylcarbonyl, lower alkoxy, lower alkoxycarbonyl, carboxyl, carbamoyl, and (N-lower alkylamino) carbonyl.

5. The compound according to claim 1, wherein A represents a bond and R$^4$ or R$^5$ represents a bond.

6. A compound of formula (II) or a pharmacologically acceptable salt thereof:

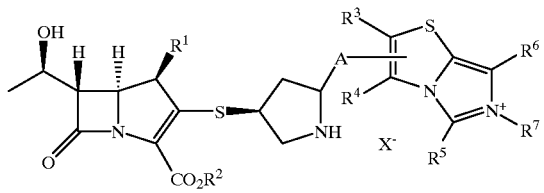

(II)

wherein

A represents a bond, —(CH$_2$)m—, —CHR$^8$—, —(CH$_2$)n—CH=CH—(CH$_2$)n'—, —C(=O)N(—R$^9$)CH$_2$— wherein R$^8$ represents hydroxyl, methoxy, halogen, or amino, R$^9$ represents hydrogen or —(CH$_2$)pCH$_3$ wherein p is an integer of 0 to 3, m is an integer of 1 to 3, and n and n' each represent an integer of 0 to 3;

R$^1$ represents hydrogen or lower alkyl;

R$^2$ represents hydrogen, sodium, or potassium;

any one of R$^3$, R$^4$, R$^5$, and R$^6$ represents a bond and is bonded to A, and the remaining three substituents, which may be the same or different, represent hydrogen, halogen, nitro, cyano, lower alkyl, lower cycloalkyl, lower alkylthio, C$_{2-4}$ alkenyl, formyl, lower alkylcarbonyl, arylcarbonyl, or aryl;

R$^7$ represents lower alkyl, lower cycloalkyl, or aryl; and one or more hydrogen atoms in said lower alkyl, lower cycloalkyl, C$_{2-4}$ alkenyl, and aryl groups as a group or a portion of a group, which may be represented by R$^3$, R$^4$, R$^5$, R$^6$, and R$^7$, may be substituted by a group selected from the group consisting of halogen, nitro, cyano, lower alkylthio, lower alkoxy, hydroxyl, amino, lower cycloalkyl, N-lower alkylamino, formyl, lower alkylcarbonyl, arylcarbonyl, carboxyl, lower alkoxycarbonyl, formylamino, lower alkylcarbonylamino, carbamoyl, (N-lower alkylamino) carbonyl, aminosulfonyl, (N-lower alkylamino) sulfonyl, aminosulfonylamino, (N-lower alkylamino) sulfonylamino, and aryl, or any two of R$^3$, R$^4$, R$^5$, and R$^6$ may form together a five-membered heterocyclic saturated ring, containing one oxygen atom and one nitrogen atom, in which the ring may be substituted by oxo (=O), or any two of R$^3$, R$^4$, R$^5$, and R$^6$ may form together C$_{3-6}$ alkylene and X$^-$ represents a pharmaceutically acceptable organic acid anion, or inorganic acid anion.

7. The compound according to claim 1, wherein R$^1$ represents hydrogen or methyl and R$^2$ represents hydrogen.

8. The compound according to claim 1, wherein R$^3$, R$^4$, R$^5$, and R$^6$ except for at representing a bond, which may be the same or different, represent hydrogen, halogen, cyano, lower alkyl, lower cycloalkyl, lower alkylthio, C$_{2-4}$ alkenyl, formyl, lower alkylcarbonyl, or aryl, and one or more hydrogen atoms in said lower alkyl, lower cycloalkyl, C$_{2-4}$ alkenyl, and aryl groups may be substituted, and $R^7$ represents a lower alkyl or lower cycloalkyl group, one or more hydrogen atoms in the lower alkyl and lower cycloalkyl groups may be substituted.

9. The compound according to claim 1, wherein A represents a bond, —$CH_2$—, —CH(OH)—, —CH=CH—, —C(=O)$NHCH_2$—, or —C(=O)N(—$CH_3$)$CH_2$—;

$R^1$ represents hydrogen or methyl;

$R^2$ represents hydrogen;

$R^3$, $R^4$, $R^5$, and $R^6$ except for at representing a bond, which may be the same or different, represent hydrogen, halogen, lower alkyl, lower cycloalkyl, or lower alkylthio, and said lower alkyl, lower cycloalkyl, and lower alkylthio groups may be substituted by a group selected from the group consisting of halogen, hydroxyl, amino, lower cycloalkyl, lower alkylcarbonyl, lower alkoxy, lower alkoxycarbonyl, carboxyl, carbamoyl, and (N-lower alkylamino) carbonyl; and $R^7$ represents lower alkyl or lower cycloalkyl, and said lower alkyl and lower cycloalkyl groups may be substituted by a group selected from the group consisting of halogen, hydroxyl, amino, lower cycloalkyl, lower alkylcarbonyl, lower alkoxy, lower alkoxycarbonyl, carboxyl, carbamoyl, and (N-lower alkylamino) carbonyl.

10. The compound according to claim 1 wherein A represents a bond and $R^4$ or $R^5$ represents a bond.

11. A pharmaceutical composition comprising a compound according to any one of claims 1 to 5, 7 to 10 together with a pharmacologically acceptable carrier.

12. A method for treating a bacterial infection, comprising administering the compound according to any one of claims 1 to 5, 7 to 10 to an animal including a human being.

* * * * *